US008053435B2

(12) United States Patent
Lee et al.

(10) Patent No.: US 8,053,435 B2
(45) Date of Patent: Nov. 8, 2011

(54) NAPHTHALENYLOXYPROPENYL DERIVATIVES HAVING INHIBITORY ACTIVITY AGAINST HISTONE DEACETYLASE AND PHARMACEUTICAL COMPOSITION COMPRISING THE SAME

(75) Inventors: Cheol Hae Lee, Gongju (KR); Hee Jung Jung, Daejeon (KR); Jae Hak Kim, Daejeon (KR); Won Jang Jeong, Daejeon (KR); Joong Myung Cho, Seoul (KR); Seong Gu Ro, Daejeon (KR); Young Lan Hyun, Seoul (KR); Cheol Soon Lee, Gwangju (KR); Dongkyu Shin, Seoul (KR)

(73) Assignees: Korea Research Institute of Chemical Technology, Daejeon (KR); Crystalgenomics, Inc., Seoul (KR)

( * ) Notice: Subject to any disclaimer, the term of this patent is extended or adjusted under 35 U.S.C. 154(b) by 0 days.

(21) Appl. No.: 12/513,021

(22) PCT Filed: Nov. 1, 2007

(86) PCT No.: PCT/KR2007/005491
§ 371 (c)(1),
(2), (4) Date: Apr. 30, 2009

(87) PCT Pub. No.: WO2008/054154
PCT Pub. Date: May 8, 2008

(65) Prior Publication Data
US 2010/0069630 A1 Mar. 18, 2010

(30) Foreign Application Priority Data

Nov. 3, 2006 (KR) .................. 10-2006-0108182
Nov. 3, 2006 (KR) .................. 10-2006-0108228
Nov. 3, 2006 (KR) .................. 10-2006-0108230
Nov. 7, 2006 (KR) .................. 10-2006-0109436

(51) Int. Cl.
| | |
|---|---|
| *A61K 31/165* | (2006.01) |
| *A61K 31/341* | (2006.01) |
| *A61K 31/381* | (2006.01) |
| *A61K 31/4164* | (2006.01) |
| *A61K 31/4166* | (2006.01) |
| *A61K 31/40* | (2006.01) |
| *A61K 31/4468* | (2006.01) |
| *A61K 31/5375* | (2006.01) |
| *C07D 207/50* | (2006.01) |
| *C07D 233/88* | (2006.01) |
| *C07D 295/027* | (2006.01) |
| *C07D 211/98* | (2006.01) |
| *C07D 307/66* | (2006.01) |
| *C07D 333/36* | (2006.01) |

(52) U.S. Cl. ............ 514/237.8; 514/315; 514/398; 514/426; 514/447; 514/472; 514/623; 544/164; 548/331.1; 548/326.5; 548/579; 548/543; 549/480; 549/69

(58) Field of Classification Search .......... None
See application file for complete search history.

(56) References Cited

FOREIGN PATENT DOCUMENTS

| | | |
|---|---|---|
| KR | 2007-0047024 A1 | 5/2007 |
| WO | 2003/076395 A1 | 9/2003 |
| WO | 2004/063146 A1 | 7/2004 |
| WO | 2004/065354 A1 | 8/2004 |
| WO | 2004/076386 A2 | 9/2004 |
| WO | 2007/052938 A1 | 5/2007 |

*Primary Examiner* — Yong Chu
*Assistant Examiner* — Michael Barker
(74) *Attorney, Agent, or Firm* — Lucas & Mercanti, LLP

(57) ABSTRACT

The present invention discloses novel naphthalenyloxypropenyl derivatives useful for inhibiting the enzyme activity of histone deacetylase, leading effective suppression of cancer cell proliferation.

13 Claims, No Drawings

NAPHTHALENYLOXYPROPENYL DERIVATIVES HAVING INHIBITORY ACTIVITY AGAINST HISTONE DEACETYLASE AND PHARMACEUTICAL COMPOSITION COMPRISING THE SAME

CROSS-REFERENCE TO RELATED APPLICATIONS

This application is a 371 of PCT/KR2007/005491 filed Nov. 1, 2007, which claims the benefit of Korean Application Nos. 10-2006-0108182 filed Nov. 3, 2006, 10-2006-0108228 filed Nov. 3, 2006, 10-2006-0108230 filed Nov. 3, 2006, and 10-2006-0109436 filed Nov. 7, 2006, the contents of each of which are incorporated herein by reference.

FIELD OF THE INVENTION

The present invention relates to novel naphthalenyloxypropenyl derivatives and an anti-cancer composition comprising the same.

BACKGROUND OF THE INVENTION

Histones associate with DNAs in the nuclei of eukaryotic cells as basic proteins and are subject to reversible acetylation at the amino group of the lysine residue. Such reversible acetylation of histones is involved in the formation of chromatin of a higher order structure, the cell division cycle and ultimately the gene expression, and can be regulated by the dynamic balance established between the opposing activities of histone acetyl transferases (HATs) and histone deacetylases (HDACs): these enzymes neutralize or restore the positive charges of lysine residues (e.g., 4 lysine residues in H4) by acetylation/deacetylation to regulate the gene transcriptional level.

HDACs play an important role in cell cancerization or differentiation and their expression is enhanced under conditions such as hypoxia, lowered glucose, and cell cancerization, to inhibit the expression of cell proliferation inhibitors. That is, histone deacetylation by HDAC causes cell proliferation, while hyperacetylation of histone facilitates the inhibition of cell proliferation and cell differentiation. Therefore, when HDACs are inhibited, cell proliferation and angiogenesis can be controlled.

Abnormal histone deacetylation has been reported to cause acute promyelocytic leukemica (APL) (Lin R. J. et. al. *Oncogene* 20: 7204, 2001; Zelent A. et. al. *Oncogene* 20: 7186, 2001). Specifically, abnormality in the regulation of HDAC activity leads to oncoprotein's inadequate transcriptional suppression and the formation of abnormal chromatin structures, which causes normal cells to become cancer. Accordingly, HDAC has been one of targets for the study of anticancer drugs as well as gene expression inhibitors and there have been attempts to develop HDAC inhibitors as anticancer drugs.

Recent studies on anticancer drug through chromatin remodeling have shown that HDAC inhibitors such as suberoylanilide hydroxamic acid (SAHA) or apicidin inhibit the proliferation of cancer cells and induce cell differentiation (Munster P. N. et al., *Cancer research* 61: 8492, 2001; Han J. W. et. al. *Cancer research* 60: 6068, 2000).

n-Butyrate, used as the first HDAC inhibitor, was reported to be useful for the treatment of large intestine cancer as well as molecular biology test. But it is not suitable for the analysis of a HDAC inhibitor due to its high concentration in the order of millimole (mM), and influence on other enzymes in cells, cytoskeleton, cell membrane, etc. Trichostatin A (TSA) which enhances the differentiation and suppresses the proliferation of Friend murine erythroleukemia cells has been reported to inhibit HDAC (Yoshida M. et al., *Cancer research* 47: 3688, 1987; Yoshida M. & Beppu T. *Exp. Cell Res.* 177: 122, 1988; Yoshida M. et al., *J of Biol. Chem.* 265: 17174, 1990).

Therefore, there has been a need for developing an improved HDAC inhibitor. The present inventors have found that novel naphthalenyloxypropenyl derivatives are efficient inhibitors against cell proliferation which can be advantageously used for treating cancer.

SUMMARY OF THE INVENTION

It is an object of the present invention to provide a novel compound which efficiently inhibits the activity of histone deacetylases, thereby suppressing the proliferation of tumor cells.

It is another object of the present invention to provide a pharmaceutical composition comprising the inventive compound as an active ingredient for preventing or treating cancers.

In accordance with one aspect of the present invention, there are provided naphthalenyloxypropenyl derivatives of formulae (1) to (4) or pharmaceutically acceptable salts thereof:

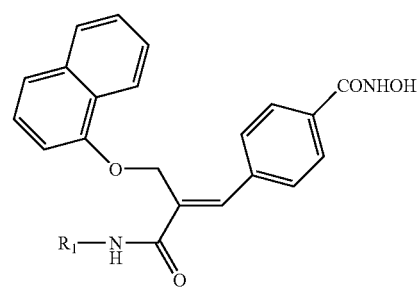

(1)

wherein, $R_1$ is substituted or unsubstituted $C_{1-6}$alkyl with one or more substituents selected from the group consisting of di$C_{1-3}$ alkylamino, pyrrolidinyl, oxopyrrolidinyl, methoxypyrrolidinyl, $C_{1-3}$alkylpiperidinyl, morpholinyl, imidazolyl, methoxy, ethoxy, tetrahydrofuranyl, $C_{3-8}$cycloalkenyl, furanyl, thiophenyl, fluorophenyl, di$C_{1-3}$alkylaminophenyl and methoxyphenyl; piperidinyl substituted with $C_{1-6}$alkyl; or $C_{3-8}$cycloalkyl;

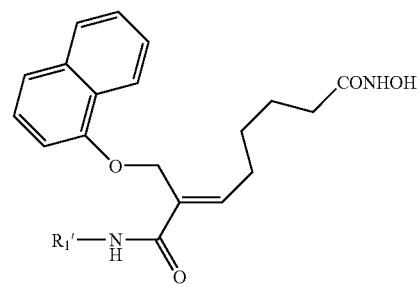

(2)

wherein,

R$_1$' is substituted or unsubstituted C$_{1-3}$alkyl with one or more substituents selected from the group consisting of halophenyl, C$_{1-3}$alkoxy, C$_{1-3}$alkoxyC$_{1-3}$alkyl, cyclohexanyl, furanyl, thiophenyl, imidazolyl, imidazolidylC$_{1-3}$alkyl, C$_{1-3}$-alkylamino, diC$_{1-3}$alkylamino, hydroxyphenyl, tetrahydrofuranyl, cyclohexyl, cyclohexenyl, oxopyrrolidinyl, thiophenyl, C$_{1-3}$alkoxyphenyl, diC$_{1-3}$-alkylaminophenyl and trifluoromethoxyphenyl; substituted or unsubstituted pyrrolidinyl with a substituent selected from C$_{3-8}$cycloalkyl, C$_{3-8}$cycloalkylC$_{1-3}$alkyl, benzyl, C$_{1-3}$-alkyl or C$_{3-8}$cycloalkylcarbonyl; piperidinyl substituted with C$_{1-3}$alkyl or C$_{3-8}$-cycloalkyl; furanyl; or C$_{3-8}$cycloalkyl;

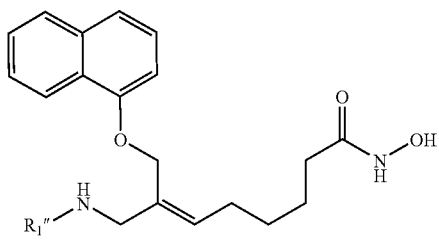

(3)

wherein,

R$_1$" is C$_{1-3}$ alkyl optionally having one or more substituents selected from the group consisting of C$_{1-3}$alkyl, C$_{1-3}$alkoxy, hydroxyC$_{1-3}$alkyl, halophenyl, piperidinyl, morpholinyl, cyanomethyl, piperazinyl, diC$_{1-3}$alkylamino, diC$_{1-3}$-alkylaminoC$_{1-3}$alkyl, piperidinylC$_{1-3}$alkyl, C$_{1-3}$alkoxyC$_{1-3}$alkyl, morpholinoC$_{1-3}$-alkyl, piperazinoC$_{1-3}$alkyl, pyrrolidinyl, oxopyrrolidinyl, C$_{1-3}$alkylpyrrolidinyl, imidazolyl, imidazolylC$_{1-3}$alkyl and thiophenyl;

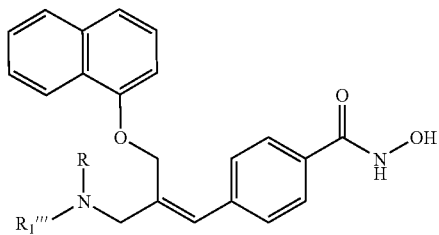

(4)

wherein,

R is hydrogen or C$_{1-3}$alkyl;

R$_1$''' is substituted or unsubstituted C$_{1-6}$alkyl with one or more substituents selected from the group consisting of diC$_{1-3}$ alkylamino, C$_{1-3}$alkylpyrrolidinyl, imidazolyl, methoxy and thiophenyl; C$_{1-6}$alkyl substituted with hydroxyphenyl, diC$_{1-3}$alkylaminophenyl, methoxyphenyl or trifluoromethoxyphenyl; substituted or unsubstituted pyrrolidine with a substituent selected from C$_{1-3}$alkyl, C$_{3-8}$cycloalkyl, C$_{3-8}$cycloalkylC$_{1-3}$alkyl, benzyl or C$_{3-8}$cycloalkylcarbonyl; piperidinyl substituted with C$_{3-8}$cycloalkyl or C$_{1-6}$alkyl; or C$_{3-8}$cycloalkyl.

In accordance with another aspect of the present invention, there is provided an anti-cancer composition comprising at least one of the compounds of formulae (1) to (4) or pharmaceutically acceptable salts thereof as an active ingredient.

DETAILED DESCRIPTION OF THE INVENTION

The inventive compounds of formulae (1) to (4) may be used in the form of pharmaceutically acceptable addition salts formed with an acid or base.

Examples of the acid include an inorganic acid such as hydrochloric, hydrobromic, phosphoric and sulfuric acids; and an organic acid such as acetic, trifluoroacetic, citric, formic, maleic, oxalic, succinic, benzoic, tartaric, fumaric, mandelic, ascorbic, malic acid, methanesulfonic and p-toluenesulfonic acids. Examples of the base include an inorganic base such as an alkali metal hydroxide (e.g., sodium hydroxide and potassium hydroxide), an alkali metal bicarbonate (e.g., sodium bicarbonate and potassium bicarbonate), an alkali metal carbonate (e.g., sodium carbonate, potassium carbonate and calcium carbonate) and an organic base such as amines.

Representative examples of preferred compounds as naphthalenyloxypropenyl derivatives of formula (1) include:

(E)-4-(3-(1-methylpiperidin-4-ylamino)-2-((naphthalen-1-yloxy)-methyl)-3-oxoprop-1-enyl)-N-hydroxybenzamide;

(E)-4-(3-(3-(1H-imidazol-1-yl)propylamino)-2-((naphthalen-1-yloxy)-methyl)-3-oxopropenyl)-N-hydroxybenzamide;

(E)-4-(3-(4-methoxyphenethylamino)-2-((naphthalen-1-yloxy)-methyl)-3-oxoprop-1-enyl)-N-hydroxybenzamide;

(E)-4-(3-(3-dimethylamino)-2,2-dimethylpropylamino)-2-((naphthalen-1-yloxy)methyl)-3-oxoprop-1-enyl)-N-hydroxybenzamide;

(E)-4-(3-(2-diisopropylamino)ethylamino)-2-((naphthalen-1-yloxy)-methyl)-3-oxoprop-1-enyl)-N-hydroxybenzamide;

(E)-4-(3-(1-methoxypropan-2-ylamino)-2-((naphthalen-1-yloxy)-methyl)-3-oxoprop-1-enyl)-N-hydroxybenzamide;

(E)-4-(3-(4-methoxybenzylamino)-2-((naphthalen-1-yloxy)methyl)-3-oxoprop-1-enyl)-N-hydroxybenzamide;

(E)-4-(3-(4-fluorophenethylamino)-2-((naphthalen-1-yloxy)methyl)-3-oxoprop-1-enyl)-N-hydroxybenzamide;

(E)-4-(3-(tetrahydrofuran-2-yl)methylamino)-2-((naphthalen-1-yloxy)methyl)-3-oxoprop-1-enyl)-N-hydroxybenzamide;

(E)-4-(3-(2-cyclohexenylethylamino)-2-((naphthalen-1-yloxy)-methyl)-3-oxoprop-1-enyl)-N-hydroxybenzamide;

(E)-4-(3-(3-(2-oxopyrrolidin-1-yl)propylamino)-2-((naphthalen-1-yloxy)methyl)-3-oxoprop-1-enyl)-N-hydroxybenzamide;

(E)-4-(3-(furan-2-ylmethylamino)-2-((naphthalen-1-yloxy)methyl)-3-oxoprop-1-enyl)-N-hydroxybenzamide;

(E)-4-(3-(4-(dimethylamino)benzylamino)-2-((naphthalen-1-yloxy)-methyl)-3-oxoprop-1-enyl)-N-hydroxybenzamide;

(E)-4-(3-(2-methoxyethylamino)-2-((naphthalen-1-yloxy)methyl)-3-oxoprop-1-enyl)-N-hydroxybenzamide;

(E)-4-(3-(cyclohexylamino)-2-((naphthalen-1-yloxy)methyl)-3-oxoprop-1-enyl)-N-hydroxybenzamide;

(E)-4-(3-(thiophen-2-ylmethylamino)-2-((naphthalen-1-yloxy)-methyl)-3-oxoprop-1-enyl)-N-hydroxybenzamide;

(E)-4-(3-(1-ethylpiperidin-4-ylamino)-2-((naphthalen-1-yloxy)-methyl)-3-oxoprop-1-enyl)-N-hydroxybenzamide, (E)-4-(3-(3-morpholinopropylamino)-2-((naphthalen-1-yloxy)methyl)-3-oxoprop-1-enyl)-N-hydroxybenzamide;

(E)-(3-(3-(2-methylpiperidin-1-yl)propylamino)-2-((naphthalen-1-yloxy)methyl)-3-oxoprop-1-enyl)-N-hydroxybenzamide;

(E)-(3-(3-pyrrolidin-1-yl)propylamino)-2-((naphthalen-1-yloxy)-methyl)-3-oxoprop-1-enyl)-N-hydroxybenzamide;

(E)-4-(3-(3-ethoxypropylamino)-2-((naphthalen-1-yloxy)methyl)-3-oxoprop-1-enyl)-N-hydroxybenzamide;

(E)-4-(3-(2-(1-methylpyrrolidin-2-yl)ethylamino)-2-((naphthalen-1-yloxy)methyl)-3-oxoprop-1-enyl)-N-hydroxybenzamide; and (E)-4-(3-(1-isopropylpiperidin-4-ylamino)-2-((naphthalen-1-yloxy)-methyl)-3-oxoprop-1-enyl)-N-hydroxybenzamide.

And the inventive naphthalenyloxypropenyl derivatives of formula (1) may be prepared by a method comprising the steps of:

1-1) allowing the compound of formula I to react with an alkyl acrylate in the presence of 1,4-diazabicyclo[2.2.2]octane (DABCO) to obtain a compound of the formula II;

1-2) reacting the compound of formula II with a brominating agent such as tribromophosphine (PBr₃) in an organic solvent to obtain a compound of formula III;

1-3) reacting the compound of formula III 1-naphthalenol to obtain a compound of formula IV;

1-4) hydrolyzing the compound of formula IV in the presence of an inorganic or organic acid to obtain a compound of formula V;

1-5) acylating the compound of formula V with an amine (R₁NH₂) to obtain a compound of formula VI;

1-6) hydrolyzing the compound of formula VI in the presence of an inorganic base to obtain a compound of formula VII;

1-7) acylating the compound of formula VII with tetrahydropyranyloxyamine (THPONH₂) to obtain a compound of formula VIII; and 1-8) treating the compound of formula VIII with trifluoroacetic acid (TFA) to remove the tetrahydropyranyl group therefrom.

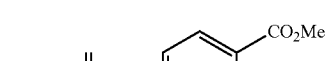

I

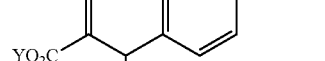

II

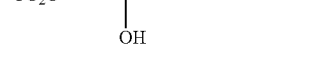

III

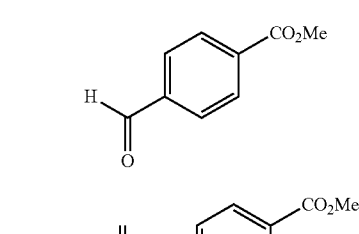

IV

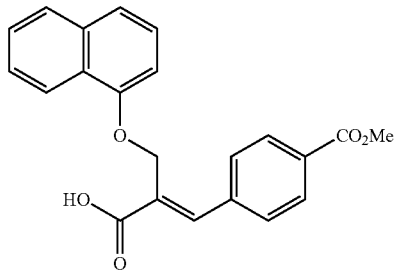

V

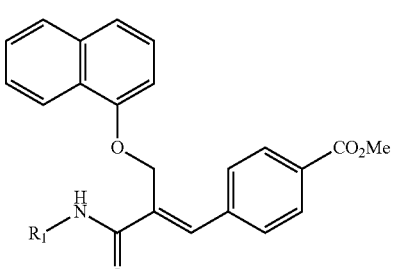

VI

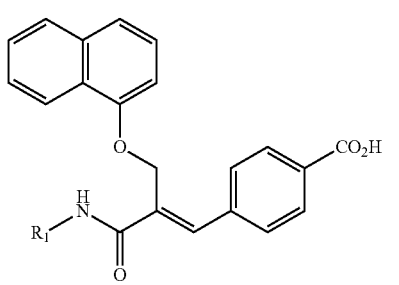

VII

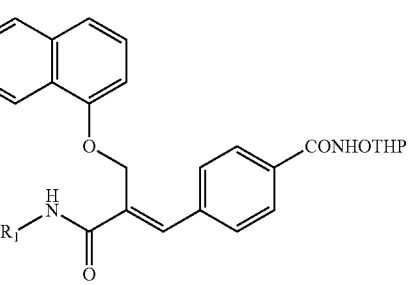

VIII wherein,

R₁ has the same meaning as defined in formula (1) above, and Y is $C_{1-4}$-alkyl.

The method described above may be represented by Reaction Scheme 1:

Reaction Scheme 1

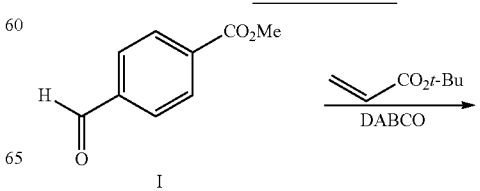

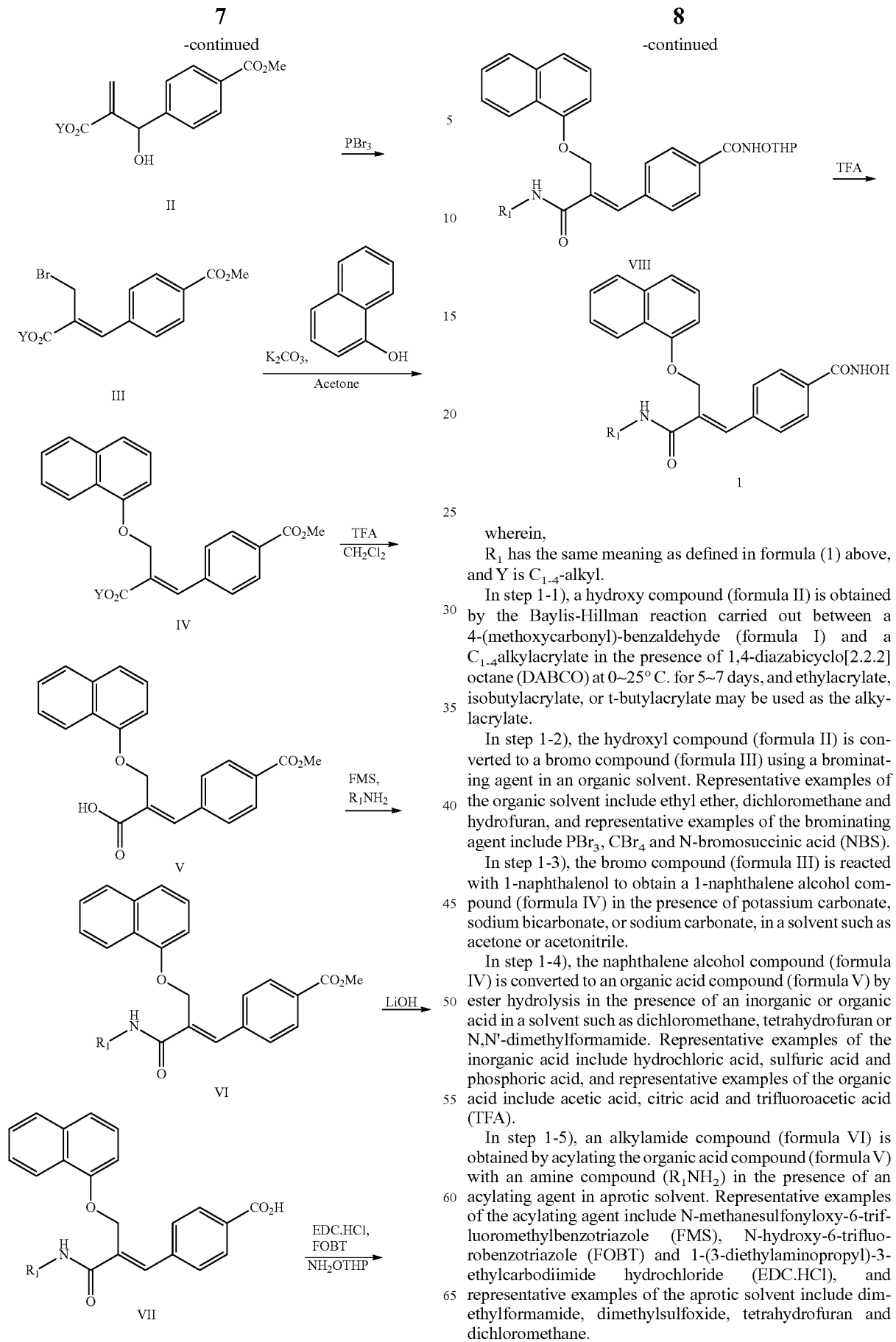

wherein, $R_1$ has the same meaning as defined in formula (1) above, and Y is $C_{1-4}$-alkyl.

In step 1-1), a hydroxy compound (formula II) is obtained by the Baylis-Hillman reaction carried out between a 4-(methoxycarbonyl)-benzaldehyde (formula I) and a $C_{1-4}$alkylacrylate in the presence of 1,4-diazabicyclo[2.2.2]octane (DABCO) at 0~25° C. for 5~7 days, and ethylacrylate, isobutylacrylate, or t-butylacrylate may be used as the alkylacrylate.

In step 1-2), the hydroxyl compound (formula II) is converted to a bromo compound (formula III) using a brominating agent in an organic solvent. Representative examples of the organic solvent include ethyl ether, dichloromethane and hydrofuran, and representative examples of the brominating agent include $PBr_3$, $CBr_4$ and N-bromosuccinic acid (NBS).

In step 1-3), the bromo compound (formula III) is reacted with 1-naphthalenol to obtain a 1-naphthalene alcohol compound (formula IV) in the presence of potassium carbonate, sodium bicarbonate, or sodium carbonate, in a solvent such as acetone or acetonitrile.

In step 1-4), the naphthalene alcohol compound (formula IV) is converted to an organic acid compound (formula V) by ester hydrolysis in the presence of an inorganic or organic acid in a solvent such as dichloromethane, tetrahydrofuran or N,N'-dimethylformamide. Representative examples of the inorganic acid include hydrochloric acid, sulfuric acid and phosphoric acid, and representative examples of the organic acid include acetic acid, citric acid and trifluoroacetic acid (TFA).

In step 1-5), an alkylamide compound (formula VI) is obtained by acylating the organic acid compound (formula V) with an amine compound ($R_1NH_2$) in the presence of an acylating agent in aprotic solvent. Representative examples of the acylating agent include N-methanesulfonyloxy-6-trifluoromethylbenzotriazole (FMS), N-hydroxy-6-trifluorobenzotriazole (FOBT) and 1-(3-diethylaminopropyl)-3-ethylcarbodiimide hydrochloride (EDC.HCl), and representative examples of the aprotic solvent include dimethylformamide, dimethylsulfoxide, tetrahydrofuran and dichloromethane.

In step 1-6), the alkylamide compound (formula VI) is hydrolyzed to an organic acid compound (formula VII) in the presence of an inorganic base in a water-soluble alcohol or tetrahydrofuran as a solvent. Representative examples of the inorganic base include lithium hydroxide monohydrate (LiOH.H$_2$O) and sodium hydroxide.

In step 1-7), the organic acid compound (formula VII) is acylated to a compound of formula VIII in an organic solvent in the presence of an acylating agent such as N-hydroxy-6-trifluorobenzotriazole (FOBT) or 1-(3-diethylaminopropyl)-3-ethylcarbodiimide hydrochloride (EDC.HCl). Representative examples of the organic solvent include N,N'-dimethylformamide, dimethylsulfoxide, tetrahydrofuran and dichloromethane.

In step 1-8), a deprotection reaction is carried out by reacting the compound of formula VIII with trifluoroacetic acid (TFA) to remove the tetrahydropyranyl group in a solvent such as methanol, ethanol, tetrahydrofuran or dichloromethane.

Representative examples of preferred compounds as naphthalenyloxypropenyl derivatives of formula (2) include:
(E)-N1-(3-(1H-imidazol-1-yl)propyl)-N8-hydroxy-2-((naphthalen-1-yloxy)methyl)octenediamide;
(E)-N8-hydroxy-N1-(4-hydroxyphenethyl)-2-((naphthalen-1-yloxy)-methyl)-2-octenediamide;
(E)-N1-(3-(dimethylamino)-2,2-dimethylpropyl)-N8-hydroxy-2-((naphthalen-1-yloxy)methyl)octenediamide;
(E)-N1-(2-(diisopropylamino)ethyl)-N8-hydroxy-2-((naphthalen-1-yloxy)methyl)octenediamide;
(E)-N8-hydroxy-N1-(1-methoxypropan-2-yl)-2-((naphthalen-1-yloxy)-methyl)-2-octenediamide;
(E)-N8-hydroxy-N1-(4-methoxybenzyl)-2-((naphthalen-1-yloxy)-methyl)-2-octenediamide;
(E)-N1-(4-fluorophenethyl)-N8-hydroxy-2-((naphthalen-1-yloxy)-methyl)-2-octenediamide;
(E)-N8-hydroxy-2-((naphthalen-1-yloxy)methyl)-N1-(tetrahydrofuran-2-yl)methyl)-2-octenediamide;
(E)-N1-(2-cyclohexenylethyl)-N8-hydroxy-2-((naphthalen-1-yloxy)-methyl)-2-octenediamide;
(E)-N8-hydroxy-2-((naphthalen-1-yloxy)methyl)-N1-(3-(2-oxopyrrolidin-1-yl)propyl)-2-octenediamide;
(E)-N1-(furan-2-ylmethyl)-N8-hydroxy-2-((naphthalen-1-yloxy)-methyl)-2-octenediamide;
(E)-N1-(4-(dimethylamino)benzyl)-N8-hydroxy-2-((naphthalen-1-yloxy)methyl)-2-octenediamide;
(E)-N8-hydroxy-N1-(2-methoxyethyl)-2-((naphthalen-1-yloxy)-methyl)-2-octenediamide;
(E)-N1-cyclohexyl-N8-hydroxy-2-((naphthalen-1-yloxy)methyl)-2-octenediamide;
(E)-N8-hydroxy-2-((naphthalen-1-yloxy)methyl)-N1-(thiophen-2-ylmethyl)-2-octenediamide;
(E)-N8-hydroxy-N1-(4-methoxyphenethyl)-2-((naphthalen-1-yloxy)-methyl)-2-octenediamide;
(E)-N8-hydroxy-2-((naphthalen-1-yloxy)methyl)-N1-(4-(trifluoromethoxy)benzyl)-2-octenediamide;
(E)-N1-(1-cyclohexylmethyl)pyrrolidin-3-yl)-N8-hydroxy-2-((naphthalen-1-yloxy)methyl)-2-octenediamide;
(E)-N1-(1-cyclopentylpiperidin-4-yl)-N8-hydroxy-2-((naphthalen-1-yloxy)methyl)-2-octenediamide;
(E)-N1-(1-benzylpyrrolidin-3-yl)-N8-hydroxy-2-((naphthalen-1-yloxy)methyl)-2-octenediamide;
(E)-N8-hydroxy-N1-(1-isopropylpyrrolidin-3-yl)-2-((naphthalen-1-yloxy)methyl)-2-octenediamide;
(E)-N1-(1-(cyclohexanecarbonyl)pyrrolidin-3-yl)-N8-hydroxy-2-((naphthalen-1-yloxy)methyl)-2-octenediamide;
t-butyl (E)-3-(8-(hydroxyamino)-2-((naphthalen-1-yloxy)methyl)-8-oxo-2-octeneamido)pyrrolidine-1-carboxylate;
(E)-N8-hydroxy-2-((naphthalen-1-yloxy)methyl)-N1-(pyrrolidin-3-yl)-2-octenediamide;
(E)-N1-(1-cyclohexylpyrrolidin-3-yl)-N8-hydroxy-2-((naphthalen-2-yloxy)methyl)-2-octenediamide;
(E)-N1-(1-cyclopropylpyrrolidin-3-yl)-N8-hydroxy-2-((naphthalen-1-yloxy)methyl)-2-octenediamide;
(E)-N1-(1-cyclopropylpiperidin-4-yl)-N8-hydroxy-2-((naphthalen-1-yloxy)methyl)-2-octenediamide;
(E)-N1-(1-ethylpiperidin-4-yl)-N8-hydroxy-2-((naphthalen-1-yloxy)-methyl)-2-octenediamide;
(E)-N1-(1-ethylpyrrolidin-3-yl)-N8-hydroxy-2-((naphthalen-1-yloxy)-methyl)-2-octenediamide; and
(E)-N8-hydroxy-N1-(1-isopropylpiperidin-4-yl)-2-((naphthalen-1-yloxy)methyl)-2-octenediamide.

Further, the inventive naphthalenyloxypropenyl derivatives of formula (2) may be prepared by a method comprising the steps of:

2-1) treating a compound of formula IX with sulfuric acid, and then with pyridinium chlorochromate (PCC) to obtain a compound of formula X;

2-2) reacting the compound of formula X with an alkyl acrylate in the presence of 1,4-diazabicyclo[2.2.2]octane (DABCO) to obtain a compound of the formula XI;

2-3) allowing the compound of formula XI to react with a brominating agent in an organic solvent to obtain a compound of formula XII;

2-4) reacting the compound of formula XII with 1-naphthalenol to obtain a compound of formula XIII;

2-5) hydrolyzing the compound of formula XIII in the presence of an inorganic or organic acid to obtain a compound of formula XIV;

2-6) reacting the compound of formula XIV with an amine (R$_1$'NH$_2$) to obtain a compound of formula XV;

2-7) hydrolyzing the compound of formula XV in the presence of an inorganic base to obtain a compound of formula XVI;

2-8) reacting the compound of formula XVI with tetrahydropyranyloxyamine (THPONH$_2$) to obtain a compound of formula XVII; and 2-9) treating the compound of formula XVII with trifluoroacetic acid (TFA) to remove the tetrahydropyranyl group therefrom.

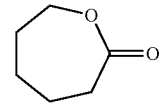

IX

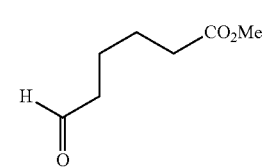

X

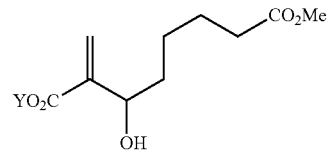

XI

-continued
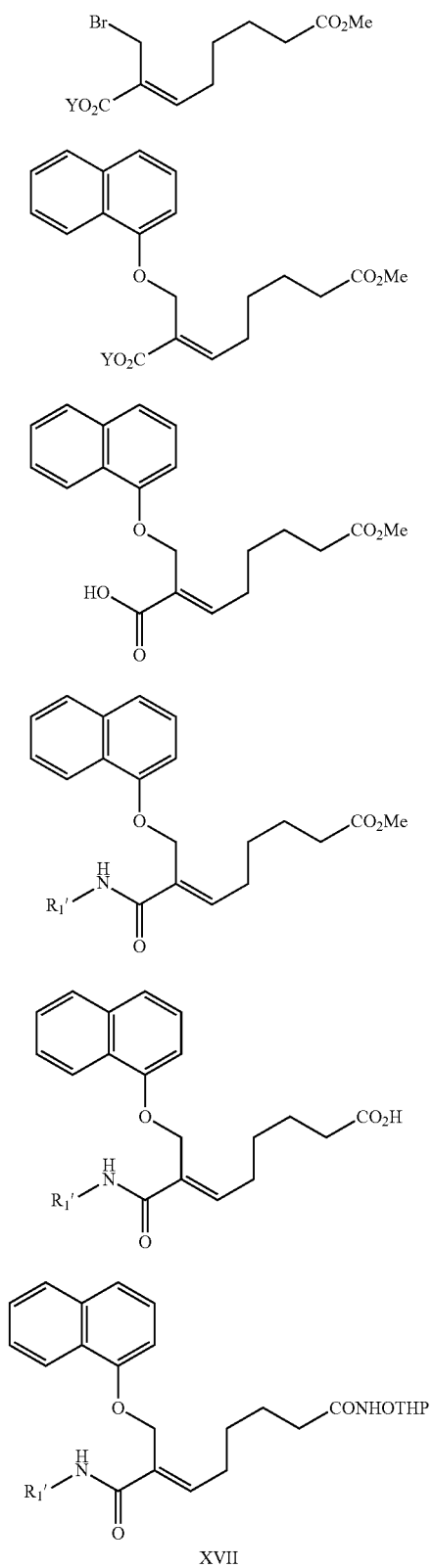
wherein,
R₁' has the same meaning as defined in formula (2) above, and Y is $C_{1-4}$ alkyl.
The method described above may be represented by Reaction Scheme 2:
Reaction Scheme 2
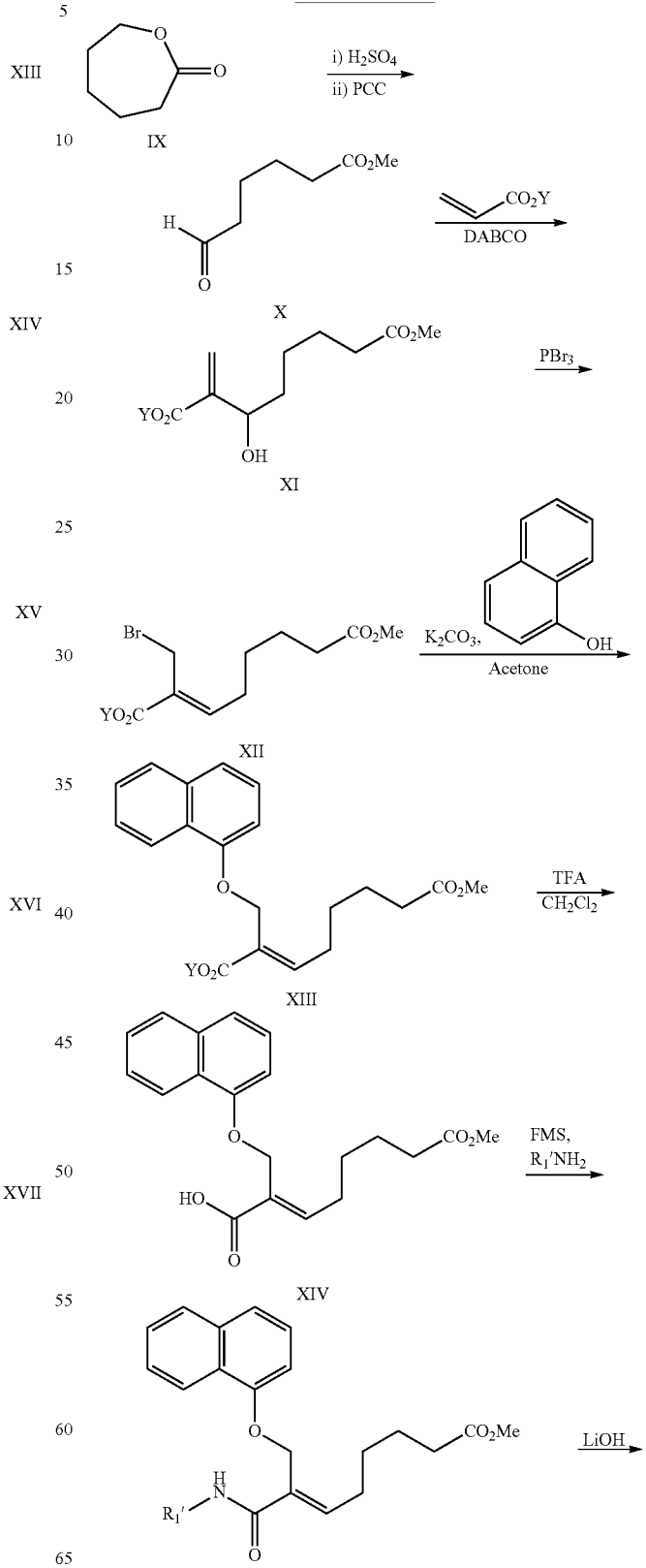

-continued

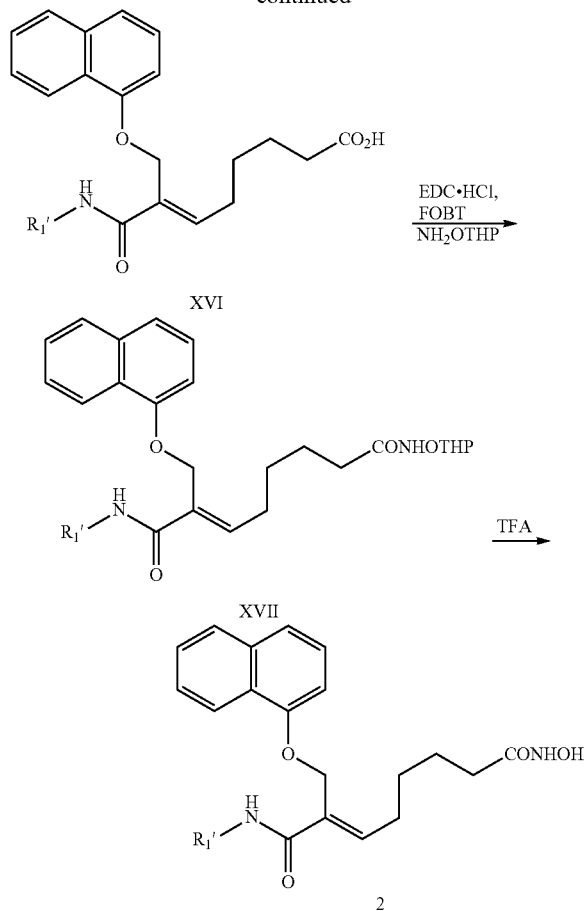

wherein,

R₁' has the same meaning as defined in formula (2) above, and Y is $C_{1-4}$alkyl.

In step 2-1), ε-caprolactone (formula IX) is dissolved in methanol and treated with concentrated sulfuric acid to form methyl 6-hydroxy-hexanoate, which is then added to pyridinium chlorochromate dissolved in an organic solvent and reacted for 1~2 hrs, preferably 2 hrs, to obtain methyl 6-oxohexanoate (formula X). The solvent suitable for use in this step may be dichloromethane, tetrahydrofuran, or dichloroethane.

In step 2-2), a hydroxy compound (formula XI) is obtained by the Baylis-Hillman reaction of the 6-oxo-hexanoate (formula X) with a $C_{1-4}$-alkylacrylate in the presence of 1,4-diazabicyclo[2.2.2]octane (DABCO) at 0~25° C. for 5~7 days. Ethylacrylate, isobutylacrylate, or t-butylacrylate may be used as the alkylacrylate.

In step 2-3), the hydroxyl compound (formula XI) is converted to a bromo compound (formula XII) using a brominating agent in an organic solvent. Representative examples of the organic solvent include ethyl ether, dichloromethane and hydrofuran, and representative examples of the brominating agent include $PBr_3$, $CBr_4$ and N-bromosuccinic acid (NBS).

In step 2-4), the bromo compound (formula XII) is reacted with 1-naphthalenol to obtain a 1-naphthalene alcohol compound (formula XIII) in a solvent such as acetone or acetonitrile in the presence of potassium carbonate, sodium bicarbonate, or sodium carbonate.

In step 2-5), the 1-naphthalene alcohol compound (formula XIII) is converted to an organic acid compound (formula XIV) by ester hydrolysis in the presence of an inorganic or organic acid in a solvent such as dichloromethane, tetrahydrofuran or N,N'-dimethylformamide. Representative examples of the inorganic acid include hydrochloric acid, sulfuric acid and phosphoric acid, and representative examples of the organic acid include trifluoroacetic acid (TFA), acetic acid and citric acid.

In step 2-6), an alkylamide compound (formula XV) is obtained by acylation between the organic acid compound (formula XIV) and an amine compound ($R_1'NH_2$) in the presence of an acylating agent in aprotic solvent. Representative examples of the acylating agent include N-methanesulfonyloxy-6-trifluoromethylbenzotriazole (FMS), N-hydroxy-6-trifluorobenzotriazole (FOBT) and 1-(3-diethylaminopropyl)-3-ethylcarbodiimide hydrochloride (EDC.HCl), and representative examples of the aprotic solvent include dimethylformamide, dimethylsulfoxide, tetrahydrofuran or dichloromethane.

In step 2-7), the alkylamide compound (formula XV) is hydrolyzed to an organic acid compound (formula XVI) in the presence of an inorganic base in a solvent such as a water-soluble alcohol or tetrahydrofuran. Representative examples of the inorganic base include sodium hydroxide and lithium hydroxide, and representative examples of the water-soluble alcohol include methanol, ethanol, isopropanol, n-butanol, t-butanol and an aqueous solution thereof.

In step 2-8), the organic acid compound (formula XVI) is acylated with tetrahydropyranyloxyamine (THPONH₂) to obtain a compound of formula XVII in an organic solvent in the presence of acylating agent such as N-hydroxy-6-trifluorobenzotriazole (FOBT) or 1-(3-diethylaminopropyl)-3-ethylcarbodiimide hydrochloride (EDC.HCl). Representative examples of the organic solvent include N,N'-dimethylformamide, dimethylsulfoxide, tetrahydrofuran and dichloromethane.

In step 2-9), a deprotection reaction is carried out by reacting the compound of formula XVII with trifluoroacetic acid (TFA) to remove the tetrahydropyranyl group therefrom in a solvent such as methanol, ethanol, tetrahydrofuran, or dichloromethane.

The starting material (formula IX) for preparing the naphthalenyloxypropenyl derivatives of formula (2) may be commercially available.

Representative examples of preferred compounds as naphthalenyloxypropenyl derivatives of formula (3) include:
(Z)—N-hydroxy-8-(2-morpholinoethylamino)-7-((naphthalen-1-yloxy)-methyl)oct-6-en-amide;
(Z)—N-hydroxy-8-(1-methoxypropan-2-ylamino)-7-((naphthalen-1-yloxy)methyl)oct-6-enamide;
(Z)—N-hydroxy-8-(naphthalen-1-yloxy)-7-((3-(2-oxopyrrolidin-1-yl)-propylamino)methyl)oct-6-enamide;
(Z)-8-(3-(1H-imidazol-1-yl)propylamino)-N-hydroxy-7-((naphthalen-1-yloxy)methyl)oct-6-enamide;
(Z)—N-hydroxy-8-(3-(2-methylpiperidin-1-yl)propylamino)-7-((naphthalen-1-yloxy)methyl)oct-6-enamide;
(Z)-8-(3-(dimethylamino)propylamino)-N-hydroxy-7-((naphthalen-1-yloxy)methyl)oct-6-enamide;
(Z)-8-(3-(dimethylamino)-2,2-dimethylpropylamino)-N-hydroxy-7-((naphthalen-1-yloxy)methyl)oct-6-enamide,
(Z)—N-hydroxy-8-(naphthalen-1-yloxy)-7-((2-(pyrrolidin-1-yl)-ethylamino)methyl)oct-6-enamide;
(Z)-8-(4-fluorophenethylamino)-N-hydroxy-7-((naphthalen-1-yloxy)-methyl)oct-6-enamide;
(Z)—N-hydroxy-8-(2-methoxyethylamino)-7-((naphthalen-1-yloxy)-methyl)oct-6-enamide;
(Z)—N-hydroxy-8-(1-isopropylpiperidin-4-ylamino)-7-((naphthalen-1-yloxy)methyl)oct-6-enamide;

(Z)-8-(3-(diethylamino)propylamino)-N-hydroxy-7-((naphthalen-1-yloxy)methyl)oct-6-enamide;

(Z)-8-(2-diisopropylamino)ethylamino))-N-hydroxy-7-((naphthalen-1-yloxy)methyl)oct-6-enamide; and (Z)—N-hydroxy-8-(naphthalen-1-yloxy)-7-(thiophen-2-ylmethylamino)methyl)oct-6-enamide.

And the inventive naphthalenyloxypropenyl derivatives of formula (3) may be prepared by a method comprising the steps of 3-1) treating a compound of formula IX with sulfuric acid, and then with pyridinium chlorochromate (PCC) to obtain a compound of formula X;

3-2) allowing the compound of formula X to react with an alkyl acrylate in the presence of 1,4-diazabicyclo[2.2.2]octane (DABCO) to obtain a compound of the formula XI;

3-3) reacting the compound of formula XI with an brominating agent in an organic solvent to obtain a compound of formula XII;

3-4) bringing the compound of formula XII to react with 1-naphthalenol to obtain a compound of formula XIII;

3-5) hydrolyzing the compound of formula XIII to produce an organic acid compound in the presence of an inorganic or organic acid, and then reacting the organic acid compound with ethylchloroformate (ECC) in the presence of a reducing agent to obtain a compound of formula XVIII;

3-6) allowing the compound of formula XVIII to react with triphenylphosphine (PPh$_3$) and tetrabromoethane (CBr$_4$) in an organic solvent to obtain a compound of formula XIX;

3-7) reacting the compound of formula XIX with an amine (R$_1$"NH$_2$) to obtain a compound of formula XX;

3-8) hydrolyzing the compound of formula XX in the presence of an inorganic base to obtain a compound of formula XXI;

3-9) acylating the compound of formula XXI with tetrahydropyranyloxyamine (THPONH$_2$) in the presence of an acylating agent to obtain a compound of formula XXII; and 3-10) reacting the compound of formula XXII with an inorganic or organic acid to remove the tetrahydropyranyl group therefrom.

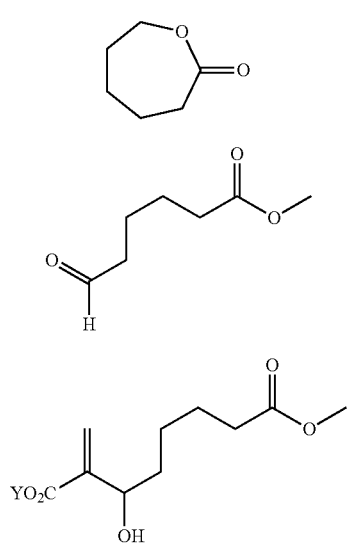

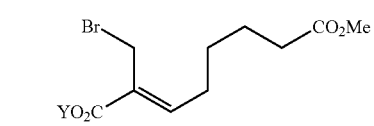

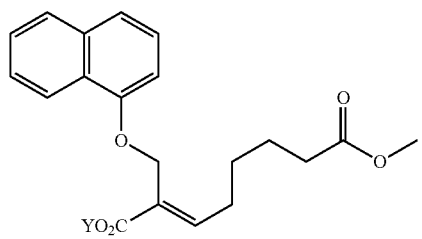

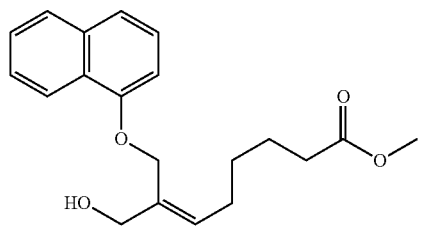

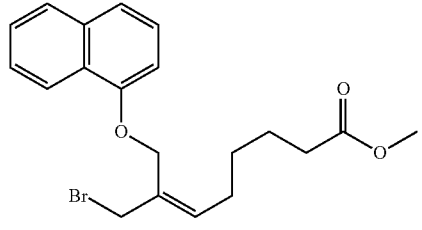

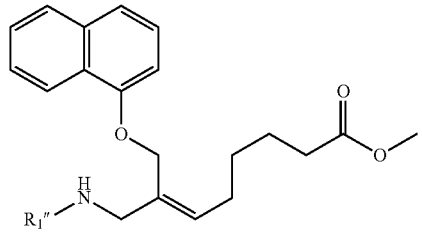

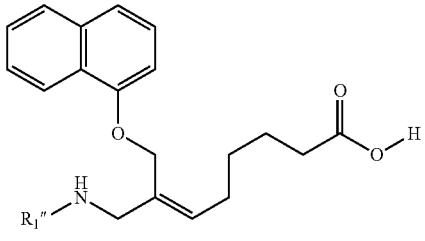

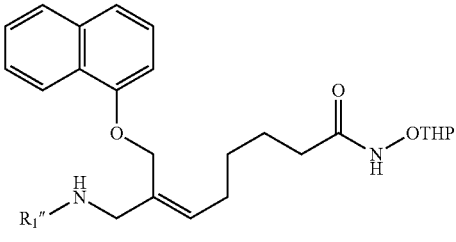

wherein,
R$_1$" has the same meaning as defined in formula (3) above, and Y is C$_{1-4}$ alkyl.

The method described above may be represented by Reaction Scheme 3:

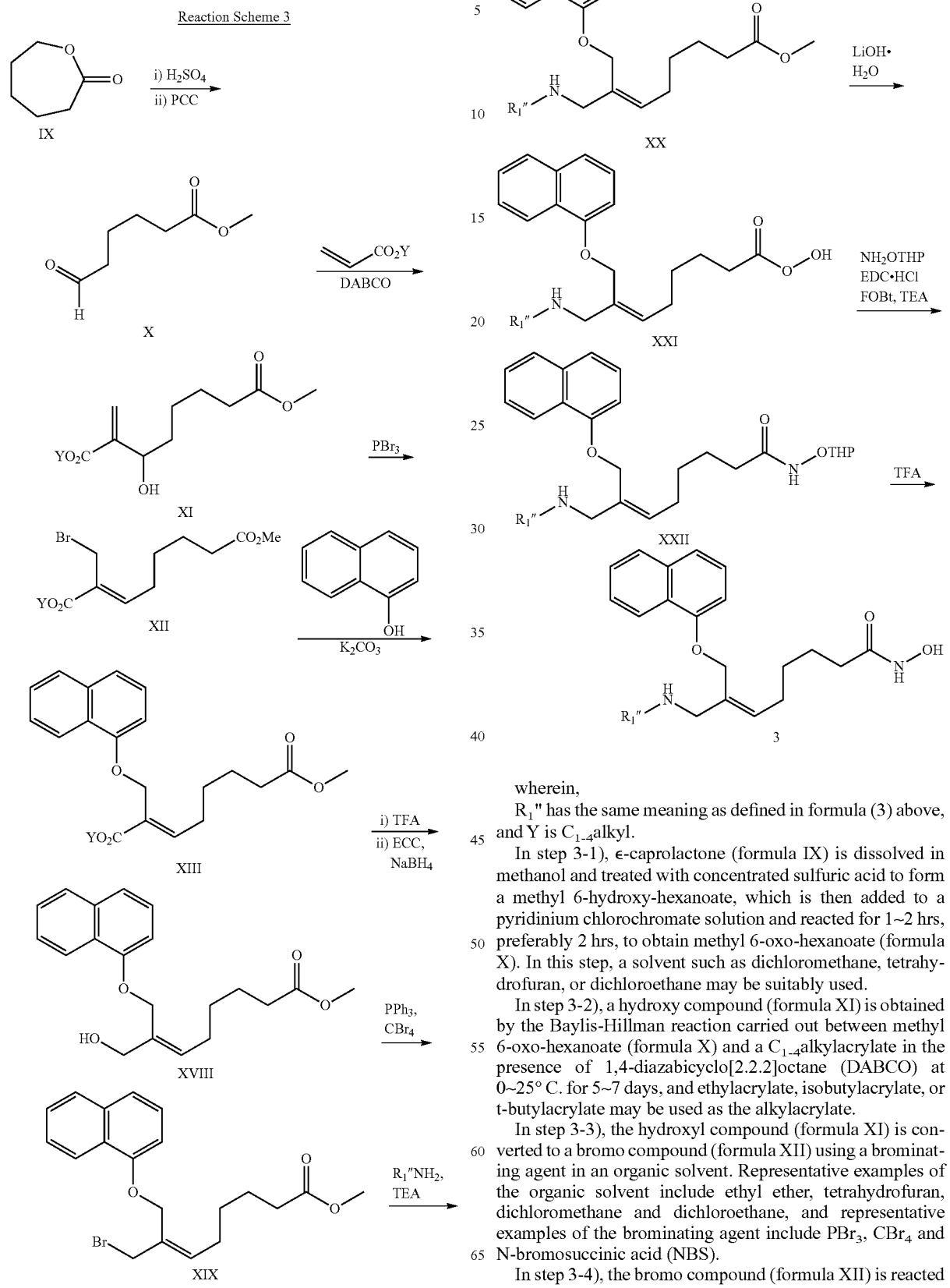

wherein,
$R_1''$ has the same meaning as defined in formula (3) above, and Y is $C_{1-4}$alkyl.

In step 3-1), ε-caprolactone (formula IX) is dissolved in methanol and treated with concentrated sulfuric acid to form a methyl 6-hydroxy-hexanoate, which is then added to a pyridinium chlorochromate solution and reacted for 1~2 hrs, preferably 2 hrs, to obtain methyl 6-oxo-hexanoate (formula X). In this step, a solvent such as dichloromethane, tetrahydrofuran, or dichloroethane may be suitably used.

In step 3-2), a hydroxy compound (formula XI) is obtained by the Baylis-Hillman reaction carried out between methyl 6-oxo-hexanoate (formula X) and a $C_{1-4}$alkylacrylate in the presence of 1,4-diazabicyclo[2.2.2]octane (DABCO) at 0~25° C. for 5~7 days, and ethylacrylate, isobutylacrylate, or t-butylacrylate may be used as the alkylacrylate.

In step 3-3), the hydroxyl compound (formula XI) is converted to a bromo compound (formula XII) using a brominating agent in an organic solvent. Representative examples of the organic solvent include ethyl ether, tetrahydrofuran, dichloromethane and dichloroethane, and representative examples of the brominating agent include $PBr_3$, $CBr_4$ and N-bromosuccinic acid (NBS).

In step 3-4), the bromo compound (formula XII) is reacted with 1-naphthalenol to obtain a 1-naphthalene alcohol compound (formula XIII) in the presence of an inorganic base such as potassium carbonate, sodium bicarbonate, or sodium carbonate, in a solvent such as acetone, acetonitrile, dichloromethane, or tetrahydrofuran.

In step 3-5), the naphthalene alcohol compound (formula XIII) is converted to an intermediate organic acid compound by ester hydrolysis in the presence of an inorganic or organic acid in a solvent such as dichloromethane, tetrahydrofuran or N,N'-dimethylformamide. And then, the intermediate organic acid compound is reduced with ethylchloroformate (ECC) to an alcohol compound (formula XVIII) in the presence of reducing agent, preferably with addition of water dropwise, preferably in an ice water bath. Representative examples of the inorganic acid include hydrochloric acid, sulfuric acid and phosphoric acid, and representative examples of the organic acid include trifluoroacetic acid (TFA), acetic acid and citric acid. Representative examples of the solvent for reduction reaction include tetrahydrofuran, 1,4-dioxane, dichloromethane, and chloroform, and representative examples of the reducing agent include sodium borohydride, sodium cyanohydride, and lithium borohydride.

In step 3-6), the alcohol compound (formula XVIII) is reacted with triphenylphosphine ($PPh_3$) and tetrabromomethane ($CBr_4$) to obtain a bromo compound (formula XIX) in a solvent such as dichloromethane, chloroform, tetrahydrofuran or dichloroethane.

In step 3-7), an alkylamide compound (formula XX) is obtained by acylation between the bromo compound (formula XIX) and an amine compound ($R_1"NH_2$) in the presence of an organic or inorganic base in an organic solvent. Representative examples of the organic solvent include acetone, acetonitrile, dichloromethane and tetrahydrofuran. Representative examples of the organic base include triethylamine, diisopropylethylamine and pyridine, and representative examples of the inorganic base include potassium carbonate, sodium bicarbonate, or sodium carbonate.

In step 3-8), the alkylamide compound (formula XX) is hydrolyzed to a compound of formula XXI in the presence of an inorganic base in a water-soluble alcohol or tetrahydrofuran as a solvent. Representative examples of the water-soluble alcohol include methanol, ethanol, isopropanol, n-butanol, t-butanol, and an aqueous solution thereof, and representative of examples of the inorganic base include lithium hydroxide, sodium hydroxide and calcium hydroxide.

In step 3-9), the compound of formula XXI is acylated with tetrahydropyranyloxyamine ($THPONH_2$) to obtain a compound of formula XXII in an organic solvent in the presence of an acylating agent. Representative examples of the organic solvent include N,N'-dimethylformamide, dimethylsulfoxide, tetrahydrofuran and dichloromethane, and representative examples of the acylating agent include N-hydroxy-6-trifluorobenzotriazole (FOBT), 1-ethyl-3-(3-dimethylaminopropyl)-carbodiimide hydrochloride (EDC.HCl) and a mixture thereof.

In step 3-10), a deprotection reaction was carried out by removing the tetrahydropyranyl group from the compound of formula XXII in an organic solvent in presence of a water-soluble inorganic or organic acid. Representative examples of the organic solvent include methanol, dichloromethane, dichloroethane, benzene and toluene. Representative examples of the water-soluble inorganic acid include hydrochloric acid, sulfuric acid and phosphoric acid, and representative examples of the organic acid include trifluoroacetic acid, acetic acid and citric acid.

Representative examples of preferred compounds as naphthalenyloxypropenyl derivatives of formula (4) include:

(Z)-4-(3-(1-ethylpiperidin-4-ylamino)-2-((naphthalen-1-yloxy)-methyl)prop-1-enyl)-N-hydroxybenzamide;
(Z)-4-(3-(1-ethylpyrrolidin-3-ylamino)-2-((naphthalen-1-yloxy)-methyl)prop-1-enyl)-N-hydroxybenzamide;
(Z)—N-hydroxy-4-(3-(naphthalen-1-yloxy)-2-((4-(trifluoromethoxy)-benzylamino)methyl)prop-1-enyl)benzamide;
t-butyl (Z)-3-(3-(4-(hydroxycarbamoyl)phenyl-2-((naphthalen-1-yloxy)methyl)allylamino)pyrrolidine-1-carboxylate;
(Z)—N-hydroxy-4-(3-(naphthalen-1-yloxy)-2-((pyrrolidin-3-ylamino)-methyl)prop-1-enyl)benzamide;
(Z)-4-(3-(1-(cyclohexylcarbonyl)pyrrolidin-3-ylamino)-2-((naphthalen-1-yloxy)methyl)prop-1-enyl)-N-hydroxybenzamide;
(Z)-4-(3-(1-cyclopentylpiperidin-4-ylamino)-2-((naphthalen-1-yloxy)-methyl)prop-1-enyl)-N-hydroxybenzamide;
(Z)-4-(3-(1-(cyclohexylmethyl)pyrrolidin-3-ylamino)-2-((naphthalen-1-yloxy)methyl)prop-1-enyl)-N-hydroxybenzamide;
(Z)-4-(3-(1-benzylpyrrolidin-3-yl-amino)-2-((naphthalen-1-yloxy)-methyl)prop-1-enyl)-N-hydroxybenzamide;
(Z)-4-(3-(1-cyclopropylpiperidin-4-ylamino)-2-((naphthalen-1-yloxy)-methyl)prop-1-enyl)-N-hydroxybenzamide;
(Z)-4-(3-(1-cyclopropylpyrrolidin-3-ylamino)-2-((naphthalen-1-yloxy)methyl)prop-1-enyl)-N-hydroxybenzamide;
(Z)-4-(3-(1-cyclohexylpyrrolidin-3-ylamino)-2-((naphthalen-1-yloxy)-methyl)prop-1-enyl)-N-hydroxybenzamide;
(Z)—N-hydroxy-4-(3-(1-methoxypropan-2-ylamino)-2-((naphthalen-1-yloxy)methyl)prop-1-enyl)benzamide;
(Z)—N-hydroxy-4-(3-(2-(1-methylpyrrolidin-2-yl)ethylamino)-2-((naphthalen-1-yloxy)methyl)prop-1-enyl)benzamide;
(Z)—N-hydroxy-4-(3-(2-(1-isopropylpiperidin-4-ylamino)-2-((naphthalen-1-yloxy)methyl)prop-1-enyl)benzamide;
(Z)-4-(3-(3-(1H-imidazol-1-yl)propylamino)-2-((naphthalen-1-yloxy)-methyl)prop-1-enyl)-N-hydroxybenzamide;
(Z)—N-hydroxy-4-(3-(4-hydroxyphenethylamino)-2-((naphthalen-1-yloxy)methyl)prop-1-enyl)benzamide;
(Z)-4-(3-(3-(dimethylamino)-2,2-dimethylpropylamino)-2-((naphthalen-1-yloxy)methyl)prop-1-enyl)-N-hydroxybenzamide;
(Z)-4-(3-(2-(diisopropylamino)ethylamino)-2-((naphthalen-1-yloxy)-methyl)prop-1-enyl)-N-hydroxybenzamide;
(Z)—N-hydroxy-4-(3-(2-methoxyethylamino)-2-((naphthalen-1-yloxy)-methyl)prop-1-enyl)benzamide;
(Z)-4-(3-(cyclohexylamino)-2-((naphthalen-1-yloxy)methyl)prop-1-enyl)-N-hydroxybenzamide;
(Z)—N-hydroxy-4-(3-(naphthalen-1-yloxy)-2-((thiophen-2-ylmethylamino)methyl)prop-1-enyl)benzamide;
(Z)—N-hydroxy-4-(3-(4-methoxyphenethylamino)-2-((naphthalen-1-lyoxy)methyl)prop-1-enyl)benzamide; and
(Z)-4-(3-(4-(dimethylamino)benzylamino))-2-((naphthalen-1-yloxy)-methyl)prop-1-enyl)-N-hydroxybenzamide.

And the inventive naphthalenyloxypropenyl derivatives of formula (4) may be prepared by a method comprising the steps of:

4-1) reacting the compound of formula I with an alkyl acrylate in the presence of 1,4-diazabicyclo[2.2.2]octane (DABCO) to obtain a compound of the formula XXIII;

4-2) allowing the compound of formula XXIII to react with tribromophosphine ($PBr_3$) in an organic solvent to obtain a compound of formula XXIV;

4-3) reacting the compound of formula XXIV with 1-naphthalenol to obtain a compound of formula XXV;

4-4) hydrolyzing the compound of formula XXV with trifluoroacetic acid to obtain methyl carboxypropenylbenzoate, and then treating the methyl carboxypropenylbenzoate with ethylchloroformate (ECC), followed by reducing with a reducing agent to obtain a compound of formula XXVI;

4-5) reacting the compound of formula XXVI to a bromination reaction with triphenylphosphine (PPh₃) and tetrabromomethane (CBr₄) in an aprotic solvent to obtain a compound of formula XXVII;

4-6) allowing the compound of formula XXVII to react with an amine (RR₁'''NH) to obtain a compound of formula XXVIII;

4-7) hydrolyzing the compound of formula XXVIII in the presence of an inorganic base to obtain a compound of formula XXIX;

4-8) acylating the compound of formula XXIX with tetrahydropyranyloxyamine (THPONH₂) in the presence of an acylating agent such as N-hydroxy-6-trifluorobenzotriazole (FOBT) or 1-ethyl-3-(3-dimethylaminopropyl)-carbodiimide hydrochloride (EDC.HCl) in an organic solvent to obtain a compound of formula XXX; and 4-9) reacting the compound of formula XXX with an inorganic or organic acid to remove the tetrahydropyranyl group therefrom.

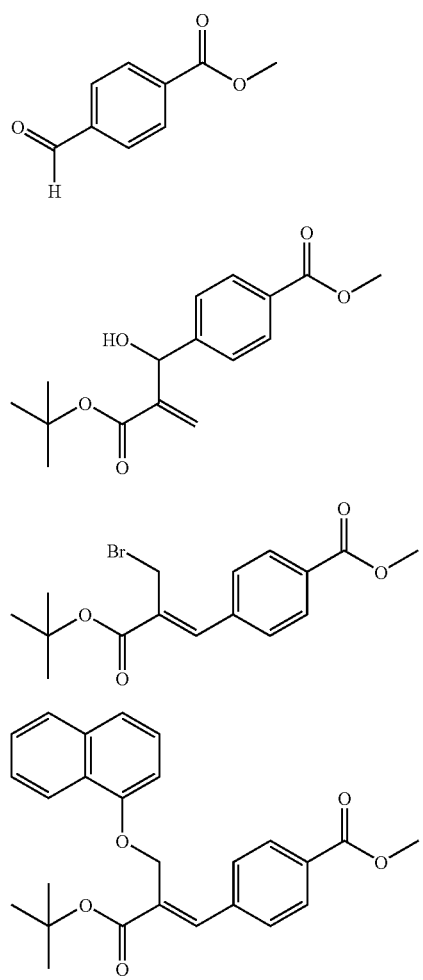

I

XXIII

XXIV

XXV

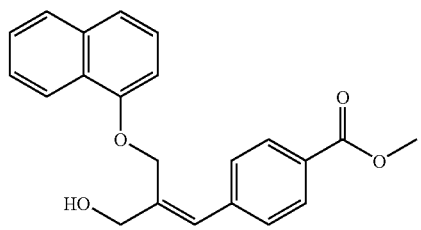

XXVI

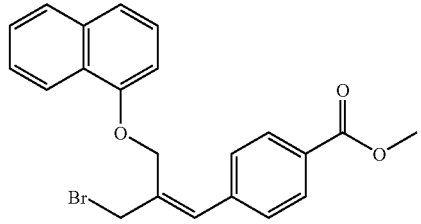

XXVII

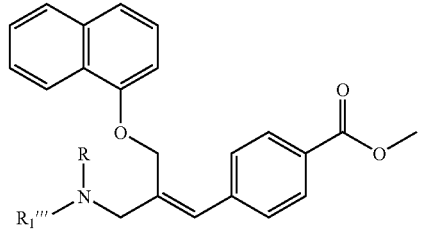

XXVIII

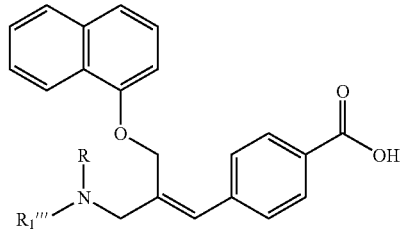

XXIX

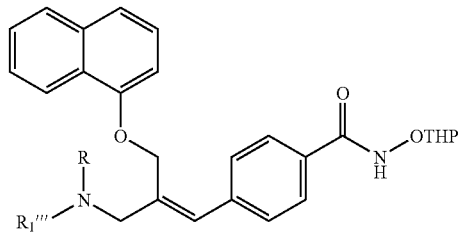

XXX wherein,
R and R₁''' have the same meanings as defined in formula (4) above.

The method described above may be represented by Reaction Scheme 4:

Reaction Scheme 4

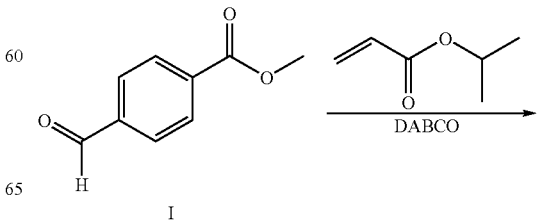

I

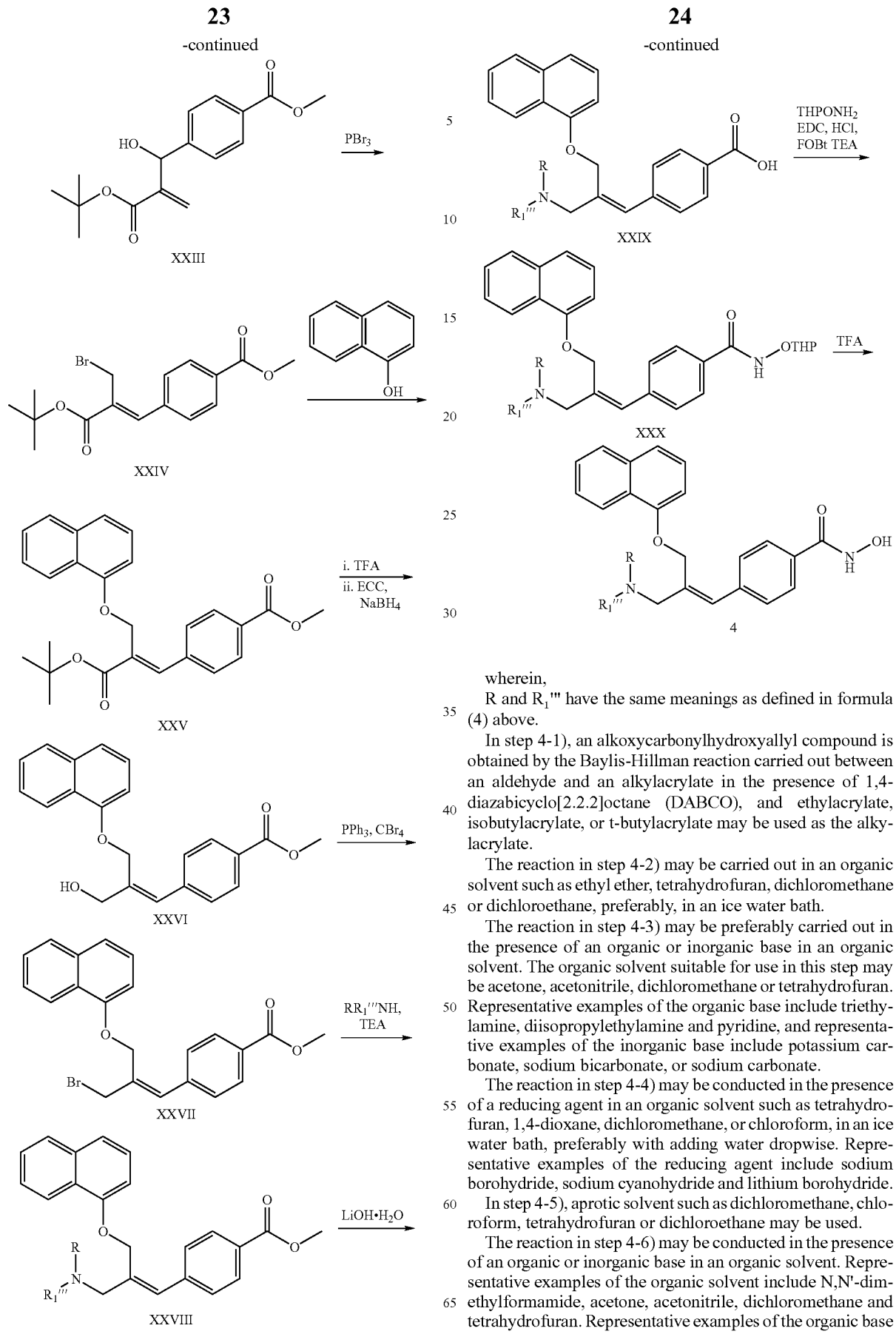

wherein,
R and $R_1'''$ have the same meanings as defined in formula (4) above.

In step 4-1), an alkoxycarbonylhydroxyallyl compound is obtained by the Baylis-Hillman reaction carried out between an aldehyde and an alkylacrylate in the presence of 1,4-diazabicyclo[2.2.2]octane (DABCO), and ethylacrylate, isobutylacrylate, or t-butylacrylate may be used as the alkylacrylate.

The reaction in step 4-2) may be carried out in an organic solvent such as ethyl ether, tetrahydrofuran, dichloromethane or dichloroethane, preferably, in an ice water bath.

The reaction in step 4-3) may be preferably carried out in the presence of an organic or inorganic base in an organic solvent. The organic solvent suitable for use in this step may be acetone, acetonitrile, dichloromethane or tetrahydrofuran. Representative examples of the organic base include triethylamine, diisopropylethylamine and pyridine, and representative examples of the inorganic base include potassium carbonate, sodium bicarbonate, or sodium carbonate.

The reaction in step 4-4) may be conducted in the presence of a reducing agent in an organic solvent such as tetrahydrofuran, 1,4-dioxane, dichloromethane, or chloroform, in an ice water bath, preferably with adding water dropwise. Representative examples of the reducing agent include sodium borohydride, sodium cyanohydride and lithium borohydride.

In step 4-5), aprotic solvent such as dichloromethane, chloroform, tetrahydrofuran or dichloroethane may be used.

The reaction in step 4-6) may be conducted in the presence of an organic or inorganic base in an organic solvent. Representative examples of the organic solvent include N,N'-dimethylformamide, acetone, acetonitrile, dichloromethane and tetrahydrofuran. Representative examples of the organic base include triethylamine, diisopropylethylamine and pyridine, and representative examples of the inorganic base include potassium carbonate, sodium bicarbonate, and sodium carbonate.

The reaction in step 4-7) may be carried out in an aqueous solution of alcohol such as methanol, ethanol, isopropanol, n-butanol or t-butanol, or tetrahydrofuran, in the presence of inorganic base such as lithium hydroxide, sodium hydroxide or calcium hydroxide.

In step 4-8), an organic solvent such as N,N'-dimethylformamide, dimethylsulfoxide, tetrahydrofuran, or dichloromethane may be used The reaction in step 4-9) may be conducted in an organic solvent such as methanol, dichloromethane, dichloroethane, benzene or toluene, in the presence of a water soluble inorganic acid such as hydrochloric acid, sulfuric acid or phosphoric acid, or an organic acid such trifluoroacetic acid, acetic acid or citric acid.

In case of the compound of formula (4) wherein R is H, it may be also prepared by a method comprising the steps of 5-1) reacting the compound of formula XXVII with a primary amine ($R_1'''NH_2$) to obtain a compound of the formula (XXVIII-1);

5-2) protecting the amine of the compound of formula (XXVIII-1) with t-butyldicarbonate in aprotic solvent to obtain a compound of formula XXXI;

5-3) hydrolyzing the compound of formula XXXI in the presence of an inorganic base to obtain a compound of formula XXXII;

5-4) acylating the compound of formula XXXII with tetrahydropyranyloxyamine ($THPONH_2$) in the presence of acylating agent such as N-hydroxy-6-trifluorobenzotriazole (FOBT) or 1-ethyl-3-(3-dimethylaminopropyl)-carbodiimide hydrochloride (EDC.HCl) in an organic solvent to obtain a compound of formula XXXIII;

5-5) reacting the compound of formula XXXIII with an inorganic or organic acid to remove the tetrahydropyranyl group and t-butoxycarbonyl group ($Boc^-$) therefrom.

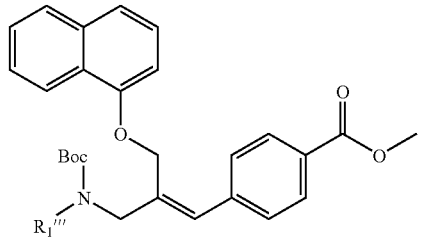

XXXI

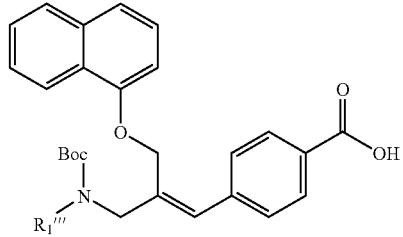

XXXII

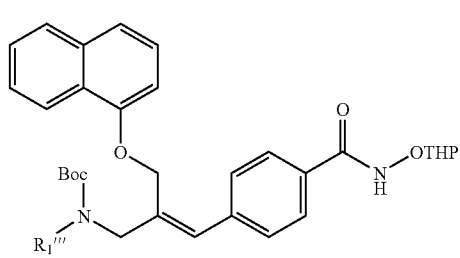

XXXIII wherein, $R_1'''$ has the same meaning as defined in formula (4) above.

The method described above may be represented by Reaction Scheme 5:

Reaction Scheme 5

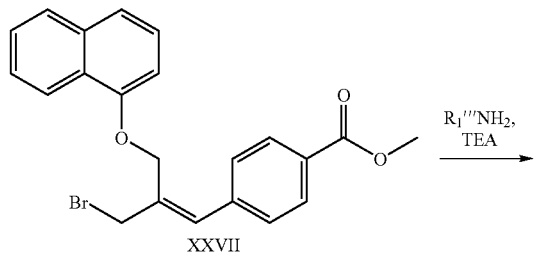

XXVII

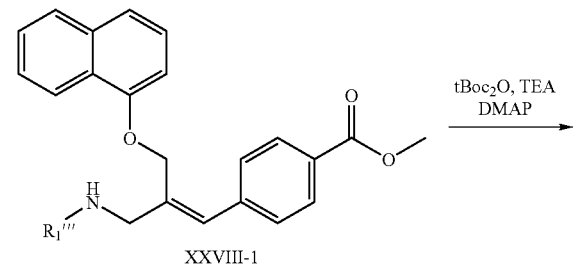

XXVIII-1

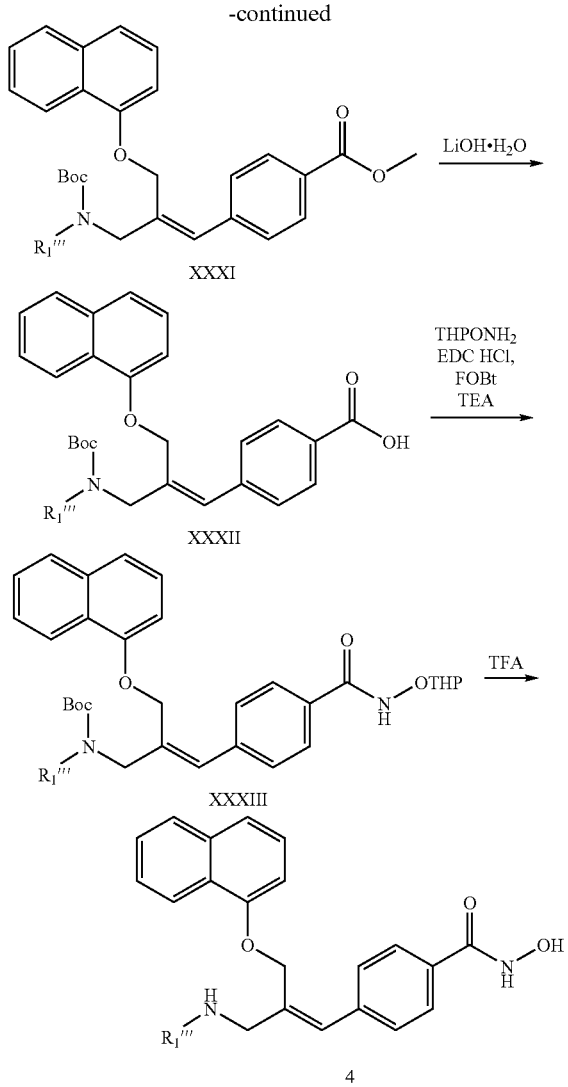

wherein,

R$_1'''$ has the same meaning as defined in formula (4) above.

The reaction in step 5-1) may be carried out in the presence of an organic or inorganic base in an organic solvent. Representative examples of the organic solvent include acetone, acetonitrile, dichloromethane and tetrahydrofuran. Representative examples of the organic base include triethylamine, diisopropylethylamine, and pyridine, and representative examples of the inorganic base include potassium carbonate, sodium bicarbonate, and sodium carbonate.

The reaction in step 5-2) may be conducted in the presence of an organic base and a catalyst in aprotic solvent. Representative examples of the aprotic solvent include dichloromethane, chloroform, tetrahydrofuran, 1,4-dioxane and dichloroethane. Representative examples of the organic base include triethylamine, diisopropylamine and pyridine, and preferred catalyst may be 4-dimethylaminopyridine (DMAP).

The reaction in step 5-3) may be preferably in the presence of an inorganic base in an aqueous solution of alcohol such as methanol, ethanol, isopropanol, N-butanol and t-butanol, or tetrahydrofuran. Representative examples of the inorganic base include lithium hydroxide, sodium hydroxide and calcium hydroxide.

In step 5-4), an organic solvent such as N,N'-dimethylformamide, dimethylsulfoxide, tetrahydrofuran or dichloromethane may be used.

In step 5-5), an organic solvent such as methanol, dichloromethane, dichloroethane, benzene or toluene may be used. Further, a water-soluble inorganic acid such as hydrochloric acid, sulfuric acid or phosphoric acid, and an organic acid such trifluoroacetic acid, acetic acid or citric acid may be used.

The starting material (formula I) for preparing the naphthalenyloxypropenyl derivatives of formula (4) can be easily synthesized using conventional methods or may be commercially available.

The inventive naphthalenyloxypropenyl derivatives of formulae (1) to (4) efficiently inhibit the activity of histone deacetylase, to suppress the differentiation of tumor cells, thereby preventing the cancer-cell proliferation.

Accordingly, the present invention also provides an anticancer composition comprising at least one of the compounds of formulae (1) to (4) as an active ingredient and a pharmaceutically acceptable carrier Further, the present invention provides a pharmaceutical composition for preventing or treating a disease caused by excessive histone deacetylase activity such as osteoporosis and central nervous system disorders (e.g., Alzheimer's disease), comprising at least one of the compounds of formulae (1) to (4) as an active ingredient and a pharmaceutically acceptable carrier.

The inventive pharmaceutical composition comprises at least one of the compounds of formulae (1) to (4) as an active ingredient in an amount ranging from 0.1 to 75 wt %, preferably 1 to 50 wt %, based on the total weight of the composition.

The inventive pharmaceutical composition may be formulated for oral or parenteral administration. The formulation for oral administration may take various forms such as tablet, pill, soft and hard capsule, solution, suspension, emulsion, syrup, granule and the like, which may contain conventional additives such as a diluent (e.g., lactose, dextrose, sucrose, mannitol, sorbitol, cellulose and/or glycine), a lubricant (e.g., silica, talc, stearic acid, or its magnesium or calcium salt, and/or polyethyleneglycol). A tablet form may also comprise a binder such as magnesium aluminum silicate, starch paste, gelatin, tragacanth, methylcellulose, sodium carboxymethylcellulose and/or polyvinylpyrrolidine, and optionally a disintegrant such as starch, agar, alginic acid or its sodium salt, or an effervescent mixture and/or an absorbent, a colorant, a flavor and a sweetener. For parenteral administration, sterile injectable formulations such as isotonic solution and suspension may be preferred.

The composition may be sterilized and/or additionally include preservatives, stabilizers, wetting agents, emulsifying agents, osmotic pressure-adjusting agents, and/or buffering agents and the like, and may be formulated through a conventional mixing, granulating or coating procedures.

A typical daily dose of the compounds of formulae (1) to (4) ranges from about 2.5 to 100 mg/kg, preferably 5 to 60 mg/kg for mammals including a human subject, and can be orally or parenterally administered in a single dose or in divided doses.

The present invention is further described and illustrated in Examples provided below, which are, however, not intended to limit the scope of the present invention.

EXAMPLE

Preparation of Naphthalenyloxypropenyl Derivatives of Formula (1)

Preparation Example 1-1

Preparation of t-butyl-3-hydroxy-2-methylene-3-(4-methoxycarbonylphenyl)propanoate (the Compound of Formula II)

4-(methoxycarbonyl)benzaldehyde (3.3 g, 20 mM), t-butylacrylate (3.5 ml, 24 mM) and 1,4-diazabicyclo[2,2,2]octane (449 mg, 4 mM) were mixed and stirred in a vessel at room temperature for 5 days. The resulting mixture was extracted with ethyl ether. The organic layer was separated, washed with 2N hydrochloric acid, water and an aqueous sodium bicarbonate solution in order, dried over anhydrous sodium sulfate, filtered and concentrated under reduced pressure. The residue thus obtained was subjected to a silica gel column chromatography (eluent: ethyl acetate/n-hexane=1/19), to obtain 4.1 g of the title compound as a white solid (yield 73%).

$^1$H-NMR (200 MHz, CDCl$_3$) δ 1.40 (s, 9H), 3.28 (m, 1H), 3.91 (s, 3H), 5.53 (d, 1H, J=5.2 Hz), 5.71 (s, 1H), 6.27 (s, 1H), 7.45 (d, 2H, J=8.0 Hz), 7.82 (d, 2H, J=8.0 Hz);

MS (EI, 70 eV) m/z 292 (M$^+$), 278, 239, 220, 187, 124, 118, 102;

Melting point: 70° C.

Preparation Example 1-2

Preparation of Methyl 4-(3-bromo-2-t-butoxycarbonylpropenyl)benzoate (the Compound of Formula III)

t-Butyl-3-hydroxy-2-methylene-3-(4-methoxycarbonylphenyl)-propanoate (994 mg, 3.4 mM) obtained in Preparation Example 1-1 was dissolved in ethyl ether (10 ml), and cooled to 0° C. To the resulting mixture, tribromophosphine (0.35 ml, 3.74 mM) was slowly added and stirred at room temperature for 1 hr. After the completion of reaction, the reaction mixture was cooled to −10° C. with adding ice water and extracted with ethyl ether. The organic layer was separated, washed with brine, dried over anhydrous MgSO$_4$, filtered, and concentrated under reduced pressure. The residue thus obtained was subjected to a silica gel column chromatography (eluent: ethyl acetate/n-hexane=1/9), to obtain 831 mg of the title compound as a yellowish green solid (yield 71%).

$^1$H-NMR (300 MHz, CDCl$_3$) δ 1.40 (s, 9H, OCH$_3$), 3.88 (s, 3H, OCH$_3$), 3.97 (s, 2H, CH$_2$), 7.41 (d, 2H, J=8.4 Hz, ArH), 7.50 (s, 1H), 7.91 (d, 2H, J=8.4 Hz, ArH);

MS (EI, 70 eV) m/z 355 (M$^+$), 338, 296, 278, 259, 219, 187, 143, 115;

Melting point: 78° C.

Preparation Example 1-3

Preparation of methyl 4-[3-(naphthalen-1-yloxy)-2-t-butoxycarbonylpropenyl]benzoate (the Compound of Formula IV)

Methyl 4-(3-bromo-2-t-butoxycarbonylpropenyl)benzoate (355 mg, 1.00 mM) obtained in Preparation Example 1-2 was dissolved in acetone (5 ml), and potassium carbonate (207 mg, 1.50 mM) and 1-naphthalenol (144 mg 1.00 mM) were added thereto. The resulting mixture was heated to reflux for 3 hrs. After the completion of reaction, the solvent of the reaction mixture was removed at room temperature under reduced pressure. The residue thus obtained was purified with a silica gel column chromatography (eluent: ethyl acetate/n-hexane=1/9) to obtain 441 mg of the title compound as a white solid (yield 100%).

$^1$H-NMR (200 MHz, CDCl$_3$) δ 1.49 (s, 9H, CH$_3$), 3.89 (s, 3H, OCH$_3$), 4.96 (s, 2H, CH$_2$), 6.84 (d, 1H, J=7.33 Hz, ArH), 7.53 (m, 5H, ArH), 7.89 (m, 1H, ArH), 8.01 (m, 3H, ArH), 8.24 (m, 3H, ArH).

Preparation Example 1-4

Preparation of methyl 4-[3-(naphthalen-1-yloxy)-2-carboxypropenyl]benzoate (the Compound of Formula V)

Methyl 4-[3-(naphthalen-1-yloxy)-2-t-butoxycarbonylpropenyl]-benzoate (372 mg, 0.89 mM) obtained in Preparation Example 1-3 was dissolved in dichloromethane (12 ml), and trifluoroacetic acid (0.90 ml, 1.00 mM) was slowly added thereto at 0° C., followed by reacting at room temperature for 30 mins. After the completion of reaction, the solvent of the reaction mixture was removed under reduced pressure. The residue was purified by adding dichloroethanol thereto, to obtain 315 mg of the title compound as a brown solid (yield 98%).

Further, amine compounds (R$_1$NH$_2$) used in Example 1-1 to 1-23 may be commercially available or can be easily synthesized using conventional methods.

Particularly, the amine compound substituted with piperidine which is substituted with C$_{1-6}$alkyl was synthesized as shown in Reaction Scheme 6:

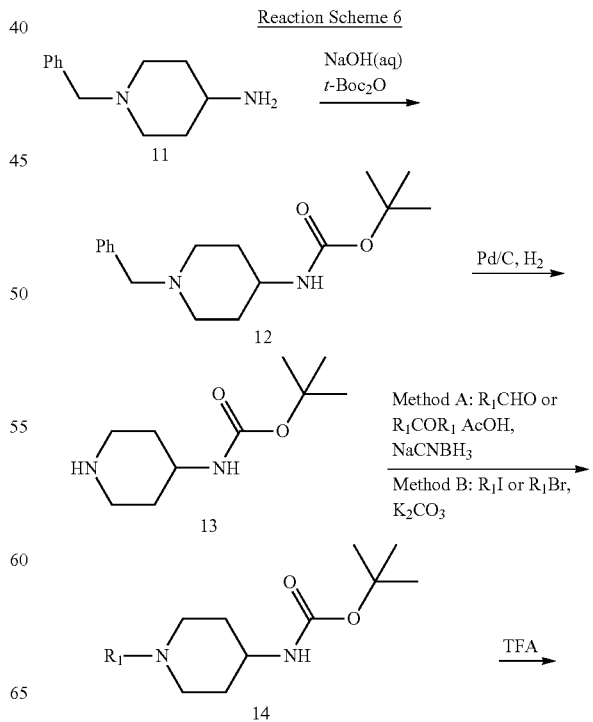

Reaction Scheme 6

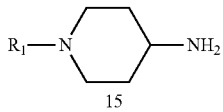

wherein, $R_1$ is $C_{1-6}$alkyl.

Preparation Examples of the Above Amine Compounds are Represented in the following.

Preparation Example 1-i

Preparation of t-butyl-1-benzylpiperidin-4-ylcarbamate (the Compound of Formula 12)

1-Benzylpiperidin-4-ylamine (3 g, 15.8 mmol), the starting material, was dissolved in 1M aqueous sodium hydroxide solution (35.8 ml) and t-butanol (32 ml) in a 250 ml vessel, and t-butyl-dicarbonate ((t-Boc)$_2$O; 3.79 g, 17.38 mmol) was added thereto while stirring, and the resulting mixture was reacted at room temperature for 12 hrs. After the completion of reaction, the reaction mixture was extracted with ethyl acetate twice. Then, the organic layer was washed with 0.1N hydrochloric acid solution and brine in order, dried over anhydrous sodium sulfate, filtered and concentrated under reduced pressure. The residue thus obtained was purified with a silica gel column chromatography to obtain 3.80 g of the title compound as a white solid (82.8%).

$^1$H-NMR (200 MHz, CDCl$_3$) δ 1.38 (s, 9H), 1.86-2.33 (m, 4H), 2.70 (m, 2H), 3.40 (m, 2H), 3.57 (br, 1H), 4.12 (s, 2H), 7.43 (m, 3H), 7.55 (m, 2H).

LC/MS (M$^+$H): 291.

Preparation Example 1-ii

Preparation of t-butylpiperidin-4-ylcarbamate (the Compound of Formula 13)

t-Butyl-1-benzylpiperidin-4-ylcarbamate (3.80 g, 13.1 mmol) obtained in Preparation Example 1-i was dissolved in 26 ml of methanol in a 100 ml vessel, and a catalytic quantity of 10% active palladium/carbon was added thereto, and the resulting mixture was reacted under a hydrogen atmosphere for 12 hrs. After the completion of reaction, the reaction mixture was filtered through a cellite pad to remove the active palladium/carbon and the solvent was removed under reduced pressure therefrom. Then, the residue was subjected to a silica gel column chromatography to obtain 2.64 g of the title compound (yield 99%).

$^1$H-NMR (200 MHz, CD$_3$OD) δ 1.36 (s, 9H), 1.84-2.36 (m, 4H), 2.74 (m, 2H), 3.42 (m, 2H), 3.60 (br, 1H).

LC/MS (M$^+$H): 201.

Preparation Example 1-iii

Preparation of t-butyl-1-R-piperidin-4-ylcarbamate (the Compound of Formula 14)

(1-iii-1) t-Butyl-1-isopropylpiperidin-4-ylcarbamate (14a)

Method A: t-Butyl piperidin-4-ylcarbamate (3 g, 15 mmol) obtained in Preparation Example 1-ii was dissolved in methanol (30 ml) in a 100 ml vessel, and acetone (7.70 ml, 105 mmol) and acetic acid (0.45 ml, 7.5 mmol) were added thereto while stirring. To the resulting mixture, NaCNBH$_3$ (1.88 mg, 30 mmol) was added dropwise in 4-divided portions and reacted for 18 hrs. After the completion of reaction, ice water was poured to the reaction product and then the resulting mixture was stirred and extracted with ethyl acetate. The organic layer was separated, washed with an aqueous sodium bicarbonate solution and brine in order. Then, the organic layer was dried over anhydrous sodium sulfate, filtered, concentrated under reduced pressure and purified with a silica gel column chromatography to obtain 2.644 g of the title compound as a white solid (yield 73.3%).

$^1$H-NMR (200 MHz, CDCl$_3$) δ 1.36 (d, J=7.0 Hz, 6H), 1.44 (s, 9H), 2.00 (m, 2H), 2.17 (m, 2H), 2.94 (m, 2H), 3.38 (m, 3H), 3.69 (m, 1H), 4.92 (br, 1H).

LC/MS (M$^+$H): 243.

(1-iii-2) t-Butyl-1-methylpiperidin-4-ylcarbamate (14b)

The procedure of Preparation Example (1-iii-1) was repeated except for using t-butyl-piperidin-4-ylcarbamate (1.67 g, 8.4 mmol) obtained in Preparation Example 1-ii and iodomethane as the starting materials, to obtain 1.43 g of the title compound as pale yellow oil (yield 79.4%).

$^1$H-NMR (200 MHz, CDCl$_3$) δ 1.44 (s, 9H), 1.45 (m, 2H), 1.92 (m, 2H), 2.07 (m, 2H), 2.27 (s, 3H), 2.74 (m, 2H), 3.44 (br, 1H), 4.43 (br, 1H).

LC/MS (M$^+$H): 215.

(1-iii-3) t-Butyl-1-ethylpiperidin-4-ylcarbamate (14c)

Method B: t-butyl piperidin-4-ylcarbamate (1.5 g, 7.49 mmol) obtained in Preparation Example 1-ii was dissolved in N,N'-dimethylformamide (19 ml) in a 25 ml vessel, and K$_2$CO$_3$ (2.07 g, 14.98 mmol, 2 eq.) and iodoethane (0.60 ml, 7.49 mmol, 1 eq.) were added thereto while stirring. The resulting mixture was heated from 0° C. to room temperature and kept for 4 hrs. After the completion of reaction, the solvent was distilled under reduced pressure and the residue thus obtained was extracted with ethyl ester. The organic layer was separated, washed with an aqueous saturated sodium bicarbonate solution and brine in order, dried over anhydrous magnesium sulfate, concentrated under reduced pressure and purified with a silica gel column chromatography to obtain 1.34 g of the title compound as pale yellow oil (yield 78%).

$^1$H-NMR (200 MHz, CDCl$_3$) δ 1.10 (t, J=7.4 Hz, 3H), 1.43 (m, 2H), 1.47 (s, 9H), 1.99 (m, 4H), 2.40 (q, J=7.2 Hz, 2H), 2.85 (m, 2H), 3.47 (br, 1H), 4.43 (br, 1H).

LC/MS (M$^+$H): 229.

Preparation Example 1-iv

Preparation of 1-R-piperidin-4-ylamine (the Compound of Formula 15)

(1-iv-1) 1-Isopropylpiperidin-4-ylamine (15a)

The compound (14a) (1.5 g, 7.49 mmol) obtained in Preparation Example (1-iii-1) was dissolved in methanol (20 ml) in a 250 ml vessel, and trifluoroacetic acid (4.06 ml, 54.5 mmol, 5 eq.) was added dropwise thereto while stirring. The resulting mixture was reacted for 18 hrs. After the completion of reaction, the mixture was concentrated under reduced pressure, and then subjected to azeotropic distillation with CHCl$_3$ 3 times. The reaction mixture was basified with aqueous KOH solution (20 ml) and extracted with $CHCl_3$ 3 times. The organic layer was separated, washed with brine, dried, filtered and distilled under reduced pressure, to obtain 1.23 g of the title compound as yellow oil (yield 79.3%).

$^1$H-NMR (200 MHz, $CDCl_3$) δ 1.02 (d, J=6.6 Hz, 6H), 1.38 (m, 2H), 1.56 (br, 2H), 1.80 (d, J=11.8 Hz, 2H), 2.17 (m, 2H), 2.71 (m, 2H), 2.80 (m, 2H).

LC/MS ($M^+H$): 143.

(1-iv-2) 1-Methylpiperidin-4-ylamine (15b)

The procedure of Preparation Example (1-iv-1) was repeated except for using the compound (14b) obtained in Preparation Example (1-iii-2) (1.80 g, 8.4 mmol) as the starting material, to obtain 820 mg of the title compound as pale yellow oil (yield 86%).

$^1$H-NMR (200 MHz, $CDCl_3$) δ 1.37 (m, 2H), 1.78 (m, 2H), 1.99 (m, 2H), 2.27 (s, 3H), 2.70 (m, 1H), 2.81 (m, 2H).

LC/MS ($M^+H$): 115.

(1-iv-3) 1-Ethylpiperidin-4-ylamine (15c)

The procedure of Preparation Example (1-iv-1) was repeated except for using the compound (14c) obtained in Preparation Example (1-iii-3) (1.34 g, 5.86 mmol) as the starting material, to obtain 672 mg of the title compound as pale yellow oil (yield 89%).

$^1$H-NMR (200 MHz, $CDCl_3$) δ 1.08 (t, J=7.2 Hz, 3H), 1.37 (m, 2H), 1.81-2.08 (m, 4H), 2.37 (q, J=7.2 Hz, 2H), 2.65 (m, 1H), 2.87 (m, 2H).

LC/MS ($M^+H$): 129.

Example 1-1

(E)-4-(3-(1-Methylpiperidin-4-ylamino)-2-((naphthalen-1-yloxy)methyl)-3-oxoprop-1-enyl)-N-hydroxybenzamide (the Compound of Formula (1))

(1-1-1) Methyl (E)-4-(3-(1-methylpiperidin-4-ylamino)-2-((naphthalen-1-yloxy)methyl)-3-oxo-prop-1-enyl)benzoate (the Compound of Formula VI)

Methyl 4-[3-(naphthalen-1-yloxy)-2-carboxypropenyl] benzoate (362 mg, 1.00 mM) obtained in Preparation Example 1-4 was dissolved in dimethylformamide (5 ml), and triethylamine (0.21 ml, 1.5 mmol) was added to the resulting solution. The resulting mixture was cooled to 0° C., and thereto were added N-hydroxy-6-trifluorobenzotriazole (FOBt; 223 mg, 1.1 mmol), 1-ethyl-3-(3-dimethylaminopropyl)carbodiimide.hydrochloride (EDC.HCl; 249 mg, 1.3 mmol), and 1-methylpiperidin-4-ylamine obtained in Preparation Example (1-iv-2) (114 mg, 1 mmol). The resulting mixture was stirred at 0° C. for 30 mins, followed by stirring at room temperature for 30 mins. After the completion of reaction, 10% potassium carbonate solution (20 ml) was added to the reaction solution, and the resulting mixture was extracted with ethyl acetate (20 ml, 15 ml×2). The organic layer was separated, washed with brine (20 ml), dried over anhydrous magnesium sulfate, concentrated under reduced pressure and subjected to a silica gel column chromatography to obtain 307 mg of the title compound (yield 66%).

$^1$H-NMR (200 MHz, $CDCl_3$) δ 1.44 (m, 3H), 1.75 (m, 1H), 2.01 (m, 2H), 2.21 (s, 3H), 2.64 (m, 2H), 3.90 (s, 3H), 3.97 (m, 1H), 4.99 (s, 2H), 6.51 (d, J=7.8 Hz, 1H), 6.74 (d, J=7.8 Hz, 1H), 7.28-7.57 (m, 6H), 7.82 (m, 1H), 7.91 (s, 1H), 7.99 (d, J=8.6 Hz, 2H), 8.20 (m, 1H).

LC/MS ($M^+H$): 459.

(1-1-2) (E)-4-(3-(1-Methylpiperidin-4-ylamino)-2-((naphthalen-1-yloxy)methyl)-3-oxo-prop-1-enyl) benzoic acid (the Compound of Formula VII)

Methyl (E)-4-(3-(1-methylpiperidin-4-ylamino)-2-((naphthalen-1-yloxy)methyl)-3-oxo-prop-1-enyl)benzoate (300 mg, 0.65 mM) obtained in Example (1-1-1) was dissolved in water (1 ml), and lithium hydroxide monohydrate ($LiOH.H_2O$) (82 mg, 1.95 mM) was added thereto. The resulting mixture was stirred at room temperature for 10 mins, and further stirred at 50° C. for 3 hrs. After the completion of reaction, the reaction mixture was cooled to room temperature and ice water was poured thereinto, followed by removing the solvent under reduced pressure. Then, the resultant was cooled to 5, acidified with 2N hydrochloride solution to pH 4, extracted with chloroform/methanol (4/1) 3 times. The organic layer was separated, dried over anhydrous sodium sulfate, filtered and concentrated under reduced pressure to obtain 281 mg of the title compound (yield 97%).

(1-1-3): (E)-4-(3-(1-Methylpiperidin-4-ylamino)-2-((naphthalen-1-yloxy)methyl)-3-oxoprop-1-enyl)-N-(tetrahydro-2H-pyran-2-yloxy)benzamide (the Compound of Formula VIII)

(E)-4-(3-(1-Methylpiperidin-4-ylamino)-2-((naphthalen-1-yloxy)-methyl)-3-oxo-prop-1-enyl)benzoic acid (339 mg, 0.56 mM) obtained in Example (1-1-2) was dissolved in dimethylformamide (4 ml) and cooled to 0° C. To the resulting mixture, triethylamine (0.16 ml, 1.14 mM), N-hydroxy-6-trifluorobenzotriazole (FOBt; 171 mg, 0.84 mmol), 1-ethyl-3-(3-dimethylaminopropyl)carbodiimide.hydrochloride (EDC.HCl; 190 mg, 0.99 mmol) and tetrahydro-2H-pyran-2-yloxyamine ($THPONH_2$; 107 mg, 0.91 mmol) were added at 0° C. and the resulting mixture was stirred at room temperature for 12 hrs. To the mixture, 10% potassium carbonate solution (20 ml) was added thereto. Then, the resultant was extracted with ethyl acetate (20 ml, 15 ml×2). The organic layer was separated, washed with brine (20 ml) and dried over anhydrous sodium sulfate, followed by removing the solvent under reduced pressure. The residue thus obtained was subjected to a silica gel column chromatography to obtain 333 mg of the title compound as a white solid (yield 80%).

$^1$H-NMR (200 MHz, $CDCl_3$) δ 1.44-1.79 (m, 5H), 1.81-2.02 (m, 5H), 2.12 (m, 2H), 2.21 (s, 3H), 2.64 (m, 2H), 3.27 (m, 1H), 3.61 (m, 1H), 3.98 (m, 1H), 4.98 (s, 2H), 5.08 (m, 1H), 6.52 (d, J=8.2 Hz, 1H), 6.75 (d, J=7.4 Hz, 1H), 7.31-7.60 (m, 6H), 7.73 (d, J=8.2 Hz, 2H), 7.84 (m, 1H), 7.89 (s, 1H), 8.20 (m, 1H).

LC/MS ($M^+H$): 544.

(1-1-4) (E)-4-(3-(1-Methylpiperidin-4-ylamino)-2-((naphthalen-1-yloxy)methyl)-3-oxoprop-1-enyl)-N-hydroxybenzamide (the Compound of Formula (1))

(E)-4-(3-(1-Methylpiperidin-4-ylamino)-2-((naphthalen-1-yloxy)-methyl)-3-oxoprop-1-enyl)-N-(tetrahydro-2H-pyran-2-yloxy)benzamide obtained in Example (1-1-3) (333 mg, 0.61 mM) was dissolved in methanol (5 ml) and the resulting solution was cooled to 0° C. To the resulting solution, trifluoroacetic acid (0.23 ml, 5 eq.) was slowly added, and the resultant was reacted at room temperature for 18 hrs. After the completion of reaction, the solvent was removed under reduced pressure. The residue thus obtained was purified with a silica gel column chromatography (eluent: ethyl acetate/n-hexane=2/1) to obtain 250 mg of the title compound as a white solid (yield 89%).

$^1$H-NMR (300 MHz, MeOH-d$_4$) δ 1.80 (m, 2H), 2.15 (m, 2H), 2.85 (s, 3H), 3.11 (q, J=1.0.5 Hz, 2H), 3.52 (d, J=12.6 Hz, 2H), 4.06 (m, 1H), 5.08 (s, 2H), 6.82 (d, J=7.5 Hz, 1H), 7.32 (t, J=7.8 Hz, 1H), 7.43 (m, 3H), 7.55 (m, 3H), 7.73 (d, J=8.1 Hz, 2H), 7.77 (d, J=7.8 Hz, 1H), 8.12 (d, J=7.8 Hz, 1H). LC/MS (M$^+$H): 460.

Example 1-2

(E)-4-(3-(3-(1H-Imidazol-1-yl)propylamino)-2-((naphthalen-1-yloxy)methyl)-3-oxopropenyl)-N-hydroxybenzamide (1-2-1) Methyl (E)-4-(3-(3-(1H-imidazol-1-yl)propylamino)-2-((naphthalen-1-yloxy)methyl)-3-oxopropenyl)benzoate The procedure of Example (1-1-1) was repeated except for using 3-(1H-imidazol-1-yl)propan-1-ylamine instead of 1-methylpiperidin-4-ylamine as the amine compound, to obtain 392 mg of the title compound (yield 96%).

$^1$H-NMR (300 MHz, CDCl$_3$) δ 1.92-2.02 (m, 2H), 2.82-2.88 (m, 2H), 3.33-3.40 (q, 2H, J=14.8, 7.6 Hz), 3.85 (s, 2H), 3.90 (s, 3H), 4.98 (s, 2H), 6.73-6.79 (t, 2H, J=7.4, 7.4 Hz), 6.95 (s, 1H), 7.29-7.34 (t, 1H, J=7.6, 7.6 Hz), 7.40-7.51 (m, 4H), 7.81 (s, 2H), 7.97-8.00 (d, 2H, J=7.4 Hz), 8.19 (s, 1H).

(1-2-2) (E)-4-(3-(3-(1H-Imidazol-1-yl)propylamino)-2-((naphthalen-1-yloxy)methyl)-3-oxopropenyl)benzoic acid The procedure of Example (1-1-2) was repeated except for using the compound obtained in Example (1-2-1) as the starting material, to obtain 361 mg of the title compound (yield 56%).

(1-2-3) (E)-4-(3-(3-(1H-Imidazol-1-yl)propylamino)-2-((naphthalen-1-yloxy)methyl)-3-oxo-1-propenyl)-N-(tetrahydro-2H-pyran-2-yloxy)benzamide The procedure of Example (1-1-3) was repeated except for using the compound obtained in Example (1-2-2) as the starting material to obtain 392 mg of the title compound (yield 85%).

$^1$H-NMR (300 MHz, CDCl$_3$) δ 1.25 (s, 2H), 1.80-1.84 (m, 2H), 1.96-2.01 (t, 2H, J=14.8, 7.6 Hz), 2.87-2.94 (m, 1H), 3.36-3.42 (m, 2H), 3.48 (s, 3H), 3.59-3.63 (m, 1H), 3.88-3.97 (m, 3H), 4.95 (s, 2H), 5.05 (s, 1H), 6.74-6.77 (d, 2H, J=7.4 Hz), 6.97 (s, 1H), 7.34-7.52 (m, 5H), 7.71-7.74 (d, 2H, J=7.4 Hz), 7.83-7.87 (t, 2H, J=7.8, 7.6 Hz), 8.18-8.20 (d, 2H, J=7.4 Hz).

(1-2-4) (E)-4-(3-(3-(1H-Imidazol-1-yl)propylamino)-2-((naphthalen-1-yloxy)methyl)-3-oxopropenyl)-N-hydroxybenzamide The procedure of Example (1-1-4) was repeated except for using the compound obtained in Example (1-2-3) as the starting material to obtain 248 mg of the title compound (yield 87%).

$^1$H-NMR (300 MHz, MeOH-d$_4$) δ 1.94-2.03 (m, 2H), 3.25 (s, 4H), 3.95-4.00 (t, 2H, J=14.8, 7.6 Hz), 5.05 (s, 2H), 6.78-6.81 (d, 1H, J=7.4 Hz), 7.00 (s, 1H), 7.12 (s, 1H), 7.27-7.42 (m, 3H), 7.48-7.54 (t, 2H, J=7.6, 7.6 Hz), 7.68-7.72 (t, 2H, J=7.6, 7.6 Hz), 7.75-7.78 (d, 2H, J=7.4 Hz), 8.08-8.11 (d, 1H, J=7.6 Hz).

Example 1-3

(E)-4-(3-(4-Methoxyphenethylamino)-2-((naphthalen-1-yloxy)methyl)-3-oxoprop-1-enyl)-N-hydroxybenzamide (1-3-1) Methyl (E)-4-(3-(4-methoxyphenethylamino)-2-((naphthalen-1-yloxy)methyl)-3-oxopropenyl)benzoate The procedure of Example (1-1-1) was repeated except for using 4-methoxyphenethylamine instead of 1-methylpiperidin-4-ylamine as the amine compound, to obtain 110 mg of the title compound (yield 92%).

$^1$H-NMR (300 MHz, CDCl$_3$) δ 2.79-2.90 (t, 2H, J=14.4, 7.2 Hz), 3.63 (s, 2H), 3.64 (s, 3H), 3.90 (s, 3H), 4.88 (s, 2H), 6.53-6.57 (d, 3H, J=7.4 Hz), 6.71-6.75 (d, 1H, J=7.6 Hz), 7.95-7.99 (d, 2H, J=7.6 Hz), 7.40-7.57 (m, 6H), 7.60-7.90 (m, 1H), 7.95-8.02 (t, 2H, J=14.8, 7.4 Hz), 8.13-8.16 (d, 1H, J=7.6 Hz).

(1-3-2) (E)-4-(3-(4-Methoxyphenethylamino)-2-((naphthalen-1-yloxy)methyl)-3-oxopropenyl)benzoic acid The procedure of Example (1-1-2) was repeated except for using the compound obtained in Example (1-3-1) as the starting material, to obtain 85 mg of the title compound (yield 97%).

(1-3-3) (E)-4-(3-(4-Methoxyphenethylamino)-2-((naphthalen-1-yloxy)methyl)-3-oxo-1-propenyl)-N-(tetrahydro-2H-pyran-2-yloxy)-benzamide The procedure of Example (1-1-3) was repeated except for using the compound obtained in Example (1-3-2) as the starting material, to obtain 392 mg of the title compound (yield 86%).

$^1$H-NMR (300 MHz, CDCl$_3$) δ 1.55-1.62 (m, 3H), 2.04 (s, 3H), 2.87 (s, 2H), 2.94 (s, 2H), 3.61 (s, 2H), 3.63 (s, 3H), 4.84 (s, 2H), 5.48 (s, 1H), 6.52-6.57 (dd, 3H, J=14.6, 7.4 Hz), 6.73-6.76 (d, 1H, J=7.4 Hz), 6.93-6.99 (dd, 2H, J=15.4, 7.4 Hz), 7.28-7.40 (m, 3H), 7.49-7.55 (m, 3H), 7.70-7.74 (d, 1H, J=7.4 Hz), 7.88-7.90 (d, 1H, J=7.6 Hz), 8.00 (s, 1H), 8.13-8.14 (d, 1H, J=7.6 Hz).

(1-3-4) (E)-4-(3-(4-Methoxyphenethylamino)-2-((naphthalen-1-yloxy)methyl)-3-oxoprop-1-enyl)-N-hydroxybenzamide The procedure of Example (1-1-4) was repeated except for using the compound obtained in Example (1-3-3) as the starting material, to obtain 54 mg of the title compound (yield 87%).

$^1$H-NMR (300 MHz, MeOH-d$_4$) δ 2.73-2.77 (t, 2H, J=14.4, 7.4 Hz), 3.67 (s, 3H), 5.01 (s, 2H), 6.76-6.79 (d, 2H, J=7.4 Hz), 7.00-7.03 (d, 1H, J=7.6 Hz), 7.11-7.14 (d, 2H, J=7.6 Hz), 7.38-7.55 (m, 6H), 7.73-7.75 (d, 2H, J=7.4 Hz), 7.87-7.90 (d, 1H, J=7.4 Hz), 8.05-8.07 (d, 1H, J=7.6 Hz), 8.41-8.43 (d, 1H, J=7.4 Hz).

Example 1-4

(E)-4-(3-(3-Dimethylamino)-2,2-dimethylpropylamino)-2-((naphthalen-1-yloxy)methyl)-3-oxoprop-1-enyl)-N-hydroxybenzamide (1-4-1) Methyl (E)-4-(3-(3-dimethylamino)-2,2-dimethylpropylamino)-2-((naphthalen-1-yloxy)methyl)-3-oxopropenyl)-benzoate The procedure of Example (1-1-1) was repeated except for using 3-(3-dimethylamino)-2,2-dimethylpropylamine instead of 1-methylpiperidin-4-ylamine as the amine compound, to obtain 331 mg of the title compound (yield 97%).
$^1$H-NMR (300 MHz, CDCl$_3$) δ 0.89 (s, 6H), 1.76 (s, 6H), 2.11 (s, 2H), 3.34-3.35 (d, 2H, J=7.4 Hz), 3.86 (s, 3H), 4.89 (s, 2H), 6.78-6.80 (d, 1H, J=7.4 Hz), 7.32-7.37 (t, 1H, J=14.8, 7.4 Hz), 7.44-7.53 (m, 5H), 7.80-7.82 (d, 1H, J=7.8 Hz), 7.93-7.96 (d, 2H, J=7.6 Hz), 8.06 (s, 1H), 8.30-8.33 (d, 1H, J=7.6 Hz).

(1-4-2) (E)-4-(3-(3-dimethylamino)-2,2-dimethylpropylamino)-2-((naphthalen-1-yloxy)methyl)-3-oxopropenyl)benzoic acid The procedure of Example (1-1-2) was repeated except for using the compound obtained in Example (1-4-1) as the starting material, to obtain 477 mg of the title compound (yield 93%).

(1-4-3) (E)-4-(3-(3-Dimethylamino)-2,2-dimethylpropylamino)-2-((naphthalen-1-yloxy)methyl)-3-oxo-1-propenyl)-N-(tetrahydro-2H-pyran-2-yloxy)benzamide The procedure of Example (1-1-3) was repeated except for using the compound obtained in Example (1-4-2) as the starting material, to obtain 392 mg of the title compound (yield 98%).
$^1$H-NMR (300 MHz, CDCl$_3$) δ 0.88 (s, 6H), 1.54-1.59 (m, 3H), 1.77-1.92 (m, 9H), 2.13-2.15 (d, 2H, J=7.4 Hz), 3.32-3.33 (d, 2H, J=7.4 Hz), 3.55-3.59 (m, 1H), 3.96-4.03 (t, 1H, J=7.4 Hz), 4.85 (s, 2H), 5.05 (s, 1H), 6.75-6.78 (d, 1H, J=7.4 Hz), 7.28-7.52 (m, 5H), 7.69-7.72 (d, 2H, J=7.8 Hz), 7.79-7.81 (d, 1H, J=7.6 Hz), 7.93-7.98 (t, 2H, J=14.8, 7.4 Hz), 8.26-8.29 (d, 1H, J=7.6 Hz).

(1-4-4) (E)-4-(3-(3-Dimethylamino)-2,2-dimethylpropylamino)-2-((naphthalen-1-yloxy)methyl)-3-oxoprop-1-enyl)-N-hydroxybenzamide The procedure of Example (1-1-4) was repeated except for using the compound obtained in Example (1-4-3) as the starting material, to obtain 180 mg of the title compound (yield 88%).
$^1$H-NMR (300 MHz, MeOH-d$_4$) δ 1.00 (s, 6H), 2.63-2.67 (m, 6H), 2.74 (s, 2H), 3.24 (s, 2H), 5.09 (s, 2H), 6.82-6.84 (d, 1H, J=7.4 Hz), 7.26-7.31 (t, 1H, J=14.8, 7.4 Hz), 7.37-7.52 (m, 5H), 7.61 (s, 1H), 7.70-7.78 (dd, 3H, J=14.8, 7.4 Hz), 8.09-8.12 (d, 1H, J=7.4 Hz).

Example 1-5

(E)-4-(3-(2-Diisopropylamino)ethylamino)-2-((naphthalen-1-yloxy)methyl)-3-oxoprop-1-enyl)-N-hydroxybenzamide (1-5-1) Methyl (E)-4-(3-(2-diisopropylamino)ethylamino)-2-((naphthalen-1-yloxy)methyl)-3-oxopropenyl)benzoate The procedure of Example (1-1-1) was repeated except for using 3-(2-diisopropylamino)ethylamine instead of 1-methylpiperidin-4-ylamine as the amine compound, to obtain 155 mg of the title compound (yield 96%).
$^1$H-NMR (300 MHz, CDCl$_3$) δ 0.82-0.84 (d, 12H, J=7.8 Hz), 2.60-2.64 (t, 2H, J=7.8 Hz), 3.37-3.43 (q, 2H, J=7.8 Hz), 3.86 (s, 3H), 4.92 (s, 2H), 6.76-6.79 (d, 1H, J=7.4 Hz), 7.30-7.36 (t, 1H, J=7.6 Hz), 7.42-7.53 (m, 5H), 7.80-7.83 (t, 1H, J=7.8 Hz), 7.93-7.96 (t, 3H, J=7.8 Hz), 8.26-8.29 (d, 1H, J=7.6 Hz).

(1-5-2) (E)-4-(3-(2-Diisopropylamino)ethylamino)-2-((naphthalen-1-yloxy)methyl)-3-oxopropenyl)benzoic acid The procedure of Example (1-1-2) was repeated except for using the compound obtained in Example (1-5-1) as the starting material, to obtain 120 mg of the title compound (yield 98%).

(1-5-3) (E)-4-(3-(2-Diisopropylamino)ethylamino)-2-((naphthalen-1-yloxy)methyl)-3-oxo-1-propenyl)-N-(tetrahydro-2H-pyran-2-yloxy)-benzamide The procedure of Example (1-1-3) was repeated except for using the compound obtained in Example (1-5-2) as the starting material, to obtain 392 mg of the title compound (yield 99%).
$^1$H-NMR (300 MHz, CDCl$_3$) δ 1.20-1.22 (d, 12H, J=7.8 Hz), 1.50-1.52 (d, 2H, J=7.8 Hz), 1.72-1.75 (d, 2H, J=7.8 Hz), 2.13-2.14 (d, 2H, J=7.8 Hz), 3.13 (s, 2H), 3.41-3.52 (m, 2H), 3.84-3.96 (m, 2H), 4.92 (s, 2H), 5.01 (s, 1H), 6.59-6.62 (d, 1H, J=7.4 Hz), 7.08 (s, 1H), 7.23-7.40 (m, 5H), 7.65-7.73 (q, 2H, J=14.9, 7.8 Hz), 7.86 (s, 2H), 8.06-8.08 (d, 1H, J=7.8 Hz).

(1-5-4) (E)-4-(3-(2-Diisopropylamino)ethylamino)-2-((naphthalen-1-yloxy)methyl)-3-oxoprop-1-enyl)-N-hydroxybenzamide The procedure of Example (1-1-4) was repeated except for using the compound obtained in Example (1-5-3) as the starting material, to obtain 84 mg of the title compound (yield 89%).
$^1$H-NMR (300 MHz, MeOH-d$_4$) δ 1.15-1.27 (m, 12H), 3.60-3.63 (d, 2H, J=7.8 Hz), 3.68-3.70 (d, 2H, J=7.8 Hz), 5.04 (s, 2H), 6.81-6.83 (d, 1H, J=7.4 Hz), 7.26-7.32 (t, 1H, J=7.6 Hz), 7.38-7.46 (m, 5H), 7.48-7.51 (d, 1H, J=7.8 Hz), 7.68-7.78 (m, 3H), 8.09-8.11 (d, 1H, J=7.6 Hz).

Example 1-6

(E)-4-(3-(1-Methoxypropan-2-ylamino)-2-((naphthalen-1-yloxy)methyl)-3-oxoprop-1-enyl)-N-hydroxybenzamide (1-6-1) Methyl (E)-4-(3-(1-methoxypropan-2-ylamino)-2-((naphthalen-1-yloxy)methyl)-3-oxopropenyl)benzoate The procedure of Example (1-1-1) was repeated except for using 1-methoxypropan-2-ylamine instead of 1-methylpiperidin-4-ylamine as the amine compound, to obtain 350 mg of the title compound (yield 98%).

$^1$H-NMR (300 MHz, CDCl$_3$) δ 1.20-1.23 (dd, 3H, J=7.8, 7.6 Hz), 3.13 (s, 2H), 3.87 (s, 3H), 4.01-4.03 (m, 1H), 4.28-4.30 (t, 3H, J=7.6 Hz), 4.98 (s, 2H), 6.73-6.76 (d, 1H, J=7.4 Hz), 6.91-6.93 (d, 1H, J=7.6 Hz), 7.29-7.51 (m, 5H), 7.80-8.00 (m, 4H), 8.26-8.27 (d, 1H, J=7.6 Hz).

(1-6-2) (E)-4-(3-(1-Methoxypropan-2-ylamino)-2-((naphthalen-1-yloxy)methyl)-3-oxopropenyl)benzoic acid The procedure of Example (1-1-2) was repeated except for using the compound obtained in Example (1-6-1) as the starting material, to obtain 312 mg of the title compound (yield 99%).

(1-6-3) (E)-4-(3-(1-Methoxypropan-2-ylamino)-2-((naphthalen-1-yloxy)methyl)-3-oxo-1-propenyl)-N-(tetrahydro-2H-pyran-2-yloxy)benzamide The procedure of Example (1-1-3) was repeated except for using the compound obtained in Example (1-6-2) as the starting material, to obtain 392 mg of the title compound (yield 98%).

$^1$H-NMR (300 MHz, CDCl$_3$) δ 1.19-1.21 (d, 3H, J=7.6 Hz), 1.52-1.60 (m, 2H), 1.74-1.82 (m, 2H), 3.13 (s, 3H), 3.32-3.36 (m, 2H), 3.57-3.61 (q, 2H, J=15.4, 7.4 Hz), 3.78-3.80 (m, 2H), 4.17-4.20 (m, 1H), 4.95 (s, 3H), 5.29 (s, 2H), 5.48 (s, 1H), 6.73-6.75 (d, 1H, J=7.4 Hz), 6.86 (s, 1H), 7.28-7.52 (m, 4H), 7.73-7.76 (d, 2H, J=7.6 Hz), 7.80-7.84 (t, 2H, J=7.6 Hz), 7.99 (s, 1H), 8.23-8.26 (d, 1H, J=7.6 Hz).

(1-6-4) (E)-4-(3-(1-methoxypropan-2-ylamino)-2-((naphthalen-1-yloxy)methyl)-3-oxoprop-1-enyl)-N-hydroxybenzamide The procedure of Example (1-1-4) was repeated except for using the compound obtained in Example (1-6-3) as the starting material, to obtain 164 mg of the title compound (yield 95%).

$^1$H-NMR (300 MHz, MeOH-d$_4$) δ 1.20-1.22 (d, 3H, J=7.8 Hz), 3.31 (s, 2H), 3.39 (s, 3H), 4.23-4.45 (m, 1H), 5.10 (s, 2H), 6.86-6.88 (d, 1H, J=7.4 Hz), 7.34 (s, 1H), 7.45-7.56 (m, 6H), 7.75-7.83 (t, 2H, J=7.4 Hz), 8.17-8.20 (d, 1H, J=7.4 Hz).

Example 1-7

(E)-4-(3-(4-Methoxybenzylamino)-2-((naphthalen-1-yloxy)methyl)-3-oxoprop-1-enyl)-N-hydroxybenzamide (1-7-1) Methyl (E)-4-(3-(4-Methoxybenzylamino)-2-((naphthalen-1-yloxy)methyl)-3-oxopropenyl)benzoate The procedure of Example (1-1-1) was repeated except for using 4-methoxybenzylamine instead of 1-methylpiperidin-4-ylamine as the amine compound, to obtain 510 mg of the title compound (yield 98%).

$^1$H-NMR (300 MHz, CDCl$_3$) δ 3.75 (s, 3H), 3.87 (s, 3H), 4.50 (s, 2H), 4.98 (s, 2H), 6.70-6.72 (d, 1H, J=7.4 Hz), 6.76-6.79 (d, 2H, J=7.4 Hz), 7.17-7.20 (d, 1H, J=7.8 Hz), 7.30-7.33 (d, 2H, J=7.8 Hz), 7.39-7.49 (m, 4H), 7.79 (s, 1H), 7.95-7.99 (m, 4H), 8.03-8.05 (d, 1H, J=7.6 Hz).

(1-7-2) (E)-4-(3-(4-Methoxybenzylamino)-2-((naphthalen-1-yloxy)methyl)-3-oxopropenyl)benzoic acid The procedure of Example (1-1-2) was repeated except for using the compound obtained in Example (1-7-1) as the starting material, to obtain 450 mg of the title compound (yield 92%).

(1-7-3) (E)-4-(3-(4-Methoxybenzylamino)-2-((naphthalen-1-yloxy)methyl)-3-oxo-1-propenyl)-N-(tetrahydro-2H-pyran-2-yloxy)benzamide The procedure of Example (1-1-3) was repeated except for using the compound obtained in Example (1-7-2) as the starting material, to obtain 392 mg of the title compound (yield 96%).

$^1$H-NMR (300 MHz, CDCl$_3$) δ 1.57-1.58 (m, 3H), 1.78-1.87 (m, 3H), 3.58-3.62 (m, 1H), 3.76 (s, 3H), 3.93-4.00 (m, 1H), 4.49-4.50 (d, 2H, J=7.8 Hz), 4.95 (s, 2H), 5.04 (s, 1H), 6.70-6.72 (d, 1H, J=7.4 Hz), 6.76-6.79 (d, 2H, J=7.4 Hz), 6.90 (s, 1H), 7.16-7.49 (m, 6H), 7.69-7.72 (d, 2H, J=7.8 Hz), 7.79-7.81 (d, 1H, J=7.8 Hz), 7.98 (s, 2H), 8.04-8.06 (d, 1H, J=7.8 Hz).

(1-7-4) (E)-4-(3-(4-Methoxybenzylamino)-2-((naphthalen-1-yloxy)methyl)-3-oxoprop-1-enyl)-N-hydroxybenzamide The procedure of Example (1-1-4) was repeated except for using the compound obtained in Example (1-7-3) as the starting material, to obtain 301 mg of the title compound (yield 94%).

$^1$H-NMR (300 MHz, MeOH-d$_4$) δ 3.69 (s, 3H), 4.40 (s, 2H), 5.06 (s, 2H), 6.70-6.73 (d, 1H, J=7.4 Hz), 6.79 (s, 2H), 7.15-7.17 (d, 2H, J=7.8 Hz), 7.33-7.49 (m, 5H), 7.68-7.76 (dd, 3H, J=15.4, 7.8 Hz), 7.92 (s, 2H), 8.02-8.05 (d, 1H, J=7.6 Hz).

Example 1-8

(E)-4-(3-(4-Fluorophenethylamino)-2-((naphthalen-1-yloxy)methyl)-3-oxoprop-1-enyl)-N-hydroxybenzamide (1-8-1) Methyl (E)-4-(3-(4-fluorophenethylamino)-2-((naphthalen-1-yloxy)methyl)-3-oxopropenyl)benzoate The procedure of Example (1-1-1) was repeated except for using 4-fluorophenethylamine instead of 1-methylpiperidin-4-ylamine as the amine compound, to obtain 388 mg of the title compound (yield 98%).

$^1$H-NMR (300 MHz, CDCl$_3$) δ 2.77-2.84 (dd, 2H, J=15.6, 7.4 Hz), 3.59-3.65 (dd, 2H, J=15.6, 7.4 Hz), 3.86 (s, 3H), 4.86 (s, 2H), 6.65-6.71 (m, 4H), 6.95-6.99 (dd, 2H, J=15.4, 7.6 Hz), 7.39-7.54 (m, 4H), 7.92-7.95 (t, 1H, J=7.8 Hz), 7.98 (s, 2H), 8.10-8.12 (d, 2H, J=7.8 Hz), 8.50-8.52 (d, 1H, J=7.8 Hz).

(1-8-2) (E)-4-(3-(4-Fluorophenethylamino)-2-((naphthalen-1-yloxy)methyl)-3-oxopropenyl)benzoic acid The procedure of Example (1-1-2) was repeated except for using the compound obtained in Example (1-8-1) as the starting material, to obtain 164 mg of the title compound (yield 87%).

(1-8-3) (E)-4-(3-(4-Fluorophenethylamino)-2-((naphthalen-1-yloxy)methyl)-3-oxo-1-propenyl)-N-(tetrahydro-2H-pyran-2-yloxy)-benzamide The procedure of Example (1-1-3) was repeated except for using the compound obtained in Example (1-8-2) as the starting material, to obtain 392 mg of the title compound (yield 81%).

$^1$H-NMR (300 MHz, CDCl$_3$) δ 1.63-1.65 (m, 3H), 1.83-1.85 (m, 2H), 2.79-2.82 (m, 2H), 2.87-2.88 (m, 2H), 2.94-2.95 (m, 2H), 3.63 (s, 3H), 3.97 (s, 1H), 4.84 (s, 2H), 5.04 (s, 1H), 6.55 (s, 1H), 6.68-6.72 (m, 3H), 6.98-7.00 (d, 2H, J=7.6 Hz), 7.26-7.55 (m, 2H), 7.68-7.71 (t, 2H, J=7.8 Hz), 7.85-7.87 (d, 2H, J=7.4 Hz), 7.90-7.91 (d, 2H, J=7.4 Hz), 8.01-8.09 (m, 2H).

(1-8-4) (E)-4-(3-(4-Fluorophenethylamino)-2-((naphthalen-1-yloxy)methyl)-3-oxoprop-1-enyl)-N-hydroxybenzamide The procedure of Example (1-1-4) was repeated except for using the compound obtained in Example (1-8-3) as the starting material, to obtain 158 mg of the title compound (yield 97%).

$^1$H-NMR (300 MHz, MeOH-d$_4$) δ 2.76-2.81 (t, 2H, J=15.6, 7.4 Hz), 3.47-3.51 (t, 2H, J=15.6, 7.4 Hz), 4.98 (s, 2H), 6.77-6.83 (t, 3H, J=7.8 Hz), 7.09-7.14 (t, 2H, J=15.4, 7.6 Hz), 7.26-7.31 (t, 1H, J=7.8 Hz), 7.36-7.51 (m, 6H), 7.65-7.68 (d, 2H, J=7.4 Hz), 7.75-7.78 (d, 1H, J=7.4 Hz), 8.06-8.09 (d, 1H, J=7.4 Hz).

Example 1-9

(E)-4-(3-(Tetrahydrofuran-2-yl)methylamino)-2-((naphthalen-1-yloxy)methyl)-3-oxoprop-1-enyl)-N-hydroxybenzamide

(1-9-1) Methyl (E)-4-(2-((naphthalen-1-yloxy)methyl)-3-oxo-3-((tetrahydrofuran-2-yl)methylamino)-1-propenyl)benzoate The procedure of Example (1-1-1) was repeated except for using (tetrahydrofuran-2-yl)methylamine instead of 1-methylpiperidin-4-ylamine as the amine compound, to obtain 362 mg of the title compound (yield 97%).

$^1$H-NMR (300 MHz, CDCl$_3$) δ 1.22-1.26 (t, 2H, J=7.8 Hz), 1.57-1.59 (d, 2H, J=7.8 Hz), 1.75-1.79 (t, 1H, J=7.8 Hz), 3.56-3.64 (m, 2H), 3.87 (s, 3H), 3.97-4.00 (t, 2H, J=7.8 Hz), 4.98 (s, 2H), 6.73-6.76 (d, 1H, J=7.4 Hz), 6.98 (s, 2H), 7.41-7.51 (m, 3H), 7.80-7.83 (t, 2H, J=7.8 Hz), 7.91 (s, 1H), 7.97-7.99 (d, 2H, J=7.8 Hz), 8.25-8.27 (d, 1H, J=7.6 Hz).

(1-9-2) (E)-4-(2-(Naphthalen-1-yloxy)methyl)-3-oxo-3-((tetrahydrofuran-2-yl)methylamino)-1-propenyl)benzoic acid The procedure of Example (1-1-2) was repeated except for using the compound obtained Example (1-9-1) as the starting material, to obtain 325 mg of the title compound (yield 90%).

(1-9-3) (E)-4-(2-(Naphthalen-1-yloxy)methyl)-3-oxo-3-((tetrahydrofuran-2-yl)methylamino)-1-propenyl))-N-(tetrahydro-2H-pyran-2-yloxy)benzamide The procedure of Example (1-1-3) was repeated except for using the compound obtained Example (1-9-2) as the starting material, to obtain 392 mg of the title compound (yield 77%).

$^1$H-NMR (300 MHz, CDCl$_3$) δ 1.23-1.28 (t, 1H, J=7.4 Hz), 1.54-1.60 (q, 5H, J=7.8 Hz), 1.75-1.93 (m, 7H), 3.35-3.37 (d, 1H, J=7.8 Hz), 3.57-3.66 (m, 4H), 3.97-4.01 (q, 2H, J=7.8, 7.8 Hz), 4.96 (s, 2H), 5.04 (s, 1H), 6.74-6.77 (d, 1H, J=15.2, 7.4 Hz), 6.90 (s, 1H), 7.31-7.52 (m, 4H), 7.70-7.73 (d, 2H, J=7.4 Hz), 7.81-7.86 (t, 2H, J=7.6 Hz), 8.00 (s, 1H), 8.25-8.28 (d, 1H, J=7.6 Hz).

(1-9-4) (E)-4-(3-((Tetrahydrofuran-2-yl)methylamino)-2-((naphthalen-1-yloxy)methyl)-3-oxoprop-1-enyl)-N-hydroxybenzamide The procedure of Example (1-1-4) was repeated except for using the compound obtained Example (1-9-3) as the starting material, to obtain 168 mg of the title compound (yield 96%).

$^1$H-NMR (300 MHz, MeOH-d$_4$) δ 1.52-1.59 (m, 1H), 1.72-1.91 (m, 211), 2.80 (s, 1H), 2.93 (s, 1H), 3.31 (s, 2H), 3.58-3.74 (m, 2H), 5.02 (s, 2H), 6.78-6.81 (d, 1H, J=7.4 Hz), 7.24-7.30 (t, 1H, J=7.6 Hz), 7.34-7.49 (m, 5H), 7.67-7.69 (d, 2H, J=7.8 Hz), 7.73-7.76 (d, 2H, J=7.8 Hz), 8.10-8.13 (d, 1H, J=7.6 Hz).

Example 1-10

(E)-4-(3-(2-Cyclohexenylethylamino)-2-((naphthalen-1-yloxy)methyl)-3-oxoprop-1-enyl)-N-hydroxybenzamide

(1-10-1) Methyl (E)-4-(3-(2-cyclohexenylethylamino)-2-((naphthalen-1-yloxy)methyl)-3-oxopropenyl)benzoic acid The procedure of Example (1-1-1) was repeated except for using 2-cyclohexenylethylamine instead of 1-methylpiperidin-4-ylamine as the amine compound, to obtain 168 mg of the title compound (yield 96%).

$^1$H-NMR (300 MHz, CDCl$_3$) δ 1.17-1.20 (m, 2H), 1.36-1.60 (m, 4H), 1.79 (s, 2H), 2.10-2.14 (t, 2H, J=7.6 Hz), 3.44-3.48 (t, 2H, J=7.6 Hz), 3.87 (s, 3H), 4.90 (s, 2H), 5.16 (s, 1H), 6.6 (s, 1H), 6.75-6.78 (d, 1H, J=7.4 Hz), 7.25-7.54 (m, 5H), 7.80-7.82 (d, 1H, J=7.4 Hz), 7.95-7.98 (t, 3H, J=7.6 Hz), 8.24-8.27 (d, 1H, J=7.6 Hz).

(1-10-2) (E)-4-(3-(2-Cyclohexenylethylamino)-2-((naphthalen-1-yloxy)methyl)-3-oxopropenyl)benzoate The procedure of Example (1-1-2) was repeated except for using the compound obtained in Example (1-10-1) as the starting material, to obtain 335 mg of the title compound (yield 81%).

(1-10-3) (E)-4-(3-(2-Cyclohexenylethylamino)-2-((naphthalen-1-yloxy)methyl)-3-oxo-1-propenyl)-N-(tetrahydro-2H-pyran-2-yloxy)benzamide The procedure of Example (1-1-3) was repeated except for using the compound obtained in Example (1-10-2) as the starting material, to obtain 392 mg of the title compound (yield 88%).

$^1$H-NMR (300 MHz, CDCl$_3$) δ 0.85-0.88 (m, 2H), 1.17-1.25 (m, 4H), 1.35-1.41 (m, 3H), 1.80-1.84 (m, 4H), 2.10-2.14 (t, 2H, J=7.6 Hz), 2.88-2.95 (m, 1H), 3.44-3.50 (q, 2H, J=7.6 Hz), 3.60-3.64 (m, 1H), 3.92-3.96 (m, 1H), 4.89 (s, 2H), 5.04 (s, 1H), 5.17 (s, 1H), 6.52-6.53 (d, 1H, J=7.6 Hz), 6.76-

6.79 (d, 1H, J=7.4 Hz), 7.33-7.56 (m, 5H), 7.68-7.71 (d, 2H, J=7.4 Hz), 7.83-7.86 (t, 1H, J=7.6 Hz), 7.94 (s, 1H), 8.23-8.26 (t, 1H, J=7.6 Hz).

(1-10-4) (E)-4-(3-(2-Cyclohexenylethylamino)-2-((naphthalen-1-yloxy)methyl)-3-oxoprop-1-enyl)-N-hydroxybenzamide The procedure of Example (1-1-4) was repeated except for using the compound obtained in Example (1-10-3) as the starting material, to obtain 192 mg of the title compound (yield 92%).
$^1$H-NMR (300 MHz, MeOH-d$_4$) δ 1.34-1.47 (m, 4H), 1.69 (s, 2H), 1.86 (s, 2H), 2.09-2.14 (t, 2H, J=7.8 Hz), 3.35-3.38 (t, 2H, J=7.8 Hz), 4.97 (s, 2H), 5.30 (s, 1H), 6.80-6.83 (d, 1H, J=7.4 Hz), 7.25-7.31 (t, 1H, J=7.4 Hz), 7.35-7.47 (m, 5H), 7.58 (s, 1H), 7.65-7.68 (d, 2H, J=7.6 Hz), 7.74-7.76 (d, 1H, J=7.6 Hz), 8.09-8.12 (d, 1H, J=7.6 Hz).

Example 1-11

(E)-4-(3-(3-(2-Oxopyrrolidin-1-yl)propylamino)-2-((naphthalen-1-yloxy)methyl)-3-oxoprop-1-enyl)-N-hydroxy-benzamide (1-11-1) Methyl (E)-4-(2-((naphthalen-1-yloxy)methyl)-3-oxo-3-(3-(2-oxopyrrolidin-1-yl)propylamino)propenyl)benzoate The procedure of Example (1-1-1) was repeated except for using 1-(3-aminopropyl)-2-pyrrolidinone instead of 1-methylpiperidin-4-ylamine as the amine compound, to obtain 266 mg of the title compound (yield 94%).
$^1$H-NMR (300 MHz, CDCl$_3$) δ 1.69-1.74 (t, 2H, J=7.4 Hz), 1.90-1.95 (t, 2H, J=7.4 Hz), 2.26-2.32 (t, 2H, J=7.2 Hz), 3.23-3.37 (m, 6H), 3.86 (s, 3H), 5.04 (s, 2H), 6.78-6.81 (d, 1H, J=7.4 Hz), 7.28-7.34 (t, 2H, J=7.6 Hz), 7.41-7.47 (m, 4H), 7.65 (s, 1H), 7.76-7.82 (dd, 1H, J=7.8 Hz), 7.94-7.97 (d, 2H), 8.22-8.25 (t, 1H, J=7.6 Hz).

(1-11-2) (E)-4-(2-(Naphthalen-1-yloxy)methyl)-3-oxo-3-(3-(2-oxopyrrolidin-1-yl)propylamino)propenyl)benzoic acid The procedure of Example (1-1-2) was repeated except for using the compound obtained in Example (1-11-1) as the starting material, to obtain 211 mg of the title compound (yield 98%).

(1-11-3) (E)-4-(2-(Naphthalen-1-yloxy)methyl)-3-oxo-3-(3-(2-oxopyrrolidin-1-yl)propylamino)propenyl)-N-(tetrahydro-2H-pyran-2-yloxy)benzamide The procedure of Example (1-1-3) was repeated except for using the compound obtained in Example (1-11-2) as the starting material, to obtain 392 mg of the title compound (yield 93%).
$^1$H-NMR (300 MHz, CDCl$_3$) δ 1.27-1.69 (m, 4H), 1.72-1.92 (m, 4H), 1.93-1.97 (d, 2H, J=7.4 Hz), 2.29-2.36 (t, 2H, J=7.4 Hz), 2.87-2.97 (dd, 4H, J=7.6 Hz), 3.27-3.30 (d, 4H, J=7.6 Hz), 4.97-5.05 (t, 3H, J=7.8 Hz), 6.78-6.81 (d, 2H, J=7.4 Hz), 7.28-7.36 (m, 4H), 7.43-7.58 (m, 4H), 7.78 (s, 1H), 8.01-8.21 (m, 1H).

(1-11-4) (E)-4-(3-(3-(2-Oxopyrrolidin-1-yl)propylamino)-2-((naphthalen-1-yloxy)methyl)-3-oxoprop-1-enyl)-N-hydroxybenzamide The procedure of Example (1-1-4) was repeated except for using the compound obtained in Example (1-11-3) as the starting material, to obtain 170 mg of the title compound (yield 89%).
$^1$H-NMR (300 MHz, MeOH-d$_4$) δ 1.66-1.70 (t, 2H, J=7.8 Hz), 1.84-1.92 (q, 2H, J=7.8, 7.4 Hz), 2.18-2.23 (t, 2H, J=7.2 Hz), 3.19-3.23 (t, 3H, J=7.4 Hz), 3.27-3.39 (m, 3H), 5.02 (s, 2H), 7.01-7.03 (d, 1H, J=7.6 Hz), 7.37-7.54 (m, 6H), 7.73-7.76 (d, 2H, J=7.6 Hz), 7.86-7.89 (d, 1H, J=7.4 Hz), 8.04-8.07 (d, 1H, J=7.6 Hz), 8.39 (s, 1H).

Example 1-12

(E)-4-(3-(Furan-2-ylmethylamino)-2-((naphthalen-1-yloxy)methyl)-3-oxoprop-1-enyl)-N-hydroxybenzamide (1-12-1) Methyl (E)-4-(3-(furan-2-ylmethylamino)-2-((naphthalen-1-yloxy)methyl)-3-oxopropenyl)benzoate The procedure of Example (1-1-1) was repeated except for using furan-2-ylmethylamine instead of 1-methylpiperidin-4-ylamine as the amine compound, to obtain 240 mg of the title compound (yield 98%).
$^1$H-NMR (300 MHz, CDCl$_3$) δ 3.84 (s, 3H), 4.57 (s, 2H), 4.95 (s, 2H), 6.20-6.25 (dd, 2H, J=7.4, 7.4 Hz), 6.69-6.71 (d, 1H, J=7.6 Hz), 7.24-7.25 (t, 1H, J=7.8 Hz), 7.29-7.48 (m, 7H), 7.77-7.80 (d, 1H, J=7.8 Hz), 7.93-7.95 (d, 2H, J=7.6 Hz), 8.13-8.15 (d, 1H, J=7.6 Hz).

(1-12-2) (E)-4-(3-(Furan-2-ylmethylamino)-2-((naphthalen-1-yloxy)methyl)-3-oxopropenyl)benzoic acid The procedure of Example (1-1-2) was repeated except for using the compound obtained in Example (1-12-1) as the starting material, to obtain 124 mg of the title compound (yield 86%).

(1-12-3) (E)-4-(3-(furan-2-ylmethylamino)-2-((naphthalen-1-yloxy)methyl)-3-oxo-1-propenyl)-N-(tetrahydro-2H-pyran-2-yloxy)-benzamide The procedure of Example (1-1-3) was repeated except for using the compound obtained in Example (1-12-2) as the starting material, to obtain 392 mg of the title compound (yield 92%).
$^1$H-NMR (300 MHz, CDCl$_3$) δ 1.58-1.69 (m, 2H), 1.82-1.89 (m, 2H), 3.56-3.61 (t, 2H, J=7.4 Hz), 3.97-4.01 (m, 2H), 4.55-4.57 (d, 2H, J=7.2 Hz), 4.94 (s, 2H), 5.04 (s, 1H), 6.25-6.28 (dd, 2H, J=7.4, 7.4 Hz), 6.70-6.74 (d, 1H, J=7.2 Hz), 7.02-7.07 (t, 1H, J=7.6 Hz), 7.25-7.53 (m, 6H), 7.68-7.72 (d, 2H, J=7.8 Hz), 7.88 (s, 1H), 7.96 (s, 1H), 8.09-8.14 (d, 1H, J=7.8 Hz).

(1-12-4) (E)-4-(3-(Furan-2-ylmethylamino)-2-((naphthalen-1-yloxy)methyl)-3-oxoprop-1-enyl)-N-hydroxybenzamide The procedure of Example (1-1-4) was repeated except for using the compound obtained in Example (1-12-3) as the starting material, to obtain 89 mg of the title compound (yield 91%).

¹H-NMR (300 MHz, MeOH-d₄) δ 4.49-4.50 (d, 2H, J=7.2 Hz), 5.09 (s, 2H), 6.33-6.34 (d, 1H, J=7.4 Hz), 6.45 (s, 1H), 7.06-7.08 (d, 1H, J=7.4 Hz), 7.42-7.68 (m, 7H), 7.79-7.82 (d, 2H, J=7.6 Hz), 7.92-7.94 (d, 1H, J=7.4 Hz), 8.06-8.09 (d, 1H, J=7.4 Hz), 8.93-8.96 (t, 1H, J=7.4 Hz).

Example 1-13

(E)-4-(3-(4-(Dimethylamino)benzylamino)-2-((naphthalen-1-yloxy)methyl)-3-oxoprop-1-enyl)-N-hydroxybenzamide (1-13-1) Methyl (E)-4-(3-(4-(dimethylamino)benzylamino)-2-((naphthalen-1-yloxy)methyl)-3-oxopropenyl)benzoate The procedure of Example (1-1-1) was repeated except for using 4-(dimethylamino)benzylamine instead of 1-methylpiperidin-4-ylamine as the amine compound, to obtain 426 mg of the title compound (yield 94%).

¹H-NMR (300 MHz, CDCl₃) δ 2.97 (s, 6H), 3.91 (s, 3H), 4.49-4.52 (d, 2H, J=7.8 Hz), 5.01 (s, 2H), 6.65-6.66 (d, 2H, J=7.4 Hz), 6.77 (s, 2H), 7.28-7.29 (d, 2H, J=7.8 Hz), 7.33 (s, 1H), 7.41-7.52 (m, 5H), 7.81-7.86 (d, 1H, J=7.4 Hz), 7.95-8.00 (t, 2H, J=7.6 Hz), 8.04-8.09 (dd, 1H, J=7.8, 7.6 Hz).

(1-13-2) (E)-4-(3-(4-(Dimethylamino)benzylamino)-2-((naphthalen-1-yloxy)methyl)-3-oxopropenyl)benzoic acid The procedure of Example (1-1-2) was repeated except for using the compound obtained in Example (1-13-1) as the starting material, to obtain 268 mg of the title compound (yield 98%).

(1-13-3) (E)-4-(3-(4-(Dimethylamino)benzylamino)-2-((naphthalen-1-yloxy)methyl)-3-oxo-1-propenyl)-N-(tetrahydro-2H-pyran-2-yloxy)benzamide The procedure of Example (1-1-3) was repeated except for using the compound obtained in Example (1-13-2) as the starting material, to obtain 392 mg of the title compound (yield 91%).

¹H-NMR (300 MHz, CDCl₃) δ 1.60 (s, 3H), 1.85 (s, 3H), 2.88 (s, 1H), 2.92 (s, 6H), 3.65-3.66 (d, 1H, J=7.4 Hz), 4.47-4.50 (d, 2H, J=7.6 Hz), 4.97 (s, 2H), 5.07 (s, 1H), 6.65-6.71 (d, 2H, J=7.4 Hz), 6.78-6.81 (d, 2H, J=7.6 Hz), 7.14-7.18 (d, 2H, J=7.6 Hz), 7.37-7.51 (m, 6H), 7.71-7.75 (d, 1H, J=7.6 Hz), 7.80-7.88 (t, 2H, J=7.4 Hz), 8.07-8.11 (d, 1H, J=7.6 Hz).

(1-13-4) (E)-4-(3-(4-(Dimethylamino)benzylamino)-2-((naphthalen-1-yloxy)methyl)-3-oxoprop-1-enyl)-N-hydroxybenzamide The procedure of Example (1-1-4) was repeated except for using the compound obtained in Example (1-13-3) as the starting material, to obtain 108 mg of the title compound (yield 91%).

¹H-NMR (300 MHz, MeOH-d₄) δ 2.71 (s, 6H), 4.15-4.17 (d, 2H, J=7.4 Hz), 4.87 (s, 2H), 6.57-6.60 (d, 2H, J=7.4 Hz), 6.81-6.83 (d, 1H, J=7.4 Hz), 6.99-7.02 (d, 2H, J=7.4 Hz), 7.20-7.37 (m, 7H), 7.56-7.58 (d, 2H, J=7.4 Hz), 7.68-7.71 (d, 1H, J=7.6 Hz), 7.85-7.87 (d, 1H, J=7.6 Hz).

Example 1-14

(E)-4-(3-(2-Methoxyethylamino)-2-((naphthalen-1-yloxy)methyl)-3-oxoprop-1-enyl)-N-hydroxybenzamide (1-14-1) Methyl (E)-4-(3-(2-methoxyethylamino)-2-((naphthalen-1-yloxy)methyl)-3-oxopropenyl)benzoate The procedure of Example (1-1-1) was repeated except for using 2-methoxyethylamine instead of 1-methylpiperidin-4-ylamine as the amine compound, to obtain 384 mg of the title compound (yield 94%).

¹H-NMR (300 MHz, CDCl₃) δ 3.18 (s, 3H), 3.47-3.49 (q, 2H, J=7.8, 7.6 Hz), 3.51-3.52 (q, 2H, J=7.8, 7.6 Hz), 3.90 (s, 3H), 5.01 (s, 2H), 6.79-7.01 (dd, 1H, J=7.4, 7.4 Hz), 7.01 (s, 1H), 7.28-7.55 (m, 5H), 7.82-7.83 (dd, 1H, J=7.8, 7.8 Hz), 7.95 (s, 1H), 8.00-8.04 (d, 2H, J=7.6 Hz), 8.27-8.32 (t, 1H, J=7.6 Hz).

(1-14-2) (E)-4-(3-(2-Methoxyethylamino)-2-((naphthalen-1-yloxy)methyl)-3-oxopropenyl)benzoic acid The procedure of Example (1-1-2) was repeated except for using the compound obtained in Example (1-14-1) as the starting material, to obtain 335 mg of the title compound (yield 98%).

(1-14-3) (E)-4-(3-(2-Methoxyethylamino)-2-((naphthalen-1-yloxy)methyl)-3-oxo-1-propenyl)-N-(tetrahydro-2H-pyran-2-yloxy)-benzamide The procedure of Example (1-1-3) was repeated except for using the compound obtained in Example (1-14-2) as the starting material, to obtain 335 mg of the title compound (yield 95%).

¹H-NMR (300 MHz, CDCl₃) δ 1.611-1.63 (m, 4H), 1.86 (s, 4H), 2.95 (s, 3H), 3.47-3.50 (d, 2H, J=7.4 Hz), 3.57-3.60 (d, 2H, J=7.4 Hz), 3.97 (s, 1H), 4.97 (s, 2H), 6.75-6.78 (d, 1H, J=7.4 Hz), 6.96 (s, 1H), 7.26-7.27 (t, 2H, J=7.6 Hz), 7.28-7.53 (m, 4H), 7.70-7.91 (m, 3H), 8.24-8.28 (t, 1H, J=7.4 Hz).

(1-14-4) (E)-4-(3-(2-Methoxyethylamino)-2-((naphthalen-1-yloxy)methyl)-3-oxoprop-1-enyl)-N-hydroxybenzamide The procedure of Example (1-1-4) was repeated except for using the compound obtained in Example (1-14-3) as the starting material, to obtain 171 mg of the title compound (yield 91%).

¹H-NMR (300 MHz, MeOH-d₄) δ 3.25 (s, 3H), 3.38-3.44 (m, 4H), 5.02 (s, 2H), 7.00-7.03 (d, 1H, J=7.4 Hz), 7.37-7.59 (m, 6H), 7.73-7.76 (d, 2H, J=7.4 Hz), 7.87-7.89 (d, 1H, J=7.4 Hz), 8.04-8.07 (d, 1H, J=7.6 Hz), 8.40-8.44 (t, 1H, J=7.6 Hz).

Example 1-15

(E)-4-(3-(Cyclohexylamino)-2-((naphthalen-1-yloxy)methyl)-3-oxoprop-1-enyl)-N-hydroxybenzamide (1-15-1) Methyl (E)-4-(3-(cyclohexylamino)-2-((naphthalen-1-yloxy)methyl)-3-oxopropenyl)benzoate The procedure of Example (1-1-1) was repeated except for using cyclohexylamine instead of 1-methylpiperidin-4-ylamine as the amine compound, to obtain 430 mg of the title compound (yield 96%).

¹H-NMR (300 MHz, CDCl₃) δ 1.11-1.16 (m, 2H), 1.22-1.29 (m, 2H), 1.61 (s, 4H), 1.93-1.98 (m, 2H), 3.88 (s, 1H), 3.89 (s, 3H), 4.98 (s, 2H), 6.49-6.53 (d, 1H, J=7.4 Hz), 6.75-6.79 (d, 1H, J=7.4 Hz), 7.35-7.55 (m, 5H), 7.83-7.85 (t, 1H, J=6.8 Hz), 7.92 (s, 1H), 7.98-8.02 (t, 2H, J=6.8 Hz), 8.23-8.27 (d, 1H, J=7.0 Hz).

(1-15-2) (E)-4-(3-(Cyclohexylamino)-2-((naphthalen-1-yloxy)methyl)-3-oxopropenyl)benzoic acid The procedure of Example (1-1-2) was repeated except for using the compound obtained in Example (1-15-1) as the starting material, to obtain 405 mg of the title compound (yield 91%).

(1-15-3) (E)-4-(3-(Cyclohexylamino)-2-((naphthalen-1-yloxy)methyl)-3-oxo-1-propenyl)-N-(tetrahydro-2H-pyran-2-yloxy)-benzamide The procedure of Example (1-1-3) was repeated except for using the compound obtained in Example (1-15-2) as the starting material, to obtain 335 mg of the title compound (yield 90%).
¹H-NMR (300 MHz, CDCl₃) δ 1.11-1.34 (m, 4H), 1.62-1.68 (d, 6H, J=7.4 Hz), 1.85-1.97 (dd, 4H, J=7.6, 7.4 Hz), 287-2.94 (dd, 2H, J=7.4, 7.2 Hz), 3.59-3.90 (m, 1H), 3.96-4.05 (m, 2H), 4.94 (s, 2H), 5.07 (s, 1H), 6.52-6.56 (d, 1H, J=7.8 Hz), 6.74-6.78 (d, 1H, J=7.6 Hz), 7.28-7.39 (m, 3H), 7.40-7.47 (m, 2H), 7.49-7.58 (m, 2H), 7.72-7.83 (t, 2H, J=7.4 Hz), 8.20-8.25 (dd, 1H, J=7.8 Hz).

(1-15-4) (E)-4-(3-(Cyclohexylamino)-2-((naphthalen-1-yloxy)methyl)-3-oxoprop-1-enyl)-N-hydroxybenzamide The procedure of Example (1-1-4) was repeated except for using the compound obtained in Example (1-15-3) as the starting material, to obtain 299 mg of the title compound (yield 93%).
¹H-NMR (300 MHz, MeOH-d₄) δ 1.15-1.34 (m, 6H), 1.57-1.81 (m, 4H), 3.69 (s, 1H), 5.03 (s, 2H), 7.00-7.02 (d, 1H, J=7.4 Hz), 7.37-7.56 (m, 6H), 7.74-7.76 (d, 2H, J=7.0 Hz), 7.86-7.89 (d, 1H, J=6.8 Hz), 8.15-8.17 (d, 2H, J=7.0 Hz).

Example 1-16

(E)-4-(3-(Thiophen-2-ylmethylamino)-2-((naphthalen-1-yloxy)methyl)-3-oxoprop-1-enyl)-N-hydroxybenzamide

(1-16-1) Methyl (E)-4-(2-((naphthalen-1-yloxy)methyl)-3-oxo-3-(thiophen-2-ylmethylamino)propenyl)benzoate The procedure of Example (1-1-1) was repeated except for using thiophen-2-ylmethylamine instead of 1-methylpiperidin-4-ylamine as the amine compound, to obtain 441 mg of the title compound (yield 92%).
¹H-NMR (300 MHz, CDCl₃) δ 1.60-1.64 (m, 1H), 2.16 (s, 1H), 3.89 (s, 3H), 4.74-4.77 (d, 2H, J=7.4 Hz), 4.99 (s, 2H), 6.73-6.77 (d, 1H, J=7.4 Hz), 6.91-6.98 (m, 2H), 7.19-7.20 (d, 1H, J=7.6 Hz), 7.26-7.55 (m, 4H), 7.81-7.85 (d, 1H, J=7.4 Hz), 7.98-8.02 (d, 2H, J=7.6 Hz), 8.10-8.14 (d, 1H, J=7.6 Hz).

(1-16-2) (E)-4-(2-((Naphthalen-1-yloxy)methyl)-3-oxo-3-(thiophen-2-ylmethylamino)propenyl)benzoic acid The procedure of Example (1-1-2) was repeated except for using the compound obtained in Example (1-16-1) as the starting material, to obtain 306 mg of the title compound (yield 95%).

(1-16-3) (E)-4-(2-(Naphthalen-1-yloxy)methyl)-3-oxo-3-(thiophen-2-ylmethylamino)-1-propenyl))-N-(tetra hydro-2H-pyran-2-yloxy)benzamide The procedure of Example (1-1-3) was repeated except for using the compound obtained in Example (1-16-2) as the starting material, to obtain 392 mg of the title compound (yield 94%).
¹H-NMR (300 MHz, CDCl₃) δ 1.61-1.85 (m, 5H), 2.88 (s, 2H), 2.95 (s, 2H), 3.59-3.65 (t, 1H, J=8.2 Hz), 3.86-3.99 (m, 1H), 4.75-4.77 (d, 2H, J=8.4 Hz), 4.97 (s, 2H), 6.74-6.77 (d, 1H, J=7.8 Hz), 6.90-6.98 (m, 2H), 7.38-7.56 (m, 5H), 7.71-7.75 (d, 1H, J=7.6 Hz), 7.81-7.85 (d, 1H, J=7.8 Hz), 7.94 (s, 1H), 8.00-8.13 (dd, 1H, J=7.6, 7.8 Hz).

(1-16-4) (E)-4-(3-(Thiophen-2-ylmethylamino)-2-((naphthalen-1-yloxy)methyl)-3-oxoprop-1-enyl)-N-hydroxybenzamide The procedure of Example (1-1-4) was repeated except for using the compound obtained in Example (1-16-3) as the starting material, to obtain 146 mg of the title compound (yield 89%).
¹H-NMR (300 MHz, MeOH-d₄) δ 2.50 (s, 2H), 4.59-4.61 (d, 2H, J=7.4 Hz), 5.04 (s, 2H), 6.95-6.97 (d, 1H, J=7.4 Hz), 7.01-7.03 (d, 2H, J=7.4 Hz), 7.39-7.55 (m, 4H), 7.63 (s, 1H), 7.73-7.76 (d, 2H, J=7.4 Hz), 7.84-7.86 (d, 1H, J=7.6 Hz), 8.01-8.03 (d, 1H, J=7.4 Hz).

Example 1-17

(E)-4-(3-(1-Ethylpiperidin-4-ylamino)-2-((naphthalen-1-yloxy)methyl)-3-oxoprop-1-enyl)-N-hydroxybenzamide

(1-17-1) Methyl (E)-4-(3-(1-ethylpiperidin-4-ylamino)-2-((naphthalen-1-yloxy)methyl)-3-oxoprop-1-enyl)benzoate The procedure of Example (1-1-1) was repeated except for using 1-ethylpiperidin-4-ylamine obtained in Preparation Example (1-iv-3) instead of 1-methylpiperidin-4-ylamine as the amine compound, to obtain 226 mg of the title compound (yield 48%).
¹H-NMR (200 MHz, CDCl₃) δ 1.04 (t, J=7.4 Hz, 3H), 1.52 (m, 2H), 1.91 (m, 2H), 2.07 (m, 2H), 2.35 (q, J=7.4 Hz, 2H), 2.88 (m, 2H), 3.90 (s, 3H), 4.00 (m, 1H), 4.98 (s, 2H), 6.53 (d, J=7.4 Hz, 1H), 6.74 (d, J=7.8 Hz, 1H), 7.34 (t, J=7.8 Hz, 1H), 7.52 (m, 5H), 7.82 (m, 1H), 7.91 (s, 1H), 7.99 (d, J=8.6 Hz, 2H), 8.22 (m, 1H).
LC/MS (M⁺H): 473.

(1-17-2) (E)-4-(3-(1-Ethylpiperidin-4-ylamino)-2-((naphthalen-1-yloxy)methyl)-3-oxo-prop-1-enyl) benzoic acid The procedure of Example (1-1-2) was repeated except for using the compound obtained in Example (1-17-1) as the starting material, to obtain 150 mg of the title compound (yield 73%).

(1-17-3) (E)-4-(3-(1-Ethylpiperidin-4-ylamino)-2-((naphthalen-1-yloxy)methyl)-3-oxoprop-1-enyl)-N-(tetrahydro-2H-pyran-2-yloxy)-benzamide The procedure of Example (1-1-3) was repeated except for using the compound obtained in Example (1-17-2) as the starting material, to obtain 160 mg of the title compound (yield 88%).

$^1$H-NMR (200 MHz, CDCl$_3$) δ 1.10 (t, J=7.8 Hz, 3H), 1.63 (m, 6H), 1.87 (m, 2H), 2.07 (m, 2H), 2.19 (m, 2H), 2.42 (q, J=7.6 Hz, 2H), 2.52 (m, 2H), 3.62 (m, 1H), 3.99 (m, 2H), 4.99 (s, 2H), 5.08 (m, 1H), 6.58 (d, J=7.4 Hz, 1H), 6.76 (d, J=7.4 Hz, 1H), 7.35-7.56 (m, 6H), 7.73 (d, J=8.6 Hz, 2H), 7.84 (m, 1H), 7.89 (s, 1H), 8.25 (m, 1H).

LC/MS (M$^+$H): 558.

(1-17-4) (E)-4-(3-(1-Ethylpiperidin-4-ylamino)-2-((naphthalen-1-yloxy)methyl)-3-oxoprop-1-enyl)-N-hydroxybenzamide The procedure of Example (1-1-4) was repeated except for using the compound obtained in Example (1-17-3) as the starting material, to obtain 80 mg of the title compound (yield 81%).

$^1$H-NMR (300 MHz, MeOH-d$_4$) δ 1.33 (t, J=7.5 Hz, 3H), 1.80 (m, 1H), 2.18 (d, J=13.5 Hz, 2H), 3.06 (t, J=12.9 Hz, 2H), 3.15 (q, J=7.2 Hz, 2H), 3.59 (d, J=12.6 Hz, 2H), 4.06 (m, 1H), 5.09 (s, 2H), 6.84 (d, J=7.2 Hz, 1H), 7.33 (t, J=7.8 Hz, 1H), 7.44 (m, 3H), 7.56 (m, 3H), 7.73 (d, J=8.4 Hz, 2H), 7.78 (d, J=7.8 Hz, 1H), 8.12 (d, J=8.1 Hz, 1H).

LC/MS (M$^+$H): 474.

Example 1-18

(E)-4-(3-(3-Morpholinopropylamino)-2-((naphthalen-1-yloxy)methyl)-3-oxoprop-1-enyl)-N-hydroxybenzamide

(1-18-1) Methyl (E)-4-(3-(3-morpholinopropylamino)-2-((naphthalen-1-yloxy)methyl)-3-oxoprop-1-enyl)benzoate The procedure of Example (1-1-1) was repeated except for using 3-morpholinopropylamine instead of 1-methylpiperidin-4-ylamine as the amine compound, to obtain 533 mg of the title compound (yield 96%).

$^1$H-NMR (200 MHz, CDCl$_3$) δ 1.70 (m, 2H), 2.25 (m, 4H), 2.35 (t, J=6.8 Hz, 2H), 3.47 (m, 6H), 3.90 (s, 3H), 5.01 (s, 2H), 6.77 (d, J=7.8 Hz, 1H), 7.28-7.57 (m, 6H), 7.82 (s, 1H), 7.84 (m, 1H), 7.99 (d, J=8.2 Hz, 2H), 8.20 (m, 1H).

LC/MS (M$^+$H): 489.

(1-18-2) (E)-4-(3-(3-Morpholinopropylamino)-2-((naphthalen-1-yloxy)methyl)-3-oxo-prop-1-enyl)benzoic acid The procedure of Example (1-1-2) was repeated except for using the compound obtained in Example (1-18-1) as the starting material, to obtain 376 mg of the title compound (yield 81%).

(1-18-3) (E)-4-(3-(3-Morpholinopropylamino)-2-((naphthalen-1-yloxy)methyl)-3-oxoprop-1-enyl)-N-(tetrahydro-2H-pyran-2-yloxy)benzamide The procedure of Example (1-1-3) was repeated except for using the compound obtained in Example (1-18-2) as the starting material, to obtain 380 mg of the title compound (yield 83%).

$^1$H-NMR (200 MHz, CDCl$_3$) δ 1.61 (m, 4H), 1.78 (m, 4H), 2.37 (m, 4H), 2.46 (t, J=7.0 Hz, 2H), 3.57 (m, 6H), 3.66 (m, 1H), 3.91 (m, 1H), 5.01 (s, 2H), 5.04 (m, 1H), 6.78 (d, J=7.6 Hz, 1H), 7.30-7.59 (m, 7H), 7.73 (m, 4H), 8.21 (m, 1H).

LC/MS (M$^+$H): 574.

(1-18-4) (E)-4-(3-(3-Morpholinopropylamino)-2-((naphthalen-1-yloxy)methyl)-3-oxoprop-1-enyl)-N-hydroxybenzamide The procedure of Example (1-1-4) was repeated except for using the compound obtained in Example (1-18-3) as the starting material, to obtain 278 mg of the title compound (yield 91%).

$^1$H-NMR (300 MHz, MeOH-d$_4$) δ 1.97 (m, 2H), 3.05 (m, 4H), 3.42 (t, J=7.4 Hz, 4H), 3.79 (m, 4H), 5.08 (s, 2H), 6.85 (d, J=7.6 Hz, 1H), 7.32 (t, J=8.2 Hz, 1H), 7.42 (m, 3H), 7.50 (m, 2H), 7.64 (s, 1H), 7.72 (d, J=8.2 Hz, 2H), 7.79 (d, J=7.9 Hz, 1H), 8.13 (d, J=7.8 Hz, 1H).

LC/MS (M$^+$H): 490.

Example 1-19

(E)-(3-(3-(2-Methylpiperidin-1-yl)propylamino)-2-((naphthalen-1-yloxy)methyl)-3-oxoprop-1-enyl)-N-hydroxybenzamide

(1-19-1) Methyl (E)-4-(3-(3-(2-methylpiperidin-1-yl)propylamino)-2-((naphthalen-1-yloxy)methyl)-3-oxo-prop-1-enyl)benzoate The procedure of Example (1-1-1) was repeated except for using 3-(2-methylpiperidin-1-yl)propan-1-ylamine instead of 1-methylpiperidin-4-ylamine as the amine compound, to obtain 211 mg of the title compound (yield 42%).

$^1$H-NMR (300 MHz, CDCl$_3$) δ 0.96 (d, J=6.3 Hz, 3H), 1.26 (m, 2H), 1.50 (m, 4H), 1.75 (m, 2H), 2.31 (m, 3H), 2.80 (m, 2H), 3.48 (m, 2H), 3.89 (s, 3H), 4.98 (s, 2H), 6.80 (d, J=7.5 Hz, 1H), 7.34 (t, J=8.1 Hz, 1H), 7.48 (m, 5H), 7.75 (s, 1H), 7.81 (d, J=7.2 Hz, 1H), 7.91 (br, 1H), 7.97 (d, J=8.4 Hz, 2H), 8.22 (d, J=7.8 Hz, 1H).

LC/MS (M$^+$H): 501.

(1-19-2) (E)-4-(3-(3-(2-Methylpiperidin-1-yl)propylamino)-2-((naphthalen-1-yloxy)methyl)-3-oxo-prop-1-enyl)benzoic acid The procedure of Example (1-1-2) was repeated except for using the compound obtained in Example (1-19-1) as the starting material, to obtain 122 mg of the title compound (yield 99%).

(1-19-3) (E)-4-(3-(3-(2-Methylpiperidin-1-yl)propylamino)-2-((naphthalen-1-yloxy)methyl)-3-oxoprop-1-enyl)-N-(tetrahydro-2H-pyran-2-yloxy)benzamide The procedure of Example (1-1-3) was repeated except for using the compound obtained in Example (1-19-2) as the starting material, to obtain 227 mg of the title compound (yield 90%).

$^1$H-NMR (200 MHz, CDCl$_3$) δ 1.10 (d, J=6.4 Hz, 3H), 1.37 (m, 2H), 1.57 (m, 4H), 1.82 (m, 6H), 2.03 (m, 2H), 2.48 (m, 1H), 2.62 (m, 2H), 3.02 (m, 2H), 3.50 (m, 2H), 3.62 (m, 1H), 3.98 (m, 1H), 5.04 (br, 1H), 5.08 (s, 2H), 6.83 (d, J=7.4 Hz, 1H), 7.27-7.52 (m, 6H), 7.68 (d, J=8. Hz, 2H), 7.81 (m, 2H), 8.05 (br, 1H), 8.21 (m, 1H).

LC/MS (M$^+$H): 586.

(1-19-4) (E)-(3-(3-(2-Methylpiperidin-1-yl)propylamino)-2-((naphthalen-1-yloxy)methyl)-3-oxoprop-1-enyl)-N-hydroxybenzamide The procedure of Example (1-1-4) was repeated except for using the compound obtained in Example (1-19-3) as the starting material, to obtain 40 mg of the title compound (yield 84%).

$^1$H-NMR (300 MHz, MeOH-$d_4$) δ 1.02 (dd, J=36.0, 6.3 Hz, 3H), 1.42 (m, 2H), 1.53 (m, 2H), 1.76 (m, 2H), 1.90 (m, 2H), 2.71 (m, 1H), 2.92 (m, 3H), 3.20 (m, 1H), 3.40 (m, 2H), 5.07 (s, 2H), 6.85 (d, J=7.5 Hz, 1H), 7.31 (t, J=8.1 Hz, 1H), 7.39 (m, 3H), 7.50 (d, J=8.1 Hz, 2H), 7.63 (s, 1H), 7.70 (d, J=8.1 Hz, 2H), 7.78 (d, J=7.8 Hz, 1H), 8.13 (d, J=8.4 Hz, 1H).

LC/MS (M$^+$H): 502.

Example 1-20

(E)-(3-(3-(Pyrrolidin-1-yl)propylamino)-2-((naphthalen-1-yloxy)methyl)-3-oxoprop-1-enyl)-N-hydroxybenzamide

(1-20-1) Methyl (E)-4-(2-((naphthalen-1-yloxy)methyl)-3-oxo-3-(3-(pyrrolidin-1-yl)propylamino)prop-1-enyl)benzoate The procedure of Example (1-1-1) was repeated except for using 3-(pyrrolidin-1-yl)propan-1-ylamine instead of 1-methylpiperidin-4-ylamine as the amine compound, to obtain 305 mg of the title compound (yield 64%).

$^1$H-NMR (200 MHz, CDCl$_3$) δ 1.57 (m, 4H), 1.75 (m, 2H), 2.38 (m, 4H), 2.54 (t, J=6.6 Hz, 2H), 3.50 (q, J=5.6 Hz, 2H), 3.89 (s, 3H), 4.99 (s, 2H), 6.77 (d, J=7.4 Hz, 2H), 7.34 (t, J=7.8 Hz, 1H), 7.46 (m, 5H), 7.81 (s, 1H), 7.85 (m, 2H), 7.97 (d, J=8.2 Hz, 2H), 8.22 (m, 1H).

LC/MS (M$^+$H): 473.

(1-20-2) (E)-4-(2-(Naphthalen-1-yloxy)methyl)-3-oxo-3-(3-(pyrrolidin-1-yl)propylamino)prop-1-enyl)benzoic acid The procedure of Example (1-1-2) was repeated except for using the compound obtained in Example (1-20-1) as the starting material, to obtain 270 mg of the title compound (yield 100%).

(1-20-3) (E)-4-(2-(Naphthalen-1-yloxy)methyl)-3-oxo-3-(3-(pyrrolidin-1-yl)propylamino)prop-1-enyl)-N-(tetrahydro-2H-pyran-2-yloxy)benzamide The procedure of Example (1-1-3) was repeated except for using the compound obtained in Example (1-20-2) as the starting material, to obtain 280 mg of the title compound (yield 85%).

$^1$H-NMR (200 MHz, CDCl$_3$) δ 1.63 (m, 6H), 1.87 (m, 6H), 2.47 (m, 4H), 2.61 (t, J=6.6 Hz, 2H), 3.58 (m, 3H), 3.77 (m, 1H), 5.02 (s, 2H), 5.09 (m, 1H), 6.79 (d, J=7.2 Hz, 1H), 7.36 (t, J=7.2 Hz, 1H), 7.48 (m, 5H), 7.83 (m, 3H), 7.99 (d, J=7.8 Hz, 2H), 8.26 (m, 1H).

LC/MS (M$^+$H): 558.

(1-20-4) (E)-(3-(3-(Pyrrolidin-1-yl)propylamino)-2-((naphthalen-1-yloxy)methyl)-3-oxoprop-1-enyl)-N-hydroxybenzamide The procedure of Example (1-1-4) was repeated except for using the compound obtained in Example (1-20-3) as the starting material, to obtain 210 mg of the title compound (yield 82%).

$^1$H-NMR (300 MHz, MeOH-$d_4$) δ 1.88 (m, 6H), 2.88 (m, 2H), 3.04 (t, J=7.7 Hz, 2H), 3.41 (m, 4H), 5.07 (s, 1H), 6.84 (d, J=7.6 Hz, 1H), 7.31 (t, J=7.8 Hz, 1H), 7.46 (m, 3H), 7.51 (d, J=8.1 Hz, 2H), 7.62 (s, 1H), 7.71 (d, J=8.0 Hz, 2H), 7.78 (d, J=7.9 Hz, 1H), 8.13 (d, J=7.8 Hz, 1H).

LC/MS (M$^+$H): 474.

Example 1-21

(E)-4-(3-(3-Ethoxypropylamino)-2-((naphthalen-1-yloxy)methyl)-3-oxoprop-1-enyl)-N-hydroxybenzamide

(1-21-1) Methyl (E)-4-(3-(3-ethoxypropylamino((naphthalen-1-yloxy)methyl)-3-oxo-prop-1-enyl)benzoate The procedure of Example (1-1-1) was repeated except for using 3-ethoxypropylamine instead of 1-methylpiperidin-4-ylamine as the amine compound, to obtain 434 mg of the title compound (yield 97%).

$^1$H-NMR (300 MHz, CDCl$_3$) δ 0.96 (t, J=7.0 Hz, 3H), 1.81 (m, 2H), 3.22 (q, J=7.0 Hz, 2H), 3.45 (t, J=5.8 Hz, 2H), 3.54 (q, J=6.2 Hz, 2H), 3.89 (s, 3H), 4.94 (s, 2H), 6.76 (d, J=7.6 Hz, 1H), 7.01 (m, 1H), 7.33 (t, J=8.0 Hz, 1H), 7.41-7.54 (m, 4H), 7.82 (d, J=7.1 Hz, 1H), 7.97 (d, J=8.3 Hz, 2H), 8.24 (d, J=7.1 Hz, 1H).

LC/MS (M$^+$H): 448.

(1-21-2) (E)-4-(3-(3-Ethoxypropylamino((naphthalen-1-yloxy)methyl)-3-oxo-prop-1-enyl)benzoic acid The procedure of Example (1-1-2) was repeated except for using the compound obtained in Example (1-21-1) as the starting material, to obtain 350 mg of the title compound (yield 91%).

(1-21-3) (E)-4-(3-(3-Ethoxypropylamino)-2-((naphthalen-1-yloxy)methyl)-3-oxoprop-1-enyl)-N-(tetrahydro-2H-pyran-2-yloxy)benzamide The procedure of Example (1-1-3) was repeated except for using the compound obtained in Example (1-21-2) as the starting material, to obtain 414 mg of the title compound (yield 96%).

$^1$H-NMR (200 MHz, CDCl$_3$) δ 0.93 (t, J=7.0 Hz, 3H), 1.56 (m, 2H), 1.82 (m, 6H), 3.19 (q, J=7.0 Hz, 2H), 3.43 (m, 4H), 3.61 (m, 1H), 3.96 (m, 1H), 4.92 (s, 2H), 5.03 (br, 1H), 6.73 (d, J=7.2 Hz, 1H), 7.03 (t, J=5.2 Hz, 1H), 7.27-7.56 (m, 6H), 7.67 (d, J=8.6 Hz, 2H), 7.81 (m, 2H), 8.24 (m, 1H), 9.21 (br, 1H).

LC/MS (M$^+$H): 533.

(1-21-4) (E)-4-(3-(3-Ethoxypropylamino)-2-((naphthalen-1-yloxy)methyl)-3-oxoprop-1-enyl)-N-hydroxybenzamide The procedure of Example (1-1-4) was repeated except for using the compound obtained in Example (1-21-3) as the starting material, to obtain 110 mg of the title compound (yield 90%).

¹H-NMR (300 MHz, MeOH-d₄) δ 1.03 (t, J=7.0 Hz, 3H), 1.77 (m, 2H), 3.32 (m, 2H), 3.38 (m, 4H), 5.03 (s, 2H), 6.80 (d, J=6.9 Hz, 1H), 7.42 (m, 5H), 7.58 (s, 1H), 7.69 (d, J=8.2 Hz, 2H), 7.76 (d, J=7.7 Hz, 1H), 8.12 (d, J=8.1 Hz, 1H).
LC/MS (M⁺H): 449.

Example 1-22

(E)-4-(3-(2-(1-Methylpyrrolidin-2-yl)ethylamino)-2-((naphthalen-1-yloxy)methyl)-3-oxo-1-propenyl)-N-hydroxy-benzamide (1-22-1) Methyl (E)-4-(3-(2-(1-1-methylpyrrolidin-2-yl)ethylamino-2-((naphthalen-1-yloxy)methyl)-3-oxo-1-propenyl)benzoate The procedure of Example (1-1-1) was repeated except for using 2-(1-methylpyrrolidin-2-yl)ethylamine instead of 1-methylpiperidin-4-ylamine as the amine compound, to obtain 501 mg of the title compound (yield 77%).
¹H-NMR (200 MHz, CDCl₃) δ 1.50 (m, 3H), 1.76 (m, 4H), 2.06 (s, 3H), 2.20 (m, 1H), 2.49 (m, 1H), 3.42 (m, 1H), 3.64 (m, 1H), 3.90 (s, 3H), 4.93 (s, 2H), 6.78 (d, J=7.8 Hz, 1H), 7.20-7.60 (m, 6H), 7.84 (m, 1H), 7.97 (m, 3H), 8.28 (m, 1H).
LC/MS (M⁺H): 473.

(1-22-2) (E)-4-(3-(2-(1-Methylpyrrolidin-2-yl)ethylamino-2-((naphthalen-1-yloxy)methyl)-3-oxo-1-propenyl)benzoic acid The procedure of Example (1-1-2) was repeated except for using the compound obtained in Example (1-22-1) as the starting material, to obtain 491 mg of the title compound (yield 100%).
¹H-NMR (200 MHz, MeOH-d₄) δ 1.65-2.02 (m, 4H), 2.15-2.39 (m, 2H), 2.74 (s, 3H), 2.87 (m, 1H), 3.16 (m, 1H), 5.15 (s, 2H), 6.86 (d, J=7.4 Hz, 1H), 7.36 (t, J=8.2 Hz, 1H), 7.30-7.61 (m, 4H), 7.68 (s, 1H), 7.81 (m, 1H), 8.01 (d, J=8.6 Hz, 2H), 8.18 (m, 1H).
LC/MS (M⁺H): 459.

(1-22-3) (E)-4-(3-(2-(1-Methylpyrrolidin-2-yl)ethylamino)-2-((naphthalen-1-yloxy)methyl)-3-oxo-1-propenyl)-N-(tetrahydro-2H-pyran-2-yloxy)benzamide The procedure of Example (1-1-3) was repeated except for using the compound obtained in Example (1-22-2) as the starting material, to obtain 170 mg of the title compound (yield 46%).
¹H-NMR (200 MHz, CDCl₃) δ 1.25 (m, 6H), 1.6 (m, 3H), 1.85 (m, 3H), 2.21 (s, 3H), 2.52 (m, 1H), 2.84 (m, 1H), 3.42 (m, 2H), 3.64 (m, 1H), 3.97 (m, 1H), 4.96 (s, 2H), 5.05 (m, 1H), 6.77 (d, J=7.4 Hz, 1H), 7.26-7.60 (m, 5H), 7.69 (d, J=7.8 Hz, 1H), 7.91 (m, 3H), 8.25 (m, 2H).
LC/MS (M⁺H): 558.

(1-22-4) (E)-4-(3-(2-(1-Methylpyrrolidin-2-yl)ethylamino)-2-((naphthalen-1-yloxy)methyl)-3-oxo-1-propenyl)-N-hydroxybenzamide The procedure of Example (1-1-4) was repeated except for using the compound obtained in Example (1-22-3) as the starting material, to obtain 130 mg of the title compound (yield 92%).
¹H-NMR (200 MHz, MeOH-d₄) δ 1.80 (m, 2H), 1.94 (m, 2H), 2.19 (m, 1H), 2.74 (s, 3H), 2.87 (q, J=10.2 Hz, 1H), 3.14 (m, 1H), 3.48 (t, J=6.2 Hz, 2H), 3.58 (m, 1H), 5.11 (s, 2H), 6.84 (d, J=7.4 Hz, 1H), 7.34 (t, J=7.8 Hz, 1H), 7.74 (m, 4H), 8.17 (d, J=7.2 Hz, 1H).
LC/MS (M⁺H): 474.

Example 1-23

(E)-4-(3-(1-Isopropylpiperidin-4-ylamino)-2-((naphthalen-1-yloxy)methyl)-3-oxoprop-1-enyl)-N-hydroxybenzamide (1-23-1) Methyl (E)-4-(3-(1-1-isopropylpiperidin-4-ylamino)-2-((naphthalen-1-yloxy)methyl)-3-oxoprop-1-enyl)benzoate The procedure of Example (1-1-1) was repeated except for using 1-isopropylpiperidin-4-ylamine obtained in Preparation Example (1-iv-1) instead of 1-methylpiperidin-4-ylamine as the amine compound, to obtain 107 mg of the title compound (yield 29%).
¹H-NMR (200 MHz, CDCl₃) δ 1.14 (d, J=7.6 Hz, 6H), 1.86 (m, 2H), 2.04 (m, 2H), 2.54 (m, 1H), 3.06 (m, 5H), 3.93 (s, 3H), 6.78 (m, 2H), 7.29-7.56 (m, 6H), 7.80 (m, 1H), 7.91 (m, 1H) 8.01 (d, J=8.6 Hz, 2H), 8.21 (m, 1H).
LC/MS (M⁺H): 487.

(1-23-2) (E)-4-(3-(1-Isopropylpiperidin-4-ylamino)-2-((naphthalen-1-yloxy)methyl)-3-oxo-prop-1-enyl) benzoic acid The procedure of Example (1-1-2) was repeated except for using the compound obtained in Example (1-23-1) as the starting material, to obtain 105 mg of the title compound (yield 100%).
LC/MS (M⁺H): 473.

(1-23-3) (E)-4-(3-(1-Isopropylpiperidin-4-ylamino)-2-((naphthalen-1-yloxy)methyl)-3-oxoprop-1-enyl)-N-(tetrahydro-2H-pyran-2-yloxy)benzamide The procedure of Example (1-1-3) was repeated except for using the compound obtained in Example (1-23-2) as the starting material, to obtain 105 mg of the title compound (yield 100%).
¹H-NMR (200 MHz, CDCl₃) δ 1.13 (d, J=7.6 Hz, 6H), 1.61-1.98 (m, 8H), 2.02 (m, 2H), 2.53 (m, 1H), 3.05 (m, 5H), 3.35 (t, J=6.0 Hz, 2H), 4.00 (m, 1H), 5.12 (m, 1H), 6.78 (m, 2H), 7.27-7.57 (m, 6H), 7.82 (m, 1H), 7.93 (m, 1H), 8.03 (d, J=8.6 Hz, 2H), 8.24 (m, 1H).
LC/MS (M⁺H): 572.

(1-23-4) (E)-4-(3-(1-Isopropylpiperidin-4-ylamino)-2-((naphthalen-1-yloxy)methyl)-3-oxoprop-1-enyl)-N-hydroxybenz amide The procedure of Example (1-1-4) was repeated except for using the compound obtained in Example (1-23-3) as the starting material, to obtain 48 mg of the title compound (yield 56%).
¹H-NMR (200 MHz, MeOH-d₄) δ 1.35 (d, J=6.4 Hz, 6H), 1.84 (m, 2H), 2.28 (m, 2H), 3.18 (m, 2H), 3.53 (m, 3H), 4.10 (m, 1H), 5.12 (s, 2H), 6.85 (d, J=7.4 Hz, 1H), 7.35 (t, J=7.8 Hz, 1H), 7.41-7.62 (m, 6H), 7.79 (m, 3H), 8.13 (d, J=8.2 Hz, 1H).
LC/MS (M⁺H): 488.

Test Example 1-1

Analysis of Inhibitory Activity Against HDAC

HDAC activity was analyzed using BIOMOL Quantizyme™ Assay system which comprised two steps of 1) enzyme reaction between HDAC and a substrate and 2) determination of the level of HDAC inhibitory activity.

In step 1), 42 µl of a buffer solution (25 mM Tris-HCl [pH 8.0], 137 mM NaCl, 2.7 mM KCl, 1 mM $MgCl_2$) and 5 µl of 250 µM Fluor de Lys™ substrate were added in order to each well of a 96-well plate, to which 2.5 µl of a test compound (compounds of Examples 1-1 to 1-23) at a concentration of 0.01, 0.1, 1, 10 and 100 µM, respectively, was added. 0.5 µl of HeLa nuclear organic layer (10 µM) (a source of HDAC enzymes) was then added thereto to a final concentration of 100 nM. The enzyme reaction was carried out for 1 hr.

Subsequently, in step 2), 2 µM tricostatin A was added to 50 µl of Flour de Lys™ developer, followed by allowing the mixture to react at room temperature for 15 minutes. The light excited at 355 nm and emitted at 460 nm from the fluorophore was measured with a fluorometric plate reader. The intensity of the fluorescence increases as the enzyme activity is higher. The HDAC inhibitory activity of each of the test compounds was determined and compared with that of the control. And suberoylanilide hydroxamic acid (SAHA) (Biomol) was used at the same level with the test compounds as a comparative control.

The HDAC inhibitory concentrations ($IC_{50}$) of the representative compounds of the above examples are shown in Table 1.

TABLE 1

| Compound | $IC_{50}$ (µM) |
| --- | --- |
| Example 1-1 | 0.006 |
| Example 1-2 | 0.028 |
| Example 1-3 | 0.080 |
| Example 1-4 | 0.014 |
| Example 1-5 | 0.014 |
| Example 1-6 | 0.023 |
| Example 1-7 | 0.010 |
| Example 1-9 | 0.060 |
| Example 1-11 | 0.040 |
| Example 1-12 | 0.007 |
| Example 1-13 | 0.020 |
| Example 1-14 | 0.030 |
| Example 1-15 | 0.040 |
| Example 1-16 | 0.010 |
| Example 1-17 | 0.008 |
| Example 1-18 | 0.021 |
| Example 1-19 | 0.009 |
| Example 1-20 | 0.006 |
| Example 1-21 | 0.021 |
| Example 1-22 | 0.013 |
| SAHA | 0.110 |

As shown in Table 1, each of the inventive naphthalenyloxypropenyl derivatives of formula (1) has a markedly higher inhibitory activity against HDAC than SAHA which is known as a HDAC inhibitor.

Test Example 1-2

Analysis of Inhibitory Activity Against Proliferation of Cancer Cells

Inhibitory activities of naphthalenyloxypropenyl derivatives synthesized in Examples 1-1 to 1-23 against proliferation of cancer cells were examined by SRB (Sulforhodamine B) analysis using cervix adenocarcinoma Hela (Korean Cell Line Bank, KCLB 10002) and colon cancer cells HCT116 (Korean Cell Line Bank, KCLB 10247) as follows:

Cancer cells were inoculated into a 96-well microplate at a concentration of $1 \times 10^3 \sim 3 \times 10^3$ cells/well and incubated under the condition of 37° C., 5% $CO_2$ for 24 hrs. After the incubation was completed, 0.2, 1, 5, 25, or 100 µM of each of the compounds of Examples was added to the plate, and then the reactant was incubated for 48 hrs. After the substrate was stained with SRB, the anti-cancer activity was determined by comparing the amount of protein in the cells treated with compounds of Examples with that of protein in untreated cells.

Specifically, after the incubation was completed, the culture medium was removed from each well, and the cells were washed 3 times with PBS (Phosphate Buffered Saline) (pH 7.4). Then, a solution of 50% trichloroacetic acid (TCA) was added to each well in an amount of 50 µl/well at 4° C. for 1 hr to fix them. Then, the microplate was washed 5 times with distilled water and dried at room temperature.

50 µl of a staining solution prepared by dissolving 0.4% SRB in 1% acetic acid was added to the wells, and the microplate was kept at room temperature for 1 hr. The well plate was then washed 5 times with 1% acetic acid to remove unbound SRB and dried at room temperature.

The stained cells were treated with 15 µl/well of 10 mM Tris-HCl solution (pH 10.5) to elute SRB from the cells, and the absorbance of the cells treated with the compounds of Examples at 540 nm was measured, based on the absorbance of an untreated cell.

The $EC_{50}$ value representing inhibition of the cancer cell growth by the extent of 50% was calculated from the measured absorbance, and the results are shown in Table 2.

When cancer cells were treated with a HDAC inhibitor, histone deacetylation would be inhibited, leading to an increase in the amount of acetyl-histone. In this test, the increased amount of acetyl-histone in the cancer cells was determined by using Western blotting, after the treatment with each of the compounds of Examples.

Hela cells were inoculated into a 6-well microplate at a concentration of $1.5 \times 10^8$ cells/well and incubated overnight under the condition of 37° C., 5% $CO_2$. 10 µM of each compound of Examples, and suberoylanilide hydroxamic acid (SAHA) as a control was added to the plate and the plate was incubated again for 24 hrs under the condition of 37° C., 5% $CO_2$.

The cells cultured in the presence of the test compound were harvested and subjected to fractionation to separate the nuclei from the cells. The cells were allowed to swell in a hypotonic solution, lysed by several rounds of freezing-thawing cycles, and then centrifuged at 1,300 rpm for 5 min to collect the nuclei. The nuclei was lysed in a lysis buffer solution (20 mM HEPES (pH 7.9), 25% glycerol, 420 mM KCl, 1.5 mM $MgCl_2$, 0.2 mM EDTA) to obtain a protein extract.

For Western blotting, the resulting protein organic layer was subjected to SDS-PAGE to separate the proteins by the size and transferred onto the nitrocellulose membrane. The following procedure was carried out by the conventional Western blotting method.

The amount of acetylated histone H4 was measured using anti-acetyl histone H4 antibody (Upstate, USA) and evaluated the HDAC inhibitory activity of the inventive compounds by comparing the degree of increase of acetylated histone H4 relative to the control (SAHA).

The results are shown in Table 2.

TABLE 2

| Compound | Inhibitory conc. against cancer cell growth ($EC_{50}\,\mu M$) HCT116 | Effect on increase of acetyl-Histone H4 compared with SAHA |
|---|---|---|
| Example 1-1 | 0.54 | + |
| Example 1-4 | 0.50 | + |
| Example 1-6 | 0.63 | + |
| Example 1-7 | 0.70 | ND |
| Example 1-12 | 0.60 | + |
| Example 1-13 | 0.80 | ND |
| Example 1-17 | 0.50 | + |
| Example 1-22 | 0.80 | ND |
| Example 1-23 | 0.70 | ND |
| SAHA | 1.60 | + |

ND: not determinded

As shown in Table 2, the inventive naphthalenyloxypropenyl derivatives of formula (1) has a markedly enhanced inhibitory activity against HDAC, which leads to effective suppression of the cancer cell proliferation.

Preparation of Naphthalenyloxypropenyl Derivatives of Formula (2)

Preparation Example 2-1

Methyl 6-hydroxy-hexanoate

ε-Caprolactone (12.50 g, 109.51 mM) was dissolved in methanol (125 ml), and a sulfuric acid solution (1 ml, 0.01 mM) was slowly added thereto. The resulting mixture was stirred at room temperature for 2 days. After the completion of reaction, methanol was removed under reduced pressure, and then ice water was poured into the residue. The resulting mixture was extracted with ethyl ether. The organic layer was separated, washed with an aqueous saturated sodium bicarbonate solution and brine in order and concentrated under reduced pressure. The residue thus obtained was subjected to a silica gel column chromatography (eluent: ethyl acetate/n-hexane=1/2) to obtain 10.18 g of the title compound (yield 64%).

$^1$H-NMR (200 MHz, $CDCl_3$) δ 1.23 (m, 2H, $CH_2$), 1.33~1.42 (m, 4H, $CH_2CH_2$), 1.44~1.74 (t, 4H, $CH_2CH_2$), 3.66 (s, 3H, $OCH_3$).

Preparation Example 2-2

Preparation of methyl 6-oxo-hexanoate (the Compound of Formula X)

Pyridinium chlorochromate (16.27 g, 75.48 mM) was dissolved in dichloromethane (140 ml), and a solution of methyl 6-hydroxy-hexanoate (10.03 g, 68.61 mM) obtained in Preparation Example 2-1 dissolved in dichloromethane (20 ml) was added dropwise thereto over 30 min. The resulting mixture was stirred at 25~30° C. for 2 hrs. After the completion of reaction, the reaction mixture was diluted with ethyl ether, filtered and concentrated under reduced pressure. The residue thus obtained was subjected to a silica gel column chromatography (eluent: ethyl acetate/n-hexane=1/4), to obtain 5.77 g of the title compound (yield 59%).

$^1$H-NMR (200 MHz, $CDCl_3$) δ 1.66 (m, 4H, $CH_2CH_2$), 2.33 (m, 2H, $CH_2$), 2.46 (m, 2H, $CH_2$), 3.66 (s, 3H, $OCH_3$), 9.74 (S, 1H, CH).

Preparation Example 2-3

Preparation of 1-t-butyl-9-methyl-3-hydroxy-2-methylene-dinonanoate (the Compound of Formula XI)

Methyl 6-oxo-hexanoate (20 g, 168.72 mM) obtained in Preparation Example 2-2 was dissolved in a mixture of water and dioxane (1:1) (100 ml), and t-butyl acrylate (60.96 ml, 461.17 mM) was added thereto. To the resulting mixture, a solution of 1,4-diazabicyclo[2.2.2]octane (DABCO) (15.56 g, 138.72 mM) dissolved in a mixture of water and dioxane (1:1) (63 ml) was slowly added. The resulting mixture was stirred at 0~25° C. for 7 days. After the completion of reaction, ice water was poured to the reaction mixture, and the resulting mixture was extracted with ethyl ether. The organic layer was separated, washed with 2N hydrochloric acid, an aqueous saturated sodium bicarbonate solution and brine in order, dried and concentrated under reduced pressure. The residue thus obtained was subjected to a silica gel column chromatography (eluent: ethyl acetate/n-hexane=1/9), to obtain 21.7 g of the title compound (yield 57%).

$^1$H-NMR (200 MHz, $CDCl_3$) δ 1.46 (m, 2H, $CH_2$), 1.47 (S, 9H, $3CH_3$), 1.62 (m, 4H, $CH_2CH_2$), 2.96 (m, 4H, $CH_2CH_2$), 3.64 (s, 3H, $OCH_3$), 5.67 (s, 1H, CH), 6.09 (s, 1H, CH).

Preparation Example 2-4

Preparation of 1-t-butyl-8-methyl-2-bromomethyl-2-dioctenoate (the Compound of Formula XII)

1-t-Butyl-9-methyl-3-hydroxy-2-methylene-dinonanoate (10.40 g, 38.20 mM) obtained in Preparation Example 2-3 was dissolved in ethyl ether (100 ml), and cooled to 0° C. To the resulting mixture, $PBr_3$ (3.93 ml, 42.02 mM) was slowly added and stirred at room temperature for 1 hr. After the completion of reaction, the reaction mixture was cooled to −10° C. by pouring ice water thereto, and extracted with ethyl ether. The organic layer was separated, washed with brine, dried over $MgSO_4$ and filtered. Then, the solvent was removed under reduced pressure, and the residue thus obtained was subjected to a silica gel column chromatography (eluent: ethyl acetate/n-hexane=1/9), to obtain 6.30 g of the title compound (yield 49%).

$^1$H-NMR (200 MHz, $CDCl_3$) δ 1.50 (s, 9H, $CH_3$), 1.65 (m, 4H, $CH_2$), 2.30 (m, 4H, $CH_2$), 3.66 (s, 3H, $OCH_3$), 4.27 (s, 2H, $CH_2$), 6.82 (m, 1H, CH).

Preparation Example 2-5

Preparation of 1-t-butyl-8-methyl-2-(naphthalen-1-yloxymethyl)-2-dioctenoate (the Compound of Formula XIII)

1-t-Butyl-8-methyl-2-bromomethyl-2-dioctenoate (11.2 g 33.41 mM) obtained in Preparation Example 2-4 was dissolved in acetone (50 ml), and potassium carbonate (6.93 g 50.11 mM) and 1-naphthalenol (5.30 g 36.75 mM) were added thereto. The resulting mixture was heated to reflux for 3 hrs. After the completion of reaction, the solvent was removed under reduced pressure at room temperature. The residue thus obtained was subjected to a silica gel column chromatography (eluent: ethyl acetate/n-hexane=1/15) to obtain 11.5 g of the title compound as a white solid (yield 86%).

$^1$H-NMR (200 MHz, $CDCl_3$) δ 1.45 (s, 9H, $CH_3$), 1.65 (m, 4H, $CH_2$), 2.30 (m, 4H, $CH_2$), 3.62 (s, 3H, $OCH_3$), 4.80 (s,

2H, CH$_2$), 6.64 (m, 1H, ArH), 6.98 (m, 1H, CH), 7.40 (m, 4H, ArH), 7.77 (m, 1H, ArH), 8.19 (m, 1H, ArH).

Preparation Example 2-6

Preparation of 8-methyl-2-(naphthalen-1-yloxymethyl)-2-dioctenoate (the Compound of Formula XIV)

1-t-Butyl-8-methyl-2-(naphthalen-1-yloxymethyl)-2-dioctenoate (5.00 g, 12.55 mM) obtained in Preparation Example 2-5 was dissolved in dichloromethane (60 ml), and trifluoroacetic acid (6.77 ml, 87.83 mM) was slowly added thereto at 0° C. The resulting mixture was reacted at room temperature for 7 hrs. After the completion of reaction, the solvent was removed under reduced pressure at room temperature. The residue thus obtained was subjected to a silica gel column chromatography (eluent: ethyl acetate/n-hexane=1/4) to obtain 2.08 g of the title compound (yield 48%).

$^1$H-NMR (200 MHz, CDCl$_3$) δ 1.46 (m, 2H, CH$_2$), 1.59 (m, 2H, CH$_2$), 2.26 (t, 2H, J=7.1 Hz, CH$_2$), 2.43 (q, 2H, J=14.9, 7.5 Hz, CH$_2$), 3.62 (s, 3H, OCH$_3$), 4.94 (s, 2H, CH$_2$), 6.89 (d, 1H, J=7.3 Hz, CH), 7.27~7.47 (m, 5H, ArH), 7.80 (dd, 1H, J=7.3, 1.7 Hz, ArH), 8.20 (t, 1H, J=7.1, 1.7 Hz, ArH).

Further, amine compounds (R$_1$'NH$_2$) used in Example 2-1 to 2-30 may be commercially available or can be easily synthesized using conventional methods.

Particularly, the amine compound such as substituted pyrrolidine or piperidine was synthesized as shown in Reaction Scheme 7 or 8:

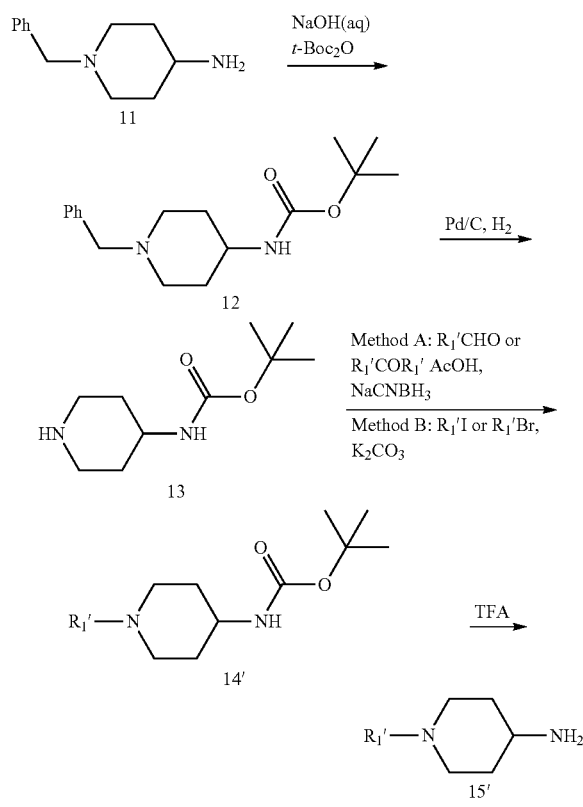

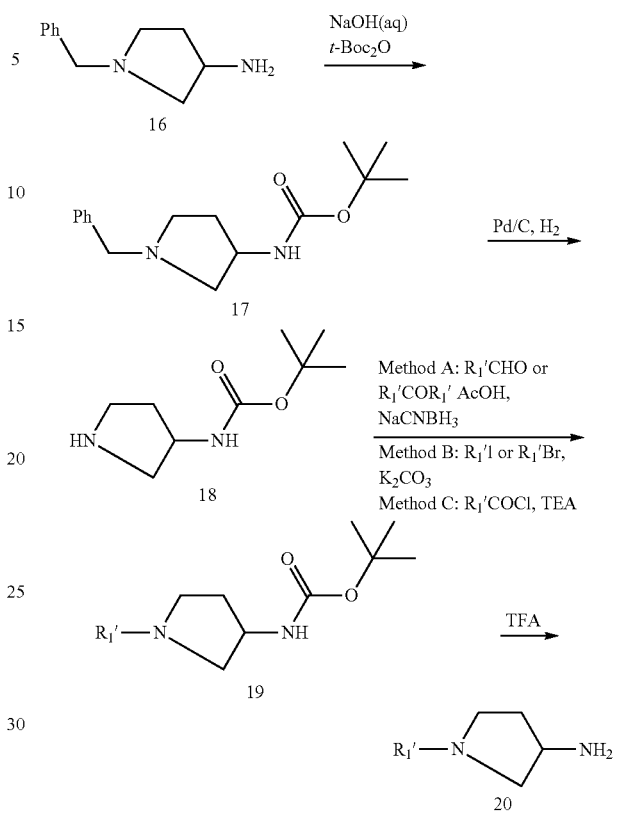

wherein,

R$_1$' is C$_{1-3}$alkyl, C$_{3-8}$cycloalkyl, C$_{3-8}$cycloalkylC$_{1-3}$alkyl, benzyl or C$_{3-8}$cycloalkylcarbonyl.

Preparation Examples of the Above Amine Compounds are Presented as follows.

Preparation Example 2-i

Preparation of t-butyl-1-benzylpiperidin-4-ylcarbamate (the Compound of Formula 12)

1-Benzylpiperidin-4-ylamine (3 g, 15.8 mmol) was dissolved in 1M aqueous sodium hydroxide solution (35.8 ml) and t-butanol (32 ml) in a 250 ml vessel, and t-butyl-dicarbonate ((t-Boc)$_2$O; 3.79 g, 17.38 mmol) was added thereto while stirring. The resulting mixture was reacted at room temperature for 12 hrs. After the completion of reaction, the reaction mixture was extracted with ethyl acetate twice. The organic layer was separated, washed with 0.1N hydrochloric acid solution and brine in order, dried over anhydrous sodium sulfate, filtered and concentrated under reduced pressure. The residue thus obtained was subjected to a silica gel column chromatography to obtain 3.80 g of the title compound as a white solid (yield 82.8%).

$^1$H-NMR (200 MHz, CDCl$_3$) δ 1.38 (s, 9H), 1.86-2.33 (m, 4H), 2.70 (m, 2H), 3.40 (m, 2H), 3.57 (br, 1H), 4.12 (s, 2H), 7.43 (m, 3H), 7.55 (m, 2H).

LC/MS (M$^+$H): 291.

Preparation Example 2-ii

Preparation of t-butyl-piperidin-4-ylcarbamate (the Compound of Formula 13)

t-Butyl-1-benzylpiperidin-4-ylcarbamate (3.80 g, 13.1 mmol) obtained in Preparation Example 2-i was dissolved in methanol (26 ml) in a 100 ml vessel, and a catalytic quantity of 10% active palladium/carbon was added thereto. The resulting mixture was reacted under a hydrogen atmosphere for 12 hrs. After the completion of reaction, the reaction mixture was filtered through a cellite pad to remove the active palladium/carbon and the solvent was removed under reduced pressure. Then, the mixture was subjected to a silica gel column chromatography to obtain 2.64 g of the title compound (yield 99%).

$^1$H-NMR (200 MHz, CD$_3$OD) δ 1.36 (s, 9H), 1.84-2.36 (m, 4H), 2.74 (m, 2H), 3.42 (m, 2H), 3.60 (br, 1H).
LC/MS (M$^+$H): 201.

Preparation Example 2-iii

Preparation of t-butyl-1-R-piperidin-4-ylcarbamate (the Compound of Formula 14')

(2-iii-1) t-Butyl-1-isopropylpiperidin-4-ylcarbamate (14'a)

t-Butyl-piperidin-4-ylcarbamate (3 g, 15 mmol) obtained in Preparation Example 2-ii was dissolved in methanol (30 ml) in a 100 ml vessel, and acetone (7.70 ml, 105 mmol) and acetic acid (0.45 ml, 7.5 mmol) were added thereto while stirring. To the resulting mixture, NaCNBH$_3$ (1.88 mg, 30 mmol) was added dropwise in 4-divided portions and reacted for 18 hrs. After the completion of reaction, ice water was poured to the reaction product while stirring, and the resulting mixture was extracted with ethyl acetate. The organic layer was separated, washed with an aqueous sodium bicarbonate solution and brine in order, dried over anhydrous sodium sulfate, filtered and concentrated under reduced pressure. The residue thus obtained was subjected to a silica gel column chromatography to obtain 2.644 g of the title compound as a white solid (yield 73.3%).

$^1$H-NMR (200 MHz, CDCl$_3$) δ 1.36 (d, J=7.0 Hz, 6H), 1.44 (s, 9H), 2.00 (m, 2H), 2.17 (m, 2H), 2.94 (m, 2H), 3.38 (m, 3H), 3.69 (m, 1H), 4.92 (br, 1H).
LC/MS (M$^+$H): 243.

(2-iii-2) t-Butyl-1-cyclopropylpiperidin-4-ylcarbamate (14'b)

The procedure of Preparation Example (2-iii-1) was repeated except for using bromocyclopropane instead of acetone as the amine substituent to obtain 0.72 g of the title compound as pale yellow oil (yield 60%).

$^1$H-NMR (200 MHz, CDCl$_3$) δ 0.44 (m, 4H), 1.31 (m, 2H), 1.47 (s, 9H), 1.58 (m, 1H), 1.90 (m, 2H), 2.29 (m, 2H), 2.94 (m, 2H), 3.49 (br, 1H), 4.42 (br, 1H).
LC/MS (M$^+$H): 241.

(2-iii-3) t-Butyl-1-cyclopentylpiperidin-4-ylcarbamate (14'c)

The procedure of Preparation Example (2-iii-1) was repeated except for using bromocyclopentane instead of acetone as the amine substituent to obtain 1.16 g of the title compound as pale yellow oil (yield 86%).

$^1$H-NMR (200 MHz, CDCl$_3$) δ 1.45 (s, 9H), 1.50-1.80 (m, 8H), 1.81-2.18 (m, 6H), 2.50 (m, 1H), 2.94 (m, 2H), 3.48 (br, 1H), 4.41 (br, 1H).
LC/MS (M$^+$H): 269.

(2-iii-4) t-Butyl-1-ethylpiperidin-4-ylcarbamate (14'd)

Method B: t-Butyl-piperidin-4-ylcarbamate (1.5 g, 7.49 mmol) obtained in Preparation Example 2-ii was dissolved in N,N'-dimethylformamide (19 ml) in a 25 ml vessel at 0° C., and K$_2$CO$_3$ (2.07 g, 14.98 mmol, 2 eq.) and iodoethane (0.60 ml, 7.49 mmol, 1 eq.) were added thereto while stirring. The resulting mixture was heated from 0° C. to room temperature and reacted for 4 hrs. After the completion of reaction, the solvent was distilled off under reduced pressure and the residue was extracted with ethyl ester. The organic layer was separated, washed with an aqueous saturated sodium bicarbonate solution and brine in order, dried over anhydrous magnesium sulfate, and concentrated under reduced pressure. The residue thus obtained was subjected to a silica gel column chromatography to obtain 1.34 g of the title compound as pale yellow oil (yield 78%).

$^1$H-NMR (200 MHz, CDCl$_3$) δ 1.10 (t, J=7.4 Hz, 3H), 1.43 (m, 2H), 1.47 (s, 9H), 1.99 (m, 4H), 2.40 (q, J=7.2 Hz, 2H), 2.85 (m, 2H), 3.47 (br, 1H), 4.43 (br, 1H).
LC/MS (M$^+$H): 229.

Preparation Example 2-iv

Preparation of 1-R-piperidin-4-ylamine (the Compound of Formula 15)

(2-iv-1) 1-Isopropylpiperidin-4-ylamine (15'a)

t-Butyl-1-isopropylpiperidin-4-ylcarbamate (2.64 g, 10.9 mmol) obtained in Preparation Example (2-iii-1) was dissolved in methanol (20 ml) in a 250 ml vessel at 0° C., and trifluoroacetic acid (TFA; 4.06 ml, 54.5 mmol, 5 eq.) was slowly added thereto while stirring. The resulting mixture was reacted for 18 hrs. After the completion of reaction, the reaction product was concentrated under reduced pressure, subjected to azeotropic distillation with CHCl$_3$ 3 times, basified with 2N aqueous KOH solution (20 ml) and extracted with CHCl$_3$ 3 times. The organic layer was separated, washed with brine, dried, filtered and distilled under reduced pressure to obtain 1.23 g of the title compound as yellow oil (yield 79.3%).

$^1$H-NMR (200 MHz, CDCl$_3$) δ 1.02 (d, J=6.6 Hz, 6H), 1.38 (m, 2H), 1.56 (br, 2H), 1.80 (d, J=11.8 Hz, 2H), 2.17 (m, 2H), 2.71 (m, 2H), 2.80 (m, 2H).
LC/MS (M$^+$H): 143.

(2-iv-2) 1-Cyclopropylpiperidin-4-ylamine (15'b)

The procedure of Preparation Example (2-iv-1) was repeated except for using the compound obtained in Preparation Example (2-iii-2) as the starting material, to obtain 286 mg of the title compound as yellow oil (yield 75%).

$^1$H-NMR (200 MHz, CDCl$_3$) δ 0.44 (m, 4H), 1.33 (m, 2H), 1.52 (m, 1H), 1.76 (m, 2H), 2.20 (m, 2H), 2.66 (m, 1H), 3.00 (m, 2H).
LC/MS (M$^+$H): 141.

(2-iv-3) 1-Cyclopentylpiperidin-4-ylamine (15'c)

The procedure of Preparation Example (2-iv-1) was repeated except for using the compound obtained in Preparation Example (2-iii-3) as the starting material, to obtain 689 mg of the title compound as pale yellow oil (yield 95%).

$^1$H-NMR (200 MHz, CDCl$_3$) δ 1.50-1.80 (m, 8H), 1.81-2.18 (m, 6H), 2.50 (m, 2H), 2.74 (m, 2H).

LC/MS (M$^+$H): 169.

(2-iv-4) 1-Ethylpiperidin-4-ylamine (15'd)

The procedure of Preparation Example (2-iv-1) was repeated except for using the compound obtained in Preparation Example (2-iii-4) as the starting material, to obtain 672 mg of the title compound as pale yellow oil (yield 89%).

$^1$H-NMR (200 MHz, CDCl$_3$) δ 1.08 (t, J=7.2 Hz, 3H), 1.37 (m, 2H), 1.81-2.08 (m, 4H), 2.37 (q, J=7.2 Hz, 2H), 2.65 (m, 1H), 2.87 (m, 2H).

LC/MS (M$^+$H): 129.

Preparation Example 2-v

Preparation of t-butyl-1-benzylpyrrolidin-3-ylcarbamate (the Compound of Formula 17)

1-benzylpyrrolidin-3-ylamine (10 g, 57 mmol) was dissolved in 3M aqueous sodium hydroxide solution (21 ml) and t-butanol (114 ml) in a 500 ml vessel, and t-butyl-dicarbonate ((t-Boc)$_2$O; 13.07 g, 59.9 mmol) was added thereto while stirring. The resulting mixture was reacted for 12 hrs. After the completion of the reaction, the reaction product was extracted with ethyl acetate twice. The organic layer was separated, washed with 0.1N hydrochloric acid solution and brine in order, dried over anhydrous sodium sulfate, filtered and concentrated under reduced pressure. The residue thus obtained was subjected to a silica gel column chromatography to obtain 15.25 g of the title compound as a white solid (yield 97%).

$^1$H-NMR (200 MHz, CDCl$_3$) δ 1.43 (s, 9H), 2.27 (m, 2H), 2.57 (m, 3H), 2.75 (m, 1H), 3.59 (s, 2H), 4.16 (br, 1H), 4.85 (br, 1H), 7.30 (m, 5H).

LC/MS (M$^+$H): 277.

Preparation Example 2-vi

Preparation of t-butylpyrrolidin-3-ylcarbamate (the Compound of Formula 18)

t-Butyl-1-benzylpyrrolidin-3-ylcarbamate (15.75 g, 57.0 mmol) obtained in Preparation Example 2-11 was dissolved in methanol and tetrabutylfuran (4:1) (114 ml) in a 500 ml vessel, and a catalytic quantity of 10% active palladium/carbon was added thereto. The resulting mixture was reacted under a hydrogen atmosphere for 12 hrs. After the completion of reaction, the reaction mixture was filtered through a cellite pad to remove the active palladium/carbon and the solvent was removed under reduced pressure therefrom. Then, the residue thus obtained was subjected to a silica gel column chromatography to obtain 9.51 g of the title compound (yield 99%).

$^1$H-NMR (200 MHz, CDCl$_3$) δ 1.41 (s, 9H), 2.26 (m, 2H), 2.55 (m, 3H), 2.74 (m, 1H), 4.84 (br, 1H).

LC/MS (M$^+$H): 187.

Preparation Example 2-vii

Preparation of t-butyl-1-R-pyrrolidin-3-ylcarbamate (the Compound of Formula 19)

(2-vii-1) t-Butyl-1-isopropylpyrrolidin-3-ylcarbamate (19a)

Method A: t-Butylpyrrolidin-3-ylcarbamate (1.24 g, 6.7 mmol) obtained in Preparation Example 2-vi was dissolved in methanol (14 ml) in a 250 ml vessel, and acetone (3.44 ml, 46.9 mmol) and acetic acid (0.19 ml, 3.35 mmol) were added thereto while stirring. To the resulting mixture, NaCNBH$_3$ (842 mg, 13.4 mmol) was added in 4-divided portions and reacted for 18 hrs. After the completion of reaction, ice water was poured to the reaction product. Then the resulting mixture was stirred and extracted with ethyl acetate. The organic layer was separated, washed with an aqueous sodium bicarbonate solution and brine in order, dried over anhydrous magnesium sulfate, and concentrated under reduced pressure. The residue thus obtained was subjected to a silica gel column chromatography to obtain 897 mg of the title compound as a white solid (yield 58%).

$^1$H-NMR (200 MHz, CDCl$_3$) δ 1.40 (d, J=6.6 Hz, 6 Hz), 1.44 (s, 9H), 2.12 (m, 1H), 2.48 (m, 1H), 3.27 (m, 1H), 3.39 (m, 3H), 3.57 (m, 1H), 4.38 (m, 1H), 5.41 (m, 1H).

LC/MS (M$^+$H): 229.

(2-vii-2) t-Butyl-1-cyclopropylpyrrolidin-3-ylcarbamate (19b)

The procedure of Preparation Example (2-vii-1) was repeated except for using bromocyclopropane instead of acetone as the amine substituent to obtain 7.17 g of the title compound as pale yellow oil (yield 59%).

$^1$H-NMR (200 MHz, CDCl$_3$) δ 0.40 (m, 4H), 1.44 (s, 9H), 1.60 (m, 2H), 2.19 (m, 1H), 2.57 (m, 2H), 2.81 (m, 2H), 4.14 (br, 1H), 4.80 (br, 1H).

LC/MS (M$^+$H): 227.

(2-vii-3) t-Butyl-1-cyclohexylpyrrolidin-3-ylcarbamate (19c)

The procedure of Preparation Example (2-vii-1) was repeated except for using cyclohexanone instead of acetone as the amine substituent to obtain 1.10 g of the title compound as pale yellow oil (yield 77%).

$^1$H-NMR (200 MHz, CDCl$_3$) δ 1.23 (m, 2H), 1.41 (m, 2H), 1.46 (s, 9H), 1.78 (m, 2H), 1.89 (m, 2H), 2.06 (m, 3H), 2.44 (m, 1H), 2.76 (m, 1H), 3.04 (m, 1H), 3.24 (m, 2H), 3.49 (m, 1H), 4.34 (m, 1H), 5.33 (m, 1H).

LC/MS (M$^+$H): 269.

(2-vii-4) t-Butyl-1-ethylpyrrolidin-3-ylcarbamate (19d)

Method B: t-Butylpyrrolidin-3-ylcarbamate (1.5 g, 8.05 mmol) obtained in Preparation Example 2-vi was dissolved in N,N'-dimethylformamide (20 ml) at 0° C. in a 100 ml vessel, and K$_2$CO$_3$ (2.23 g, 16.1 mmol, 2 eq.) and iodoethane (0.64 ml, 8.05 mmol, 1 eq.) were added thereto while stirring. The resulting mixture was heated from 0° C. to room temperature, and reacted for 12 hrs. After the completion of reaction, the solvent was distilled off under reduced pressure and the residue was extracted with ethyl ester. The organic layer was separated, washed with an aqueous saturated sodium bicarbonate and brine in order, dried over anhydrous magnesium sulfate, and concentrated under reduced pressure. The residue thus obtained was subjected to a silica gel column chromatography to obtain 1.13 g of the title compound as pale yellow oil (yield 66%).

$^1$H-NMR (200 MHz, CDCl$_3$) δ 1.10 (t, J=7.4 Hz, 3H), 1.44 (s, 9H), 1.69 (m, 1H), 2.27 (m, 2H), 2.48 (q, J=7.0 Hz, 2H), 2.57 (m, 1H), 2.81 (m, 1H), 4.16 (br, 1H), 4.86 (br, 1H).

LC/MS (M$^+$H): 215.

(2-vii-5) t-Butyl-1-(cyclohexanecarbonyl)pyrrolidin-3-ylcarbamate (19e)

Method C: t-Butylpyrrolidin-3-ylcarbamate (1 g, 5.4 mmol) obtained in Preparation Example 2-vi was dissolved in dichloromethane (14 ml) at 0° C. in a 50 ml vessel, and triethylamine (0.83 ml, 5.94 mmol, 1.1 eq.) and cyclohexylcarbonyl chloride (0.79 ml, 5.94 mmol, 1.1 were added thereto while stirring. The resulting mixture was heated from 0° C. to room temperature, and reacted for 4 hrs. After the completion of reaction, the solvent was distilled off under reduced pressure and the residue was extracted with dichloromethane. The organic layer was separated, washed with an aqueous saturated sodium bicarbonate solution and brine in order, dried over anhydrous magnesium sulfate and concentrated under reduced pressure. The residue thus obtained was subjected to a silica gel column chromatography to obtain 1.57 g of the title compound as pale yellow oil (yield 98%).

$^1$H-NMR (200 MHz, CDCl$_3$) δ 1.26 (m, 4H), 1.46 (s, 9H), 1.79 (m, 6H), 1.98 (m, 1H), 2.08-2.49 (m, 2H), 3.39 (m, 1H), 3.59 (m, 2H), 3.73 (m, 1H), 4.22 (m, 1H), 4.63 (m, 1H).

LC/MS (M$^+$H): 297.

Preparation Example 2-viii

Preparation of 1-R-pyrrolidin-3-ylamine (the Compound of Formula 20)

(2-viii-1) 1-Isopropylpyrrolidin-3-ylamine (20a)

t-Butyl-1-isopropylpyrrolidin-3-ylcarbamate (0.90 g, 3.9 mmol) obtained in Preparation Example (2-vii-1) was dissolved in dichloromethane (10 ml) in a 50 ml vessel, and trifluoroacetic acid (1.45 ml, 1.95 mmol, 5 eq.) was slowly added dropwise thereto while stirring. The resulting mixture was reacted for 18 hrs. After the completion of reaction, the reaction mixture was distilled and concentrated under reduced pressure, and then subjected to azeotropic distillation with CHCl$_3$ 3 times. The resultant was basified with aqueous 2N potassium hydroxide solution (20 ml) and extracted with CHCl$_3$ 3 times. The organic layer was separated, washed with brine, dried over anhydrous magnesium sulfate, filtered and distilled under reduced pressure to obtain 433 mg of the title compound as yellow oil (yield 86%).

$^1$H-NMR (200 MHz, CDCl$_3$) δ 1.38 (d, J=6.6 Hz, 6 Hz), 2.11 (m, 1H), 2.47 (m, 1H), 3.15 (m, 1H), 3.29 (m, 4H), 3.57 (m, 1H).

LC/MS (M$^+$H): 129.

(2-viii-2) 1-Cyclopropylpyrrolidin-3-ylamine (20b)

The procedure of Preparation Example (2-viii-1) was repeated except for using the compound obtained in Preparation Example (2-vii-2) as the starting material, to obtain 477 mg of the title compound as pale yellow oil (yield 79%).

$^1$H-NMR (200 MHz, CDCl$_3$) δ 0.41 (m, 4H), 1.55 (m, 2H), 2.16 (m, 1H), 2.40 (m, 1H), 2.68 (m, 1H), 2.80 (m, 1H), 2.93 (m, 1H), 3.47 (m, 1H).

LC/MS (M$^+$H): 127.

(2-viii-3) 1-Cyclohexylpyrrolidin-3-ylamine (20c)

The procedure of Preparation Example (2-viii-1) was repeated except for using the compound obtained in Preparation Example (2-vii-3) as the starting material, to obtain 513 mg of the title compound as pale yellow oil (yield 74%).

$^1$H-NMR (200 MHz, CDCl$_3$) δ 1.19 (m, 4H), 1.39-1.62 (m, 4H), 1.72 (m, 1H), 1.93 (m, 3H), 2.14 (m, 1H), 2.31 (m, 1H), 2.58-2.78 (m, 2H), 2.85 (m, 1H), 3.47 (m, 1H).

LC/MS (M$^+$H): 169.

(2-viii-4) 1-Ethylpyrrolidin-3-ylamine (20d)

The procedure of Preparation Example (2-viii-1) was repeated except for using the compound obtained in Preparation Example (2-vii-4) as the starting material, to obtain 477 mg of the title compound as pale yellow oil (yield 79%).

$^1$H-NMR (200 MHz, CDCl$_3$) δ 1.13 (t, J=7.2 Hz, 3H), 1.51 (m, 2H), 2.31 (m, 2H), 2.47 (m, 3H), 2.73 (m, 1H), 3.54 (m, 1H).

LC/MS (M$^+$H): 115.

(2-viii-5) (3-Aminopyrrolidin-1-yl)(cyclohexyl)methanone (20e)

The procedure of Preparation Example (2-viii-1) was repeated except for using the compound obtained in Preparation Example (2-vii-5) as the starting material, to obtain 1.51 g of the title compound as pale yellow oil (yield 99%).

$^1$H-NMR (200 MHz, CDCl$_3$) δ 1.26 (m, 4H), 1.79 (m, 6H), 1.98 (m, 1H), 2.08-2.49 (m, 2H), 3.39 (m, 1H), 3.59 (m, 2H), 3.73 (m, 1H).

LC/MS (M$^+$H): 197.

Example 2-1

Preparation of (E)-N1-(3-(1H-imidazol-1-yl)propyl)-N8-hydroxy-2-((naphthalen-1-yloxy)methyl)octenediamide (the Compound of Formula (2))

(2-1-1): Preparation of methyl (E)-8-(3-(1H-imidazol-1-yl)propylamino)-7-((naphthalen-1-yloxy)methyl)-8-oxo-6-octenoate (the Compound of Formula XV)

8-Methyl-2-(naphthalen-1-yloxymethyl)-2-dioctenoate (343 mg, 1.00 mM) obtained in Preparation Example 2-6 was dissolved in dichloromethane (3 ml) in a 50 ml vessel, and the resulting solution was cooled to 0° C. Then, triethylamine (209 μl, 1.50 mM) and N-methanesulfonyloxy-6-trifluorobenzotriazole (420 mg, 1.50 mM) were added to the solution, and the resulting mixture was reacted at 0° C. for 30 mins. To the resultant, 3-(1H-imidazol-1-yl)propan-1-ylamine (155 μl, 1.30 mM) was slowly added and the resulting mixture was stirred at room temperature for 1 hr. After the completion of reaction, the reaction mixture was cooled to room temperature and ice water was poured thereto. The resulting mixture was extracted with ethyl acetate. The organic layer was separated, washed with 1N hydrochloric acid, an aqueous sodium bicarbonate solution and brine in order, filtered and dried over anhydrous magnesium sulfate. The solvent was removed under reduced pressure, and the residue thus obtained subjected to a silica gel column chromatography (eluent: dichloromethane/methanol=12/1) to obtain 449 mg of the title compound as a yellow solid (yield 77%).

$^1$H-NMR (300 MHz, CDCl$_3$) δ 1.53-1.84 (m, 4H), 2.05 (m, 2H), 2.39 (m, 4H), 3.42 (q, J=6.3 Hz, 2H), 3.72 (s, 3H), 3.98 (t, J=7.0 Hz, 2H), 5.02 (s, 2H), 6.72 (t, J=6.0 Hz, 1H), 6.88-7.07 (m, 4H), 7.36-7.65 (m, 4H), 7.90 (d, J=6.7 Hz, 1H), 8.22 (d, J=7.3 Hz, 1H).

LC/MS (M$^+$H): 450.23.

(2-1-2): Preparation of (E)-8-(3-(1H-imidazol-1-yl) propylamino)-7-((naphthalen-1-yloxy)methyl)-8-oxo-6-octenoic acid (the Compound of Formula XVI)

Methyl (E)-8-(3-(1H-imidazol-1-yl)propylamino)-7-((naphthalen-1-yloxy)-methyl)-8-oxo-6-octenoate (350 mg, 0.77 mM) obtained in Example (2-1-1) was dissolved in water (1 ml), and lithium hydroxide monohydrate (LiOH.H$_2$O) (96 mg, 2.31 mM) and tetrahydrofuran (4 ml) were added thereto. The resulting mixture was stirred at room temperature for 10 mins, followed by stirring at 50° C. for 3 hrs. After the completion of reaction, the reaction mixture was cooled to room temperature, followed by adding ice water thereto. Then, the solvent was removed under reduced pressure, and the residue was cooled to 5° C. again and acidified (pH 4) with 2N hydrochloric acid. The resultant was filtered and dried over anhydrous magnesium sulfate to obtain the 350 mg of the title compound as a white solid (yield 85%).

(2-1-3): Preparation of (E)-N1-(3-(1H-imidazol-1-yl) propyl)-2-((naphthalen-1-yloxy)methyl)-N8-(tetra hydro-2H-pyran-2-yloxy)-2-octenediamide (the Compound of Formula XVII)

(E)-8-(3-(1H-imidazol-1-yl)propylamino)-7-((naphthalen-1-yloxy)-methyl)-8-oxo-6-octenoic acid (286 mg, 0.65 mM) obtained in Example (2-1-2) was dissolved in dimethylformamide (3 ml), and triethylamine (136 μl, 0.98 mM) was added thereto. Then, the resulting mixture was cooled to 0° C., and to the mixture, N-hydroxy-6-trifluorobenzotriazole (144 mg, 0.72 mM), 1-(3-diethylaminopropyl)-3-ethylcarbodiimide hydrochloride (EDC.HCl) (162 mg, 0.85 mM) and tetrahydropyranyloxyamine (114 mg, 0.98 mM) were added and stirred at room temperature for 18 hrs. After the completion of reaction, ice water was added to the reaction mixture. The resulting mixture was extracted with ethyl acetate. The organic layer was separated, washed with an aqueous saturated sodium bicarbonate solution and brine in order, dried over anhydrous magnesium sulfate, and concentrated under reduced pressure. The residue thus obtained was subjected to a silica gel column chromatography to obtain 220 mg of the title compound (yield 63%).

$^1$H-NMR (200 MHz, CDCl$_3$) δ 1.40-1.75 (m, 11H), 1.81 (t, J=6.4 Hz, 2H), 1.96 (m, 2H), 2.15 (m, 2H), 3.19 (q, J=6.1 Hz, 2H), 3.38 (d, J=11.8 Hz, 1H), 3.76 (t, J=6.9 Hz, 3H), 4.74 (s, 2H), 6.46 (m, 1H), 6.67 (m, 2H), 6.83 (m, 2H) 7.32 (m, 5H), 7.65 (d, J=6.5 Hz, 1H), 7.96 (d, J=7.7 Hz, 1H), 9.33 (br, 1H).

LC/MS (M$^+$H): 535.28.

(2-1-4): Preparation of (E)-N1-(3-(1H-imidazol-1-yl) propyl)-N8-hydroxy-2-((naphthalen-1-yloxy)methyl) octenediamide (the Compound of Formula (2))

(E)-N1-(3-(1H-imidazol-1-yl)propyl)-2-((naphthalen-1-yloxy)-methyl)-N8-(tetrahydro-2H-pyran-2-yloxy)-2-octenediamide (203 mg, 0.38 mM) obtained in Example (2-1-3) was dissolved in methanol (2 ml), and trifluoroacetic acid (146 μl, 1.90 mM) was slowly added thereto at 0° C. Then, the resulting mixture was heated to room temperature and reacted for 18 hrs. After the completion of reaction, the solvent was removed under reduced pressure. The residue thus obtained was subjected to a silica gel column chromatography (eluent: methanol/dichloromethane=1/9) to obtain 63 mg of the title compound (yield 37%).

HPLC purification: 46 mg (Purity: 97%)

$^1$H-NMR (300 MHz, MeOH-d$_4$) δ 1.52 (m, 2H), 1.68 (m, 2H), 2.03 (t, J=6.6 Hz, 2H), 2.11 (t, J=6.6 Hz, 2H), 2.35 (q, J=7.2 Hz, 2H), 5.04 (s, 2H), 6.57 (t, J=6.3 Hz, 2H), 7.01 (d, J=7.2 Hz, 1H), 7.18 (s, 1H), 7.26 (s, 1H), 7.43 (m, 4H), 7.78 (d, J=7.8 Hz, 1H), 8.09 (s, 1H), 8.13 (d, J=5.1 Hz, 1H).

LC/MS (M$^+$H): 451.23.

Example 2-2

(E)-N8-Hydroxy-N1-(4-hydroxyphenethyl)-2-((naphthalen-1-yloxy)methyl)-2-octenediamide (2-2-1): Methyl (E)-8-(4-hydroxyphenethylamino)-7-((naphthalen-1-yloxy)methyl)-8-oxo-6-octenoate The procedure of Example (2-1-1) was repeated except for using 4-hydroxyphenethylamine as the amine compound, to obtain 461 mg of the title compound (yield 95%).

$^1$H-NMR (300 MHz, CDCl$_3$) δ 1.50-1.80 (m, 4H), 2.38 (m, 4H), 2.82 (t, J=6.9 Hz, 2H), 3.63 (m, 2H), 3.72 (s, 3H), 4.92 (s, 2H), 6.44 (br, 1H), 6.53-6.59 (t, J=5.4 Hz, 1H), 6.66 (d, J=8.4 Hz, 2H), 6.95 (m, 4H), 7.37 (m, 4H), 7.90 (d, J=9.1 Hz, 1H), 8.12 (d, J=9.7 Hz, 1H).

LC/MS (M$^+$H): 412.20.

(2-2-2): (E)-8-(4-Hydroxyphenethylamino)-7-((naphthalen-1-yloxy)methyl)-8-oxo-6-octenoic acid The procedure of Example (2-1-2) was repeated except for using the compound obtained in Example (2-2-1) as the starting material, to obtain 439 mg of the title compound (yield 92%).

$^1$H-NMR (300 MHz, MeOH-d$_4$) δ 1.52 (m, 2H, CH$_2$), 1.64 (m, 2H, CH$_2$), 2.20 (m, 2H, CH$_2$), 2.27 (s, 6H, N(CH$_3$)$_2$), 2.38 (m, 2H, CH$_2$), 2.55 (m, 2H, CH$_2$), 3.42 (m, 2H, CH$_2$), 4.97 (s, 2H, CH$_2$), 6.67 (s, 1H, CH), 6.99 (t, 1H, J=7.0, 1.8 Hz, ArH), 7.41 (m, 4H, ArH), 7.77 (d, 1H, J=7.0, 1.8 Hz, ArH), 8.14 (d, 1H, J=7.2 Hz, ArH).

(2-2-3): (E)-N1-(4-Hydroxyphenethyl)-2-((naphthalen-1-yloxy)methyl)-N8-(tetrahydro-2H-pyran-2-yloxy)-2-octenediamide The procedure of Example (2-1-3) was repeated except for using the compound obtained in Example (2-2-2) as the starting material, to obtain 394 mg of the title compound (yield 75%).

$^1$H-NMR (200 MHz, CDCl$_3$) δ 1.42-1.85 (m, 12H), 2.04 (m, 2H), 2.22 (m, 2H), 2.71 (t, J=6.4 Hz, 2H), 3.50 (m, 3H), 3.92 (m, 1H), 4.79 (s, 2H), 4.92 (m, 1H), 6.38 (t, J=5.4 Hz, 1H), 6.67 (m, 3H), 6.86 (m, 3H) 7.18 (br, 1H), 7.44 (m, 4H), 7.77 (m, 1H), 8.00 (m, 1H), 8.93 (br, 1H).

LC/MS (M$^+$H): 497.26.

(2-2-4): (E)-N8-Hydroxy-N1-(4-hydroxyphenethyl)-2-((naphthalen-1-yloxy)methyl)-2-octenediamide The procedure of Example (2-1-4) was repeated except for using the compound obtained in Example (2-2-3) as the starting material, to obtain 121 mg of the title compound (yield 78%).

HPLC purification: 61 mg (Purity: 95%)

$^1$H-NMR (200 MHz, MeOH-d$_4$) δ 1.48-1.72 (m, 4H), 2.08 (t, J=7.2 Hz, 2H), 2.34 (q, J=6.8 Hz, 2H), 2.73 (t, J=7.2 Hz, 2H), 3.45 (t, 7.0 Hz, 2H), 4.98 (s, 2H), 6.53 (t, J=7.4 Hz, 1H), 6.63 (d, J=7.8 Hz, 2H), 6.97 (d, J=8.2 Hz, 3H), 7.43 (m, 4H), 7.78 (d, J=7.0 Hz, 1H), 8.10 (d, J=9.2 Hz, 1H).

LC/MS (M$^+$H): 413.20.

Example 2-3

(E)-N1-(3-(Dimethylamino)-2,2-dimethylpropyl)-N8-hydroxy-2-((naphthalen-1-yloxy)methyl)octene-diamide (2-3-1): Methyl (E)-8-(3-(dimethylamino)-2,2-dimethylpropylamino)-7-((naphthalen-1-yloxy)methyl)-8-oxo-6-octenoate The procedure of Example (2-1-1) was repeated except for using 3-dimethylamino-2,2-dimethylpropylamine as the amine compound, to obtain 454 mg of the title compound (yield 75%).

$^1$H-NMR (200 MHz, CDCl$_3$) δ 0.87 (s, 6H), 1.45-1.73 (m, 4H), 1.85 (s, 6H), 2.11 (s, 2H), 2.27 (m, 2H), 3.25 (d, J=4.4 Hz, 2H), 3.60 (s, 3H), 4.87 (s, 2H), 6.92 (m, 2H), 7.42 (m, 4H), 7.72 (d, J=7.4 Hz, 1H), 8.19 (d, J=9.0 Hz, 1H).

LC/MS (M$^+$H): 405.27.

(2-3-2): (E)-8-(3-(Dimethylamino)-2,2-dimethylpropylamino)-7-((naphthalen-1-yloxy)methyl)-8-oxo-6-octenoic acid The procedure of Example (2-1-2) was repeated except for using the compound obtained in Example (2-3-1) as the starting material, to obtain 339 mg of the title compound (yield 93%).

$^1$H-NMR (200 MHz, MeOH-d$_4$) δ 1.6 (m, 4H, CH$_2$CH$_2$), 2.4 (m, 6H, CH$_2$CH$_2$CH$_2$), 2.50 (m, 4H, CH$_2$CH$_2$), 2.80 (m, 2H, CH$_2$), 3.01 (s, 3H, NCH$_3$), 3.29 (m, 1H, CH), 3.65 (m, 1H, CH), 4.95 (s, 2H, PhCH$_2$), 6.00 (m, 1H, CH), 7.00 (t, 1H, J=16.6, 9.4 Hz, ArH), 7.46 (m, 4H, ArH), 7.82 (m, 1H, ArH), 8.18 (m, 1H, ArH).

(2-3-3): (E)-N1-(3-(Dimethylamino)-2,2-dimethylpropyl)-2-((naphthalen-1-yloxy)methyl)-N8-(tetrahydro-2H-pyran-2-yloxy)-2-octenediamide The procedure of Example (2-1-3) was repeated except for using the compound obtained in Example (2-3-2) as the starting material, to obtain 304 mg of the title compound (yield 52%).

$^1$H-NMR (200 MHz, CDCl$_3$) δ 0.88 (s, 6H), 1.49-1.82 (m, 10H), 1.86 (s, 6H), 2.02 (m, 2H), 2.13 (s, 2H), 2.31 (q, J=7.4 Hz, 2H), 3.27 (d, J=4.6 Hz, 2H), 3.58 (m, 1H), 3.93 (m, 1H), 4.88 (s, 2H), 4.90 (m, 1H), 6.95 (t, J=7.4 Hz, 2H), 7.45 (m, 4H), 7.78 (d, J=6.0 Hz, 1H), 8.21 (d, J=7.0 Hz, 1H), 8.48 (br, 1H), 8.62 (br, 1H).

LC/MS (M$^+$H): 490.32.

(2-3-4): (E)-N1-(3-(Dimethylamino)-2,2-dimethylpropyl)-N8-hydroxy-2-((naphthalen-1-yloxy)methyl)octenediamide The procedure of Example (2-1-4) was repeated except for using the compound obtained in Example (2-3-3) as the starting material, to obtain 144 mg of the title compound (yield 74%).

HPLC purification: 101 mg (Purity: 92%)

$^1$H-NMR (200 MHz, MeOH-d$_4$) δ 0.98 (s, 6H), 1.54 (m, 2H), 1.66 (m, 2H), 2.12 (t, J=7.4 Hz, 2H), 2.40 (s, 6H), 2.46 (m, 4H), 3.26 (s, 2H), 5.04 (s, 2H), 6.71 (t, J=8.2 Hz, 1H), 7.04 (m, 1H), 7.45 (m, 4H), 7.80 (d, J=7.8 Hz, 1H), 8.13 (d, J=8.6 Hz, 1H).

LC/MS (M$^+$H): 406.26.

Example 2-4

(E)-N1-(2-(Diisopropylamino)ethyl)-N8-hydroxy-2-((naphthalen-1-yloxy)methyl)octenediamide (2-4-1): Methyl (E)-8-(2-(diisopropylamino)ethylamino)-8-oxo-7-((naphthalen-1-yloxy)methyl)-6-octenoate The procedure of Example (2-1-1) was repeated except for using 2-(diisopropylamino)ethylamine as the amine compound, to obtain 420 mg of the title compound (yield 89%).

$^1$H-NMR (200 MHz, CDCl$_3$) δ 0.87 (d, J=7.0 Hz, 12H), 1.51 (m, 2H), 1.64 (m, 2H), 2.26 (m, 4H), 2.57 (t, J=6.0 Hz, 2H), 2.86 (m, 2H), 3.31 (q, J=5.6 Hz, 2H), 3.61 (s, 3H), 4.90 (s, 1H), 6.90 (m, 3H), 7.44 (m, 4H), 7.77 (d, J=7.2 Hz, 1H), 8.17 (d, J=7.0 Hz, 1H).

LC/MS (M$^+$H): 419.28.

(2-4-2): (E)-8-(2-(Diisopropylamino)ethylamino)-8-oxo-7-((naphthalen-1-yloxy)methyl)-6-octenoic acid The procedure of Example (2-1-2) was repeated except for using the compound obtained in Example (2-4-1) as the starting material, to obtain 420 mg of the title compound (yield 78%).

(2-4-3): (E)-N1-(2-(Diisopropylamino)ethyl)-2-((naphthalen-1-yloxy)methyl)-N8-(tetrahydro-2H-pyran-2-yloxy)-2-octenediamide The procedure of Example (2-1-3) was repeated except for using the compound obtained in Example (2-4-2) as the starting material, to obtain 319 mg of the title compound (yield 50%).

$^1$H-NMR (200 MHz, CDCl$_3$) δ 0.95 (br, 9H), 1.50-1.95 (m, 10H), 2.10 (m, 2H), 2.31 (q, J=6.8 Hz, 2H), 2.67 (m, 2H), 2.96 (s, 2H), 3.46 (m, 2H), 3.57 (m, 2H), 3.97 (m, 1H), 4.93 (s, 2H), 4.94 (m, 1H), 6.87 (m, 3H), 7.49 (m, 4H), 7.78 (d, J=6.8 Hz, 1H), 8.15 (d, J=8.6 Hz, 1H).

LC/MS (M$^+$H): 504.34.

(2-4-4): (E)-N1-(2-(Diisopropylamino)ethyl)-N8-hydroxy-2-((naphthalen-1-yloxy)methyl)octenediamide The procedure of Example (2-1-4) was repeated except for using the compound obtained in Example (2-4-3) as the starting material, to obtain 145 mg of the title compound (yield 85%).

HPLC purification: 59 mg (Purity: 92%)

$^1$H-NMR (200 MHz, MeOH-d$_4$) δ 1.32 (t, J=6.2 Hz, 9H), 1.46-1.78 (m, 4H), 2.10 (t, J=7.0 Hz, 2H), 2.41 (q, J=6.8 Hz, 2H), 3.23 (t, J=6.2 Hz, 2H), 3.63 (t, J=7.0 Hz, 1H), 3.74 (m, 2H), 5.05 (s, 2H), 6.76 (t, J=6.6 Hz, 1H), 7.02 (d, J=7.0 Hz, 1H), 7.45 (m, 4H), 7.80 (d, J=7.6 Hz, 1H), 8.12 (d, J=7.8 Hz, 1H).

LC/MS (M$^+$H): 420.28.

Example 2-5

(E)-N8-Hydroxy-N1-(1-methoxypropan-2-yl)-2-((naphthalen-1-yloxy)methyl)-2-octenediamide (2-5-1): Methyl (E)-8-(1-methoxypropan-2-ylamino)-7-((naphthalen-1-yloxy)methyl)-8-oxo-6-octenoate The procedure of Example (2-1-1) was repeated except for using 1-methoxypropan-2-ylamine as the amine compound, to obtain 413 mg of the title compound (yield 83%).
$^1$H-NMR (200 MHz, CDCl$_3$) δ 1.15 (d, J=6.8 Hz, 3H), 1.50 (m, 2H), 1.63 (m, 2H), 2.29 (m, 4H), 3.15 (s, 3H), 3.31 (d, J=4.0 Hz, 2H), 3.62 (s, 3H), 4.24 (m, 1H), 4.93 (s, 2H), 6.64 (d, J=7.8 Hz, 1H), 6.84 (t, J=7.8 Hz, 1H), 6.91 (d, J=7.2 Hz, 1H), 7.46 (m, 4H), 7.83 (m, 1H), 8.19 (m, 1H).
LC/MS (M$^+$H): 414.22.

(2-5-2): (E)-8-(1-Methoxypropan-2-ylamino)-7-((naphthalen-1-yloxy)methyl)-8-oxo-6-octenoic acid The procedure of Example (2-1-2) was repeated except for using the compound obtained in Example (2-5-1) as the starting material, to obtain 346 mg of the title compound (yield 81%).

(2-5-3): (E)-N1-(1-Methoxypropan-2-yl)-2-((naphthalen-1-yloxy)methyl)-N8-(tetrahydro-2H-pyran-2-yloxy)-2-octenediamide The procedure of Example (2-1-3) was repeated except for using the compound obtained in Example (2-5-2) as the starting material, to obtain 289 mg of the title compound (yield 75%).
$^1$H-NMR (200 MHz, CDCl$_3$) δ 1.17 (d, J=6.8 Hz, 3H), 1.41-1.89 (m, 10H), 2.09 (m, 2H), 2.31 (q, J=7.0 Hz, 2H), 3.17 (s, 3H), 3.57 (m, 1H), 3.93 (m, 1H), 4.24 (m, 1H), 4.93 (m, 1H), 6.69 (d, J=7.8 Hz, 1H), 6.84 (t, J=6.6 Hz, 1H), 6.91 (d, J=7.8 Hz, 1H), 7.41 (m, 4H), 7.80 (d, J=7.8 Hz, 1H), 8.19 (d, J=7.8 Hz, 1H).
LC/MS (M$^+$H): 499.27.

(2-5-4): (E)-N8-Hydroxy-N1-(1-methoxypropan-2-yl)-2-((naphthalen-1-yloxy)methyl)-2-octenediamide The procedure of Example (2-1-4) was repeated except for using the compound obtained in Example (2-5-3) as the starting material, to obtain 125 mg of the title compound (yield 88%).
HPLC purification: 63 mg (Purity: 97%)
$^1$H-NMR (200 MHz, DMSO-d$_4$) δ 1.07 (d, J=7.0 Hz, 3H), 1.45 (m, 2H), 1.51 (m, 2H), 1.96 (t, J=7.0 Hz, 2H), 2.29 (m, 2H), 3.24 (s, 3H), 3.36 (s, 2H), 4.09 (m, 1H), 4.96 (s, 2H), 6.51 (t, J=7.8 Hz, 1H), 7.07 (d, J=6.8 Hz, 1H), 7.47 (m, 4H), 7.86 (m, 2H), 8.06 (d, J=9.0 Hz, 1H), 8.70 (br, 4H), 10.35 (br, 1H).
LC/MS (M$^+$H): 415.22.

Example 2-6

(E)-N8-Hydroxy-N1-(4-methoxybenzyl)-2-((naphthalen-1-yloxy)methyl)-2-octenediamide (2-6-1): Methyl (E)-8-(4-methoxybenzylamino)-7-((naphthalen-1-yloxy)methyl)-8-oxo-6-octenoate The procedure of Example (2-1-1) was repeated except for using 4-methoxybenzylamine as the amine compound, to obtain 461 mg of the title compound (yield 98%).
$^1$H-NMR (200 MHz, CDCl$_3$) δ 1.49 (m, 2H), 1.59 (m, 2H), 2.29 (m, 4H), 3.62 (s, 3H), 3.77 (s, 3H), 4.44 (d, J=5.8 Hz, 2H), 4.94 (s, 2H), 6.75 (m, 3H), 6.88 (d, J=7.4 Hz, 2H), 7.15 (d, J=8.6 Hz, 2H), 7.44 (m, 4H), 7.78 (d, J=7.4 Hz, 1H), 7.99 (d, J=7.4 Hz, 1H).
LC/MS (M$^+$H): 462.22.

(2-6-2): (E)-8-(4-Methoxybenzylamino)-7-((naphthalen-1-yloxy)methyl)-8-oxo-6-octenoic acid The procedure of Example (2-1-2) was repeated except for using the compound obtained in Example (2-6-1) as the starting material, to obtain 454 mg of the title compound (yield 86%).

(2-6-3): (E)-N1-(4-Methoxybenzyl)-2-((naphthalen-1-yloxy)methyl)-N8-(tetrahydro-2H-pyran-2-yloxy)-2-octenediamide The procedure of Example (2-1-3) was repeated except for using the compound obtained in Example (2-6-2) as the starting material, to obtain 378 mg of the title compound (yield 85%).
$^1$H-NMR (200 MHz, CDCl$_3$) δ 1.52-1.95 (m, 10H), 2.07 (m, 2H), 2.29 (q, J=7.2 Hz, 2H), 3.75 (s, 3H), 3.91 (m, 1H), 4.43 (d, J=5.8 Hz, 2H), 4.90 (m, 1H), 4.92 (s, 2H), 6.79 (m, 3H), 6.87 (d, J=7.6 Hz, 2H), 7.14 (d, J=8.4 Hz, 2H), 7.47 (m, 4H), 7.77 (d, J=8.0 Hz, 1H), 7.98 (d, J=7.8 Hz, 1H), 8.65 (br, 1H).
LC/MS (M$^+$H): 547.27.

(2-6-4): (E)-N8-Hydroxy-N1-(4-methoxybenzyl)-2-((naphthalen-1-yloxy)methyl)-2-octenediamide The procedure of Example (2-1-4) was repeated except for using the compound obtained in Example (2-6-3) as the starting material, to obtain 142 mg of the title compound (yield 80%).
HPLC purification: 81 mg (Purity: 92%)
$^1$H-NMR (200 MHz, MeOH-d$_4$) δ 1.52 (m, 2H), 1.58 (m, 2H), 2.08 (t, J=7.4 Hz, 2H), 2.34 (q, J=7.6 Hz, 2H), 3.37 (s, 3H), 3.74 (s, 1H), 5.03 (s, 2H), 6.59 (t, J=7.4 Hz, 1H), 6.74 (d, J=8.2 Hz, 2H), 6.96 (d, J=6.6 Hz, 1H), 7.16 (d, J=8.4 Hz, 2H), 7.42 (m, 4H), 7.77 (d, J=7.8 Hz, 1H), 8.06 (d, J=7.4 Hz, 1H).
LC/MS (M$^+$H): 463.22.

Example 2-7

(E)-N1-(4-Fluorophenethyl)-N8-hydroxy-2-((naphthalen-1-yloxy)methyl)-2-octenediamide (2-7-1): Methyl (E)-8-(4-fluorophenethylamino)-7-((naphthalen-1-yloxy)methyl)-8-oxo-6-octenoate The procedure of Example (2-1-1) was repeated except for using 4-fluorophenethylamine as the amine compound, to obtain 463 mg of the title compound (yield 93%).
$^1$H-NMR (200 MHz, CDCl$_3$) δ 1.52 (m, 2H), 1.62 (m, 2H), 2.28 (m, 4H), 2.76 (t, J=6.8 Hz, 2H), 3.54 (q, J=5.6 Hz, 2H), 3.61 (s, 3H), 4.82 (s, 2H), 6.66 (br, 1H), 6.70 (m, 2H), 6.86 (m, 2H), 6.96 (m, 2H), 7.48 (m, 4H), 7.80 (d, J=7.4 Hz, 1H), 7.99 (d, J=7.0 Hz, 1H)
LC/MS (M$^+$H): 464.21. .

(2-7-2): (E)-8-(4-Fluorophenethylamino)-7-((naphthalen-1-yloxy)methyl)-8-oxo-6-octenoic acid The procedure of Example (2-1-2) was repeated except for using the compound obtained in Example (2-7-1) as the starting material, to obtain 434 mg of the title compound (yield 86%).

(2-7-3): (E)-N1-(4-Fluorophenethyl)-2-((naphthalen-1-yloxy)methyl)-N8-(tetrahydro-2H-pyran-2-yloxy)-2-octenediamide The procedure of Example (2-1-3) was repeated except for using the compound obtained in Example (2-7-2) as the starting material, to obtain 362 mg of the title compound (yield 65%).
$^1$H-NMR (200 MHz, CDCl$_3$) δ 1.48-1.89 (m, 10H), 2.16 (m, 2H), 2.28 (q, J=7.2 Hz, 2H), 2.75 (t, J=6.8 Hz, 2H), 3.53 (q, J=5.8 Hz, 2H), 3.60 (m, 1H), 3.91 (m, 1H), 4.81 (s, 2H), 4.90 (m, 1H), 6.49 (m, 1H), 6.70 (m, 2H), 6.85 (m, 2H), 6.96 (m, 2H), 7.42 (m, 4H), 7.81 (d, J=7.4 Hz, 1H), 7.98 (d, J=7.6 Hz, 1H), 8.56 (br, 1H).
LC/MS (M$^+$H): 549.27.

(2-7-4): (E)-N1-(4-Fluorophenethyl)-N8-hydroxy-2-((naphthalen-1-yloxy)methyl)-2-octenediamide The procedure of Example (2-1-4) was repeated except for using the compound obtained in Example (2-7-3) as the starting material, to obtain 83 mg of the title compound (yield 76%).
HPLC purification: 36 mg (Purity: 92%)
$^1$H-NMR (200 MHz, MeOH-d$_4$) δ 1.49 (m, 2H), 1.69 (m, 2H), 2.09 (t, J=6.8 Hz, 2H), 2.34 (q, J=7.2 Hz, 2H), 2.80 (t, J=6.8 Hz, 2H), 3.48 (m, 2H), 4.97 (s, 2H), 6.55 (t, J=7.8 Hz, 1H), 6.86 (m, 2H), 6.97 (d, J=7.6 Hz, 1H), 7.14 (m, 2H), 7.45 (m, 4H), 7.79 (d, J=7.8 Hz, 1H), 8.10 (d, J=8.0 Hz, 1H).
LC/MS (M$^+$H): 465.21.

Example 2-8

(E)-N8-Hydroxy-2-((naphthalen-1-yloxy)methyl)-N1-(tetrahydrofuran-2-yl)methyl)-2-octenediamide (2-8-1): Methyl (E)-7-(((naphthalen-1-yloxy)methyl)-8-oxo-8-((tetrahydrofuran-2-yl)methylamino)-6-octenoate The procedure of Example (2-1-1) was repeated except for using (tetrahydrofuran-2-yl)methylamine as the amine compound, to obtain 426 mg of the title compound (yield 87%).
$^1$H-NMR (200 MHz, CDCl$_3$) δ 1.45-1.99 (m, 8H), 2.28 (m, 4H), 3.26 (m, 1H), 3.78 (m, 3H), 3.61 (s, 3H), 3.97 (m, 1H), 4.93 (s, 2H), 6.79 (m, 1H), 6.90 (m, 2H), 7.47 (m, 4H), 7.78 (m, 1H), 8.20 (m, 1H).
LC/MS (M$^+$H): 426.22.

(2-8-2): (E)-7-(((Naphthalen-1-yloxy)methyl)-8-oxo-8-((tetrahydrofuran-2-yl)methylamino)-6-octenoic acid The procedure of Example (2-1-2) was repeated except for using the compound obtained in Example (2-8-1) as the starting material, to obtain 370 mg of the title compound (yield 90%).

(2-8-3): (E)-2-(Naphthalen-1-yloxy)methyl)-N8-(tetrahydro-2H-pyran-2-yloxy)-N1-(tetrahydrofuran-2-ylmethyl)-2-octenediamide The procedure of Example (2-1-3) was repeated except for using the compound obtained in Example (2-8-2) as the starting material, to obtain 323 mg of the title compound (yield 65%).
$^1$H-NMR (200 MHz, CDCl$_3$) δ 1.42-1.95 (m, 14H), 2.08 (m, 2H), 2.25 (q, J=7.6 Hz, 2H), 3.28 (m, 1H), 3.59 (m, 3H), 3.89 (m, 2H), 4.88 (s, 2H), 4.90 (m, 1H), 6.77 (m, 2H), 6.85 (d, J=7.2 Hz, 1H), 7.40 (m, 4H), 7.77 (m, 1H), 8.14 (m, 1H), 8.68 (br, 1H).
LC/MS (M$^+$H): 511.27.

(2-8-4): (E)-N8-Hydroxy-2-((naphthalen-1-yloxy)methyl)-N1-(tetrahydrofuran-2-yl)methyl)-2-octenediamide The procedure of Example (2-1-4) was repeated except for using the compound obtained in Example (2-8-3) as the starting material, to obtain 85 mg of the title compound (yield 85%).
HPLC purification: 32 mg (Purity: 95%)
$^1$H-NMR (200 MHz, MeOH-d$_4$) δ 1.60 (m, 6H), 1.81 (m, 2H), 2.09 (t, J=7.2 Hz, 2H), 2.37 (q, J=7.4 Hz, 2H), 3.35 (m, 2H), 3.68 (m, 2H), 4.00 (m, 1H), 5.02 (s, 2H), 6.65 (t, J=7.8 Hz, 1H), 7.01 (d, J=6.8 Hz, 1H), 7.44 (m, 4H), 7.78 (d, J=8.6 Hz, 1H), 8.15 (d, J=9.4 Hz, 1H).
LC/MS (M$^+$H): 427.22.

Example 2-9

(E)-N1-(2-Cyclohexenylethyl)-N8-hydroxy-2-((naphthalen-1-yloxy)methyl)-2-octenediamide (2-9-1): Methyl (E)-8-(2-cyclohexenylethylamino)-7-((naphthalen-1-yloxy)methyl)-8-oxo-6-octenoate The procedure of Example (2-1-1) was repeated except for using 2-cyclohexenylethylamine as the amine compound, to obtain 449 mg of the title compound (yield 89%).
$^1$H-NMR (200 MHz, CDCl$_3$) δ 1.25 (m, 2H), 1.30-1.71 (m, 8H), 1.79 (m, 2H), 2.09 (t, J=7.4 Hz, 2H), 2.28 (m, 4H), 3.39 (q, J=5.4 Hz, 2H), 3.60 (s, 3H), 4.86 (s, 2H), 5.28 (br, 1H), 6.41 (br, 1H), 6.89 (t, J=7.6 Hz, 2H), 7.46 (m, 4H), 7.79 (m, 1H), 8.14 (m, 1H).
LC/MS (M$^+$H): 450.26.

(2-9-2): (E)-8-(2-Cyclohexenylethylamino)-7-((naphthalen-1-yloxy)methyl)-8-oxo-6-octenoic acid The procedure of Example (2-1-2) was repeated except for using the compound obtained in Example (2-9-1) as the starting material, to obtain 401 mg of the title compound (yield 95%).

(2-9-3): (E)-N1-(2-Cyclohexenylethyl)-2-((naphthalen-1-yloxy)methyl)-N8-(tetrahydro-2H-pyran-2-yloxy)-2-octenediamide The procedure of Example (2-1-3) was repeated except for using the compound obtained in Example (2-9-2) as the starting material, to obtain 370 mg of the title compound (yield 82%).
$^1$H-NMR (200 MHz, CDCl$_3$) δ 1.27 (m, 2H), 1.35-2.02 (m, 16H), 2.10 (m, 4H), 2.30 (q, J=6.8 Hz, 2H), 3.40 (q, J=5.8 Hz, 2H), 3.63 (m, 1H), 3.96 (m, 1H), 4.87 (s, 2H), 4.92 (m, 1H), 5.18 (br, 1H), 6.44 (br, 1H), 6.90 (t, J=7.6 Hz, 2H), 7.44 (m, 4H), 7.80 (m, 1H), 8.15 (m, 1H), 8.80 (br, 1H).

LC/MS (M$^+$H): 535.31.

(2-9-4): (E)-N1-(2-Cyclohexenylethyl)-N8-hydroxy-2-((naphthalen-1-yloxy)methyl)-2-octenediamide The procedure of Example (2-1-4) was repeated except for using the compound obtained in Example (2-9-3) as the starting material, to obtain 112 mg of the title compound (yield 91%).

HPLC purification: 62 mg (Purity: 92%)

$^1$H-NMR (200 MHz, MeOH-d$_4$) δ 1.36-1.82 (m, 10H), 1.91 (m, 2H), 2.09 (m, 4H), 2.36 (q, J=7.4 Hz, 2H), 3.34 (m, 2H), 4.99 (s, 2H), 5.34 (br, 1H), 6.63 (t, J=7.8 Hz, 1H), 7.01 (d, J=6.8 Hz, 1H), 7.45 (m, 4H), 7.79 (d, J=9.4 Hz, 1H), 8.13 (d, J=9.0 Hz, 1H).

LC/MS (M$^+$H): 451.25.

Example 2-10

(E)-N8-Hydroxy-2-((naphthalen-1-yloxy)methyl)-N1-(3-(2-oxopyrrolidin-1-yl)propyl)-2-octenediamide (2-10-1): Methyl (E)-7-((naphthalen-1-yloxy)methyl)-8-oxo-8-(3-(2-oxopyrrolidin-1-yl)propylamino)-6-octenoate The procedure of Example (2-1-1) was repeated except for using 3-(2-oxopyrrolidine)-1-propylamine as the amine compound, to obtain 466 mg of the title compound (yield 79%).

$^1$H-NMR (200 MHz, CDCl$_3$) δ 1.44 (m, 2H), 1.63 (m, 4H), 1.95 (m, 2H), 2.26 (m, 6H), 3.21 (m, 6H), 3.56 (s, 3H), 4.93 (s, 2H), 6.72 (t, J=7.6 Hz, 1H), 6.88 (d, J=7.6 Hz, 1H), 7.23 (m, 1H), 7.39 (m, 1H), 7.74 (m, 1H), 8.12 (m, 1H).

LC/MS (M$^+$H): 467.25.

(2-10-2): (E)-7-((Naphthalen-1-yloxy)methyl)-8-oxo-8-(3-(2-oxopyrrolidin-1-yl)propylamino)-6-octenoic acid The procedure of Example (2-1-2) was repeated except for using the compound obtained in Example (2-10-1) as the starting material, to obtain 370 mg of the title compound (yield 88%).

(2-10-3): (E)-2-(Naphthalen-1-yloxy)methyl)-N1-(3-(2-oxopyrrolidin-1-yl)propyl)-N8-(tetrahydro-2H-pyran-2-yloxy)-2-octenediamide The procedure of Example (2-1-3) was repeated except for using the compound obtained in Example (2-10-2) as the starting material, to obtain 316 mg of the title compound (yield 80%).

$^1$H-NMR (200 MHz, CDCl$_3$) δ 1.42-1.90 (m, 12H), 2.04 (m, 4H), 2.39 (m, 4H), 3.27 (m, 6H), 3.59 (m, 1H), 3.95 (m, 1H), 4.94 (m, 1H), 4.99 (s, 2H), 6.73 (t, J=7.6 Hz, 1H), 6.91 (d, J=7.4 Hz, 1H), 7.25 (br, 4H), 7.45 (m, 4H), 7.78 (d, J=7.8 Hz, 1H), 8.13 (d, J=7.8 Hz, 1H), 9.25 (br, 1H).

LC/MS (M$^+$H): 552.30.

(2-10-4): (E)-N8-Hydroxy-2-((naphthalen-1-yloxy)methyl)-N1-(3-(2-oxopyrrolidin-1-yl)propyl)-2-octenediamide The procedure of Example (2-1-4) was repeated except for using the compound obtained in Example (2-10-3) as the starting material, to obtain 166 mg of the title compound (yield 82%).

HPLC purification: 49 mg (Purity: 97%)

$^1$H-NMR (200 MHz, MeOH-d$_4$) δ 1.53 (m, 2H), 1.74 (m, 4H), 2.06 (m, 4H), 2.36 (m, 4H), 3.33 (m, 6H), 4.86 (s, 2H), 6.61 (t, J=7.4 Hz, 1H), 7.00 (d, J=6.8 Hz, 1H), 7.43 (m, 4H), 7.78 (d, J=7.4 Hz, 1H), 8.14 (d, J=7.4 Hz, 1H).

LC/MS (M$^+$H): 468.24.

Example 2-11

(E)-N1-(Furan-2-ylmethyl)-N8-hydroxy-2-((naphthalen-1-yloxy)methyl)-2-octenediamide (2-11-1): Methyl (E)-8-(furan-2-ylmethylamino)-7-((naphthalen-1-yloxy)methyl)-8-oxo-6-octenoate The procedure of Example (2-1-1) was repeated except for using furan-2-ylmethylamine as the amine compound, to obtain 421 mg of the title compound (yield 83%).

$^1$H-NMR (200 MHz, CDCl$_3$) δ 1.48 (m, 2H), 1.60 (m, 2H), 2.27 (m, 4H), 3.61 (s, 3H), 4.51 (d, J=5.4 Hz, 2H), 4.93 (s, 2H), 6.20 (dd, J=10.6 Hz, 3.2 Hz, 2H), 6.90 (m, 3H), 7.45 (m, 4H), 7.78 (d, J=7.6 Hz, 1H), 8.07 (d, J=7.6 Hz, 1H).

LC/MS (M$^+$H): 408.17.

(2-11-2): (E)-8-(Furan-2-ylmethylamino)-7-((naphthalen-1-yloxy)methyl)-8-oxo-6-octenoic acid The procedure of Example (2-1-2) was repeated except for using the compound obtained in Example (2-11-1) as the starting material, to obtain 353 mg of the title compound (yield 90%).

(2-11-3): (E)-N1-(Furan-2-ylmethyl)-2-((naphthalen-1-yloxy)methyl)-N8-(tetrahydro-2H-pyran-2-yloxy)-2-octenediamide The procedure of Example (2-1-3) was repeated except for using the compound obtained in Example (2-11-2) as the starting material, to obtain 306 mg of the title compound (yield 55%).

$^1$H-NMR (200 MHz, CDCl$_3$) δ 1.55-1.98 (m, 10H), 2.17 (m, 2H), 2.41 (q, J=7.4 Hz, 2H), 3.66 (m, 1H), 3.97 (m, 1H), 4.61 (d, J=5.4 Hz, 2H), 4.88 (m, 1H), 4.90 (s, 2H), 6.31 (d, J=11.2 Hz, 2H), 6.96 (m, 3H), 7.52 (m, 4H), 7.89 (d, J=6.8 Hz, 1H), 7.17 (d, J=6.6 Hz, 1H), 8.45 (br, 1H).

LC/MS (M$^+$H): 493.23

(2-11-4): (E)-N1-(Furan-2-ylmethyl)-N8-hydroxy-2-((naphthalen-1-yloxy)methyl)-2-octenediamide The procedure of Example (2-1-4) was repeated except for using the compound obtained in Example (2-11-3) as the starting material, to obtain 156 mg of the title compound (yield 79%).

HPLC purification: 68 mg (Purity: 92%)

$^1$H-NMR (200 MHz, MeOH-d$_4$) δ 1.50 (m, 2H), 1.62 (m, 2H), 2.08 (t, J=6.8 Hz, 2H), 2.37 (q, J=7.4 Hz, 2H), 4.47 (s,

2H), 5.03 (s, 2H), 6.24 (dd, J=14.6 Hz, 3.0 Hz, 2H), 6.62 (t, J=7.4 Hz, 1H), 6.99 (d, J=7.2 Hz, 1H), 7.43 (m, 4H), 7.78 (d, J=9.0 Hz, 1H), 8.08 (d, J=8.2 Hz, 1H).

LC/MS (M$^+$H): 409.17.

Example 2-12

(E)-N1-(4-(Dimethylamino)benzyl)-N8-hydroxy-2-((naphthalen-1-yloxy)methyl)-2-octenediamide (2-12-1): Methyl (E)-8-(4-(dimethylamino)benzylamino)-7-((naphthalen-1-yloxy)methyl)-8-oxo-6-octenoate The procedure of Example (2-1-1) was repeated except for using 4-(dimethylamino)benzylamine as the amine compound, to obtain 547 mg of the title compound (yield 72%).

$^1$H-NMR (200 MHz, CDCl$_3$) δ 1.45-1.75 (m, 4H), 2.31 (m, 4H), 2.93 (s, 6H), 3.64 (s, 3H), 4.44 (d, J=5.4 Hz, 2H), 4.96 (s, 2H), 6.62 (m, 3H), 6.91 (m, 2H), 7.14 (d, J=8.4 Hz, 2H), 7.40 (m, 4H), 7.84 (d, J=7.4 Hz, 1H), 8.05 (d, J=7.8 Hz, 1H).

LC/MS (M$^+$H): 475.

(2-12-2): (E)-8-(4-(Dimethylamino)benzylamino)-7-((naphthalen-1-yloxy)methyl)-8-oxo-6-octenoic acid The procedure of Example (2-1-2) was repeated except for using the compound obtained in Example (2-12-1) as the starting material, to obtain 397 mg of the title compound (yield 99%).

(2-12-3): (E)-N1-(4-Dimethylamino)benzyl)-2-((naphthalen-1-yloxy)methyl)-N8-(tetrahydro-2H-pyran-2-yloxy)-2-octenediamide The procedure of Example (2-1-3) was repeated except for using the compound obtained in Example (2-12-2) as the starting material, to obtain 380 mg of the title compound (yield 96%).

$^1$H-NMR (200 MHz, CDCl$_3$) δ 1.50-1.92 (m, 10H), 2.05 (m, 2H), 2.30 (q, J=7.4 Hz, 2H), 2.92 (s, 2H), 2.96 (m, 1H), 3.57 (m, 1H), 3.92 (m, 1H), 4.41 (d, J=5.2 Hz, 2H), 4.81 (m, 1H), 4.94 (s, 2H), 6.60 (m, 3H), 6.89 (m, 2H), 7.12 (d, J=8.4 Hz, 2H), 7.41 (m, 4H), 7.78 (d, J=8.0 Hz, 1H), 8.02 (d, J=8.2 Hz, 1H), 8.37 (br, 1H).

LC/MS (M$^+$H): 560.

(2-12-4): (E)-N1-(4-(Dimethylamino)benzyl)-N8-hydroxy-2-((naphthalen-1-yloxy)methyl)-2-octenediamide The procedure of Example (2-1-4) was repeated except for using the compound obtained in Example (2-12-3) as the starting material, to obtain 305 mg of the title compound (yield 92%).

HPLC purification: 287 mg (Purity: 98%)

$^1$H-NMR (300 MHz, MeOH-d$_4$) δ 1.44 (m, 2H), 1.59 (m, 2H), 2.00 (t, J=7.2 Hz, 2H), 2.28 (q, J=7.2 Hz, 2H), 3.04 (s, 6H), 4.38 (s, 2H), 5.01 (s, 2H), 6.54 (t, J=7.5 Hz, 1H), 6.88 (d, J=7.2 Hz, 1H), 7.17 (d, J=8.4 Hz, 2H), 7.33 (m, 6H), 7.70 (d, J=8.1 Hz, 1H), 8.01 (d, J=8.1 Hz, 1H).

LC/MS (M$^+$H): 476.25.

Example 2-13

(E)-N8-Hydroxy-N1-(2-methoxyethyl)-2-((naphthalen-1-yloxy)methyl)-2-octenediamide (2-13-1): Methyl (E)-8-(2-methoxyethylamino)-7-((naphthalen-1-yloxy)methyl)-8-oxo-6-octenoate The procedure of Example (2-1-1) was repeated except for using 2-methoxyethylamine as the amine compound, to obtain 399 mg of the title compound (yield 85%).

$^1$H-NMR (200 MHz, CDCl$_3$) δ 1.44-1.79 (m, 4H), 2.31 (m, 4H), 3.19 (s, 1H), 3.49 (m, 4H), 3.64 (s, 3H), 4.95 (s, 2H), 6.92 (m, 3H), 7.48 (m, 4H), 7.81 (m, 1H), 7.81 (m, 1H), 8.20 (m, 1H).

LC/MS (M$^+$H): 400.20.

(2-13-2): (E)-8-(2-Methoxyethylamino)-7-((naphthalen-1-yloxy)methyl)-8-oxo-6-octenoic acid The procedure of Example (2-1-2) was repeated except for using the compound obtained in Example (2-13-1) as the starting material, to obtain 339 mg of the title compound (yield 95%).

(2-13-3): (E)-N1-(2-Methoxyethyl)-2-((naphthalen-1-yloxy)methyl)-N8-(tetrahydro-2H-pyran-2-yloxy)-2-octenediamide The procedure of Example (2-1-3) was repeated except for using the compound obtained in Example (2-13-2) as the starting material, to obtain 313 mg of the title compound (yield 70%).

$^1$H-NMR (200 MHz, CDCl$_3$) δ 1.41-1.97 (m, 10H), 2.07 (m, 2H), 2.30 (q, J=7.4 Hz, 2H), 3.17 (s, 3H), 3.46 (m, 5H), 3.92 (m, 1H), 4.90 (m, 1H), 4.92 (s, 2H), 6.85 (m, 3H), 7.46 (m, 4H), 7.81 (m, 1H), 8.17 (m, 1H), 8.67 (m, 1H).

LC/MS (M$^+$H): 485.26.

(2-13-4): (E)-N8-Hydroxy-N1-(2-methoxyethyl)-2-((naphthalen-1-yloxy)methyl)-2-octenediamide The procedure of Example (2-1-4) was repeated except for using the compound obtained in Example (2-13-3) as the starting material, to obtain 87 mg of the title compound (yield 68%).

HPLC purification: 42 mg (Purity: 98%)

$^1$H-NMR (300 MHz, MeOH-d$_4$) δ 1.44 (m, 2H), 1.57 (m, 2H), 2.02 (t, J=7.2 Hz, 2H), 2.30 (q, J=7.2 Hz, 2H), 3.19 (s, 3H), 3.40 (s, 4H), 4.95 (s, 2H), 6.57 (t, J=7.5 Hz, 1H), 6.96 (d, J=6.3 Hz, 1H), 7.38 (m, 4H), 7.73 (d, J=6.9 Hz, 1H), 8.09 (d, J=7.2 Hz, 1H).

LC/MS (M$^+$H): 401.20.

Example 2-14

(E)-N1-Cyclohexyl-N8-hydroxy-2-((naphthalen-1-yloxy)methyl)-2-octenediamide (2-14-1): Methyl (E)-8-(cyclohexylamino)-7-((naphthalen-1-yloxy)methyl)-8-oxo-6-octenoate The procedure of Example (2-1-1) was repeated except for using cyclohexylamine as the amine compound, to obtain 423 mg of the title compound (yield 94%).

¹H-NMR (200 MHz, CDCl₃) δ 1.13 (m, 2H), 1.33 (m, 2H), 1.42-1.79 (m, 8H), 1.88 (m, 2H), 2.29 (m, 4H), 3.62 (s, 3H), 3.82 (m, 1H), 4.92 (s, 2H), 6.34 (d, J=7.4 Hz, 1H), 6.84 (t, J=7.8 Hz, 1H), 6.91 (d, J=7.2 Hz, 1H), 7.47 (m, 4H), 7.81 (m, 1H), 8.15 (m, 1H).
LC/MS (M⁺H): 424.24.

(2-14-2): (E)-8-(Cyclohexylamino)-7-((naphthalen-1-yloxy)methyl)-8-oxo-6-octenoic acid The procedure of Example (2-1-2) was repeated except for using the compound obtained in Example (2-14-1) as the starting material, to obtain 397 mg of the title compound (yield 67%).

(2-14-3): (E)-N1-Cyclohexyl-2-((naphthalen-1-yloxy)methyl)-N8-(tetrahydro-2H-pyran-2-yloxy)-2-octenediamide The procedure of Example (2-1-3) was repeated except for using the compound obtained in Example (2-14-2) as the starting material, to obtain 257 mg of the title compound (yield 95%).
¹H-NMR (200 MHz, CDCl₃) δ 1.14 (m, 2H), 1.34 (m, 2H), 1.40-2.00 (m, 16H), 2.08 (m, 2H), 2.30 (q, J=7.2 Hz, 2H), 3.62 (m, 1H), 3.90 (m, 2H), 4.72 (m, 1H), 4.93 (s, 2H), 6.40 (d, J=7.8 Hz, 1H), 6.83 (t, J=7.8 Hz, 1H), 6.96 (d, J=8.6 Hz, 1H), 7.48 (m, 4H), 7.81 (m, 1H), 8.16 (m, 1H), 8.81 (br, 1H).
LC/MS (M⁺H): 509.29.

(2-14-4): (E)-N1-Cyclohexyl-N8-hydroxy-2-((naphthalen-1-yloxy)methyl)-2-octenediamide The procedure of Example (2-1-4) was repeated except for using the compound obtained in Example (2-14-3) as the starting material, to obtain 122 mg of the title compound (yield 83%).
HPLC purification: 78 mg (Purity: 93%)
¹H-NMR (300 MHz, MeOH-d₄) δ 1.11-1.39 (m, 5H), 1.40-1.71 (m, 7H), 1.79 (m, 2H), 2.03 (t, J=6.9 Hz, 2H), 2.29 (m, 2H), 3.69 (m, 1H), 4.96 (s, 1H), 6.47 (t, J=7.2 Hz, 1H), 6.93 (d, J=7.2 Hz, 1H), 7.37 (m, 4H), 7.75 (d, J=7.5 Hz, 1H), 8.08 (d, J=7.8 Hz, 1H).
LC/MS (M⁺H): 425.24.

Example 2-15

(E)-N8-Hydroxy-2-((naphthalen-1-yloxy)methyl)-N1-(thiophen-2-ylmethyl)-2-octenediamide (2-15-1): Methyl (E)-7-((naphthalen-1-yloxy)methyl)-8-oxo-8-(thiophen-2-ylmethylamino)-6-octenoate The procedure of Example (2-1-1) was repeated except for using thiophen-2-ylmethylamine as the amine compound, to obtain 438 mg of the title compound (yield 100%).
¹H-NMR (200 MHz, CDCl₃) δ 1.43-1.75 (m, 4H), 2.29 (m, 4H), 3.62 (s, 3H), 4.68 (d, J=5.8 Hz, 2H), 4.90 (s, 2H), 6.93 (m, 5H), 7.18 (d, J=4.8 Hz, 1H), 7.46 (m, 4H), 7.78 (d, J=8.0 Hz, 1H), 8.04 (d, J=8.0 Hz, 1H)
LC/MS (M⁺H): 438.17.

(2-15-2): (E)-7-((Naphthalen-1-yloxy)methyl)-8-oxo-8-(thiophen-2-ylmethylamino)-6-octenoic acid The procedure of Example (2-1-2) was repeated except for using the compound obtained in Example (2-15-1) as the starting material, to obtain 438 mg of the title compound (yield 92%).

(2-15-3): (E)-2-(Naphthalen-1-yloxy)methyl)-N8-(tetrahydro-2H-pyran-2-yloxy)-N1-(thiophen-2-ylmethyl)-2-octenediamide The procedure of Example (2-1-3) was repeated except for using the compound obtained in Example (2-15-2) as the starting material, to obtain 390 mg of the title compound (yield 66%).
¹H-NMR (200 MHz, CDCl₃) δ 1.46-1.94 (m, 10H), 2.10 (m, 2H), 2.32 (q, J=7.0 Hz, 2H), 3.64 (m, 1H), 3.93 (m, 1H), 4.70 (d, J=5.2 Hz, 2H), 4.90 (m, 5H), 4.95 (s, 1H), 6.91 (m, 5H), 7.19 (d, J=4.8 Hz, 1H), 7.47 (m, 4H), 7.80 (d, J=8.8 Hz, 1H), 8.09 (d, J=10.0 Hz, 1H), 8.41 (br, 1H).
LC/MS (M⁺H): 523.22.

(2-15-4): (E)-N8-Hydroxy-2-((naphthalen-1-yloxy)methyl)-N1-(thiophen-2-ylmethyl)-2-octenediamide The procedure of Example (2-1-4) was repeated except for using the compound obtained in Example (2-15-3) as the starting material, to obtain 168 mg of the title compound (yield 87%).
HPLC purification: 55 mg (Purity: 95%)
¹H-NMR (300 MHz, MeOH-d₄) δ 1.34 (m, 2H), 1.58 (m, 2H), 2.10 (m, 2H), 2.32 (m, 2H), 4.58 (s, 2H), 4.96 (s, 2H), 6.55 (m, 1H), 6.86 (m, 3H), 7.19 (d, J=4.8 Hz, 1H), 7.36 (m, 4H), 7.71 (d, J=7.8 Hz, 1H), 8.01 (d, J=7.8 Hz, 1H).
LC/MS (M⁺H): 439.16.

Example 2-16

(E)-N8-Hydroxy-N1-(4-methoxyphenethyl)-2-((naphthalen-1-yloxy)methyl)-2-octenediamide (2-16-1): Methyl (E)-8-(4-methoxyphenethylamino)-7-((naphthalen-1-yloxy)methyl)-8-oxo-6-octenoate The procedure of Example (2-1-1) was repeated except for using 4-methoxyphenethylamine as the amine compound, to obtain 476 mg of the title compound (yield 100%).
¹H-NMR (200 MHz, CDCl₃) δ 1.45-1.73 (m, 4H), 2.30 (m, 4H), 2.75 (t, J=6.4 Hz, 2H), 3.56 (q, J=6.6 Hz, 2H), 3.63 (s, 3H), 3.66 (s, 3H), 4.84 (s, 2H), 6.46 (m, 1H), 6.56 (d, J=8.6 Hz, 2H), 6.88 (m, 2H), 6.95 (d, J=8.6 Hz, 2H), 7.50 (m, 4H), 7.82 (d, J=8.4 Hz, 1H), 8.05 (d, J=8.1 Hz, 1H).
LC/MS (M⁺H): 476.24.

(2-16-2): (E)-8-(4-Methoxyphenethylamino)-7-((naphthalen-1-yloxy)methyl)-8-oxo-6-octenoic acid The procedure of Example (2-1-2) was repeated except for using the compound obtained in Example (2-16-1) as the starting material, to obtain 476 mg of the title compound (yield 90%).

(2-16-3): (E)-N1-(4-Methoxyphenethyl)-2-((naphthalen-1-yloxy)methyl)-N8-(tetrahydro-2H-pyran-2-yloxy)-2-octenediamide The procedure of Example (2-1-3) was repeated except for using the compound obtained in Example (2-16-2) as the starting material, to obtain 415 mg of the title compound (yield 93%).
$^1$H-NMR (200 MHz, CDCl$_3$) δ 1.50-1.90 (m, 10H), 2.19 (m, 2H), 2.30 (m, 2H), 2.86 (m, 2H), 3.67 (m, 3H), 3.81 (s, 3H), 3.92 (m, 1H), 4.85 (s, 2H), 4.92 (m, 1H), 6.61 (m, 1H), 6.87 (m, 2H), 7.15 (m, 4H), 7.46 (m, 4H), 7.82 (d, J=8.0 Hz, 1H), 8.09 (d, J=8.0 Hz, 1H), 8.39 (br, 1H).
LC/MS (M$^+$H): 561.29.

(2-16-4): (E)-N8-Hydroxy-N1-(4-methoxyphenethyl)-2-((naphthalen-1-yloxy)methyl)-2-octenediamide The procedure of Example (2-1-4) was repeated except for using the compound obtained in Example (2-16-3) as the starting material, to obtain 155 mg of the title compound (yield 84%).
HPLC purification: 50 mg (Purity: 95%)
$^1$H-NMR (300 MHz, MeOH-d$_4$) δ 1.44 (m, 2H), 1.57 (m, 2H), 2.03 (t, J=6.9 Hz, 2H), 2.28 (q, J=6.9 Hz, 2H), 2.70 (t, J=6.9 Hz, 2H), 3.41 (t, J=7.2 Hz, 2H), 3.61 (s, 3H), 4.91 (s, 2H), 6.50 (t, J=7.2 Hz, 1H), 6.61 (d, J=8.1 Hz, 2H), 6.92 (d, J=7.2 Hz, 1H), 6.98 (d, J=8.1 Hz, 2H), 7.39 (m, 4H), 7.74 (d, J=7.8 Hz, 1H), 8.05 (d, J=7.8 Hz, 1H).
LC/MS (M$^+$H): 478.23.

Example 2-17

(E)-N8-Hydroxy-2-((naphthalen-1-yloxy)methyl)-N1-(4-(trifluoromethoxy)benzyl)-2-octenediamide (2-17-1): Methyl (E)-7-((naphthalen-1-yloxy)methyl)-8-oxo-8-(4-trifluoromethoxy)benzylamino)-6-octenoate The procedure of Example (2-1-1) was repeated except for using 4-(trifluoromethoxy)benzylamine as the amine compound, to obtain 515 mg of the title compound (yield 57%).
$^1$H-NMR (200 MHz, CDCl$_3$) δ 1.52-1.71 (m, 6H), 2.32 (m, 4H), 3.62 (s, 3H), 4.52 (d, J=5.6 Hz, 2H), 4.96 (s, 2H), 6.82 (br, 1H), 6.94 (m, 2H), 7.10 (d, J=8.2 Hz, 2H), 7.38 (m, 2H), 7.48 (m, 2H), 7.82 (d, J=8.2 Hz, 1H), 8.02 (d, J=8.2 Hz, 1H).
LC/MS (M$^+$H): 516.19.

(2-17-2): (E)-7-(Naphthalen-1-yloxy)methyl)-8-oxo-8-(4-trifluoromethoxy)benzylamino)-6-octenoic acid The procedure of Example (2-1-2) was repeated except for using the compound obtained in Example (2-17-1) as the starting material, to obtain 293 mg of the title compound (yield 95%).

(2-17-3): (E)-2-(Naphthalen-1-yloxy)methyl)-N8-(tetrahydro-2H-pyran-2-yloxy)-N1-(4-(trifluoromethoxy)benzyl)-2-octenediamide The procedure of Example (2-1-3) was repeated except for using the compound obtained in Example (2-17-2) as the starting material, to obtain 291 mg of the title compound (yield 60%).
$^1$H-NMR (200 MHz, CDCl$_3$) δ 0.86 (m, 2H), 1.28 (m, 2H), 1.44-1.79 (m, 8H), 2.34 (m, 2H), 3.64 (br, 1H), 3.92 (br, 1H), 4.52 (d, J=5.8 Hz, 2H), 4.90 (m, 1H), 4.98 (s, 2H), 6.92 (m, 3H), 7.10 (m, 2H), 7.32 (m, 2H), 7.42 (m, 2H), 7.82 (d, J=8.2 Hz, 1H), 8.02 (d, J=8.2 Hz, 1H), 8.29 (br, 1H).
LC/MS (M$^+$H): 601.24.

(2-17-4): (E)-N8-Hydroxy-2-((naphthalen-1-yloxy)methyl)-N1-(4-(trifluoromethoxy)benzyl)-2-octenediamide The procedure of Example (2-1-4) was repeated except for using the compound obtained in Example (2-17-3) as the starting material, to obtain 74 mg of the title compound (yield 52%).
HPLC purification: 15 mg (Purity: 95%)
$^1$H-NMR (300 MHz, MeOH-d$_4$) δ 1.30 (m, 2H), 1.57 (m, 2H), 1.63 (m, 2H), 2.07 (t, J=8.2 Hz, 2H), 2.38 (q, J=7.4 Hz, 2H), 4.46 (s, 2H), 5.05 (s, 2H), 5.47 (s, 2H), 6.61 (t, J=7.6 Hz, 1H), 6.97 (d, J=7.4 Hz, 1H), 7.06 (d, J=8.6 Hz, 1H), 7.38 (m, 6H), 7.77 (d, J=8.0 Hz, 1H), 8.07 (d, J=8.2 Hz, 1H).
LC/MS (M$^+$H): 517.19.

Example 2-18

(E)-N1-(1-(Cyclohexylmethyl)pyrrolidin-3-yl)-N8-hydroxy-2-((naphthalen-1-yloxy)methyl)-2-octenediamide (2-18-1): Methyl (E)-8-(1-(cyclohexylmethyl)pyrrolidin-3-ylamino)-7-((naphthalen-1-yloxy)methyl)-8-oxo-6-octenoate The procedure of Example (2-1-1) was repeated except for using 1-(cyclohexylmethyl)pyrrolidin-3-ylamine as the amine compound, to obtain 506 mg of the title compound (yield 26%).
$^1$H-NMR (200 MHz, CDCl$_3$) δ 0.86 (m, 4H), 1.05-1.33 (m, 8H), 1.42-1.87 (m, 4H), 2.09 (m, 2H), 2.17-2.34 (m, 4H), 2.57 (m, 2H), 2.84 (m, 1H), 3.62 (s, 3H),
4.53 (br, 1H), 4.93 (s, 2H), 5.30 (s, 2H), 6.84 (m, 2H), 7.47 (m, 4H), 7.78 (m, 1H), 8.15 (m, 1H).
LC/MS (M$^+$H): 507.31.

(2-18-2): (E)-8-(1-(Cyclohexylmethyl)pyrrolidin-3-ylamino)-7-((naphthalen-1-yloxy)methyl)-8-oxo-6-octenoic acid The procedure of Example (2-1-2) was repeated except for using the compound obtained in Example (2-18-1) as the starting material, to obtain 135 mg of the title compound (yield 89%).

(2-18-3): (E)-N1-(1-(Cyclohexylmethyl)pyrrolidin-3-yl)-2-((naphthalen-1-yloxy)methyl)-N8-(tetrahydro-2H-pyran-2-yloxy)-2-octenediamide
The procedure of Example (2-1-3) was repeated except for using the compound obtained in Example (2-18-2) as the starting material, to obtain 117 mg of the title compound (yield 53%).
$^1$H-NMR (200 MHz, CDCl$_3$) δ 0.83 (m, 4H), 1.07 (m, 2H), 1.28 (m, 4H), 1.42 (m, 1H), 1.57-1.78 (m, 12H), 2.17 (m, 2H), 2.31 (m, 6H), 2.61-2.89 (m, 3H), 3.60 (m, 1H), 3.92 (m, 1H), 4.57 (m, 1H), 4.93 (s, 2H), 6.82 (t, J=7.4 Hz, 1H), 6.91 (d, J=7.2 Hz, 1H), 7.46 (m, 4H), 7.78 (d, J=7.2 Hz, 1H), 8.16 (d, J=7.4 Hz, 1H), 8.43 (br, 1H).
LC/MS (M$^+$H): 592.37.

(2-18-4): (E)-N1-(1-(Cyclohexylmethyl)pyrrolidin-3-yl)-N8-hydroxy-2-((naphthalen-1-yloxy)methyl)-2-octenediamide The procedure of Example (2-1-4) was repeated except for using the compound obtained in Example (2-18-3) as the starting material, to obtain 58 mg of the title compound (yield 77%).

HPLC purification: 24 mg (Purity: 95%)
$^1$H-NMR (300 MHz, MeOH-$d_4$) δ 0.92 (m, 2H), 1.15 (m, 4H), 1.46 (m, 2H), 1.50-1.70 (m, 8H), 2.04 (m, 3H), 2.36 (q, J=7.2 Hz, 2H), 2.50 (m, 1H), 2.96 (m, 3H), 3.56 (m, 1H), 3.79 (m, 1H), 4.34 (br, 1H), 4.97 (s, 2H), 6.53 (t, J=7.0 Hz, 1H), 6.94 (d, J=7.2 Hz, 1H), 7.38 (m, 4H), 7.73 (d, J=7.6 Hz, 1H), 8.06 (d, J=7.6 Hz, 1H).
LC/MS (M$^+$H): 508.31.

Example 2-19

(E)-N1-(1-Cyclopentylpiperidin-4-yl)-N8-hydroxy-2-((naphthalen-1-yloxy)methyl)-2-octenediamide (2-19-1): Methyl (E)-8-(1-cyclopentylpiperidin-4-ylamino)-7-((naphthalen-1-yloxy)methyl)-8-oxo-6-octenoate The procedure of Example (2-1-1) was repeated except for using 1-cyclopentylpiperidin-4-ylamine obtained in Preparation Example (2-iv-3) as the amine compound, to obtain 492 mg of the title compound (yield 55%).
$^1$H-NMR (200 MHz, CDCl$_3$) δ 0.83-1.04 (m, 4H), 1.28 (m, 6H), 1.42-1.70 (m, 8H), 1.92-2.59 (m, 6H), 2.85 (m, 1H), 3.62 (s, 3H), 3.94 (m, 1H), 4.92 (s, 2H), 6.39 (d, J=7.8 Hz, 1H), 6.84 (m, 2H), 7.48 (m, 4H), 7.79 (m, 1H), 8.17 (m, 1H).
LC/MS (M$^+$H): 493.30.

(2-19-2): (E)-8-(1-Cyclopentylpiperidin-4-ylamino)-7-((naphthalen-1-yloxy)methyl)-8-oxo-6-octenoic acid The procedure of Example (2-1-2) was repeated except for using the compound obtained in Example (2-19-1) as the starting material, to obtain 274 mg of the title compound (yield 96%).

(2-19-3): (E)-N1-(1-Cyclopentylpiperidin-4-yl)-2-((naphthalen-1-yloxy)methyl)-N8-(tetrahydro-2H-pyran-2-yloxy)-2-octenediamide The procedure of Example (2-1-3) was repeated except for using the compound obtained in Example (2-19-2) as the starting material, to obtain 257 mg of the title compound (yield 48%).
$^1$H-NMR (200 MHz, CDCl$_3$) δ 0.82 (m, 2H), 1.25-1.77 (m, 22H), 1.93-2.37 (m, 6H), 2.49 (m, 1H), 2.90 (m, 2H), 3.61 (br, 1H), 3.91 (br, 1H), 4.91 (s, 2H), 6.52 (br, 1H), 6.89 (m, 2H), 7.50 (m, 4H), 7.79 (m, 1H), 8.16 (m, 1H), 8.52 (br, 1H).
LC/MS (M$^+$H): 578.35.

(2-19-4): (E)-N1-(1-Cyclopentylpiperidin-4-yl)-N8-hydroxy-2-((naphthalen-1-yloxy)methyl)-2-octenediamide The procedure of Example (2-1-4) was repeated except for using the compound obtained in Example (2-19-3) as the starting material, to obtain 122 mg of the title compound (yield 70%).

HPLC purification: 42 mg (Purity: 95%)
$^1$H-NMR (300 MHz, MeOH-$d_4$) δ 1.46 (m, 2H), 1.54-1.78 (m, 12H), 1.99-2.11 (m, 6H), 2.32 (q, J=7.4 Hz, 2H), 2.98 (t, J=12.6 Hz, 2H), 3.39 (m, 1H), 3.57 (d, J=12.4 Hz, 2H), 3.94 (m, 1H), 4.96 (s, 2H), 6.47 (t, J=7.2 Hz, 1H), 6.92 (d, J=7.2 Hz, 1H), 7.34 (m, 4H), 7.74 (d, J=8.0 Hz, 1H), 7.82 (s, 1H), 8.07 (d, J=7.8 Hz, 1H).
LC/MS (M$^+$H): 494.29.

Example 2-20

(E)-N1-(1-Benzylpyrrolidin-3-yl)-N8-hydroxy-2-((naphthalen-1-yloxy)methyl)-2-octenediamide (2-20-1): Methyl (E)-8-(1-benzylpyrrolidin-3-ylamino)-7-((naphthalen-1-yloxy)methyl)-8-oxo-6-octenoate The procedure of Example (2-1-1) was repeated except for using 1-benzylpyrrolidin-3-ylamine as the amine compound, to obtain 501 mg of the title compound (yield 70%).
$^1$H-NMR (200 MHz, CDCl$_3$) δ 0.84 (m, 2H), 1.29 (m, 2H), 1.62 (m, 4H), 2.30 (m, 6H), 2.55 (m, 2H), 3.48 (m, 3H), 3.63 (s, 3H), 4.94 (s, 2H), 6.86 (m, 2H), 7.14 (m, 2H), 7.18 (m, 2H), 7.46 (m, 4H), 7.81 (d, J=7.8 Hz, 1H), 8.19 (d, J=7.4 Hz, 1H).
LC/MS (M$^+$H): 501.27.

(2-20-2): (E)-8-(1-Benzylpyrrolidin-3-ylamino)-7-((naphthalen-1-yloxy)methyl)-8-oxo-6-octenoic acid The procedure of Example (2-1-2) was repeated except for using the compound obtained in Example (2-20-1) as the starting material, to obtain 352 mg of the title compound (yield 55%).

(2-20-3): (E)-N1-(1-Benzylpyrrolidin-3-yl)-2-((naphthalen-1-yloxy)methyl)-N8-(tetrahydro-2H-pyran-2-yloxy)-2-octenediamide The procedure of Example (2-1-3) was repeated except for using the compound obtained in Example (2-20-2) as the starting material, to obtain 188 mg of the title compound (yield 67%).
$^1$H-NMR (200 MHz, CDCl$_3$) δ 0.86 (m, 2H), 1.28 (m, 2H), 1.42-1.77 (m, 8H), 2.08-2.37 (m, 6H), 2.54 (m, 2H), 2.75 (m, 1H), 3.48 (m, 3H), 3.91 (br, 1H), 4.53 (br, 1H), 4.85 (m, 1H), 4.92 (s, 2H), 6.94 (m, 3H), 7.16 (m, 4H), 7.40 (m, 4H), 7.84 (d, J=7.0 Hz, 1H), 8.21 (d, J=9.6 Hz, 1H), 8.60 (br, 1H).
LC/MS (M$^+$H): 586.32.

(2-20-4): (E)-N1-(1-Benzylpyrrolidin-3-yl)-N8-hydroxy-2-((naphthalen-1-yloxy)methyl)-2-octenediamide The procedure of Example (2-1-4) was repeated except for using the compound obtained in Example (2-20-3) as the starting material, to obtain 64 mg of the title compound (yield 68%).

HPLC purification: 23 mg (Purity: 95%)
$^1$H-NMR (300 MHz, MeOH-$d_4$) δ 1.30 (m, 2H), 1.52 (m, 2H), 1.64 (m, 2H), 2.07 (t, J=7.0 Hz, 2H), 2.39 (q, J=7.2 Hz, 2H), 4.32 (m, 3H), 4.94 (m, 3H), 5.47 (s, 2H), 6.57 (t, J=7.4 Hz, 1H), 7.02 (d, J=7.2 Hz, 1H), 7.36-7.44 (m, 8H), 7.77 (d, J=8.4 Hz, 1H), 7.86 (m, 1H), 8.08 (d, J=6.4 Hz, 1H), 8.75 (br, 1H)
LC/MS (M$^+$H): 502.26. .

Example 2-21

(E)-N8-Hydroxy-N1-(1-isopropylpyrrolidin-3-yl)-2-((naphthalen-1-yloxy)methyl)-2-octenediamide (2-21-1): Methyl (E)-8-(1-isopropylpyrrolidin-3-ylamino)-7-((naphthalen-1-yloxy)methyl)-8-oxo-6-octenoate The procedure of Example (2-1-1) was repeated except for using 1-isopropylpyrrolidin-3-ylamine obtained in Preparation Example (2-14-1) as the amine compound, to obtain 452 mg of the title compound (yield 41%).

$^1$H-NMR (200 MHz, CDCl$_3$) δ 0.84 (m, 2H), 1.02 (m, 4H), 1.26 (m, 3H), 1.61 (m, 4H), 2.18 (m, 2H), 2.30 (m, 5H), 2.70 (t, J=6.6 Hz, 2H), 3.63 (s, 3H), 4.95 (s, 2H), 6.86 (m, 3H), 7.46 (m, 4H), 7.79 (d, J=8.2 Hz, 1H), 8.17 (d, J=8.6 Hz, 1H).

LC/MS (M$^+$H): 453.27.

(2-21-2): (E)-8-(1-Isopropylpyrrolidin-3-ylamino)-7-((naphthalen-1-yloxy)methyl)-8-oxo-6-octenoic acid The procedure of Example (2-1-2) was repeated except for using the compound obtained in Example (2-21-1) as the starting material, to obtain 184 mg of the title compound (yield 83%).

(2-21-3): (E)-N1-(1-Isopropylpyrrolidin-3-yl)-2-((naphthalen-1-yloxy)methyl)-N8-(tetrahydro-2H-pyran-2-yloxy)-2-octenediamide The procedure of Example (2-1-3) was repeated except for using the compound obtained in Example (2-21-2) as the starting material, to obtain 151 mg of the title compound (yield 69%).

$^1$H-NMR (200 MHz, CDCl$_3$) δ 0.83 (m, 4H), 1.05 (m, 6H), 1.25 (m, 4H), 1.59 (m, 6H), 2.09 (m, 2H), 2.34 (m, 4H), 2.76 (d, J=5.4 Hz, 2H), 3.62 (m, 1H), 3.92 (m, 1H), 4.94 (s, 2H), 6.79 (t, J=7.8 Hz, 1H), 6.94 (d, J=7.4 Hz, 1H), 7.14 (m, 1H), 7.44 (m, 4H), 7.77 (m, 1H), 8.16 (m, 1H).

LC/MS (M$^+$H): 538.32.

(2-21-4): (E)-N8-Hydroxy-N1-(1-isopropylpyrrolidin-3-yl)-2-((naphthalen-1-yloxy)methyl)-2-octenediamide The procedure of Example (2-1-4) was repeated except for using the compound obtained in Example (2-21-3) as the starting material, to obtain 101 mg of the title compound (yield 82%).

HPLC purification: 39 mg (Purity: 96%)

$^1$H-NMR (300 MHz, MeOH-d$_4$) δ 1.26 (m, 6H), 1.47 (q, J=7.2 Hz, 2H), 1.62 (q, J=7.2 Hz, 2H), 2.04 (t, J=7.0 Hz, 3H), 2.34 (q, J=7.2 Hz, 3H), 3.25-3.53 (m, 4H), 3.69 (m, 1H), 4.43 (m, 1H), 4.97 (m, 2H), 6.58 (m, 1H), 6.95 (d, J=7.2 Hz, 1H), 7.34 (m, 4H), 7.74 (d, J=7.6 Hz, 1H), 8.06 (d, J=8.0 Hz, 1H).

LC/MS (M$^+$H): 454.26.

Example 2-22

(E)-N1-(1-(Cyclohexanecarbonyl)pyrrolidin-3-yl)-N8-hydroxy-2-((naphthalen-1-yloxy)methyl)-2-octenediamide (2-22-1): Methyl (E)-8-(1-(cyclohexanecarbonyl)pyrrolidin-3-ylamino)-7-((naphthalen-1-yloxy)methyl)-8-oxo-6-octenoate The procedure of Example (2-1-1) was repeated except for using 1-(cyclohexanecarbonyl)pyrrolidin-3-ylamine as the amine compound, to obtain 520 mg of the title compound (yield 66%).

$^1$H-NMR (200 MHz, CDCl$_3$) δ 1.17-1.76 (m, 14H), 2.16-2.35 (m, 7H), 3.46 (m, 2H), 3.62 (s, 3H), 3.83 (m, 2H), 4.54 (m, 1H), 4.93 (s, 2H), 6.60 (m, 1H), 6.88 (m, 1H), 7.47 (m, 4H), 7.80 (d, J=7.2 Hz, 1H), 8.12 (d, J=6.8 Hz, 1H).

LC/MS (M$^+$H): 521.29.

(2-22-2): (E)-8-(1-(Cyclohexanecarbonyl)pyrrolidin-3-ylamino)-7-((naphthalen-1-yloxy)methyl)-8-oxo-6-octenoic acid The procedure of Example (2-1-2) was repeated except for using the compound obtained in Example (2-22-1) as the starting material, to obtain 342 mg of the title compound (yield 78%).

(2-22-3): (E)-N1-(1-(Cyclohexanecarbonyl)pyrrolidin-3-yl)-2-((naphthalen-1-yloxy)methyl)-N8-(tetrahydro-2H-pyran-2-yloxy)-2-octenediamide The procedure of Example (2-1-3) was repeated except for using the compound obtained in Example (2-22-2) as the starting material, to obtain 262 mg of the title compound (yield 40%).

$^1$H-NMR (300 MHz, CDCl$_3$) δ 1.20 (m, 4H), 1.42-1.77 (m, 16H), 2.11 (m, 4H), 2.32 (m, 3H), 3.37 (m, 2H), 3.44 (m, 1H), 3.60 (m, 2H), 3.86 (m, 1H), 4.53 (q, J=5.6 Hz, 1H), 4.93 (s, 2H), 6.89 (m, 3H), 7.45 (m, 4H), 7.80 (d, J=7.4 Hz, 1H), 8.10 (d, J=7.6 Hz, 1H), 8.41 (br, 1H).

LC/MS (M$^+$H): 606.35.

(2-22-4): (E)-N1-(1-(cyclohexanecarbonyl)pyrrolidin-3-yl)-N8-hydroxy-2-((naphthalen-1-yloxy)methyl)-2-octenediamide The procedure of Example (2-1-4) was repeated except for using the compound obtained in Example (2-22-3) as the starting material, to obtain 154 mg of the title compound (yield 80%).

HPLC purification: 67 mg (Purity: 96%)

$^1$H-NMR (300 MHz, MeOH-d$_4$) δ 1.18-1.69 (m, 14H), 2.03 (m, 4H), 2.32 (q, J=7.0 Hz, 3H), 3.49 (m, 2H), 3.80 (m, 1H), 3.93 (s, 1H), 4.40 (m, 1H), 4.98 (s, 2H), 6.48 (t, J=7.8 Hz, 1H), 6.94 (d, J=5.4 Hz, 1H), 7.37 (m, 4H), 7.73 (d, J=7.8 Hz, 1H), 8.08 (d, J=8.8 Hz, 1H).

LC/MS (M$^+$H): 522.29.

Example 2-23 t-Butyl (E)-3-(8-(hydroxyamino)-2-((naphthalen-1-yloxy)methyl)-8-oxo-2-octeneamido)pyrrolidine-1-carboxylate (2-23-1): t-Butyl (E)-3-(8-methoxy-2-((naphthalen-1-yloxy)methyl)-8-oxo-2-octeneamido)pyrrolidine-1-carboxylate The procedure of Example (2-1-1) was repeated except for using t-butyl 3-aminopyrrolidine-1-carboxylate as the amine compound, to obtain 510 mg of the title compound (yield 83%).

$^1$H-NMR (300 MHz, CDCl$_3$) δ 1.33 (m, 2H), 1.39 (s, 9H), 1.60 (m, 2H), 2.15 (m, 2H), 2.31 (m, 4H), 3.36 (m, 4H), 3.62 (s, 3H), 4.93 (s, 2H), 6.66 (br, 1H), 6.90 (m, 2H), 7.38 (t, J=7.8 Hz, 2H), 7.49 (m, 2H), 7.80 (m, 1H), 8.10 (m, 1H).

LC/MS (M$^+$H): 511.27.

(2-23-2): (E)-8-(1-(t-Butoxycarbonyl)pyrrolidin-3-ylamino)-7-((naphthalen-1-yloxy)methyl)-8-oxo-6-octenoic acid The procedure of Example (2-1-2) was repeated except for using the compound obtained in Example (2-23-1) as the starting material, to obtain 423 mg of the title compound (yield 77%).

(2-23-3): t-Butyl (E)-3-(2-((naphthalen-1-yloxy)methyl)-8-oxo-8-(tetrahydro-2H-pyran-2-yloxyamino)-2-octeneamido)pyrrolidine-1-carboxylate The procedure of Example (2-1-3) was repeated except for using the compound obtained in Example (2-23-2) as the starting material, to obtain 320 mg of the title compound (yield 72%).

$^1$H-NMR (300 MHz, CDCl$_3$) δ 1.25 (m, 2H), 1.39 (s, 9H), 1.45 (m, 2H), 1.50-1.77 (m, 6H), 1.92 (m, 1H), 2.04 (m, 4H), 2.30 (q, J=7.2 Hz, 2H), 3.36 (m, 4H), 3.60 (br, 1H), 3.92 (br, 1H), 4.92 (s, 2H), 6.74 (br, 1H), 6.83 (t, J=7.6 Hz, 1H), 6.92 (d, J=7.4 Hz, 1H), 7.46 (m, 4H), 7.80 (m, 1H), 8.10 (m, 1H), 8.71 (br, 1H).

LC/MS (M$^+$H): 596.33.

(2-23-4): t-Butyl (E)-3-(8-(hydroxyamino)-2-((naphthalen-1-yloxy)methyl)-8-oxo-2-octeneamido)pyrrolidine-1-carboxylate The procedure of Example (2-1-4) was repeated except for using the compound obtained in Example (2-23-3) as the starting material, to obtain 255 mg of the title compound (yield 95%).

HPLC purification: 5 mg (Purity: 96%)

$^1$H-NMR (300 MHz, MeOH-d$_4$) δ 1.29 (m, 2H), 1.42 (s, 9H), 1.62 (m, 2H), 1.89-2.09 (m, 4H), 2.33 (m, 2H), 3.20 (m, 2H), 3.57 (m, 2H), 4.41 (t, J=5.4 Hz, 1H), 5.48 (s, 2H), 6.52 (t, J=7.4 Hz, 1H), 7.00 (d, J=7.2 Hz, 2H), 7.40 (m, 4H), 7.79 (d, J=8.4 Hz, 1H), 8.10 (d, J=7.4 Hz, 1H).

LC/MS (M$^+$H): 512.27.

Example 2-24

(E)-N8-Hydroxy-2-((naphthalen-1-yloxy)methyl)-N1-(pyrrolidin-3-yl)-2-octenediamide (2-24-1): t-Butyl (E)-3-(8-methoxy-2-((naphthalen-1-yloxy)methyl)-8-oxo-2-octeneamido)pyrrolidine-1-carboxylate The procedure of Example (2-1-1) was repeated except for using t-butyl 3-aminopyrrolidine-1-carboxylate as the amine compound, to obtain 510 mg of the title compound (yield 83%).

$^1$H-NMR (300 MHz, CDCl$_3$) δ 1.33 (m, 2H), 1.39 (s, 9H), 1.60 (m, 2H), 2.15 (m, 2H), 2.31 (m, 4H), 3.36 (m, 4H), 3.62 (s, 3H), 4.93 (s, 2H), 6.66 (br, 1H), 6.90 (m, 2H), 7.38 (t, J=7.8 Hz, 2H), 7.49 (m, 2H), 7.80 (m, 1H), 8.10 (m, 1H).

LC/MS (M$^+$H): 511.27.

(2-24-2): (E)-8-(1-(t-Butoxycarbonyl)pyrrolidin-3-ylamino)-7-((naphthalen-1-yloxy)methyl)-8-oxo-6-octenoic acid The procedure of Example (2-1-2) was repeated except for using the compound obtained in Example (2-24-1) as the starting material, to obtain 423 mg of the title compound (yield 77%).

(2-24-3): t-Butyl (E)-3-(2-((naphthalen-1-yloxy)methyl)-8-oxo-8-(tetrahydro-2H-pyran-2-yloxyamino)-2-octeneamido)pyrrolidine-1-carboxylate The procedure of Example (2-4-3) was repeated except for using the compound obtained in Example (2-24-2) as the starting material, to obtain 320 mg of the title compound (yield 72%).

$^1$H-NMR (300 MHz, CDCl$_3$) δ 1.25 (m, 2H), 1.39 (s, 9H), 1.45 (m, 2H), 1.50-1.77 (m, 6H), 1.92 (m, 1H), 2.04 (m, 4H), 2.30 (q, J=7.2 Hz, 2H), 3.36 (m, 4H), 3.60 (br, 1H), 3.92 (br, 1H), 4.92 (s, 2H), 6.74 (br, 1H), 6.83 (t, J=7.6 Hz, 1H), 6.92 (d, J=7.4 Hz, 1H), 7.46 (m, 4H), 7.80 (m, 1H), 8.10 (m, 1H), 8.71 (br, 1H).

LC/MS (M$^+$H): 596.33.

(2-24-4): t-Butyl (E)-3-(8-(hydroxyamino)-2-((naphthalen-1-yloxy)methyl)-8-oxo-2-octeneamido)pyrrolidine-1-carboxylate The procedure of Example (2-4-4) was repeated except for using the compound obtained in Example (2-24-3) as the starting material, to obtain 255 mg of the title compound (yield 95%).

HPLC purification: 5 mg (Purity: 96%)

$^1$H-NMR (300 MHz, MeOH-d$_4$) δ 1.29 (m, 2H), 1.42 (s, 9H), 1.62 (m, 2H), 1.89-2.09 (m, 4H), 2.33 (m, 2H), 3.20 (m, 2H), 3.57 (m, 2H), 4.41 (t, J=5.4 Hz, 1H), 5.48 (s, 2H), 6.52 (t, J=7.4 Hz, 1H), 7.00 (d, J=7.2 Hz, 2H), 7.40 (m, 4H), 7.79 (d, J=8.4 Hz, 1H), 8.10 (d, J=7.4 Hz, 1H).

LC/MS (M$^+$H): 512.27.

(2-24-5): (E)-N8-Hydroxy-2-((naphthalen-1-yloxy)methyl)-N1-(pyrrolidin-3-yl)-2-octenediamide The procedure of Example (2-4-4) was repeated except for using the compound obtained in Example (2-24-4) as the starting material, to obtain 172 mg of the title compound (yield 92%).

HPLC purification: 58 mg (Purity: 96%)
¹H-NMR (300 MHz, MeOH-d₄) δ 1.46 (m, 2H), 1.58 (m, 2H), 2.04 (t, J=7.0 Hz, 2H), 2.34 (m, 4H), 3.22 (m, 2H), 3.44 (m, 2H), 4.43 (m, 1H), 4.97 (s, 2H), 6.55 (m, 1H), 6.95 (d, J=6.8 Hz, 1H), 7.38 (m, 4H), 7.73 (d, J=7.4 Hz, 1H), 8.08 (d, J=7.8 Hz, 1H).
LC/MS (M⁺H): 412.22.

Example 2-25

(E)-N1-(1-Cyclohexylpyrrolidin-3-yl)-N8-hydroxy-2-((naphthalen-2-yloxy)methyl)-2-octenediamide (2-25-1): Methyl (E)-8-(1-cyclohexylpyrrolidin-3-ylamino)-7-((naphthalen-2-yloxy)methyl)-8-oxo-6-octenoate The procedure of Example (2-1-1) was repeated except for using 1-cyclohexylpyrrolidin-3-ylamine obtained in Preparation Example (2-viii-3) as the amine compound, to obtain 492 mg of the title compound (yield 54%).
¹H-NMR (200 MHz, CDCl₃) δ 1.08-1.42 (m, 4H), 1.51-1.78 (m, 10H), 1.94 (m, 2H), 2.29 (m, 6H), 2.64 (d, J=5.4 Hz, 2H), 2.82 (m, 1H), 3.63 (s, 3H), 4.53 (m, 1H), 4.93 (s, 2H), 6.90 (m, 2H), 7.48 (m, 4H), 7.78 (m, 1H), 8.17 (d, J=7.2 Hz, 1H).
LC/MS (M⁺H): 493.30.

(2-25-2): (E)-8-(1-Cyclohexylpyrrolidin-3-ylamino)-7-((naphthalen-2-yloxy)methyl)-8-oxo-6-octenoic acid The procedure of Example (2-1-2) was repeated except for using the compound obtained in Example (2-25-1) as the starting material, to obtain 269 mg of the title compound (yield 100%).

(2-25-3): (E)-N1-(1-Cyclohexylpyrrolidin-3-yl)-2-((naphthalen-2-yloxy)methyl)-N8-(tetrahydro-2H-pyran-2-yloxy)-2-octenediamide The procedure of Example (2-1-3) was repeated except for using the compound obtained in Example (2-25-2) as the starting material, to obtain 269 mg of the title compound (yield 43%).
¹H-NMR (200 MHz, CDCl₃) δ 0.83 (m 4H), 1.13-1.42 (m, 6H), 1.56-1.89 (m, 12H), 2.16 (m, 6H), 2.32 (m, 2H), 2.77 (m, 1H), 3.62 (br, 1H), 3.94 (br, 1H), 4.61 (m, 1H), 4.80 (m, 1H), 4.94 (s, 2H), 6.82 (t, J=7.8 Hz, 1H), 6.91 (d, J=7.6 Hz, 2H), 7.44 (m, 4H), 7.82 (m, 1H), 8.16 (m, 1H).
LC/MS (M⁺H): 578.35.

(2-25-4): (E)-N1-(1-Cyclohexylpyrrolidin-3-yl)-N8-hydroxy-2-((naphthalen-2-yloxy)methyl)-2-octenediamide The procedure of Example (2-1-4) was repeated except for using the compound obtained in Example (2-25-3) as the starting material, to obtain 140 mg of the title compound (yield 88%).
HPLC purification: 16 mg (Purity: 97%)
¹H-NMR (300 MHz, MeOH-d₄) δ 1.24-1.34 (m, 8H), 1.47-1.65 (m, 6H), 1.77 (m, 1H), 1.98 (m, 2H), 2.05 (t, J=7.2 Hz, 2H), 2.11 (s, 2H), 2.34 (m, 2H), 2.76 (br, 1H), 4.41 (m, 1H), 4.99 (s, 2H), 6.59 (t, J=7.4 Hz, 2H), 6.98 (d, J=7.0 Hz, 1H), 7.39 (m, 4H), 7.74 (d, J=7.6 Hz, 1H), 8.07 (d, J=8.2 Hz, 1H).
LC/MS (M⁺H): 494.29.

Example 2-26

(E)-N1-(1-Cyclopropylpyrrolidin-3-yl)-N8-hydroxy-2-((naphthalen-1-yloxy)methyl)-2-octenediamide (2-26-1): Methyl (E)-8-(1-cyclopropylpyrrolidin-3-ylamino)-7-((naphthalen-2-yloxy)methyl)-8-oxo-6-octenoate The procedure of Example (2-1-1) was repeated except for using 1-cyclopropylpyrrolidin-3-ylamine obtained in Preparation Example (2-viii-2) as the amine compound, to obtain 450 mg of the title compound (yield 78%).
¹H-NMR (200 MHz, CDCl₃) δ 0.15 (m, 2H), 0.28 (m, 2H), 1.28-1.93 (m, 8H), 2.29 (m, 6H), 2.80 (m, 2H), 3.62 (s, 3H), 4.92 (s, 2H), 6.69 (d, J=7.8 Hz, 1H), 6.82 (m, 1H), 7.47 (m, 4H), 7.82 (m, 1H), 8.15 (m, 1H).
LC/MS (M⁺H): 451.25.

(2-26-2): (E)-8-(1-Cyclopropylpyrrolidin-3-ylamino)-7-((naphthalen-2-yloxy)methyl)-8-oxo-6-octenoic acid The procedure of Example (2-1-2) was repeated except for using the compound obtained in Example (2-26-1) as the starting material, to obtain 355 mg of the title compound (yield 98%).

(2-26-3): (E)-N1-(1-Cyclopropylpyrrolidin-3-yl)-2-(naphthalen-1-yloxy)methyl)-N8-(tetrahydro-2H-pyran-2-yloxy)-2-octenediamide The procedure of Example (2-1-3) was repeated except for using the compound obtained in Example (2-26-2) as the starting material, to obtain 334 mg of the title compound (yield 61%).
¹H-NMR (200 MHz, CDCl₃) δ 0.16 (m, 2H), 0.31 (m, 2H), 1.47-1.83 (m, 12H), 2.15 (m, 2H), 2.17 (s, 2H), 2.30 (m, 2H), 2.37 (m, 2H), 2.81 (m, 2H), 3.62 (br, 1H), 3.91 (br, 1H), 4.90 (m, 1H), 4.92 (s, 2H), 6.80 (t, J=7.8 Hz, 1H), 6.90 (d, J=7.6 Hz, 1H), 7.46 (m, 4H), 7.80 (m, 1H), 8.14 (m, 1H), 8.44 (br, 1H).
LC/MS (M⁺H): 536.30.

(2-26-4): (E)-N1-(1-Cyclopropylpyrrolidin-3-yl)-N8-hydroxy-2-((naphthalen-1-yloxy)methyl)-2-octenediamide The procedure of Example (2-1-4) was repeated except for using the compound obtained in Example (2-26-3) as the starting material, to obtain 154 mg of the title compound (yield 89%).
HPLC purification: 65 mg (Purity: 95%)
¹H-NMR (300 MHz, MeOH-d₄) δ 0.42 (m, 4H), 1.44 (q, J=7.4 Hz, 2H), 1.59 (m, 3H), 1.82 (br, 1H), 2.02 (t, J=7.2 Hz, 1H), 2.09 (s, 1H), 2.27 (m, 1H), 2.32 (q, J=7.2 Hz, 2H), 2.71 (m, 2H), 3.01 (m, 2H), 4.94 (s, 2H), 6.53 (t, J=7.4 Hz, 1H), 6.92 (d, J=7.2 Hz, 1H), 7.36 (m, 4H), 7.74 (d, J=7.8 Hz, 1H), 7.81 (s, 1H), 8.08 (d, J=7.8 Hz, 1H).

Example 2-27

(E)-N1-(1-Cyclopropylpiperidin-4-yl)-N8-hydroxy-2-((naphthalen-1-yloxy)methyl)-2-octenediamide (2-27-1): Methyl (E)-8-(1-cyclopropylpiperidin-4-ylamino)-7-((naphthalen-1-yloxy)methyl)-8-oxo-6-octenoate The procedure of Example (2-1-1) was repeated except for using 1-cyclopropylpiperidin-4-ylamine obtained in Preparation Example (2-iv-2) as the amine compound, to obtain 464 mg of the title compound (yield 47%).
$^1$H-NMR (200 MHz, CDCl$_3$) δ 0.33-0.40 (m, 4H), 1.24-1.73 (m, 9H), 1.88 (m, 2H), 2.17 (m, 1H), 2.29 (m, 6H), 3.62 (s, 3H), 3.92 (m, 1H), 4.91 (s, 2H), 6.35 (d, J=8.0 Hz, 1H), 6.90 (m, 2H), 7.48 (m, 4H), 7.80 (m, 1H), 8.12 (m, 1H).
LC/MS (M$^+$H): 465.27.

(2-27-2): (E)-8-(1-Cyclopropylpiperidin-4-ylamino)-7-((naphthalen-1-yloxy)methyl)-8-oxo-6-octenoic acid The procedure of Example (2-1-2) was repeated except for using the compound obtained in Example (2-27-1) as the starting material, to obtain 221 mg of the title compound (yield 100%).

(2-27-3): (E)-N1-(1-Cyclopropylpiperidin-4-yl)-2-((naphthalen-1-yloxy)methyl)-N8-(tetrahydro-2H-pyran-2-yloxy)-2-octenediamide The procedure of Example (2-1-3) was repeated except for using the compound obtained in Example (2-27-2) as the starting material, to obtain 221 mg of the title compound (yield 51%).
$^1$H-NMR (200 MHz, CDCl$_3$) δ 0.38 (m, 4H), 1.28-1.94 (m, 18H), 2.10 (m, 2H), 2.32 (m, 4H), 3.64 (m, 1H), 3.95 (m, 1H), 4.88 (m, 1H), 4.92 (s, 2H), 6.40 (d, J=8.2 Hz, 1H), 6.92 (m, 2H), 7.48 (m, 4H), 7.84 (m, 1H), 8.14 (m, 1H), 8.42 (br, 1H).
LC/MS (M$^+$H): 550.32.

(2-27-4): (E)-N1-(1-Cyclopropylpiperidin-4-yl)-N8-hydroxy-2-((naphthalen-1-yloxy)methyl)-2-octenediamide The procedure of Example (2-1-4) was repeated except for using the compound obtained in Example (2-27-3) as the starting material, to obtain 150 mg of the title compound (yield 90%).
HPLC purification: 107 mg (Purity: 95%)
$^1$H-NMR (300 MHz, MeOH-d$_4$) δ 0.89 (m, 4H), 1.25 (m, 4H), 1.46 (m, 2H), 1.62 (m, 2H), 2.04 (t, J=7.2 Hz, 2H), 2.10 (m, 2H), 2.33 (q, J=7.4, 2H), 2.73 (m, 1H), 3.59 (m, 2H), 3.99 (m, 1H), 4.98 (s, 2H), 6.49 (m, 1H), 6.94 (d, J=7.2 Hz, 1H), 7.36 (m, 4H), 7.73 (d, J=7.8 Hz, 1H), 8.06 (d, J=7.8 Hz, 1H).
LC/MS (M$^+$H): 466.26.

Example 2-28

(E)-N1-(1-Ethylpiperidin-4-yl)-N8-hydroxy-2-((naphthalen-1-yloxy)methyl)-2-octenediamide (2-28-1): Methyl (E)-8-(1-ethylpiperidin-4-ylamino)-7-((naphthalen-1-yloxy)methyl)-8-oxo-6-octenoate The procedure of Example (2-1-1) was repeated except for using 1-ethylpiperidin-4-ylamine obtained in Preparation Example (2-iv-5) as the amine compound, to obtain 452 mg of the title compound (yield 62%).
$^1$H-NMR (200 MHz, CDCl$_3$) δ 1.02 (t, J=7.4, 3H), 1.26-1.74 (m, 8H), 1.92-2.17 (m, 4H), 2.32 (m, 4H), 2.72 (m, 2H), 3.63 (s, 3H), 4.92 (s, 2H), 6.38 (d, J=8.0 Hz, 1H), 6.80 (t, J=7.8 Hz, 1H), 6.90 (d, J=7.6 Hz, 1H), 7.48 (m, 4H), 7.82 (m, 1H), 8.14 (m, 1H).
LC/MS (M$^+$H): 453.27.

(2-28-2): (E)-8-(1-Ethylpiperidin-4-ylamino)-7-((naphthalen-1-yloxy)methyl)-8-oxo-6-octenoic acid The procedure of Example (2-1-2) was repeated except for using the compound obtained in Example (2-28-1) as the starting material, to obtain 279 mg of the title compound (yield 100%).

(2-28-3): (E)-N1-(1-Ethylpiperidin-4-yl)-2-((naphthalen-1-yloxy)methyl)-N8-(tetrahydro-2H-pyran-2-yloxy)-2-octenediamide The procedure of Example (2-1-3) was repeated except for using the compound obtained in Example (2-28-2) as the starting material, to obtain 279 mg of the title compound (yield 80%).
$^1$H-NMR (200 MHz, CDCl$_3$) δ 0.84 (m, 2H), 1.05 (t, J=7.4 Hz, 3H), 1.27 (m, 2H), 1.44-1.79 (m, 10H), 1.94-2.26 (m, 4H), 2.35 (m, 4H), 2.90 (m, 2H), 3.62 (m, 1H), 3.93 (m, 1H), 4.94 (s, 2H), 4.97 (m, 1H), 6.46 (d, J=7.8 Hz, 1H), 6.84 (t, J=7.8 Hz, 1H), 6.92 (d, J=7.0 Hz, 1H), 7.48 (m, 4H), 7.82 (m, 1H), 8.14 (m, 1H), 8.43 (br, 1H).
LC/MS (M$^+$H): 538.32.

(2-28-4): (E)-N1-(1-Ethylpiperidin-4-yl)-N8-hydroxy-2-((naphthalen-1-yloxy)methyl)-2-octenediamide The procedure of Example (2-1-4) was repeated except for using the compound obtained in Example (2-28-3) as the starting material, to obtain 146 mg of the title compound (yield 94%).
HPLC purification: 114 mg (Purity: 95%)
$^1$H-NMR (300 MHz, MeOH-d$_4$) δ 1.24 (t, J=7.2 Hz, 3H), 1.45-1.81 (m, 7H), 1.93-2.10 (m, 5H), 2.32 (q, J=7.2 Hz, 2H), 2.98 (m, 2H), 3.09 (q, J=7.2 Hz, 2H), 3.51 (m, 1H), 4.97 (s, 2H), 6.46 (t, J=7.6 Hz, 1H), 6.94 (d, J=7.0 Hz, 1H), 7.38 (m, 4H), 7.72 (d, J=7.6 Hz, 1H), 8.05 (d, J=7.8 Hz, 1H).
LC/MS (M$^+$H): 454.26.

Example 2-29

(E)-N1-(1-Ethylpyrrolidin-3-yl)-N8-hydroxy-2-((naphthalen-1-yloxy)methyl)-2-octenediamide (2-29-1): Methyl (E)-8-(1-ethylpyrrolidin-3-ylamino)-7-((naphthalen-1-yloxy)methyl)-8-oxo-6-octenoate The procedure of Example (2-1-1) was repeated except for using 1-ethylpyrrolidin-3-ylamine obtained in Preparation Example (2-viii-4) as the amine compound, to obtain 438 mg of the title compound (yield 52%).
$^1$H-NMR (200 MHz, CDCl$_3$) δ 0.99 (t, J=7.2 Hz, 3H), 1.26-1.73 (m, 6H), 2.16-2.47 (m, 8H), 2.60 (m, 2H), 2.80 (m, 1H), 3.63 (s, 3H), 4.95 (s, 2H), 6.81 (t, J=7.6 Hz, 1H), 6.90 (d, J=7.4 Hz, 1H), 7.46 (m, 4H), 7.79 (m, 1H), 8.16 (m, 1H).
LC/MS (M$^+$H): 469.30.

(2-29-2): (E)-8-(1-Ethylpyrrolidin-3-ylamino)-7-((naphthalen-1-yloxy)methyl)-8-oxo-6-octenoic acid The procedure of Example (2-1-2) was repeated except for using the compound obtained in Example (2-29-1) as the starting material, to obtain 224 mg of the title compound (yield 100%).

(2-29-3): (E)-N1-(1-Ethylpyrrolidin-3-yl)-2-((naphthalen-1-yloxy)methyl)-N8-(tetrahydro-2H-pyran-2-yloxy)-2-octenediamide The procedure of Example (2-1-3) was repeated except for using the compound obtained in Example (2-29-2) as the starting material, to obtain 224 mg of the title compound (yield 69%).

$^1$H-NMR (200 MHz, CDCl$_3$) δ 0.82 (m, 2H), 1.06 (t, J=7.4 Hz, 3H), 1.24 (m, 4H), 1.41-2.20 (m, 8H), 2.31 (m, 4H), 2.51 (m, 3H), 2.57 (m, 1H), 2.62 (m, 1H), 3.61 (br, 1H), 3.92 (br, 1H), 4.91 (m, 1H), 4.94 (s, 2H), 6.79 (t, J=7.8 Hz, 1H), 6.94 (d, J=7.0 Hz, 1H), 7.44 (m, 4H), 7.82 (m, 1H), 8.20 (m, 1H).

LC/MS (M$^+$H): 524.30.

(2-29-4): (E)-N1-(1-Ethylpyrrolidin-3-yl)-N8-hydroxy-2-((naphthalen-1-yloxy)methyl)-2-octenediamide The procedure of Example (2-1-4) was repeated except for using the compound obtained in Example (2-29-3) as the starting material, to obtain 184 mg of the title compound (yield 91%).

HPLC purification: 128 mg (Purity: 96%)

$^1$H-NMR (300 MHz, MeOH-d$_4$) δ 1.22 (m, 4H), 1.46-1.62 (m, 6H), 1.79 (m, 1H), 2.03 (m, 3H), 2.33 (m, 6H), 4.97 (s, 2H), 6.54 (m, 1H), 6.94 (d, J=6.4 Hz, 1H), 7.38 (m, 4H), 7.73 (d, J=7.8 Hz, 1H), 8.04 (d, J=8.2 Hz, 1H).

LC/MS (M$^+$H): 440.25.

Example 2-30

(E)-N8-Hydroxy-N1-(1-isopropylpiperidin-4-yl)-2-((naphthalen-1-yloxy)methyl)-2-octenediamide (2-30-1): Methyl (E)-8-(1-isopropylpiperidin-4-ylamino)-7-((naphthalen-1-yloxy)methyl)-8-oxo-6-octenoate The procedure of Example (2-1-1) was repeated except for using 1-isopropylpiperidin-4-ylamine obtained in Preparation Example (2-iv-1) as the amine compound, to obtain 283 mg of the title compound (yield 42%).

$^1$H-NMR (200 MHz, CDCl$_3$) δ 1.03 (d, J=6.4 Hz, 6H), 1.45-1.78 (m, 6H), 1.98 (m, 2H), 2.35 (m, 6H), 2.79 (m, 3H), 3.64 (s, 3H), 3.92 (m, 1H), 4.94 (s, 2H), 6.45 (d, J=8.2 Hz, 1H), 6.84 (t, J=7.8 Hz, 1H), 6.92 (d, J=7.8 Hz, 1H), 7.31-7.58 (m, 4H), 7.81 (m, 1H), 8.14 (m, 1H).

LC/MS (M$^+$H): 467.

(2-30-2): (E)-8-(1-Isopropylpiperidin-4-ylamino)-7-((naphthalen-1-yloxy)methyl)-8-oxo-6-octenoic acid The procedure of Example (2-1-2) was repeated except for using the compound obtained in Example (2-30-1) as the starting material, to obtain 278 mg of the title compound (yield 100%).

LC/MS (M$^+$H): 453.

(2-30-3): (E)-N1-(1-Isopropylpiperidin-4-yl)-2-((naphthalen-1-yloxy)methyl)-N8-(tetrahydro-2H-pyran-2-yloxy)-2-octenediamide The procedure of Example (2-1-3) was repeated except for using the compound obtained in Example (2-30-2) as the starting material, to obtain 350 mg of the title compound (yield 100%).

$^1$H-NMR (200 MHz, CDCl$_3$) δ 0.94 (d, J=6.4 Hz, 6H), 1.38-1.84 (m, 12H), 1.85-2.19 (m, 4H), 2.26 (m, 5H), 2.70 (m, 3H), 3.55 (m, 1H), 3.90 (m, 2H), 4.76 (m, 1H), 4.90 (s, 2H), 6.42 (d, J=8.0 Hz, 1H), 6.82 (t, J=7.4 Hz, 1H), 6.89 (d, J=7.4 Hz, 1H), 7.45 (m, 4H), 7.80 (m, 1H), 8.01 (s, 1H), 8.14 (m, 1H).

LC/MS (M$^+$H): 552.

(2-30-4): (E)-N8-Hydroxy-N1-(1-isopropylpiperidin-4-yl)-2-((naphthalen-1-yloxy)methyl)-2-octenediamide The procedure of Example (2-1-4) was repeated except for using the compound obtained in Example (2-30-3) as the starting material, to obtain 168 mg of the title compound (yield 57%).

HPLC purification: 78 mg (Purity: 94%)

$^1$H-NMR (300 MHz, MeOH-d$_4$) δ 1.32 (d, J=6.2 Hz, 6H), 1.43-1.92 (m, 6H), 2.09-2.34 (m, 4H), 2.43 (m, 2H), 3.17 (m, 2H), 3.47 (m, 3H), 4.03 (m, 1H), 5.05 (s, 2H), 6.56 (t, J=7.4 Hz, 1H), 7.04 (m, 1H), 7.44 (m, 4H), 7.80 (m, 1H), 8.13 (m, 1H).

LC/MS (M$^+$H): 468.

Test Example 2-1

Analysis of Inhibitory Activity Against HDAC

HDAC activity was analyzed using BIOMOL Quantizyme™ Assay system which comprised two steps of 1) enzyme reaction between HDAC and a substrate and 2) determination of the level of HDAC inhibitory activity.

In step 1), 42 µl of a buffer solution (25 mM Tris-HCl [pH 8.0], 137 mM NaCl, 2.7 mM KCl, 1 mM MgCl$_2$) and 5 µl of 250 µM Fluor de Lys™ substrate were added to each well of a 96-well plate, to which 2.5 µl of a test compound (compounds of Examples 2-1 to 2-30) at a concentration of 0.01, 0.1, 1, 10 and 100 µM, respectively, was added. 0.5 µl of HeLa nuclear organic layer (10 µM) (a source of HDAC enzymes) was then added thereto to a final concentration of 100 nM, The enzyme reaction was carried out for 1 hr.

Subsequently, in step 2), 2 µM tricostatin A was added to 50 µl of Flour de Lys™ developer, followed by allowing the mixture to react at room temperature for 15 minutes. The light excited at 355 nm and emitted at 460 nm from the fluorophore was measured with a fluorometric plate reader. The intensity of the fluorescence increases as the enzyme activity is higher. The HDAC inhibitory activity of each of the test compounds was determined and compared with that of the control. And suberoylanilide hydroxamic acid (SAHA) (Biomol) was used at the same level with the test compounds as a comparative control.

The HDAC inhibitory concentrations (IC$_{50}$) of the test compounds of Examples 2-1 to 2-30 are shown in Table 3.

TABLE 3

| Compound | IC$_{50}$(μM) |
| --- | --- |
| Example 2-1 | 0.023 |
| Example 2-2 | 0.009 |
| Example 2-3 | 0.021 |
| Example 2-4 | 0.009 |
| Example 2-5 | 0.017 |
| Example 2-6 | 0.005 |
| Example 2-7 | 0.020 |
| Example 2-8 | 0.014 |
| Example 2-9 | 0.027 |
| Example 2-10 | 0.016 |
| Example 2-11 | 0.006 |
| Example 2-12 | 0.006 |
| Example 2-13 | 0.024 |
| Example 2-15 | 0.008 |
| Example 2-16 | 0.017 |
| Example 2-17 | 0.007 |
| Example 2-18 | 0.010 |
| Example 2-19 | 0.013 |
| Example 2-20 | 0.007 |
| Example 2-21 | 0.012 |
| Example 2-22 | 0.022 |
| Example 2-24 | 0.012 |
| Example 2-25 | 0.010 |
| Example 2-26 | 0.011 |
| Example 2-27 | 0.016 |
| Example 2-28 | 0.013 |
| Example 2-29 | 0.010 |
| Example 2-30 | 0.015 |
| SAHA | 0.110 |

As shown in Table 3, each of the inventive naphthalenyloxypropenyl derivatives of formula (2) has an inhibitory activity against HDAC, which is comparable to or markedly higher than that of SAHA known as a HDAC inhibitor.

Test Example 2-2

Analysis of Inhibitory Activity Against Proliferation of Cancer Cells

Inhibitory activities of naphthalenyloxypropenyl derivatives synthesized in Examples 2-1 to 2-30 against proliferation of cancer cells were examined by SRB (Sulforhodamine B) analysis using cervix adenocarcinoma Hela (Korean Cell. Line Bank, KCLB 10002) and colon cancer cells HCT116 (Korean Cell Line Bank, KCLB 10247) as follows:

Cancer cells were inoculated into a 96-well microplate at a concentration of $1 \times 10^3 \sim 3 \times 10^3$ cells/well and incubated under the condition of 37° C., 5% CO$_2$ for 24 hrs. After the incubation was completed, 0.2, 1, 5, 25, or 100 μM of each of the compounds of Examples was added to the plate, and then the reactant was incubated for 48 hrs. After the substrate was stained with SRB, the anti-cancer activity was determined by comparing the amount of protein in the cells treated with the compound of Examples with that of protein in untreated cells.

Specifically, after the incubation was completed, the culture medium was removed from each well, and the cells were washed 3 times with PBS (pH 7.4). Then, a solution of 50% trichloroacetic acid (TCA) was added to each well in an amount of 50 μl/well at 4° C. for 1 hr to fix them. Then, the microplate was washed 5 times with distilled water and dried in air.

50 μl of a staining solution prepared by dissolving 0.4% SRB in 1% acetic acid was added to the wells, and the microplate was kept at room temperature for 1 hr. The well plate was then washed 5 times with 1% acetic acid to remove unbound SRB and dried in air. The stained cells were treated with 150 μl/well of 10 mM Tris-HCl solution (pH 10.5) to elute SRB from the cells, and the absorbance of the cells treated with the compounds of examples at 540 nm was measured, based on the absorbance of an untreated cell. The EC$_{50}$ value representing inhibition of the cancer cell growth by the extent of 50% was calculated from the measured absorbance, and the results are shown in Table 4.

When cancer cells were treated with a HDAC inhibitor, histone deacetylation would be inhibited, leading to an increase in the amount of acetyl-histone. In this test, the increased amount of acetyl-histone in the cancer cells was determined by using Western blotting, after the treatment with each of the compounds of Examples.

The cells to be tested were inoculated into a 6-well microplate at a concentration of $1.5 \times 10^8$ cells/well and incubated overnight under the condition of 37° C., 5% CO$_2$. 10 μM of each compound of Examples, and suberoylanilide hydroxamic acid (SAHA) as a control was added to the plate and the plate was incubated again for 24 hrs.

The cells cultured in the presence of the test compound were harvested and subjected to fractionation to separate the nuclei from the cells. The cells were allowed to swell in a hypotonic solution, lysed by several rounds of freezing-thawing cycles, and then centrifuged of 1,300 rpm for 5 min to collect the nuclei. The nuclei was lysed in a lysis buffer solution (20 mM HEPES (pH 7.9), 25% glycerol, 420 mM KCl, 1.5 mM MgCl$_2$, 0.2 mM EDTA) to obtain a protein extract. In order to conduct Western blotting, the resulting protein organic layer was subjected to SDS-PAGE to separate the proteins by the size and transferred onto the nitrocellulose membrane according to the conventional method. The amount of acetylated histone H4 was measured using anti-acetyl histone H4 antibody (Upstate, USA) and evaluated the HDAC inhibitory activity of the inventive compounds by comparing the degree of increase of acetylated histone H4 relative to the control (SAHA). The results are shown in Table 4.

TABLE 4

| Compound | Inhibitory conc. against cancer cell growth (EC$_{50}$ μM) HCT116 | Effect on increase of acetyl-Histone H4 compared with SAHA |
| --- | --- | --- |
| Example 2-6 | 0.80 | + |
| Example 2-8 | 0.70 | + |
| Example 2-11 | 0.60 | + |
| Example 2-12 | 0.50 | + |
| Example 2-13 | 0.60 | + |
| Example 2-14 | 0.80 | + |
| Example 2-15 | 0.40 | + |
| Example 2-16 | 0.70 | + |
| Example 2-19 | 0.80 | + |
| Example 2-20 | 0.90 | + |
| Example 2-21 | 1.00 | + |
| Example 2-25 | 0.50 | + |
| Example 2-26 | <0.2 | + |
| Example 2-27 | 0.32 | + |
| Example 2-29 | 0.90 | + |
| Example 2-30 | 0.70 | + |
| SAHA | 1.60 | + |

As shown in Table 4, the inventive naphthalenyloxypropenyl derivatives of formula (2) has a markedly enhanced inhibitory activity against HDAC, which leads to effective suppression of the cancer cell proliferation.

Preparation of Naphthalenyloxypropenyl Derivatives of Formula (3)

Preparation Example 3-1

Methyl 6-hydroxy-hexanoate

ε-Caprolactone (12.50 g, 109.51 mM) was dissolved in methanol (125 ml), and a sulfuric acid solution (1 ml, 0.01 mM) was slowly added thereto. The resulting mixture was stirred at room temperature for 2 days. After the completion of reaction, methanol was removed under reduced pressure, and then ice water was poured into the residue. The resulting mixture was extracted with ethyl ether. The organic layer was separated, washed with an aqueous saturated sodium bicarbonate solution and brine in order and concentrated under reduced pressure. The residue thus obtained was subjected to a silica gel column chromatography (eluent: ethyl acetate/n-hexane=1/2) to obtain 10.18 g of the title compound (yield 64%).

$^1$H-NMR (200 MHz, CDCl$_3$) δ 1.23 (m, 2H, CH$_2$), 1.33~1.42 (m, 4H, CH$_2$CH$_2$), 1.44~1.74 (t, 4H, CH$_2$CH$_2$), 3.66 (s, 3H, OCH$_3$).

Preparation Example 3-2

Preparation of methyl 6-oxo-hexanoate (the Compound of Formula X)

Pyridinium chlorochromate (16.27 g, 75.48 mM) was dissolved in dichloromethane (140 ml), and a solution of methyl 6-hydroxy-hexanoate (10.03 g, 68.61 mM) obtained in Preparation Example 3-1 dissolved in dichloromethane (20 ml) was added dropwise thereto for 30 min. The resulting mixture was stirred at 25~30° C. for 2 hrs. After the completion of reaction, the reaction mixture was diluted with ethyl ether, filtered and concentrated under reduced pressure. The residue thus obtained was subjected to a silica gel column chromatography (eluent: ethyl acetate/n-hexane=1/4) to obtain 5.77 g of the title compound (yield 59%).

$^1$H-NMR (200 MHz, CDCl$_3$) δ 1.66 (m, 4H, CH$_2$CH$_2$), 2.33 (m, 2H, CH$_2$), 2.46 (m, 2H, CH$_2$), 3.66 (s, 3H, OCH$_3$), 9.74 (S, 1H, CH).

Preparation Example 3-3

Preparation of 1-t-butyl-9-methyl-3-hydroxy-2-methylene-dinonanoate (the Compound of Formula XI)

Methyl 6-oxo-hexanoate (20 g, 168.72 mM) obtained in Preparation Example 3-2 was dissolved in a mixture of water and dioxane (1:1) (100 ml), and t-butyl acrylate (60.96 ml, 461.17 mM) was added thereto. To the resulting mixture, a solution of 1,4-diazabicyclo[2.2.2]octane (DABCO) (15.56 g, 138.72 mM) dissolved in a mixture of water and dioxane (1:1) (63 ml) was slowly added. The resulting mixture was stirred at 0~25° C. for 7 days. After the completion of reaction, ice water was poured to the reaction mixture, and the resulting mixture was extracted with ethyl ether. The organic layer was separated, washed with 2N hydrochloric acid, an aqueous saturated sodium bicarbonate solution and brine in order, dried and concentrated under reduced pressure. The residue thus obtained was subjected to a silica gel column chromatography (eluent: ethyl acetate/n-hexane=1/9), to obtain 21.7 g of the title compound (yield 57%).

$^1$H-NMR (200 MHz, CDCl$_3$) δ 1.46 (m, 2H, CH$_2$), 1.47 (S, 9H, 3CH$_3$), 1.62 (m, 4H, CH$_2$CH$_2$), 2.96 (m, 4H, CH$_2$CH$_2$), 3.64 (s, 3H, OCH$_3$), 5.67 (s, 1H, CH), 6.09 (s, 1H, CH).

Preparation Example 3-4

Preparation of 1-t-butyl-8-methyl-2-bromomethyl-2-dioctenoate (the Compound of Formula XII)

1-t-Butyl-9-methyl-3-hydroxy-2-methylene-dinonanoate (10.40 g, 38.20 mM) obtained in Preparation Example 3-3 was dissolved in ethyl ether (100 ml), and cooled to 0° C. To the resulting mixture, PBr$_3$ (3.93 ml, 42.02 mM) was slowly added and stirred at room temperature for 1 hr. After the completion of reaction, the reaction mixture was cooled to −10° C. by pouring ice water thereto. The resulting mixture was extracted with ethyl ether. The organic layer was separated, washed with brine, dried over MgSO$_4$ and filtered. Then, the solvent was removed under reduced pressure, and the residue thus obtained was subjected to a silica gel column chromatography (eluent: ethyl acetate/n-hexane=1/9), to obtain 6.30 g of the title compound (yield 49%).

$^1$H-NMR (200 MHz, CDCl$_3$) δ 1.50 (s, 9H, CH$_3$), 1.65 (m, 4H, CH$_2$), 2.30 (m, 4H, CH$_2$), 3.66 (s, 3H, OCH$_3$), 4.27 (s, 2H, CH$_2$), 6.82 (m, 1H, CH).

Preparation Example 3-5

Preparation of 1-t-butyl-8-methyl-2-(naphthalen-1-yloxymethyl)-2-dioctenoate (the Compound of Formula XIII)

1-t-Butyl-8-methyl-2-bromomethyl-2-dioctenoate (11.2 g 33.41 mM) obtained in Preparation Example 3-4 was dissolved in acetone (50 ml), and potassium carbonate (6.93 g 50.11 mM) and 1-naphthalenol (5.30 g 36.75 mM) were added thereto. The resulting mixture was heated to reflux for 3 hrs. After the completion of reaction, the solvent was removed under reduced pressure at room temperature. The residue thus obtained was subjected to a silica gel column chromatography (eluent: ethyl acetate/n-hexane=1/15) to obtain 11.5 g of the title compound as a white solid (yield 86%).

$^1$H-NMR (200 MHz, CDCl$_3$) δ 1.45 (s, 9H, CH$_3$), 1.65 (m, 4H, CH$_2$), 2.30 (m, 4H, CH$_2$), 3.62 (s, 3H, OCH$_3$), 4.80 (s, 2H, CH$_2$), 6.64 (m, 1H, ArH), 6.98 (m, 1H, CH), 7.40 (m, 4H, ArH), 7.77 (m, 1H, ArH), 8.19 (m, 1H, ArH).

Preparation Example 3-6

Preparation of (Z)-methyl-8-hydroxy-7-((naphthalen-1-yloxy)methyl)oct-6-enoate (the Compound of Formula XVIII)

Step 1: Preparation of 8-methyl-2-(naphthalen-1-yloxymethyl)-2-dioctenoate 1-t-Butyl-8-methyl-2-(naphthalen-1-yloxymethyl)-2-dioctenoate (5.00 g, 12.55 mM) obtained in Preparation Example 3-5 was dissolved in dichloromethane (60 ml), and trifluoroacetic acid (6.77 ml, 87.83 mM) was slowly added thereto at 0° C. The resulting mixture was reacted at room temperature for 7 hrs. After the completion of reaction, the solvent was removed under reduced pressure at room temperature. The residue thus obtained was subjected to a silica gel column chromatography (eluent: ethyl acetate/n-hexane=1/4) to obtain 2.08 g of the title compound (yield 48%).

$^1$H-NMR (200 MHz, CDCl$_3$) δ 1.46 (m, 2H, CH$_2$), 1.59 (m, 2H, CH$_2$), 2.26 (t, 2H, J=7.1 Hz, CH$_2$), 2.43 (q, 2H, J=14.9, 7.5 Hz, CH$_2$), 3.62 (s, 3H, OCH$_3$), 4.94 (s, 2H, CH$_2$), 6.89 (d, 1H, J=7.3 Hz, CH), 7.27~7.47 (m, 5H, ArH), 7.80 (dd, 1H, J=7.3, 1.7 Hz, ArH), 8.20 (t, 1H, J=7.1, 1.7 Hz, ArH).

Step 2: Preparation of (Z)-methyl-8-hydroxy-7-((naphthalen-1-yloxy)methyl)oct-6-enoate 8-Methyl-2-(naphthalen-1-yloxymethyl)-2-dioctenoate (2 g, 5.02 mM) obtained in the step 1 of Preparation Example 3-6 was dissolved in tetrahydrofuran (30 ml), and cooled to 0° C. To the resulting mixture, triethylamine (1.05 ml, 7.53 mM) and ethylchloroformate (0.72 ml, 7.53 mM) was slowly added dropwise and stirred for 1 hr. To the reaction mixture, sodium borohydride (1.264 g, 20.08 mM) and distilled water (10 ml) were added in order, and stirred at room temperature for 2.5 hrs. Then, the reaction mixture was acidified (pH 2) with 1N hydrochloric acid and extracted with ethyl acetate. The organic layer was separated, washed with an aqueous saturated sodium bicarbonate solution and brine in order, dried over anhydrous magnesium sulfate, and filtered. The residue thus obtained was subjected to a silica gel column chromatography to obtain 1.00 g of the title compound as pale yellow oil (yield 61%).

$^1$H-NMR (200 MHz, CDCl$_3$) δ 1.45 (m, 2H), 1.64 (m, 2H), 2.22 (m, 2H), 2.28 (m, 2H), 3.65 (s, 3H), 4.15 (s, 2H), 4.84 (s, 2H), 5.77 (t, J=7.2 Hz, 1H), 6.85 (d, J=7.2 Hz, 1H), 7.39 (m, 4H), 7.77 (m, 1H), 8.19 (m, 1H).

Preparation Example 3-8

Preparation of (E)-methyl-8-bromo-7-((naphthalen-1-yloxy)methyl)oct-6-enoate (the Compound of Formula XIX)

(Z)-Methyl-8-hydroxy-7-((naphthalen-1-yloxy)methyl) oct-6-enoate (2 g, 6.0 mM) obtained in Preparation Example 3-7 was dissolved in dichloromethane (25 ml), and triphenylphosphine (1.73 g, 6.6 mM) was added thereto. Then, the resulting mixture was cooled to 0° C. To the mixture, tetrabromomethane (2.19 g, 6.6 mM) was added and stirred for 6 hrs. After the solvent was removed under reduced pressure, the residue thus obtained was subjected to a silica gel column chromatography to obtain 1.81 g of the title compound as a white solid (yield 77%).

$^1$H-NMR (200 MHz, CDCl$_3$) 1.43 (m, 2H), 1.65 (m, 2H), 2.20 (m, 2H), 2.26 (m, 2H), 3.66 (s, 3H), 3.86 (s, 2H), 4.81 (s, 2H), 5.76 (t, J=7.2 Hz, 1H), 6.83 (d, J=7.2 Hz, 1H), 7.36 (m, 4H), 7.76 (m, 1H), 8.15 (m, 1H).

Example 3-1

Preparation of (Z)—N-hydroxy-8-(2-morpholinoethylamino)-7-((naphthalen-1-yloxy)methyl)oct-6-enamide (the Compound of Formula (3))

(3-1-1): Preparation of (Z)-methyl-8-(2-morpholinoethylamino)-7-((naphthalen-1-yloxy)-methyl)oct-6-enoate (the Compound of Formula XX)

(E)-Methyl-8-bromo-7-((naphthalen-1-yloxy)-methyl) oct-6-enoate (500 mg, 1.28 mmol) obtained in Preparation Example 3-8 was dissolved in acetonitrile (5 ml) in a 25 ml vessel at 0° C., and triethylamine (0.21 ml, 1.54 mmol, 1.2 eq.) and 2-morpholinoethylamine (0.20 ml, 1.54 mmol, 1.2 eq.) were added thereto. The resulting mixture was heated to room temperature and reacted for 4 hrs. After the completion of reaction, the solvent was distilled under reduced pressure. Then, the resultant was extracted with ethyl ester. The organic layer was separated, washed with an aqueous saturated sodium bicarbonate solution and brine in order, dried over anhydrous magnesium sulfate, and concentrated under reduced pressure. The residue thus obtained was subjected to a silica gel column chromatography to obtain 278 mg of the title compound as pale yellow oil (yield 49%).

$^1$H-NMR (200 MHz, CDCl$_3$) δ 1.49 (m, 2H), 1.65 (m, 2H), 2.33 (m, 4H), 2.41 (m, 4H), 2.51 (t, J=6.0 Hz, 2H), 2.73 (t, J=6.0 Hz, 2H), 3.50 (s, 2H), 3.55 (m, 4H), 3.66 (s, 3H), 4.79 (s, 2H), 5.73 (t, J=7.2 Hz, 1H), 6.88 (d, J=7.0 Hz, 1H), 7.45 (t, J=7.2 Hz, 1H), 7.80 (m, 1H), 8.23 (m, 1H)

LC/MS (M$^+$H): 441.

(3-1-2): Preparation of (Z)-8-(2-Morpholinoethylamino)-7-((naphthalen-1-yloxy)methyl)oct-6-enoic acid (the Compound of Formula XXI)

(Z)-Methyl-8-(2-morpholinoethylamino)-7-((naphthalen-1-yloxy)-methyl)oct-6-enoate (278 mg, 0.63 mmol) obtained in Example (3-1-1) was dissolved in tetrahydrofuran (2.52 ml) in a 25 ml vessel and stirred. To the resulting mixture, a solution of lithium hydroxide monohydrate (LiOH.H$_2$O) (79 mg, 1.89 mmol, 3 eq.) dissolved in water (0.63 ml) was added and stirred at room temperature for 12 hrs. After the completion of reaction, the aqueous layer was washed with ethyl ester and acidified (pH 4) with 6N hydrochloric acid. The resultant was distilled under reduced pressure and extracted with ethyl acetate twice. The organic layer was separated, washed with brine, dried over anhydrous sodium sulfate and filtered. The solvent was removed under reduced pressure. The residue thus obtained was purified with a silica gel column chromatography to obtain 268 mg of the title compound as pale yellow foam (100%).

$^1$H-NMR (200 MHz, CD$_3$OD) δ 1.62 (m, 4H), 2.32 (m, 4H), 2.58 (m, 4H), 2.82 (m, 2H), 3.49 (m, 4H), 3.75 (m, 2H), 3.98 (s, 2H), 4.91 (s, 2H), 6.18 (t, J=7.8 Hz, 1H), 7.06 (d, J=7.2 Hz, 1H), 7.45 (m, 4H), 7.84 (m, 1H), 8.21 (m, 1H)

LC/MS (M$^+$H): 427.

(3-1-3): Preparation of (Z)-8-(2-morpholinoethylamino)-7-((naphthalen-1-yloxy)methyl)-N-(tetrahydro-2H-pyran-2-yloxy)oct-6-enamide (the Compound of Formula XXII)

(Z)-8-(2-morpholinoethylamino)-7-((naphthalen-1-yloxy)methyl)oct-6-enoic acid (268 mg, 0.63 mmol) obtained in Example (3-1-2) was dissolved in N,N'-dimethylformal (3.2 ml) in a 25 ml vessel, and to the resulting mixture, N-hydroxy-6-trifluorobenzotriazole (FOBt; 140 mg, 0.69 mmol, 1.1 eq.), 1-ethyl-3-(3-dimethylaminopropyl) carbodiimide hydrochloride (EDC.HCl; 157 mg, 0.82 mmol, 1.3 eq.), tetrahydro-2H-pyran-2-yloxyamine (THPONH$_2$; 111 mg, 0.95 mmol, 1.5 eq.), and triethylamine (0.18 ml, 1.26 mmol, 1.5 eq.) were added at 0° C., while stirring. The resulting mixture was heated to room temperature and stirred for 12 hrs. After the completion of reaction, 10% aqueous potassium carbonate solution was added to the reaction mixture, and then the resultant was extracted with ethyl acetate. The organic layer was separated, washed with an aqueous saturated sodium bicarbonate solution and brine in order, dried over anhydrous magnesium sulfate, and concentrated under reduced pressure. The residue thus obtained was subjected to a silica gel column chromatography to obtain 142 mg of the title compound as dark yellow foam (yield 43%).

$^1$H-NMR (200 MHz, CDCl$_3$) δ 1.53 (m, 6H), 1.67 (m, 4H), 2.21 (m, 4H), 2.36 (m, 4H), 2.51 (t, J=6.4 Hz, 2H), 2.78 (t, J=6.2 Hz, 2H), 3.46 (m, 4H), 3.51 (s, 2H), 3.62 (m, 1H), 3.98 (m, 1H), 4.77 (s, 2H), 4.92 (br, 1H), 5.77 (t, J=7.2 Hz, 1H), 6.80 (d, J=7.0 Hz, 1H), 7.47 (m, 4H), 7.78 (m, 1H), 8.18 (m, 1H)

LC/MS (M$^+$H): 526.

(3-1-4): Preparation of (Z)—N-hydroxy-8-(2-morpholinoethylamino)-7-((naphthalen-1-yloxy)methyl) oct-6-enamide (the Compound of Formula (3))

(Z)-8-(2-morpholinoethylamino)-7-((naphthalen-1-yloxy)methyl)-N-(tetrahydro-2H-furan-2-yloxy)oct-6-enamide (63 mg, 0.09 mmol) obtained in Example (3-1-3) was dissolved in methanol (1.5 ml), and trifluoroacetic acid (0.04 ml, 0.45 mmol) was slowly added thereto at room temperature. The resulting mixture was reacted for 8 hours to conduct a deprotection reaction of THP. After the completion of reaction, the reaction solution was concentrated under reduced pressure. The residue thus obtained was purified by a preparative HPLC to obtain 21 mg of the title compound as pale orange oil (yield 53%), which was used in the subsequent analysis.

$^1$H-NMR (300 MHz, CD$_3$OD) δ 1.46 (m, 2H), 1.63 (m, 2H), 2.05 (t, J=7.1 Hz, 2H), 2.28 (q, J=6.9 Hz, 2H), 3.06 (m, 4H), 3.27 (t, J=7.1 Hz, 2H), 3.47 (t, J=7.1 Hz, 2H), 3.72 (m, 2H), 3.92 (s, 2H), 4.86 (s, 2H), 6.10 (t, J=7.5 Hz, 1H), 6.96 (d, J=7.5 Hz, 1H), 7.36 (t, J=8.2 Hz, 1H), 7.43 (m, 3H), 7.78 (m, 1H), 8.14 (m, 1H)

LC/MS (M$^+$H): 442.

Example 3-2

(Z)—N-Hydroxy-8-(1-methoxypropan-2-ylamino)-7-((naphthalen-1-yloxy)methyl)oct-6-enamide (3-2-1): (Z)-Methyl-8-(1-methoxypropan-2-ylamino)-7-((naphthalen-1-yloxy)methyl)oct-6-enoate The procedure of Example (3-1-1) was repeated except for using 1-methoxypropan-2-ylamine as the alkylamine compound to obtain 357 mg of the title compound as pale yellow oil (yield 70%).

$^1$H-NMR (200 MHz, CDCl$_3$) δ 1.03 (d, J=6.2 Hz, 3H), 1.49 (m, 2H), 1.70 (m, 2H), 2.30 (m, 4H), 2.96 (m, 1H), 3.31 (s, 2H), 3.32 (s, 3H), 3.43 (dd, J=20.4 Hz, 13.4 Hz, 2H), 3.67 (s, 3H), 4.80 (s, 2H), 5.73 (t, J=7.4 Hz, 1H), 6.99 (d, J=7.0 Hz, 1H), 7.45 (m, 4H), 7.81 (m, 1H), 8.27 (m, 1H)

LC/MS (M$^+$H): 400.

(3-2-2): (Z)-8-(1-Methoxypropan-2-ylamino)-7-((naphthalen-1-yloxy)methyl)oct-6-enoic acid The procedure of Example (3-1-2) was repeated except for using the compound obtained in Example (3-2-1) as the starting material, to obtain 342 mg of the title compound as pale yellow foam (yield 100%).

$^1$H-NMR (200 MHz, CDCl$_3$) δ 1.35 (d, J=7.6 Hz, 3H), 1.67 (m, 4H), 2.32 (m, 4H), 3.28 (s, 3H), 3.50 (m, 1H), 3.74 (m, 2H), 3.92 (s, 2H), 6.16 (t, J=7.4 Hz, 1H), 7.02 (d, J=7.4 Hz, 1H), 7.49 (m, 4H), 7.83 (m, 1H), 8.19 (m, 1H)

LC/MS (M$^+$H): 386.

(3-2-3): (Z)-8-(1-Methoxylpropan-2-ylamino)-7-((naphthalen-1-yloxy)methyl)-N-(tetrahydro-2H-pyran-2-yloxy)oct-6-enamide The procedure of Example (3-1-3) was repeated except for using the compound obtained in Example (3-2-2) as the starting material, to obtain 240 mg of the title compound as pale yellow foam (yield 56%).

$^1$H-NMR (200 MHz, CDCl$_3$) δ 1.02 (d, J=6.4 Hz, 3H), 1.43-1.98 (m, 10H), 2.23 (m, 4H), 2.94 (m, 1H), 3.28 (s, 3H), 3.41 (dd, J=19.6 Hz, 13.8 Hz, 2H), 3.62 (m, 1H), 3.95 (m, 1H), 4.77 (s, 2H), 4.91 (br, 1H), 5.72 (t, J=7.6 Hz, 1H), 6.86 (t, J=7.2 Hz, 1H), 7.47 (m, 4H), 7.81 (m, 1H), 8.22 (m, 1H)

LC/MS (M$^+$H): 485.

(3-2-4): (Z)—N-Hydroxy-8-(1-methoxypropan-2-ylamino)-7-((naphthalen-1-yloxy)methyl)oct-6-enamide The procedure of Example (3-1-4) was repeated except for using the compound obtained in Example (3-2-3) as the starting material, to obtain 28 mg of the title compound as pale yellow oil (yield 62%), which was used in the subsequent analysis.

$^1$H-NMR (300 MHz, CD$_3$OD) δ 1.28 (d, J=6.5 Hz, 3H), 1.46 (m, 2H), 1.61 (m, 2H), 2.04 (t, J=7.2 Hz, 2H), 2.26 (q, J=7.2 Hz, 2H), 3.19 (s, 3H), 3.40 (m, 1H), 3.51 (m, 2H), 3.84 (s, 2H), 4.86 (s, 2H), 6.05 (t, J=7.4 Hz, 1H), 6.95 (d, J=7.5 Hz, 1H), 7.36 (t, J=7.7 Hz, 1H), 7.44 (m, 3H), 7.77 (m, 1H), 8.14 (m, 1H)

LC/MS (M$^+$H): 401.

Example 3-3

(Z)—N-Hydroxy-8-(naphthalen-1-yloxy)-7-((3-(2-oxopyrrolidin-1-yl)propylamino)methyl)oct-6-enamide (3-3-1): (Z)-Methyl-8-(naphthalen-1-yloxy)-7-((3-(2-oxopyrrolidin-1-yl) propylamino)methyl)oct-6-enoate The procedure of Example (3-1-1) was repeated except for using 2-oxopyrrolidin-1-ylpropylamine as the alkylamine compound to obtain 324 mg of the title compound as pale yellow oil (yield 56%).

$^1$H-NMR (200 MHz, CDCl$_3$) δ 1.47 (m, 2H), 1.63 (m, 2H), 1.76 (m, 1H), 1.93 (m, 2H), 2.27 (m, 6H), 2.65 (t, J=6.6 Hz, 2H), 3.30 (m, 4H), 3.46 (s, 2H), 3.63 (s, 3H), 4.78 (s, 2H), 5.75 (t, J=7.6 Hz, 1H), 6.87 (d, J=6.8 Hz, 1H), 7.41 (m, 4H), 7.78 (m, 1H), 8.19 (m, 1H)

LC/MS (M$^+$H): 453.

(3-3-2): (Z)-8-(Naphthalen-1-yloxy)-7-((3-(2-oxopyrrolidin-1-yl)propylamino)methyl)oct-6-enoic acid The procedure of Example (3-1-2) was repeated except for using the compound obtained in Example (3-3-1) as the starting material, to obtain 333 mg of the title compound as pale yellow foam (yield 100%).

$^1$H-NMR (200 MHz, CDCl$_3$) δ 1.50 (m, 2H), 1.64 (m, 2H), 1.88 (m, 3H), 2.04 (m, 2H), 2.21 (m, 5H), 2.90 (m, 2H), 3.28 (m, 4H), 3.70 (s, 2H), 4.88 (s, 2H), 6.08 (t, J=7.2 Hz, 1H), 6.87 (d, J=7.2 Hz, 1H), 7.47 (m, 4H), 7.78 (m, 1H), 7.98 (br, 1H), 8.17 (m, 1H)

LC/MS (M$^+$H): 439.

(3-3-3): (Z)-8-(Naphthalen-1-yloxy)-7-((3-(2-oxopyrrolidin-1-yl)propylamino)methyl)-N-(tetrahydro-2H-pyran-2-yloxy)oct-6-enamide)

The procedure of Example (3-1-3) was repeated except for using the compound obtained in Example (3-3-2) as the starting material, to obtain 210 mg of the title compound as pale yellow foam (yield 54%).

$^1$H-NMR (200 MHz, CDCl$_3$) δ 1.56 (m, 4H), 1.77 (m, 6H), 1.97 (m, 2H), 2.34 (m, 6H), 2.68 (t, J=7.0 Hz, 2H), 3.34 (m, 1H), 3.50 (s, 2H), 3.62 (m, 1H), 3.97 (m, 1H), 4.80 (s, 2H), 4.95 (br, 1H), 5.81 (t, J=7.0 Hz, 1H), 6.88 (d, J=7.0 Hz, 1H), 7.43 (m, 4H), 7.79 (m, 1H), 8.20 (m, 1H)

LC/MS (M$^+$H): 538.

(3-3-4): (Z)—N-Hydroxy-8-(naphthalen-1-yloxy)-7-((3-(2-oxopyrrolidin-1-yl)propylamino)methyl)oct-6-enamide The procedure of Example (3-1-4) was repeated except for using the compound obtained in Example (3-3-3) as the starting material, to obtain 18 mg of the title compound (yield 47%), which was used in the subsequent analysis.

$^1$H-NMR (300 MHz, CD$_3$OD) δ 1.45 (m, 2H), 1.60 (m, 2H), 1.90 (m, 4H), 2.00 (t, J=7.3 Hz, 2H), 2.25 (t, J=8.2 Hz, 4H), 2.99 (t, J=7.2 Hz, 2H), 3.30 (t, J=6.4 Hz, 2H), 3.36 (t, J=7.0 Hz, 2H), 3.80 (s, 2H), 4.85 (s, 2H), 6.04 (t, J=7.4 Hz, 1H), 6.94 (d, J=7.5 Hz, 1H), 7.35 (t, J=8.2 Hz, 1H), 7.43 (m, 3H), 7.75 (m, 1H), 8.15 (m, 1H)

LC/MS (M$^+$H): 454.

Example 3-4

(Z)-8-(3-(1H-Imidazol-1-yl)propylamino)-N-hydroxy-7-((naphthalen-1-yloxy)methyl)oct-6-enamide

(3-4-1): (Z)-Methyl-8-(3-(1H-imidazol-1-yl)propylamino)-7-((naphthalen-1-yloxy)methyl)oct-6-enoate The procedure of Example (3-1-1) was repeated except for using 1H-imidazol-2-ylpropylamine as the alkylamine compound to obtain 240 mg of the title compound as pale yellow oil (yield 54%).

$^1$H-NMR (200 MHz, CDCl$_3$) δ 1.46 (m, 2H), 1.63 (m, 2H), 1.88 (m, 2H), 2.31 (m, 4H), 2.59 (t, J=6.6 Hz, 2H), 3.40 (s, 2H), 3.64 (s, 3H), 3.95 (t, J=7.0 Hz, 2H). 4.75 (s, 2H), 5.66 (t, J=7.8 Hz, 1H), 6.83 (s, 1H), 6.85 (d, J=7.2 Hz, 1H), 6.99 (s, 1H), 7.41 (m, 5H), 7.78 (m, 1H), 8.19 (m, 1H)

LC/MS (M$^+$H): 436.

(3-4-2): (Z)-8-(3-(1H-Imidazol-1-yl)propylamino)-7-((naphthalen-1-yloxy)methyl)oct-6-enoic acid The procedure of Example (3-1-2) was repeated except for using the compound obtained in Example (3-4-1) as the starting material, to obtain 165 mg of the title compound as pale yellow foam (yield 71%).

LC/MS (M$^+$H): 422.

(3-4-3): (Z)-8-(3-(1H-Imidazol-1-yl)propylamino)-7-((naphthalen-1-yloxy)methyl)-N-(tetrahydro-2H-pyran-2-yloxy)oct-6-enamide The procedure of Example (3-1-3) was repeated except for using the compound obtained in Example (3-4-2) as the starting material, to obtain 109 mg of the title compound as pale yellow foam (yield 54%).

$^1$H-NMR (200 MHz, CDCl$_3$) δ 1.30-1.72 (m, 6H), 1.73-2.06 (m, 6H), 2.17 (m, 4H), 2.56 (t, J=7.0 Hz, 2H), 3.41 (s, 2H), 3.61 (m, 1H), 3.98 (m, 3H), 4.72 (s, 2H), 4.97 (m, 1H), 5.62 (t, J=6.8 Hz, 1H), 6.85 (s, 1H), 6.86 (d, J=6.2 Hz, 1H), 7.02 (s, 1H), 7.45 (m, 5H), 7.78 (m, 1H), 8.16 (m, 1H)

LC/MS (M$^+$H): 521.

(3-4-4): (Z)-8-(3-(1H-Imidazol-1-yl)propylamino)-N-hydroxy-7-((naphthalen-1-yloxy)methyl)oct-6-enamide The procedure of Example (3-1-4) was repeated except for using the compound obtained in Example (3-4-3) as the starting material, to obtain 23 mg of the title compound as pale yellow oil (yield 59%).

$^1$H-NMR (300 MHz, CD$_3$OD) δ 1.47 (m, 2H), 1.62 (m, 2H), 2.03 (t, J=7.1 Hz, 2H), 2.27 (m, 4H), 3.10 (t, J=7.5 Hz, 2H), 3.83 (s, 2H), 4.33 (t, J=7.4 Hz, 2H), 4.83 (s, 2H), 6.04 (t, J=7.4 Hz, 1H), 6.92 (d, J=7.5 Hz, 1H), 7.42 (m, 4H), 7.51 (s, 1H), 7.58 (s, 1H), 7.76 (m, 1H), 8.13 (m, 1H), 8.93 (s, 1H)

LC/MS (M$^+$H): 437.

Example 3-5

(Z)—N-Hydroxy-8-(3-(2-methylpiperidin-1-yl)propylamino)-7-((naphthalen-1-yloxy)methyl)oct-6-enamide

(3-5-1): (Z)-Methyl-8-(3-(2-methylpiperidin-1-yl)propylamino)-7-((naphthalen-1-yloxy)methyl)oct-6-enoate The procedure of Example (3-1-1) was repeated except for using 2-methylpiperidin-1-ylpropylamine as the alkylamine compound to obtain 105 mg of the title compound as pale yellow oil (yield 23%).

$^1$H-NMR (300 MHz, CDCl$_3$) δ 0.99 (d, J=6.2 Hz, 3H), 1.23 (m, 2H), 1.44-1.69 (m, 10H), 2.05 (m, 1H), 2.16-2.36 (m, 6H), 2.61 (t, J=6.9 Hz, 2H), 2.63-2.87 (m, 2H), 3.41 (s, 2H), 3.62 (s, 3H), 4.74 (s, 2H), 5.67 (t, J=7.4 Hz, 1H), 6.85 (d, J=7.1 Hz, 1H), 7.31-7.50 (m, 4H), 7.77 (d, J=6.9 Hz, 1H), 8.21 (d, J=7.0 Hz, 1H)

LC/MS (M$^+$H): 467.

(3-5-2): (Z)-8-(3-(2-Methylpiperidin-1-yl)propylamino)-7-((naphthalen-1-yloxy)methyl)oct-6-enoic acid The procedure of Example (3-1-2) was repeated except for using the compound obtained in Example (3-5-1) as the starting material, to obtain 93 mg of the title compound as pale yellow foam (yield 96%).

LC/MS (M$^+$H): 453.

(3-5-3): (Z)-8-(3-(2-Methylpiperidin-1-yl)propylamino)-7-((naphthalen-1-yloxy)methyl)-N-(tetrahydro-2H-pyran-2-yloxy)oct-6-enamide The procedure of Example (3-1-3) was repeated except for using the compound obtained in Example (3-5-2) as the starting material, to obtain 93 mg of the title compound as pale yellow foam (yield 77%).

$^1$H-NMR (200 MHz, CDCl$_3$) δ 0.77 (d, J=6.2 Hz, 3H), 1.25 (m, 2H), 1.32-1.84 (m, 16H), 2.01-2.42 (m, 7H), 2.54 (m, 2H), 3.03 (m, 1H), 3.22 (m, 1H), 3.52 (m, 1H), 3.61 (s, 2H), 3.91 (m, 1H), 4.37 (s, 2H), 4.89 (m, 1H), 5.66 (t, J=7.6 Hz,

1H), 6.25 (m, 1H), 7.25 (t, J=7.6 Hz, 1H), 7.43 (m, 3H), 7.77 (d, J=7.2 Hz, 1H), 8.13 (d, J=7.4 Hz, 1H)
LC/MS (M$^+$H): 552.

(3-5-4): (Z)—N-Hydroxy-8-(3-(2-methylpiperidin-1-yl)propylamino)-7-((naphthalen-1-yloxy)methyl)oct-6-enamide The procedure of Example (3-1-4) was repeated except for using the compound obtained in Example (3-5-3) as the starting material, to obtain 7.1 mg of the title compound as pale yellow oil (yield 68%), which was used in the subsequent analysis.
$^1$H-NMR (300 MHz, CD$_3$OD) δ 1.06 (d, J=6.2 Hz, 3H), 1.44 (m, 6H), 1.62 (m, 6H), 2.08 (m, 4H), 2.30 (m, 3H), 2.81-3.24 (m, 4H), 3.38 (s, 2H), 4.75 (s, 2H), 6.06 (t, J=7.3 Hz, 1H), 6.67 (d, J=7.0 Hz, 1H), 7.32 (t, J=7.7 Hz, 1H), 7.46 (m, 3H), 7.85 (d, J=7.7 Hz, 1H), 8.10 (d, J=7.6 Hz, 1H)
LC/MS (M$^+$H): 468.

Example 3-6

(Z)-8-(3-(Dimethylamino)propylamino)-N-hydroxy-7-((naphthalen-1-yloxy)methyl)oct-6-enamide (3-6-1): (Z)-Methyl-8-(naphthalen-1-yloxy)-7-((3-(2-oxopyrrolidin-1-yl) propylamino)methyl)oct-6-enoate The procedure of Example (3-1-1) was repeated except for using 2-oxopyrrolidin-1-ylpropylamine as the alkylamine compound to obtain 68 mg of the title compound as pale yellow oil (yield 17%).
$^1$H-NMR (200 MHz, CDCl$_3$) δ 1.36-1.75 (m, 4H), 2.10 (s, 6H), 2.29 (m, 4H), 2.55 (t, J=6.2 Hz, 2H), 2.80-3.15 (m, 4H), 3.65 (s, 3H), 3.68 (s, 2H), 4.84 (s, 2H), 5.92 (t, J=7.6 Hz, 1H), 6.88 (d, J=7.2 Hz, 1H), 7.27-7.55 (m, 4H), 7.79 (m, 1H), 8.15 (m, 1H)
LC/MS (M$^+$H): 413.

(3-6-2): (Z)-8-(3-(Dimethylamino)propylamino)-7-((naphthalen-1-yloxy)methyl)oct-6-enoic acid The procedure of Example (3-1-2) was repeated except for using the compound obtained in Example (3-6-1) as the starting material, to obtain 63 mg of the title compound as pale yellow foam (yield 41%).
LC/MS (M$^+$H): 399.

(3-6-3): (Z)-8-(3-(Dimethylamino)propylamino)-7-((naphthalen-1-yloxy)methyl)-N-(tetrahydro-2H-pyran-2-yloxy)oct-6-enamide The procedure of Example (3-1-3) was repeated except for using the compound obtained in Example (3-6-2) as the starting material, to obtain 63 mg of the title compound as pale yellow foam (yield 87%).
$^1$H-NMR (200 MHz, CDCl$_3$) δ 1.47-1.85 (m, 8H), 2.22 (m, 6H), 2.28 (s, 6H), 2.45 (m, 2H), 3.21 (m, 2H), 3.49 (s, 2H), 3.60 (m, 1H), 3.93 (m, 1H), 4.77 (s, 2H), 4.95 (m, 1H), 5.81 (t, J=6.4 Hz, 1H), 6.82 (d, J=6.2 Hz, 1H), 7.42 (m, 4H), 7.80 (m, 1H), 8.21 (m, 1H)
LC/MS (M$^+$H): 498.

(3-6-4): (Z)-8-(3-(Dimethylamino)propylamino)-N-hydroxy-7-((naphthalen-1-yloxy)methyl)oct-6-enamide The procedure of Example (3-1-4) was repeated except for using the compound obtained in Example (3-6-3) as the starting material, to obtain 11 mg of the title compound as pale yellow oil (yield 75%), which was used in the subsequent analysis.
$^1$H-NMR (300 MHz, CD$_3$OD) δ 1.55 (m, 2H), 1.68 (m, 2H), 2.13 (m, 4H), 2.17 (q, J=5.5 Hz, 2H), 2.89 (s, 6H), 3.20 (m, 4H), 3.93 (s, 2H), 4.94 (s, 2H), 6.15 (t, J=7.1 Hz, 1H), 6.97 (d, J=6.7 Hz, 1H), 7.45 (m, 4H), 7.83 (m, 1H), 8.22 (m, 1H)
LC/MS (M$^+$H): 414.

Example 3-7

(Z)-8-(3-(Dimethylamino)-2,2-dimethylpropylamino)-N-hydroxy-7-((naphthalen-1-yloxy)methyl)oct-6-enamide (3-7-1): (Z)-Methyl-8-(3-(dimethylamino)-2,2-dimethylpropylamino)-7-((naphthalen-1-yloxy)methyl)oct-6-enoate The procedure of Example (3-1-1) was repeated except for using 3-dimethylamino-2,2-dimethylpropylamine as the alkylamine compound to obtain 101 mg of the title compound as pale yellow oil (yield 29%).
$^1$H-NMR (200 MHz, CDCl$_3$) δ 0.91 (s, 6H), 1.46 (m, 2H), 1.68 (m, 2H), 2.19 (m, 2H), 2.19 (s, 6H), 2.20 (m, 4H), 2.52 (s, 2H), 3.48 (s, 2H), 3.64 (s, 3H), 4.77 (s, 2H), 5.74 (t, J=7.4 Hz, 1H), 6.87 (m, 1H), 7.26-7.53 (m, 4H), 7.82 (m, 1H), 8.22 (m, 1H)
LC/MS (M$^+$H): 441.

(3-7-2): (Z)-8-(3-(Dimethylamino)-2,2-dimethylpropylamino)-7-((naphthalen-1-yloxy)methyl)oct-6-enoic acid The procedure of Example (3-1-2) was repeated except for using the compound obtained in Example (3-7-1) as the starting material, to obtain 99 mg of the title compound as pale yellow foam (yield 100%).
LC/MS (M$^+$H): 427.

(3-7-3): (Z)-8-(3-(Dimethylamino)-2,2-dimethylpropylamino)-7-((naphthalen-1-yloxy)methyl)-N-(tetrahydro-2H-pyran-2-yloxy)oct-6-enamide The procedure of Example (3-1-3) was repeated except for using the compound obtained in Example (3-7-2) as the starting material, to obtain 98 mg of the title compound as pale yellow foam (yield 66%).
$^1$H-NMR (200 MHz, CDCl$_3$) δ 0.92 (s, 6H), 1.43-1.88 (m, 10H), 2.21 (m, 2H), 2.20 (s, 6H), 2.21 (m, 4H), 2.53 (s, 2H), 3.49 (s, 2H), 3.64 (s, 3H), 3.65 (m, 1H), 3.97 (m, 1H), 4.77 (s, 2H), 5.01 (m, 1H), 5.73 (t, J=7.4 Hz, 1H), 6.86 (m, 1H), 7.24-7.57 (m, 4H), 7.78 (m, 1H), 8.19 (m, 1H)
LC/MS (M$^+$H): 526.

(3-7-4): (Z)-8-(3-(Dimethylamino)-2,2-dimethylpropylamino)-N-hydroxy-7-((naphthalen-1-yloxy)methyl)oct-6-enamide The procedure of Example (3-1-2) was repeated except for using the compound obtained in Example (3-7-3) as the starting material, to obtain 12 mg of the title compound as pale yellow oil (yield 75%), which was used in the subsequent analysis.
$^1$H-NMR (300 MHz, CD$_3$OD) δ 1.18 (s, 6H), 1.50 (m, 2H), 1.60 (m, 2H), 2.04 (m, 2H), 2.28 (m, 2H), 2.86 (s, 6H), 3.17 (s, 2H), 3.20 (s, 2H), 3.91 (s, 2H), 3.89 (s, 2H), 6.10 (t, J=7.6

Hz, 1H), 6.96 (d, J=7.1 Hz, 1H), 7.53 (t, J=7.6 Hz, 1H), 7.44 (m, 4H), 7.77 (m, 1H), 8.13 (m, 1H)
LC/MS (M$^+$H): 442.

Example 3-8

(Z)—N-Hydroxy-8-(naphthalen-1-yloxy)-7-((2-(pyrrolidin-1-yl)ethylamino)methyl)oct-6-enamide (3-8-1): (Z)-Methyl-8-(naphthalen-1-yloxy)-7-((2-(pyrrolidin-1-yl)ethylamino)methyl)oct-6-enoate The procedure of Example (3-1-1) was repeated except for using 2-pyrrolidin-1-ylethylamine as the alkylamine compound to obtain 256 mg of the title compound as pale yellow oil (yield 49%).
$^1$H-NMR (300 MHz, CDCl$_3$) δ 1.43 (m, 2H), 1.59 (m, 6H), 2.20 (m, 4H), 2.74 (m, 6H), 2.91 (d, J=5.7 Hz, 2H), 3.47 (d, J=7.8 Hz, 2H), 3.66 (s, 3H), 4.77 (s, 2H), 5.73 (s, 1H), 6.87 (d, J=6.9 Hz, 1H), 7.48 (m, 4H), 7.80 (dd, J=7.5, 1.2 Hz, 1H), 8.18 (dd, J=6.6, 3.6 Hz, 1H).

(3-8-2): (Z)-8-(Naphthalen-1-yloxy)-7-((2-(pyrrolidin-1-yl)ethylamino)methyl)oct-6-enoic acid The procedure of Example (3-1-2) was repeated except for using the compound obtained in Example (3-8-1) as the starting material, to obtain 99 mg of the title compound as pale yellow foam (yield 87%).

(3-8-3): (Z)-8-(Naphthalen-1-yloxy)-7-((2-(pyrrolidin-1-yl)ethylamino)methyl))-N-(tetrahydro-2H-pyran-2-yloxy)oct-6-enamide The procedure of Example (3-1-3) was repeated except for using the compound obtained in Example (3-8-2) as the starting material, to obtain 132 mg of the title compound as pale yellow foam (yield 35%).
$^1$H-NMR (300 MHz, CDCl$_3$) δ 1.42-1.67 (m, 12H), 2.11 (m, 5H), 2.84 (m, 5H), 3.52 (m, 5H), 3.72 (m, 5H), 4.04 (t, J=7.8 Hz, 3H), 4.63 (d, J=5.9 Hz, 2H), 4.94 (s, 1H), 5.80 (s, 1H), 6.79 (d, J=6.9 Hz, 1H), 7.31 (m, 4H), 7.77 (d, J=8.7 Hz, 1H), 8.14 (d, J=7.5 Hz, 1H).

(3-8-4): (Z)—N-hydroxy-8-(Naphthalen-1-yloxy)-7-((2-(pyrrolidin-1-yl)ethylamino)methyl)oct-6-enamide The procedure of Example (3-1-4) was repeated except for using the compound obtained in Example (3-8-3) as the starting material, to obtain 21 mg of the title compound as pale yellow oil (yield 44%), which was used in the subsequent analysis.
$^1$H-NMR (300 MHz, CD$_3$OD) δ 1.51 (m, 2H), 1.69 (m, 2H), 2.08 (m, 6H), 2.35-2.37 (m, 2H), 3.13-3.54 (m, 4H), 3.58 (s, 2H), 3.59 (s, 2H), 3.92 (s, 2H), 6.15 (t, J=7.8 Hz, 1H), 6.99 (t, J=7.6 Hz, 1H), 7.37 (m, 4H), 7.83 (d, J=5.4 Hz, 1H), 8.20 (t, J=6.1 Hz, 1H).

Example 3-9

(Z)-8-(4-Fluorophenethylamino)-N-hydroxy-7-((naphthalen-1-yloxy)methyl)oct-enamide (3-9-1): (Z)-Methyl-8-(4-fluorophenethylamino)-7-((naphthalen-1-yloxy)methyl)oct-6-enoate The procedure of Example (3-1-1) was repeated except for using 4-fluorophenethylamine as the alkylamine compound to obtain 355 mg of the title compound as pale yellow oil (yield 69%).
$^1$H-NMR (300 MHz, CDCl$_3$) δ 1.59 (m, 2H), 1.96 (t, J=7.2 Hz, 2H), 2.27 (m, 3H), 2.76 (m, 4H), 3.18 (s, 1H), 3.44 (s, 1H), 3.62 (s, 1H), 3.66 (s, 3H), 4.68 (s, 1H), 4.80 (d, J=7.8 Hz, 1H), 5.64 (d, J=7.4 Hz, 1H), 6.94 (m, 4H), 7.08 (m, 2H), 7.42 (m, 3H), 7.78 (d, J=7.6 Hz, 1H), 8.16 (d, J=7.8 Hz, 1H).

(3-9-2): (Z)-8-(4-Fluorophenethylamino)-7-((naphthalene-1-oxy)methyl)oct-6-enoic acid The procedure of Example (3-1-2) was repeated except for using the compound obtained in Example (3-9-1) as the starting material, to obtain 175 mg of the title compound as pale yellow foam (yield 50%).

(3-9-3): (Z)-8-(4-Fluorophenethylamino)-7-((naphthalen-1-yloxy)methyl)-N-(tetrahydro-2H-pyran-2-yloxy)oct-6-enamide The procedure of Example (3-1-3) was repeated except for using the compound obtained in Example (3-9-2) as the starting material, to obtain 201 mg of the title compound as pale yellow foam (yield 54%).
$^1$H-NMR (300 MHz, CDCl$_3$) δ 1.25 (m, 4H), 1.61 (m, 4H), 2.08 (m, 4H), 2.72 (m, 6H), 3.43 (d, J=10.1 Hz, 1H), 3.55 (d, J=8.8 Hz, 1H), 3.90 (s, 2H), 4.67 (s, 2H), 4.91 (s, 1H), 5.65 (t, J=7.6 Hz, 1H), 6.80 (m, 4H), 7.06 (m, 2H), 7.41 (m, 3H), 7.80 (d, J=7.8 Hz, 1H), 8.14 (d, J=8.0 Hz, 1H).

(3-9-4): (Z)-8-(4-Fluorophenethylamino)-N-hydroxy-7-((naphthalen-1-yloxy)methyl)oct-enamide The procedure of Example (3-1-4) was repeated except for using the compound obtained in Example (3-9-3) as the starting material, to obtain 54 mg of the title compound as pale yellow oil (yield 48%), which was used in the subsequent analysis, which was used in the subsequent analysis.
$^1$H-NMR (300 MHz, CD$_3$OD) δ 1.59 (m, 2H), 1.96 (t, J=7.2 Hz, 2H), 2.27 (m, 3H), 2.76 (m, 4H), 3.18 (s, 1H), 3.44 (s, 1H), 4.68 (s, 2H), 4.80 (d, J=7.8 Hz, 1H), 5.64 (d, J=7.4 Hz, 1H), 6.94 (m, 4H), 7.08 (m, 2H), 7.46 (m, 3H), 7.78 (d, J=7.6 Hz, 1H), 8.16 (d, J=7.8 Hz, 1H).

Example 3-10

(Z)—N-Hydroxy-8-(2-methoxyethylamino)-7-((naphthalen-1-yloxy)methyl)oct-6-enamide (3-10-1): (Z)-Methyl-8-(2-methoxyethylamino)-7-((naphthalen-1-yloxy)methyl)oct-6-enoate The procedure of Example (3-1-1) was repeated except for using 2-methoxyethylamine as the alkylamine compound to obtain 301 mg of the title compound as pale yellow oil (yield 43%).
$^1$H-NMR (300 MHz, CDCl$_3$) δ 1.25 (m, 2H), 1.43 (d, J=6.6 Hz, 4H), 1.63 (m, 2H), 2.01 (m, 2H), 2.76 (m, 2H), 3.49 (s, 2H), 3.62 (s, 3H), 3.66 (s, 3H), 4.92 (s, 2H), 5.70 (s, 1H), 6.85 (d, J=6.9 Hz, 1H), 7.49 (m, 4H), 7.76 (d, J=7.2 Hz, 1H), 8.21 (t, J=6.6 Hz, 1H).

(3-10-2): (Z)-8-(2-Methoxyethylamino)-7-((naphthalen-1-yloxy)methyl)oct-6-enoic acid The procedure of Example (3-1-2) was repeated except for using the compound obtained in Example (3-10-1) as the starting material, to obtain 248 mg of the title compound as pale yellow foam (yield 65%).

(3-10-3): (Z)-8-(2-Methoxyethylamino)-7-((naphthalen-1-yloxy)methyl)-N-(tetrahydro-2H-pyran-2-yloxy)oct-6-enamide The procedure of Example (3-1-3) was repeated except for using the compound obtained in Example (3-10-2) as the starting material, to obtain 180 mg of the title compound as pale yellow foam (yield 61%).
$^1$H-NMR (300 MHz, CDCl$_3$) δ 1.44 (m, 4H), 1.56 (m, 5H), 2.17 (m, J=7.1 Hz, 5H), 2.82 (t, J=5.1 Hz, 2H), 3.30 (s, 3H), 3.47 (m, 3H), 3.60 (s, 2H), 3.92 (s, 1H), 4.75 (s, 2H), 4.91 (s, 1H), 5.71 (t, J=7.2 Hz, 1H), 6.85 (d, J=7.2 Hz, 1H), 7.34-7.50 (m, 4H), 7.77 (d, J=5.8 Hz, 1H), 8.19 (m, 1H).

(3-10-4): (Z)—N-Hydroxy-8-(2-methoxyethylamino)-7-((naphthalen-1-yloxy)methyl)oct-6-enamide The procedure of Example (3-1-4) was repeated except for using the compound obtained in Example (3-10-3) as the starting material, to obtain 38 mg of the title compound as pale yellow oil (yield 72%), which was used in the subsequent analysis.
$^1$H-NMR (300 MHz, CD$_3$OD) δ 1.25 (m, 2H), 1.43 (m, 4H), 1.63 (m, 2H), 2.01 (m, 2H), 2.76 (m, 2H), 3.49 (s, 2H), 3.62 (s, 3H), 4.92 (s, 2H), 5.70 (s, 1H), 6.85 (d, J=6.9 Hz, 1H), 7.36-7.49 (m, 4H), 7.76 (m, 1H), 8.21 (m, 1H).

Example 3-11

(Z)—N-Hydroxy-8-(1-isopropylpiperidin-4-ylamino)-7-((naphthalen-1-yloxy)methyl)oct-6-enamide (3-11-1): (Z)-Methyl-8-(1-isopropylpiperidin-4-ylamino)-7-((naphthalen-1-yloxy)methyl)oct-6-enoate The procedure of Example (3-1-1) was repeated except for using 1-isopropylpiperidin-4-ylamine as the alkylamine compound to obtain 324 mg of the title compound as pale yellow oil (yield 41%).
$^1$H-NMR (300 MHz, CDCl$_3$) δ 1.21 (m, 6H), 1.43 (m, 4H), 2.03 (d, J=7.4 Hz, 4H), 2.10 (m, 5H), 2.71 (m, 1H), 3.08 (s, 2H), 3.37 (s, 2H), 3.67 (s, 3H), 4.40 (s, 2H), 5.62 (t, J=7.4 Hz, 1H), 6.28 (d, J=7.6 Hz, 1H), 7.27 (m, 1H), 7.37 (m, 4H), 7.78 (m, 1H), 8.17 (m, 1H).

(3-11-2): (Z)-8-(1-Isopropylpiperidin-4-ylamino)-7-((naphthalen-1-yloxy)methyl)oct-6-enoic acid The procedure of Example (3-1-2) was repeated except for using the compound obtained in Example (3-11-1) as the starting material, to obtain 315 mg of the title compound as pale yellow foam (yield 100%).

(3-11-3): (Z)-8-(1-Isopropylpiperidin-4-ylamino)-7-((naphthalen-1-yloxy)methyl)-N-(tetrahydro-2H-pyran-2-yloxy)oct-6-enamide The procedure of Example (3-1-3) was repeated except for using the compound obtained in Example (3-11-2) as the starting material, to obtain 340 mg of the title compound as pale yellow foam (yield 76%).
$^1$H-NMR (300 MHz, CDCl$_3$) δ 0.95 (d, J=6.4 Hz, 2H), 1.36 (m, 8H), 1.75 (s, 4H), 1.97-2.07 (m, 8H), 2.47 (s, 1H), 2.64 (s, 1H), 2.75 (t, J=6.6 Hz, 1H), 2.94 (s, 1H), 3.25 (s, 2H), 3.54 (d, J=11.4 Hz, 1H), 3.87 (s, 1H), 4.41 (s, 2H), 4.86 (s, 1H), 5.60 (t, J=7.1 Hz, 1H), 6.36 (d, J=7.5 Hz, 1H), 7.22 (d, J=8.0 Hz, 1H), 7.37 (m, 4H), 7.77 (m, 1H), 8.14 (m, 1H).

(3-11-4): (Z)—N-Hydroxy-8-(1-isopropylpiperidin-4-ylamino)-7-((naphthalen-1-yloxy)methyl)oct-6-enamide The procedure of Example (3-1-4) was repeated except for using the compound obtained in Example (3-11-3) as the starting material, to obtain 43 mg of the title compound as pale yellow oil (yield 64%), which was used in the subsequent analysis.
$^1$H-NMR (300 MHz, CD$_3$OD) δ 1.21 (m, 6H), 1.43 (m, 4H), 2.03 (d, J=7.4 Hz, 4H), 2.10 (m, 5H), 2.71 (m, 1H), 3.08 (s, 2H), 3.37 (s, 2H), 4.40 (s, 2H), 5.62 (t, J=7.4 Hz, 1H), 6.28 (d, J=7.6 Hz, 1H), 7.27 (m, 1H), 7.37 (m, 4H), 7.78 (m, 1H), 8.1 (m, 1H).

Example 3-12

(Z)-8-(3-(Diethylamino)propylamino)-N-hydroxy-7-((naphthalen-1-yloxy)methyl)oct-6-enamide (3-12-1): (Z)-Methyl-8-(3-(diethylamino)propylamino)-7-((naphthalen-1-yloxy)methyl)oct-6-enoate The procedure of Example (3-1-1) was repeated except for using 3-diethylaminopropylamine as the alkylamine compound to obtain 187 mg of the title compound as pale yellow oil (yield 38%).
$^1$H-NMR (300 MHz, CDCl$_3$) δ 0.56 (t, J=6.6 Hz, 6H), 1.40 (t, J=7.2 Hz, 4H), 1.59 (t, J=7.8 Hz, 2H), 1.96 (m, 1H), 2.10 (t, J=7.2 Hz, 4H), 2.25 (t, J=7.2 Hz, 4H), 2.42 (t, J=5.4 Hz, 2H), 3.14 (s, 2H), 3.61 (s, 3H), 4.37 (s, 2H), 5.67 (t, J=7.2 Hz, 1H), 6.16 (d, J=7.5 Hz, 1H), 7.14 (t, J=7.8 Hz, 1H), 7.48 (m, 4H), 7.77 (m, 1H), 8.14 (m, 1H).

(3-12-2): (Z)-Methyl-8-(3-(diethylamino)propylamino)-7-((naphthalen-1-yloxy)methyl)oct-6-enoic acid The procedure of Example (3-1-2) was repeated except for using the compound obtained in Example (3-12-1) as the starting material, to obtain 177 mg of the title compound as pale yellow foam (yield 100%).

(3-12-3): (Z)-8-(3-(Diethylamino)propylamino)-7-((naphthalen-1-yloxy)methyl)-N-(tetrahydro-2H-pyran-2-yloxy)oct-6-enamide The procedure of Example (3-1-3) was repeated except for using the compound obtained in Example (3-12-2) as the starting material, to obtain 202 mg of the title compound as pale yellow foam (yield 80%).
$^1$H-NMR (300 MHz, CDCl$_3$) δ 0.56 (m, 6H), 1.40 (m, 6H), 1.75 (m, 5H), 2.21 (m, 6H), 2.37 (m, 4H), 3.12 (m, 2H), 3.46 (m, 2H), 3.86 (s, 1H), 4.38 (s, 2H), 4.89 (s, 1H), 5.62 (t, J=7.5 Hz, 2H), 6.25 (s, 1H), 7.20 (d, J=8.1 Hz, 1H), 7.48 (m, 4H), 7.78 (d, J=7.8 Hz, 1H), 8.12 (d, J=8.4 Hz, 1H).

(3-12-4): (Z)-8-(3-(Diethylamino)propylamino)-N-hydroxy-7-((naphthalen-1-yloxy)methyl)oct-6-enamide The procedure of Example (3-1-4) was repeated except for using the compound obtained in Example (3-12-3) as the starting material, to obtain 19 mg of the title compound as pale yellow oil (yield 77%), which was used in the subsequent analysis.

$^1$H-NMR (300 MHz, CD$_3$OD) δ 0.61 (t, J=6.6 Hz, 6H), 1.40 (t, J=7.2 Hz, 4H), 1.59 (t, J=7.4 Hz, 2H), 1.96 (m, 1H), 2.10 (t, J=7.4 Hz, 4H), 2.25 (t, J=7.2 Hz, 4H), 2.42 (t, J=5.4 Hz, 2H), 3.14 (s, 2H), 4.37 (s, 2H), 5.67 (t, J=7.2 Hz, 1H), 6.16 (d, J=7.4 Hz, 1H), 7.14 (t, J=7.8 Hz, 1H), 7.37 (m, 4H), 7.77 (d, J=8.7 Hz, 1H), 8.11 (d, J=8.7 Hz, 1H).

Example 3-13

(Z)-8-(2-(Diisopropylamino)ethylamino))-N-hydroxy-7-((naphthalen-1-yloxy)methyl)oct-6-enamide (3-13-1): (Z)-Methyl-8-(2-(diisopropylamino)ethylamino)-7-((naphthalen-1-yloxy)methyl)oct-6-enoate The procedure of Example (3-1-1) was repeated except for using 2-diisopropylaminoethylamine as the alkylamine compound to obtain 344 mg of the title compound as pale yellow oil (yield 78%).

$^1$H-NMR (300 MHz, CDCl$_3$) δ 0.80 (m, 7H), 0.96 (m, 2H), 1.25-1.42 (m, 6H), 1.58 (m, 3H), 1.80 (m, 2H), 2.04 (q, J=7.4 Hz, 2H), 2.23 (m, 4H), 3.18 (s, 2H), 3.60 (s, 3H), 4.44 (s, 2H), 5.63 (t, J=7.2 Hz, 1H), 6.37 (d, J=7.6 Hz, 1H), 7.38 (m, 4H), 7.75 (d, J=7.8 Hz, 1H), 8.14 (d, J=8.2 Hz, 1H)

LC/MS (M$^+$H): 455.32.

(3-13-2): (Z)-8-(2-(Diisopropylamino)ethylamino)-7-((naphthalen-1-yloxy)methyl)oct-6-enoic acid The procedure of Example (3-1-2) was repeated except for using the compound obtained in Example (3-13-1) as the starting material, to obtain 338 mg of the title compound as pale yellow foam (yield 100%).

(3-13-3): (Z)-8-(2-(Diisopropylamino)ethylamino)-7-((naphthalen-1-yloxy)methyl)-N-(tetrahydro-2H-pyran-2-yloxy)oct)-6-enamide The procedure of Example (3-1-3) was repeated except for using the compound obtained in Example (3-13-2) as the starting material, to obtain 341 mg of the title compound as pale yellow foam (yield 97%).

$^1$H-NMR (200 MHz, CDCl$_3$) δ 0.77 (m, 7H), 1.38 (m, 4H), 1.56-1.75 (m, 10H), 2.03 (m, 6H), 2.28 (m, 4H), 2.72 (m, 1H), 3.17 (s, 2H), 3.58 (m, 1H), 3.87 (m, 1H), 4.45 (s, 2H), 4.86 (m, 1H), 5.62 (t, J=6.8 Hz, 1H), 6.37 (d, J=7.6 Hz, 1H), 7.37 (m, 4H), 7.74 (d, J=7.4 Hz, 1H), 8.15 (d, J=8.0 Hz, 1H)

LC/MS (M$^+$H): 540.37.

(3-13-4): (Z)-8-(2-(Diisopropylamino)ethylamino))-N-hydroxy-7-((naphthalen-1-yloxy)methyl)oct-6-enamide The procedure of Example (3-1-4) was repeated except for using the compound obtained in Example (3-13-3) as the starting material, to obtain 23 mg of the title compound as pale yellow oil (yield 85%), which was used in the subsequent analysis.

$^1$H-NMR (300 MHz, CD$_3$OD) δ 0.86 (m, 8H), 1.30-1.37 (m, 4H), 1.50-1.58 (m, 3H), 1.93-2.11 (m, 6H), 2.67 (m, 3H), 3.08 (m, 2H), 3.11 (m, 2H), 4.47 (s, 2H), 5.70 (t, J=7.2 Hz, 1H), 6.36 (d, J=7.6 Hz, 1H), 7.23 (t, J=8.0 Hz, 1H), 7.41 (m, 3H), 7.77 (d, J=7.8 Hz, 1H), 8.06 (d, J=8.0 Hz, 1H)

LC/MS (M$^+$H): 456.31.

Example 3-14

(Z)—N-Hydroxy-8-(naphthalen-1-yloxy)-7-((thiophen-2-ylmethylamino)methyl)oct-6-enamide (3-14-1): (Z)-Methyl-8-(naphthalen-1-yloxy)-7-((thiophen-2-ylmethylamino)methyl)oct-6-enoate The procedure of Example (3-1-1) was repeated except for using thiophen-2-ylmethylamine as the alkylamine compound to obtain 358 mg of the title compound as pale yellow oil (yield 79%).

$^1$H-NMR (200 MHz, CDCl$_3$) δ 1.30 (m, 1H), 1.51 (m, 1H), 1.67 (m, 4H), 2.32 (m, 2H), 3.53 (s, 2H), 3.68 (s, 3H), 4.04 (s, 2H), 4.82 (s, 2H), 5.75 (t, J=7.0 Hz, 1H), 6.95 (m, 3H), 7.21 (m, 1H), 7.47 (m, 4H), 7.82 (m, 1H), 8.22 (m, 1H)

LC/MS (M$^+$H): 424.19.

(3-14-2): (Z)-8-(Naphthalen-1-yloxy)-7-((thiophen-3-ylmethylamino)methyl)oct-6-enoic acid The procedure of Example (3-1-2) was repeated except for using the compound obtained in Example (3-14-1) as the starting material, to obtain 349 mg of the title compound as pale yellow foam (yield 100%).

TLC (MeOH/MC=1/6) Rf 0.70.

(3-14-3): (Z)-8-(Naphthalen-1-yloxy)-N-(tetrahydro-2H-pyran-2-yloxy)-7-((thiophen-2-ylmethylamino)methyl)oct-6-enamide The procedure of Example (3-1-3) was repeated except for using the compound obtained in Example (3-14-2) as the starting material, to obtain 321 mg of the title compound as pale yellow foam (yield 82%).

$^1$H-NMR (300 MHz, CDCl$_3$) δ 1.44-1.77 (m, 10H), 2.08 (m, 2H), 2.20 (q, J=7.2 Hz, 2H), 3.47 (s, 2H), 3.58 (m, 1H), 3.89 (m, 1H), 3.99 (s, 2H), 4.76 (s, 2H), 4.89 (m, 1H), 5.70 (t, J=7.2 Hz, 1H), 6.90 (m, 3H), 7.17 (m, 1H), 7.44 (m, 4H), 7.77 (d, J=7.6 Hz, 1H), 8.15 (d, J=8.0 Hz, 1H), 8.50 (br, 1H)

LC/MS (M$^+$H): 509.24.

(3-14-4): (Z)—N-Hydroxy-8-(naphthalen-1-yloxy)-7-((thiophen-2-ylmethylamino)methyl)oct-6-enamide The procedure of Example (3-1-4) was repeated except for using the compound obtained in Example (3-14-3) as the starting material, to obtain 68 mg of the title compound as pale yellow oil (yield 77%), which was used in the subsequent analysis.

$^1$H-NMR (300 MHz, CD$_3$OD) δ 1.47 (q, J=7.9 Hz, 2H), 1.62 (m, 2H), 2.05 (t, J=7.0 Hz, 2H), 2.28 (q, J=7.2 Hz, 2H), 3.86 (s, 2H), 4.47 (s, 2H), 4.85 (s, 2H), 6.04 (t, J=7.4 Hz, 1H), 6.93 (d, J=7.4 Hz, 1H), 7.02 (m, 1H), 7.22 (m, 2H), 7.44 (m, 5H), 7.76 (d, J=8.0 Hz, 1H), 8.02 (d, J=8.2 Hz, 1H)

LC/MS (M$^+$H): 425.18.

Test Example 3-1

Analysis of Inhibitory Activity Against HDAC

HDAC activity was analyzed using BIOMOL Quantizyme™ Assay system which comprised two steps of 1)

enzyme reaction between HDAC and a substrate and 2) determination of the level of HDAC inhibitory activity.

In step 1), 42 μl of a buffer solution (25 mM Tris-HCl [pH 8.0], 137 mM NaCl, 2.7 mM KCl, 1 mM MgCl$_2$) and 5 μl of 250 μM Fluor de Lys™ substrate were added to each well of a 96-well plate, to which 2.5 μl of a test compound (compounds of Examples 3-1 to 3-14) at a concentration of 0.01, 0.1, 1, 10 and 100 μM, respectively, was added. 0.5 μl of HeLa nuclear organic layer (10 μM) (a source of HDAC enzymes) was then added thereto to a final concentration of 100 nM. The enzyme reaction was carried out for 1 hr.

Subsequently, in step 2), 2 μM tricostatin A was added to 50 μl of Flour de Lys™ developer, followed by allowing the mixture to react at room temperature for 15 minutes. The light excited at 355 nm and emitted at 460 nm from the fluorophore was measured with a fluorometric plate reader. The intensity of the fluorescence increases as the enzyme activity is higher. The HDAC inhibitory activity of each of the test compounds was determined and compared with that of the control. And suberoylanilide hydroxamic acid (SAHA) (Biomol) was used at the same level with the test compounds as a comparative control.

The HDAC inhibitory concentrations (IC$_{50}$) of the test compounds of Examples 3-1 to 3-14 are shown in Table 5.

TABLE 5

| Inhibitory conc. (IC$_{50}$, μM/ml) | |
|---|---|
| Compound | IC$_{50}$ (μM/ml) |
| SAHA | 0.140 |
| Example 3-1 | 0.002 |
| Example 3-2 | 0.005 |
| Example 3-3 | 0.003 |
| Example 3-4 | 0.003 |
| Example 3-5 | 0.062 |
| Example 3-6 | 0.002 |
| Example 3-7 | 0.012 |
| Example 3-8 | 0.005 |
| Example 3-9 | 0.003 |
| Example 3-10 | 0.006 |
| Example 3-11 | 0.012 |
| Example 3-12 | 0.113 |
| Example 3-13 | 0.042 |
| Example 3-14 | 0.002 |

As shown in Table 5, each of the inventive naphthalenyloxypropenyl derivatives of formula (3) has an inhibitory activity against HDAC, which is comparable to or markedly higher than that of SAHA known as a HDAC inhibitor.

Test Example 3-2

Analysis of Inhibitory Activity Against Proliferation of Cancer Cells

Inhibitory activities of naphthalenyloxypropenyl derivatives synthesized in Examples 3-1 to 3-14 against proliferation of cancer cells were examined by SRB (Sulforhodamine B) analysis using cervix adenocarcinoma Hela (Korean Cell Line Bank, KCLB 10002) and colon cancer cells HCT116 (Korean Cell Line Bank, KCLB 10247) as follows:

Cancer cells were inoculated into a 96-well microplate at a concentration of $1 \times 10^3 \sim 3 \times 10^3$ cells/well and incubated under the condition of 37° C., 5% CO$_2$ for 24 hrs. After the incubation was completed, 0.2, 1, 5, 25, or 100 μM of each of the compounds of Examples was added to the plate, and then the reactant was incubated for 48 hrs. After the substrate was stained with SRB, the anti-cancer activity was determined by comparing the amount of protein in the cells treated with the compound of Examples with that of protein in untreated cells.

Specifically, after the incubation was completed, the culture medium was removed from each well, and the cells were washed 3 times with PBS (pH 7.4). Then, a solution of 50% trichloroacetic acid (TCA) was added to each well in an amount of 50 μl/well at 4° C. for 1 hr to fix them. Then, the microplate was washed 5 times with distilled water and dried in air.

50 μl of a staining solution prepared by dissolving 0.4% SRB in 1% acetic acid was added to the wells, and the microplate was kept at room temperature for 1 hr. The well plate was then washed 5 times with 1% acetic acid to remove unbound SRB and dried in air. The stained cells were treated with 150 μl/well of 10 mM Tris-HCl solution (pH 10.5) to elute SRB from the cells, and the absorbance of the cells treated with the compounds of examples at 540 nm was measured, based on the absorbance of an untreated cell. The EC$_{50}$ value representing inhibition of the cancer cell growth by the extent of 50% was calculated from the measured absorbance, and the results are shown in Table 6.

When cancer cells were treated with a HDAC inhibitor, histone deacetylation would be inhibited, leading to an increase in the amount of acetyl-histone. In this test, the increased amount of acetyl-histone in the cancer cells was determined by using Western blotting, after the treatment with each of the compounds of Examples.

The cells to be tested were inoculated into a 6-well microplate at a concentration of $1.5 \times 10^8$ cells/well and incubated overnight under the condition of 37° C., 5% CO$_2$. 10 μM of each compound of Examples, and suberoylanilide hydroxamic acid (SAHA) as a control was added to the plate and the plate was incubated again for 24 hrs.

The cells cultured in the presence of the test compound were harvested and subjected to fractionation to separate the nuclei from the cells. The cells were allowed to swell in a hypotonic solution, lysed by several rounds of freezing-thawing cycles, and then centrifuged of 1,300 rpm for 5 min to collect the nuclei. The nuclei was lysed in a lysis buffer solution (20 mM HEPES (pH 7.9), 25% glycerol, 420 mH KCl, 1.5 mM MgCl$_2$, 0.2 mM EDTA) to obtain a protein extract. In order to conduct Western blotting, the resulting protein organic layer was subjected to SDS-PAGE to separate the proteins by the size and transferred onto the nitrocellulose membrane according to the conventional method. The amount of acetylated histone H4 was measured using anti-acetyl histone H4 antibody (Upstate, USA) and evaluated the HDAC inhibitory activity of the inventive compounds by comparing the degree of increase of acetylated histone H4 relative to the control (SAHA). The results are shown in Table 6.

TABLE 6

| Compound | Inhibitory conc. against cancer cell growth (EC$_{50}$ μM) HCT116 | Effect on increase of acetyl-Histone H4 compared with SAHA |
|---|---|---|
| Example 3-1 | 0.2 | + |
| Example 3-2 | 0.2 | + |
| Example 3-3 | 0.5 | + |
| Example 3-4 | 0.7 | + |
| Example 3-7 | 1.2 | + |
| Example 3-8 | 0.5 | + |
| Example 3-9 | 0.4 | + |
| Example 3-10 | <0.2 | + |
| Example 3-11 | 1.3 | + |
| Example 3-14 | 0.3 | + |
| SAHA | 1.6 | + |

As shown in Table 6, the inventive naphthalenyloxypropenyl derivatives of formula (3) has a markedly enhanced inhibitory activity against HDAC, which leads to effective suppression of the cancer cell proliferation.

Preparation of Naphthalenyloxypropenyl Derivatives of Formula (4)

Preparation Example 4-1

Preparation of t-butyl-3-hydroxy-2-methylene-3-(4-methoxycarbonylphenyl)propanoate (the Compound of Formula XXIII)

4-(Methoxycarbonyl)benzaldehyde (3.3 g, 20 mM), t-butylacrylate (3.5 ml, 24 mM) and 1,4-diazabicyclo[2,2,2]octane (449 mg, 4 mM) were mixed and stirred in a vessel at room temperature for 5 days. The resulting mixture was extracted with diethyl ether. The organic layer was separated, washed with 2N hydrochloric acid, water, and sodium bicarbonate in order, dried over anhydrous sodium sulfate, filtered and concentrated under reduced pressure. The residue thus obtained was subjected to a silica gel column chromatography, to obtain 4.2 g of the title compound as a white solid (yield 73%).
$^1$H-NMR (300 MHz, CDCl$_3$) δ 1.40 (s, 9H), 3.28 (m, 1H), 3.91 (s, 3H), 5.53 (d, 1H, J=5.2 Hz), 5.71 (s, 1H), 6.27 (s, 1H), 7.45 (d, 2H, J=8.0 Hz), 7.81 (d, 2H, J=8.0 Hz);
MS (EI, 70 eV) m/z 292 (M$^+$), 283, 255, 241, 227, 201, 189, 179, 150, 135;
Melting point: 70° C.

Preparation Example 4-2

Preparation of methyl 4-(3-bromo-2-t-butoxycarbonylpropenyl)benzoate (the Compound of Formula XXIV)

t-Butyl-3-hydroxy-2-methylene-3-(4-methoxycarbonylphenyl)-propanoate (994 mg, 3.4 mM) obtained in Preparation Example 4-1 was dissolved in ethyl ether (10 ml), and cooled to 0° C. To the resulting mixture, tribromophosphine (0.35 ml, 3.74 mM) was slowly added and stirred at room temperature for 1 hr. After the completion of reaction, the reaction mixture was poured to ice water, and the resulting mixture was extracted with ethyl ether. The organic layer was separated, washed with brine, dried over anhydrous MgSO$_4$, filtered and concentrated under reduced pressure. The residue thus obtained was subjected to a silica gel column chromatography, to obtain 943 mg of the title compound as a yellowish green solid (yield 71%)
$^1$H-NMR (300 MHz, CDCl$_3$) δ 1.40 (S, 9H, OCH$_3$), 3.88 (S, 3H, OCH$_3$), 3.97 (S, 2H, CH$_2$), 7.41 (d, 2H, J=8.4 Hz, ArH), 7.50 (s, 1H), 7.91 (d, 2H, J=8.4 Hz, ArH);
MS (EI, 70 eV) m/z 355 (M$^+$), 338, 296, 278, 259, 219, 187, 143, 115;
Melting point: 78° C.

Preparation Example 4-3

Preparation of methyl 4-[3-(naphthalen-1-yloxy)-2-t-butoxycarbonylpropenyl]benzoate (the Compound of Formula XXV)

Methyl 4-(3-bromo-2-t-butoxycarbonylpropenyl)benzoate (355 mg, 1.00 mM) obtained in Preparation Example 4-2 was dissolved in acetone (5 ml), and potassium carbonate (207 mg, 1.50 mM) and 1-naphthalenol (144 mg 1.00 mM) were added thereto. The resulting mixture was heated to reflux for 3 hrs. After the completion of reaction, the reaction mixture was cooled to room temperature, and filtered to remove the solvent therefrom. The residue thus obtained was subjected to a silica gel column chromatography to obtain 438 mg of the title compound as a white solid (yield 99%).
$^1$H-NMR (200 MHz, CDCl$_3$) δ 1.49 (S, 9H, CH$_3$), 3.89 (S, 3H, OCH$_3$), 4.96 (S, 2H, CH$_2$), 6.84 (d, 1H, J=7.33 Hz, ArH), 7.53 (m, 5H, ArH), 7.89 (m, 1H, ArH), 8.01 (m, 3H, ArH), 8.24 (m, 3H, ArH)

Preparation Example 4-4

Preparation of methyl 4-[2-hydroxymethyl-3-(naphthalen-1-yloxy)-propenyl]-benzoate (the Compound of Formula XXVI)

Methyl 4-[3-(naphthalen-1-yloxy)-2-t-butoxycarbonylpropenyl]-benzoate (2 g, 5.52 mM) obtained in Preparation Example 4-3 was dissolved in tetrahydrofuran (30 ml), and triethylamine (1.15 ml, 8.27 mM) and ethyl chloroformate (0.792 ml, 8.279 mM) were slowly added thereto at 0° C. The resulting mixture was stirred for 1 hour, and thereto added were sodium borohydride (1.462 mg, 38.64 mM) and distilled water (10 ml) in order, and the resulting mixture was stirred at room temperature for 2.5 hours. The reaction mixture was adjusted to pH 2 with 1N HCl aqueous solution, and extracted with ethyl acetate. The organic layer was separated, washed with an aqueous saturated sodium bicarbonate solution and then brine, dried over anhydrous magnesium sulfate, and filtered. The residue thus obtained was subjected to a silica gel column chromatography, to obtain 1.58 g of the title compound as a white solid (yield 82%).
$^1$H-NMR (200 MHz, CDCl$_3$) δ 3.89 (S, 3H, OCH$_3$), 4.55 (S, 2H, CH$_2$), 4.88 (S, 2H, CH$_2$), 6.71 (d, 1H, J=7.5 Hz, ArH), 6.96 (S, 1H, CH), 7.28-7.54 (m, 6H, ArH), 7.83 (m, 1H, ArH), 8.03 (d, 2H, J=8.1 Hz, ArH), 8.30 (m, 1H, ArH)

Preparation Example 4-5

Preparation of methyl 4-[2-bromomethyl-3-(naphthalen-1-yloxy)-propenyl]-benzoate (the Compound of Formula XXVII)

Methyl 4-[2-hydroxymethyl-3-(naphthalen-1-yloxy)-propenyl]-benzoate (1.57 g, 4.52 mM) obtained in Preparation Example 4-4 was dissolved in dichloromethane (15 ml), and triphenylphosphine (1.78 g, 6.79 mM) was added thereto. The resulting mixture was cooled to 0° C., and tetrabromomethane (2.25 g, 6.79 mM) was added thereto. The resulting mixture was stirred for 6 hours, and concentrated under reduced pressure. The residue thus obtained was subjected to a silica gel column chromatography to obtain 1.36 g of the title compound as a white solid (yield 73%).
$^1$H-NMR (200 MHz, CDCl$_3$) δ 3.91 (S, 3H, OCH$_3$), 4.42 (S, 2H, CH$_2$), 4.98 (S, 2H, CH$_2$), 6.71 (d, 1H, J=7.5 Hz, ArH), 7.05 (S, 1H, CH), 7.27-7.56 (m, 6H, ArH), 7.83 (m, 1H, ArH), 8.03 (d, 2H, J=8.1 Hz, ArH), 8.30 (m, 1H, ArH)
Further, amine compounds (RR$_1$'''NH) used in Examples 4-1 to 4-24 may be commercially available or can be easily synthesized using conventional methods.
Particularly, amine compounds substituted with pyrrolidine or piperidine, which is substituted with $C_{1-6}$alkyl, were synthesized as shown in Reaction Scheme 9 or 10:

Reaction Scheme 9

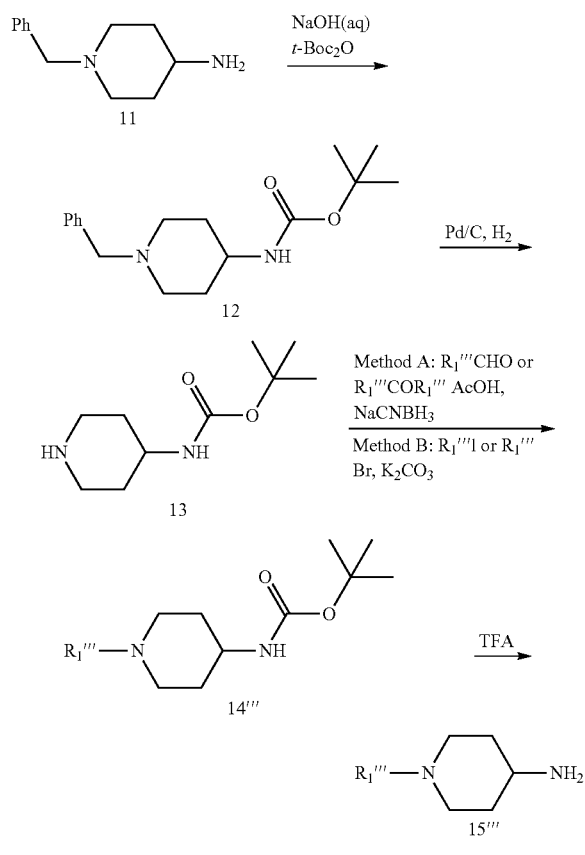

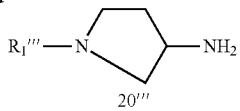

wherein,
$R_1'''$ is $C_{1-6}$alkyl.

Preparation Examples of the Above Amine Compounds were represented in the following.

Preparation Example 4-i

Preparation of
t-butyl-1-benzylpiperidin-4-ylcarbamate (the Compound of Formula 12)

1-Benzylpiperidin-4-ylamine (3 g, 15.8 mmol) as a starting material was dissolved in 1M aqueous sodium hydroxide solution (35.8 ml) and t-butanol (32 ml) in a 250 ml vessel, and t-butyl-dicarbonate ((t-Boc)$_2$O; 3.79 g, 17.38 mmol) was added thereto while stirring. The resulting mixture was reacted at room temperature for 12 hrs. After the completion of reaction, the reaction mixture was extracted with ethyl acetate twice. The organic layer was separated, washed with 0.1N hydrochloric acid aqueous solution and brine in order, dried over anhydrous sodium sulfate, filtered, and concentrated under reduced pressure. The residue thus obtained was subjected to a silica gel column chromatography to obtain 3.801 g of the title compound as a white solid (82.8%).

$^1$H-NMR (200 MHz, CDCl$_3$) δ 1.38 (s, 9H), 1.86-2.33 (m, 4H), 2.70 (m, 2H), 3.40 (m, 2H), 3.57 (br, 1H), 4.12 (s, 2H), 7.43 (m, 3H), 7.55 (m, 2H).
LC/MS (M$^+$H): 291.

Preparation Example 4-ii

Preparation of t-butylpiperidin-4-ylcarbamate (the Compound of Formula 13)

t-Butyl-1-benzylpiperidin-4-ylcarbamate (3.801 g, 13.1 mmol) obtained in Preparation Example 4-i was dissolved in 26 ml of methanol in a 100 ml vessel, and a catalytic quantity of 10% active palladium/carbon was added thereto, and the resulting mixture was reacted under a hydrogen atmosphere for 12 hrs. After the completion of reaction, the reaction mixture was filtered through a cellite pad to remove the active palladium/carbon catalyst and the solvent was removed under reduced pressure therefrom. Then, the residue thus obtained was subjected to a silica gel column chromatography to obtain 2.64 g of the title compound (yield 99%).

$^1$H-NMR (200 MHz, CD$_3$OD) δ 1.36 (s, 9H), 1.84-2.36 (m, 4H), 2.74 (m, 2H), 3.42 (m, 2H), 3.60 (br, 1H).
LC/MS (M$^+$H): 201.

Preparation Example 4-iii

Preparation of t-butyl-1-R-piperidin-4-ylcarbamate (the Compound of Formula 14''')

(4-iii-1) t-Butyl-1-isopropylpiperidin-4-ylcarbamate (14'''a)

Method A: t-Butyl piperidin-4-ylcarbamate (3 g, 15 mmol) obtained in Preparation Example 4-ii was dissolved in methanol (30 ml) in a 100 ml vessel, and acetone (7.70 ml, 105

Reaction Scheme 10

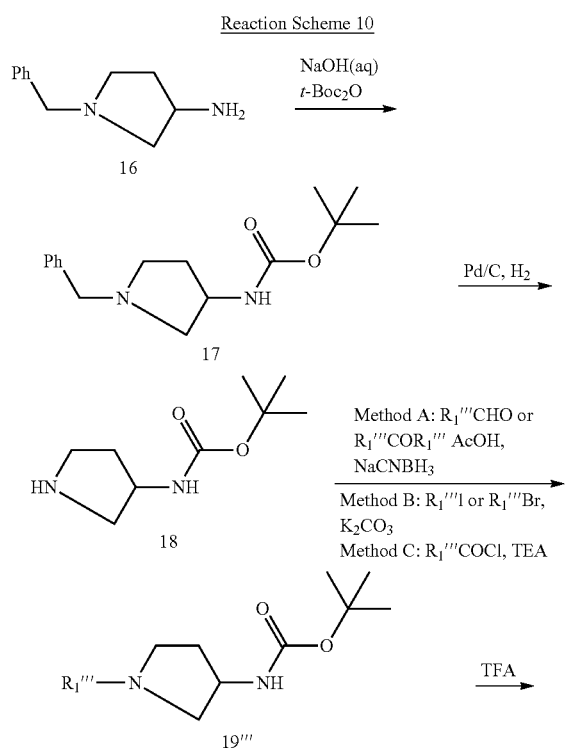

mmol) and acetic acid (0.45 ml, 7.5 mmol) were added thereto while stirring. To the resulting mixture, NaCNBH$_3$ (1.885 mg, 30 mmol) was added in 4-divided portions and reacted for 18 hrs. After the completion of reaction, ice water was poured to the reaction product and then the resulting mixture was stirred and extracted with ethyl acetate. The organic layer was separated, washed with aqueous sodium bicarbonate and brine in order, dried over anhydrous sodium sulfate, filtered, and concentrated under reduced pressure. The residue thus obtained was subjected to a silica gel column chromatography to obtain 2.644 g of the title compound as a white solid (yield 73.3%).

$^1$H-NMR (200 MHz, CDCl$_3$) δ 1.36 (d, J=7.0 Hz, 6H), 1.44 (s, 9H), 2.00 (m, 2H), 2.17 (m, 2H), 2.94 (m, 2H), 3.38 (m, 3H), 3.69 (m, 1H), 4.92 (br, 1H).

LC/MS (M$^+$H): 243.

(4-iii-2) t-Butyl-1-cyclopropylpiperidin-4-ylcarbamate (14'''b)

The procedure of Preparation Example (4-iii-1) was repeated except for using bromocyclopropane instead of acetone as the amine substituent, to obtain 0.716 g of the title compound as pale yellow oil (yield 60%).

$^1$H-NMR (200 MHz, CDCl$_3$) δ 0.44 (m, 4H), 1.31 (m, 2H), 1.47 (s, 9H), 1.58 (m, 1H), 1.90 (m, 2H), 2.29 (m, 2H), 2.94 (m, 2H), 3.49 (br, 1H), 4.42 (br, 1H)

LC/MS (M$^+$H): 241

(4-iii-3) t-Butyl-1-cyclopentylpiperidin-4-ylcarbamate (14'''c)

The procedure of Preparation Example (4-iii-1) was repeated except for using bromocyclopentane instead of acetone as the amine substituent, to obtain 1.16 g of the title compound as pale yellow oil (yield 86%).

$^1$H-NMR (200 MHz, CDCl$_3$) δ 1.45 (s, 9H), 1.50-1.80 (m, 8H), 1.81-2.18 (m, 6H), 2.50 (m, 1H), 2.94 (m, 2H), 3.48 (br, 1H), 4.41 (br, 1H)

LC/MS (M$^+$H): 269

(4-iii-4) t-Butyl-1-methylpiperidin-4-ylcarbamate (14'''d)

The procedure of Preparation Example (4-iii-1) was repeated except for using iodomethane instead of acetone as the amine substituent, to obtain 1.43 g of the title compound as pale yellow oil (yield 79.4%).

$^1$H-NMR (200 MHz, CDCl$_3$) δ 1.44 (s, 9H), 1.45 (m, 2H), 1.92 (m, 2H), 2.07 (m, 2H), 2.27 (s, 3H), 2.74 (m, 2H), 3.44 (br, 1H), 4.43 (br, 1H).

LC/MS (M$^+$H): 215.

(4-iii-5) t-Butyl-1-ethylpiperidin-4-ylcarbamate (14'''e)

Method B: t-Butyl piperidin-4-ylcarbamate (1.5 g, 7.49 mmol) obtained in Preparation Example 4-ii was dissolved in N,N'-dimethylformamide (19 ml) in a 25 ml vessel at 0° C., and K$_2$CO$_3$ (2.07 g, 14.98 mmol, 2 eq.) and iodoethane (0.60 ml, 7.49 mmol, 1 eq.) were added thereto while stirring. The resulting mixture was heated from 0° C. to room temperature and reacted for 4 hrs. After the completion of reaction, the solvent was distilled off under reduced pressure and the residue thus obtained was extracted with ethyl ester. The organic layer was separated, washed with an aqueous saturated sodium bicarbonate solution and brine in order, dried over anhydrous magnesium sulfate, and concentrated under reduced pressure. The residue thus obtained was subjected to a silica gel column chromatography to obtain 1.337 g of the title compound as pale yellow oil (yield 78%).

$^1$H-NMR (200 MHz, CDCl$_3$) δ 1.10 (t, J=7.4 Hz, 3H), 1.43 (m, 2H), 1.47 (s, 9H), 1.99 (m, 4H), 2.40 (q, J=7.2 Hz, 2H), 2.85 (m, 2H), 3.47 (br, 1H), 4.43 (br, 1H).

LC/MS (M$^+$H): 229.

Preparation Example 4-iv

Preparation of 1-R-piperidin-4-ylamine (the Compound of Formula 15''')

(4-iv-1) 1-Isopropylpiperidin-4-ylamine (15'''a)

The compound (14'''a) (2.64 g, 10.9 mmol) obtained in Preparation Example (4-iii-1) was dissolved in methanol (20 ml) in a 250 ml vessel, and trifluoroacetic acid (4.06 ml, 54.5 mmol, 5 eq.) was added dropwise thereto while stirring. The resulting mixture was reacted for 18 hrs. After the completion of reaction, the mixture was concentrated under reduced pressure, and then subjected to azeotropic distillation with CHCl$_3$ 3 times. The reaction mixture was basified with aqueous KOH solution (20 ml) and extracted with CHCl$_3$ 3 times. The organic layer was separated, washed with brine, dried, filtered and distilled under reduced pressure, to obtain 1.229 g of the title compound as yellow oil (yield 79.3%).

$^1$H-NMR (200 MHz, CDCl$_3$) δ 1.02 (d, J=6.6 Hz, 6H), 1.38 (m, 2H), 1.56 (br, 2H), 1.80 (d, J=11.8 Hz, 2H), 2.17 (m, 2H), 2.71 (m, 2H), 2.80 (m, 2H).

LC/MS (M$^+$H): 143.

(4-iv-2) 1-Cyclopropylpiperidin-4-ylamine (15'''b)

The procedure of Preparation Example (4-iv-1) was repeated except for using the compound (716 mg, 2.98 mmol) obtained in Preparation Example (4-iii-2) as the starting material, to obtain 286 mg of the title compound as pale yellow oil (yield 75%).

$^1$H-NMR (200 MHz, CDCl$_3$) δ 0.44 (m, 4H), 1.33 (m, 2H), 1.52 (m, 1H), 1.76 (m, 2H), 2.20 (m, 2H), 2.66 (m, 1H), 3.00 (m, 2H)

LC/MS (M$^+$H): 141

(4-iv-3) 1-Cyclopentylpiperidin-4-ylamine (15'''c)

The procedure of Preparation Example (4-iv-1) was repeated except for using the compound (1.16 g, 4.3 mmol) obtained in Preparation Example (4-iii-3) as the starting material, to obtain 689 mg of the title compound as pale yellow oil (yield 95%).

$^1$H-NMR (200 MHz, CDCl$_3$) δ 1.50-1.80 (m, 8H), 1.81-2.18 (m, 6H), 2.50 (m, 2H), 2.74 (m, 2H)

LC/MS (M$^+$H): 169

(4-iv-4) 1-Methylpiperidin-4-ylamine (15'''d)

The procedure of Preparation Example (4-iv-1) was repeated except for using the compound (1.80 g, 8.4 mmol) obtained in Preparation Example (4-iii-4) as the starting material, to obtain 820 mg of the title compound as pale yellow oil (yield 86%).

$^1$H-NMR (200 MHz, CDCl$_3$) δ 1.37 (m, 2H), 1.78 (m, 2H), 1.99 (m, 2H), 2.27 (s, 3H), 2.70 (m, 1H), 2.81 (m, 2H).

LC/MS (M$^+$H): 115.

(4-iv-5) 1-Ethylpiperidin-4-ylamine (15'''e)

The procedure of Preparation Example (4-iv-1) was repeated except for using the compound (1.34 g, 5.86 mmol) obtained in Preparation Example (4-iii-5) as the starting material, to obtain 672 mg of the title compound as pale yellow oil (yield 89%).

$^1$H-NMR (200 MHz, CDCl$_3$) δ 1.08 (t, J=7.2 Hz, 3H), 1.37 (m, 2H), 1.81-2.08 (m, 4H), 2.37 (q, J=7.2 Hz, 2H), 2.65 (m, 1H), 2.87 (m, 2H).

LC/MS (M$^+$H): 129.

Preparation Example 4-v

Preparation of t-butyl-1-benzylpyrrolidin-3-ylcarbamate (the Compound of Formula 17)

1-benzylpyrrolidin-4-ylamine (10 g, 57 mmol) was dissolved in 3M sodium hydroxide aqueous solution (21 ml) and t-butanol (114 ml) in a 500 ml vessel, and t-butyl-dicarbonate ((t-Boc)$_2$O; 13.07 g, 59.9 mmol) wad added thereto while stirring. The resulting mixture was reacted at room temperature for 12 hrs, extracted with ethyl acetate twice. The organic layer was separated, washed with 0.1N hydrochloric acid solution and brine, dried over anhydrous sodium sulfate, filtered, and concentrated under reduced pressure. The residue thus obtained was subjected to a silica gel column chromatography to obtain 15.25 g of the title compound as a white solid (yield 97%).

$^1$H-NMR (200 MHz, CDCl$_3$) δ 1.43 (s, 9H), 2.27 (m, 2H), 2.57 (m, 3H), 2.75 (m, 1H), 3.59 (s, 2H), 4.16 (br, 1H), 4.85 (br, 1H), 7.30 (m, 5H)

LC/MS (M$^+$H): 277

Preparation Example 4-vi

Preparation of t-butyl-pyrrolidin-3-ylcarbamate (the Compound of Formula 18)

t-Butyl-1-benzylpyrrolidin-3-ylcarbamate (15.75 g, 57.0 mmol) obtained in Preparation Example 4-v was dissolved in 114 ml of a mixture of methanol and tetrabutylfuran (4:1) in a 100 ml vessel. To the resulting mixture, a catalytic quantity of 10% active palladium/carbon was added, and the resulting mixture was reacted under a hydrogen atmosphere for 12 hrs. After the completion of reaction, the reaction mixture was filtered through a cellite pad to remove the active palladium/carbon catalyst and the solvent was removed under reduced pressure therefrom. Then, the residue thus obtained was subjected to a silica gel column chromatography to obtain 9.51 g of the title compound (yield 99%).

$^1$H-NMR (200 MHz, CDCl$_3$) δ 1.41 (s, 9H), 2.26 (m, 2H), 2.55 (m, 3H), 2.74 (m, 1H), 4.84 (br, 1H),

LC/MS (M$^+$H): 187

Preparation Example 4-vii

Preparation of t-butyl-1-R-pyrrolidin-3-ylcarbamate (the Compound of Formula 19''')

(4-vii-1) t-Butyl-1-isopropylpyrrolidin-3-ylcarbamate (19'''a)

Method A: t-Butyl pyrrolidin-4-ylcarbamate (1.24 g, 6.7 mmol) obtained in Preparation Example 4-vi was dissolved in methanol (14 ml) in a 250 ml vessel, and acetone (3.44 ml, 46.9 mmol) and acetic acid (0.19 ml, 3.35 mmol) were added thereto while stirring. To the resulting mixture, NaCNBH$_3$ (842 ml, 13.4 mmol) was added in 4-divided portions and reacted for 18 hrs. After the completion of reaction, ice water was poured to the reaction product and then the resulting mixture was stirred and extracted with ethyl acetate. The organic layer was separated, washed with aqueous sodium bicarbonate and brine in order, dried over anhydrous sodium sulfate, filtered, and concentrated under reduced pressure. The residue thus obtained was subjected to a silica gel column chromatography to obtain 897 mg of the title compound as a white solid (yield 58%).

$^1$H-NMR (200 MHz, CDCl$_3$) δ 1.40 (d, J=6.6 Hz, 6 Hz), 1.44 (s, 9H), 2.12 (m, 1H), 2.48 (m, 1H), 3.27 (m, 1H), 3.39 (m, 3H), 3.57 (m, 1H), 4.38 (m, 1H), 5.41 (m, 1H)

LC/MS (M$^+$H): 229

(4-vii-2) t-Butyl-1-cyclopropylpyrrolidin-3-ylcarbamate (19'''b)

The procedure of Preparation Example (4-vii-1) was repeated except for using bromocyclopropane instead of acetone as the amine substituent, to obtain 7.17 g of the title compound as pale yellow oil (yield 59%).

$^1$H-NMR (200 MHz, CDCl$_3$) δ 0.40 (m, 4H), 1.44 (s, 9H), 1.60 (m, 2H), 2.19 (m, 1H), 2.57 (m, 2H), 2.81 (m, 2H), 4.14 (br, 1H), 4.80 (br, 1H)

LC/MS (M$^+$H): 227

(4-vii-3) t-Butyl-1-cyclohexylpyrrolidin-3-ylcarbamate (19'''c)

The procedure of Preparation Example (4-vii-1) was repeated except for using cyclohexanone instead of acetone as the amine substituent, to obtain 1.103 g of the title compound as pale yellow oil (yield 77%).

$^1$H-NMR (200 MHz, CDCl$_3$) δ 1.23 (m, 2H), 1.41 (m, 2H), 1.46 (s, 9H), 1.78 (m, 2H), 1.89 (m, 2H), 2.06 (m, 3H), 2.44 (m, 1H), 2.76 (m, 1H), 3.04 (m, 1H), 3.24 (m, 2H), 3.49 (m, 1H), 4.34 (m, 1H), 5.33 (m, 1H)

LC/MS (M$^+$H): 269

(4-vii-4) t-Butyl-1-ethylpyrrolidin-3-ylcarbamate (19'''d)

Method B: t-butyl pyrrolidin-4-ylcarbamate (1.5 g, 8.05 mmol) obtained in Preparation Example 4-vi was dissolved in N,N'-dimethylformamide (20 ml) in a 100 ml vessel at 0° C., and K$_2$CO$_3$ (2.23 g, 16.1 mmol, 2 eq.) and iodoethane (0.64 ml, 8.05 mmol, 1 eq.) were added thereto while stirring. The resulting mixture was heated from 0° C. to room temperature and reacted for 12 hrs. After the completion of reaction, the solvent was distilled off under reduced pressure and the residue thus obtained was extracted with ethyl ester. The organic layer was separated, washed with an aqueous saturated sodium bicarbonate solution and brine in order, dried over anhydrous magnesium sulfate, and concentrated under reduced pressure. The residue thus obtained was subjected to a silica gel column chromatography to obtain 1.13 g of the title compound as pale yellow oil (yield 66%).

$^1$H-NMR (200 MHz, CDCl$_3$) δ 1.10 (t, J=7.4 Hz, 3H), 1.44 (s, 9H), 1.69 (m, 1H), 2.27 (m, 2H), 2.48 (q, J=7.0 Hz, 2H), 2.57 (m, 1H), 2.81 (m, 1H), 4.16 (br, 1H), 4.86 (br, 1H)

LC/MS (M$^+$H): 215

(4-vii-5) t-Butyl-1-(cyclohexanecarbonyl)pyrrolidin-3-ylcarbamate (19'''e)

Method C: t-Butyl-pyrrolidin-4-ylcarbamate (1 g, 5.4 mmol) obtained in Preparation Example 4-vi was dissolved in dichloromethane (14 ml) in a 50 ml vessel at 0° C., and triethylamine (0.83 ml, 5.94 mmol, 1.1 eq.) and cyclohexylcarbonyl chloride (0.79 ml, 5.94 mmol, 1.1 eq.) were added thereto while stirring. The resulting mixture was heated from 0° C. to room temperature and kept for 4 hrs. After the completion of reaction, the solvent was distilled off under reduced pressure and the residue thus obtained was extracted with dichloromethane. The organic layer was separated, washed with an aqueous saturated sodium bicarbonate solution and brine in order, dried over anhydrous magnesium sulfate, and concentrated under reduced pressure. The residue thus obtained was subjected to a silica gel column chromatography to obtain 1.57 g of the title compound as pale yellow oil (yield 98%).

$^1$H-NMR (200 MHz, CDCl$_3$) δ 1.26 (m, 4H), 1.46 (s, 9H), 1.79 (m, 6H), 1.98 (m, 1H), 2.08-2.49 (m, 2H), 3.39 (m, 1H), 3.59 (m, 2H), 3.73 (m, 1H), 4.22 (m, 1H), 4.63 (m, 1H)

LC/MS (M$^+$H): 297

Preparation Example 4-viii

Preparation of 1-R-pyrrolidin-3-ylamine (the Compound of Formula 20''')

(4-viii-1) 1-Isopropylpyrrolidin-3-ylamine (20'''a)

The compound (19'''a) (0.897 g, 3.9 mmol) obtained in Preparation Example (4-vii-1) was dissolved in dichloromethane (10 ml) in a 50 ml vessel, and trifluoroacetic acid (1.45 ml, 1.95 mmol, 5 eq.) was added dropwise thereto while stirring. The resulting mixture was reacted for 18 hrs. After the completion of reaction, the mixture was concentrated under reduced pressure, and then subjected to azeotropic distillation with CHCl$_3$ 3 times. The reaction mixture was basified with 2N aqueous KOH solution (20 ml) and extracted with CHCl$_3$ 3 times. The organic layer was separated, washed with brine, dried, filtered and distilled under reduced pressure, to obtain 433 mg of the title compound as yellow oil (yield 86%).

$^1$H-NMR (200 MHz, CDCl$_3$) δ 1.38 (d, J=6.6 Hz, 6 Hz), 2.11 (m, 1H), 2.47 (m, 1H), 3.15 (m, 1H), 3.29 (m, 4H), 3.57 (m, 1H)

LC/MS (M$^+$H): 129

(4-viii-2) 1-Cyclopropylpyrrolidin-3-ylamine (20'''b)

The procedure of Preparation Example (4-viii-1) was repeated except for using the compound obtained in Preparation Example (4-vii-2) (1.129 g, 5.27 mmol) as the starting material, to obtain 477 mg of the title compound as pale yellow oil (yield 79%).

$^1$H-NMR (200 MHz, CDCl$_3$) δ 0.41 (m, 4H), 1.55 (m, 2H), 2.16 (m, 1H), 2.40 (m, 1H), 2.68 (m, 1H), 2.80 (m, 1H), 2.93 (m, 1H), 3.47 (m, 1H)

LC/MS (M$^+$H): 127

(4-viii-3) 1-Cyclohexylpyrrolidin-3-ylamine (20'''c)

The procedure of Preparation Example (4-viii-1) was repeated except for using the compound obtained in Preparation Example (4-vii-3) (1.10 g, 4.11 mmol) as the starting material, to obtain 513 mg of the title compound as pale yellow oil (yield 74%).

$^1$H-NMR (200 MHz, CDCl$_3$) δ 1.19 (m, 4H), 1.39-1.62 (m, 4H), 1.72 (m, 1H), 1.93 (m, 3H), 2.14 (m, 1H), 2.31 (m, 1H), 2.58-2.78 (m, 2H), 2.85 (m, 1H), 3.47 (m, 1H)

LC/MS (M$^+$H): 169

(4-viii-4) 1-Ethylpyrrolidin-3-ylamine (20'''d)

The procedure of Preparation Example (4-viii-1) was repeated except for using the compound obtained in Preparation Example (4-vii-4) (1.129 g, 5.27 mmol) as the starting material, to obtain 477 mg of the title compound as pale yellow oil (yield 79%).

$^1$H-NMR (200 MHz, CDCl$_3$) δ 1.13 (t, J=7.2 Hz, 3H), 1.51 (m, 2H), 2.31 (m, 2H), 2.47 (m, 3H), 2.73 (m, 1H), 3.54 (m, 1H)

LC/MS (M$^+$H): 115

(4-viii-5) (3-Aminopyrrolidin-1-yl)(cyclohexyl)methanone (20'''e)

The procedure of Preparation Example (4-viii-1) was repeated except for using the compound obtained in Preparation Example (4-vii-5) (1.57 g, 5.3 mmol) as the starting material, to obtain 1.51 g of the title compound as pale yellow oil (yield 99%).

$^1$H-NMR (200 MHz, CDCl$_3$) δ 1.26 (m, 4H), 1.79 (m, 6H), 1.98 (m, 1H), 2.08-2.49 (m, 2H), 3.39 (m, 1H), 3.59 (m, 2H), 3.73 (m, 1H)

LC/MS (M$^+$H): 197

Preparation Example 4-6

Preparation of the compound of formula XXVIII

(4-6-1) (Z)-Methyl 4-(3-(1-ethylpiperidin-4-ylamino)-2-((naphthalen-1-yloxy)methyl)prop-1-enyl)benzoate (XXVIIIa)

Methyl 4-[2-bromomethyl-3-(naphthalen-1-yloxy)-propenyl]-benzoate (412 mg, 1 mmol) was dissolved in N,N'-dimethylformamide (2.5 ml) in a 100 ml flask at 0° C., and to the resulting solution, triethylamine (0.17 ml, 1.2 mmol, 1.2 eq.) and 1-ethylpiperidin-4-ylamine (128 ml, 1.0 mmol, 1.0 eq.) were added while stirring. The resulting mixture was heated from 0° C. to room temperature, and then reacted for 4 hours. After the completion of reaction, the mixture was concentrated under reduced pressure, and the residue thus obtained was extracted with ethyl ester. The organic layer was separated, washed with an aqueous saturated sodium bicarbonate solution and brine in order, dried over anhydrous magnesium sulfate, and concentrated under reduced pressure. The residue thus obtained was subjected to a silica gel column chromatography to obtain 211 mg of the title compound as pale yellow oil (yield 46%).

$^1$H-NMR (200 MHz, CDCl$_3$) δ 1.29 (m, 5H), 1.72 (m, 4H), 2.63 (m, 3H), 2.96 (m, 2H), 3.63 (s, 2H), 3.91 (s, 3H), 4.87 (s, 2H), 6.70 (s, J=7.8 Hz, 1H), 6.89 (s, 1H), 7.28-7.57 (m, 6H), 7.80 (m, 1H), 7.99 (d, J=8.2 Hz, 2H), 8.22 (m, 1H)

LC/MS (M$^+$H): 459

(4-6-2) ((Z)-Methyl 4-(3-(1-ethylpyrrolidin-3-ylamino)-2-(naphthalen-1-yloxy)methylprop-1-enyl)benzoate (XXVIIIb)

The procedure of Preparation Example (4-6-1) was repeated except for using 1-ethylpyrrolidin-3-ylamine instead of 1-ethylpiperidin-4-ylamine as the amine compound, to obtain 160 mg of the title compound as pale yellow oil (yield 36%).

$^1$H-NMR (200 MHz, CDCl$_3$) δ 1.26 (t, J=7.8 Hz, 3H), 1.81 (m, 2H), 2.32 (m, 2H), 2.86 (q, J=7.2 Hz, 2H), 3.15 (m, 2H), 3.49 (s, 2H), 3.60 (m, 1H), 3.90 (s, 3H), 4.86 (s, 2H), 6.69 (d, J=7.5 Hz, 1H), 6.90 (s, 1H), 7.28-7.52 (m, 6H), 7.80 (d, J=7.2 Hz, 1H), 7.98 (d, J=8.1 Hz, 2H), 8.22 (d, J=7.2 Hz, 1H)

LC/MS (M$^+$H): 445

(4-6-3) (Z)-Methyl 4-(2-((4-(trifluoromethoxy)benzylamino)-methyl)-3-(naphthalen-1-yloxy)prop-1-enyl)benzoate (XXVIIIc)

The procedure of Preparation Example (4-6-1) was repeated except for using 1-(trifluoromethoxy)benzylamine instead of 1-ethylpiperidin-4-ylamine as the amine compound, to obtain 421 mg of the title compound as pale yellow oil (yield 92%).

TLC (EtOAc/Hex=1/4) Rf 0.20

$^1$H-NMR (300 MHz, CDCl$_3$) δ 3.65 (s, 2H), 3.86 (s, 2H), 3.89 (s, 3H), 4.86 (s, 2H), 6.69 (d, J=7.4 Hz, 1H), 6.89 (s, 1H), 7.10 (d, J=7.6 Hz, 2H), 7.25-7.50 (m, 8H), 7.79 (d, J=7.4 Hz, 1H), 7.96 (d, J=7.8 Hz, 2H), 8.18 (d, J=7.4 Hz, 1H)

LC/MS (M$^+$H): 506

(4-6-4) (Z)-t-Butyl-3-(3-(4-(methoxycarbonyl)phenyl)-2-((naphthalen-1-yloxy)methyl)allylamino)-pyrrolidine-1-carboxylate (XXVIIId)

The procedure of Preparation Example (4-6-1) was repeated except for using 4-(methoxycarbonyl)phenylamine instead of 1-ethylpiperidin-4-ylamine as the amine compound, to obtain 466 mg of the title compound as pale yellow oil (yield 98%).

TLC (MeOH/MC=1/12) Rf 0.45

$^1$H-NMR (300 MHz, CDCl$_3$) δ 1.44 (s, 9H), 1.60-1.74 (m, 2H), 2.01-2.07 (q, J=7.4 Hz, 1H), 2.86 (d, J=7.6 Hz, 2H), 3.10 (m, 1H), 3.35-3.63 (m, 3H), 3.88 (s, 3H), 4.84 (s, 2H), 6.68 (d, J=7.4 Hz, 1H), 6.88 (s, 1H), 7.26-7.50 (m, 6H), 7.78 (t, J=7.8 Hz, 1H), 7.96 (d, J=7.6 Hz, 2H), 8.23 (d, J=7.6 Hz, 1H)

LC/MS (M$^+$H): 517

(4-6-5) (Z)-Methyl 4-(3-(1-(cyclohexanecarbonyl)pyrrolidin-3-ylamino)-2-((naphthalen-1-yloxy)-methyl)prop-1-enyl)benzoate (XXVIIIe)

The procedure of Preparation Example (4-6-1) was repeated except for using 1-(cyclohexanecarbonyl)pyrrolidin-3-ylamine instead of 1-ethylpiperidin-4-ylamine as the amine compound, to obtain 401 mg of the title compound as pale yellow oil (yield 79%).

TLC (MeOH/MC=1/12) Rf 0.25

$^1$H-NMR (300 MHz, CDCl$_3$) δ 1.23 (m, 5H), 1.43 (m, 5H), 2.09 (q, J=7.4 Hz, 3H), 3.58 (m, 4H), 3.87 (d, J=7.4 Hz, 3H), 4.81 (t, J=7.4 Hz, 3H), 4.93 (s, 2H), 6.71 (s, 1H), 6.77 (d, J=7.6 Hz, 1H), 7.31 (m, 2H), 7.46 (m, 4H), 7.82 (d, J=7.6 Hz, 2H), 7.94 (dd, J=7.8, 7.8 Hz, 1H), 8.22 (d, J=7.6 Hz, 1H)

LC/MS (M$^+$H): 527

(4-6-6) (Z)-Methyl 4-(3-(1-cyclopentylpiperidin-4-ylamino)-2-((naphthalen-1-yloxy)methyl)prop-1-enyl)benzoate (XXVIIIf)

The procedure of Preparation Example (4-6-1) was repeated except for using 1-cyclopentylpiperidin-4-ylamine instead of 1-ethylpiperidin-4-ylamine as the amine compound, to obtain 433 mg of the title compound as pale yellow oil (yield 86%).

TLC (MeOH/MC=1/6) Rf 0.40

$^1$H-NMR (300 MHz, CDCl$_3$) δ 1.39 (m, 9H), 2.47 (s, 1H), 3.45 (s, 1H), 3.57 (m, 6H), 3.86 (s, 3H), 4.63 (s, 2H), 4.90 (s, 2H), 5.29 (s, 1H), 6.74 (d, J=7.4 Hz, 1H), 7.27 (s, 1H), 7.48 (m, 5H), 7.64 (s, 1H), 7.83 (t, J=7.8 Hz, 1H), 7.93 (d, J=7.8 Hz, 2H), 8.09 (t, J=7.6 Hz, 1H)

LC/MS (M$^+$H): 499

(4-6-7) (Z)-Methyl 4-(3-(1-(cyclohexylmethyl)pyrrolidin-3-ylamino)-2-((naphthalen-1-yloxy)-methyl-prop-1-enyl)benzoate (XXVIIIg)

The procedure of Preparation Example (4-6-1) was repeated except for using 1-(cyclohexylmethyl)pyrrolidin-3-ylamine instead of 1-ethylpiperidin-4-ylamine as the amine compound, to obtain 477 mg of the title compound as pale yellow oil (yield 90%).

TLC (MeOH/MC=1/6) Rf 0.80

$^1$H-NMR (300 MHz, CDCl$_3$) δ 0.83 (m, 3H), 1.07-1.33 (m, 4H), 1.60 (m, 5H), 2.02 (d, J=7.6 Hz, 2H), 2.17 (m, 5H), 3.46-3.63 (m, 2H), 3.89 (s, 3H), 4.57 (s, 1H), 4.79 (m, 2H), 6.69 (d, J=7.4 Hz, 1H), 6.86 (t, J=7.6 Hz, 2H), 7.18-7.48 (m, 5H), 7.83 (d, J=7.8 Hz, 1H), 7.95 (d, J=7.6 Hz, 2H), 8.26 (d, J=7.6 Hz, 1H)

LC/MS (M$^+$H): 513

(4-6-8) (Z)-Methyl 4-(3-(1-benzylpyrrolidin-3-ylamino)-2-naphthalen-1-yloxy)methylprop-1-enyl)benzoate (XXVIIIh)

The procedure of Preparation Example (4-6-1) was repeated except for using 1-benzylpyrrolidin-3-ylamine instead of 1-ethylpiperidin-4-ylamine as the amine compound, to obtain 485 mg of the title compound as pale yellow oil (yield 94%).

TLC (MeOH/MC=1/12) Rf 0.25

$^1$H-NMR (300 MHz, CDCl$_3$) δ 1.61 (t, J=7.6 Hz, 1H), 2.15 (m, 2H), 2.41 (q, J=7.6 Hz, 1H), 2.51 (d, J=7.6 Hz, 1H), 2.64 (d, J=7.6 Hz, 1H), 2.73 (m, 1H), 3.39 (m, 1H), 3.55 (m, 3H), 3.85 (s, 3H), 4.81 (s, 2H), 6.66 (d, J=7.6 Hz, 1H), 6.85 (s, 1H), 7.35 (m, 6H), 7.47 (m, 5H), 7.76 (t, J=7.8 Hz, 1H), 7.94 (d, J=7.6 Hz, 2H), 8.23 (d, J=7.6 Hz, 1H)

LC/MS (M$^+$H): 507

(4-6-9) (Z)-Methyl 4-(3-(1-cyclopropylpiperidin-4-ylamino)-2-((naphthalen-1-yloxy)methyl)prop-1-enyl)benzoate (XXVIIIi)

The procedure of Preparation Example (4-6-1) was repeated except for using 1-cyclopropylpiperidin-4-ylamine instead of 1-ethylpiperidin-4-ylamine as the amine compound, to obtain 320 mg of the title compound as pale yellow oil (yield 30%).

TLC (MeOH/MC=1/6) Rf 0.55

$^1$H-NMR (300 MHz, CDCl$_3$) δ 0.47 (m, 2H), 1.47 (m, 3H), 1.64 (t, J=7.4 Hz, 3H), 2.32 (m, 1H), 2.57 (s, 1H), 3.04 (q, J=7.4 Hz, 1H), 3.25 (m, 1H), 3.62 (m, 4H), 3.87 (s, 3H), 4.86 (s, 2H), 6.69 (d, J=7.4 Hz, 1H), 6.96 (s, 1H), 7.27-7.50 (m, 4H), 7.78 (d, J=7.4 Hz, 1H), 7.95 (t, J=7.4 Hz, 4H), 8.21 (d, J=7.6 Hz, 1H)

(4-6-10) (Z)-Methyl 4-(3-(1-cyclopropylpyrrolidin-3-ylamino)-2-((naphthalen-1-yloxy)methyl)prop-1-enyl)benzoate (XXVIIIj)

The procedure of Preparation Example (4-6-1) was repeated except for using 1-cyclopropylpyrrolidin-3-ylamine instead of 1-ethylpiperidin-4-ylamine as the amine compound, to obtain 394 mg of the title compound as pale yellow oil (yield 60%).

TLC (MeOH/MC=1/12) Rf 0.80

$^1$H-NMR (300 MHz, CDCl$_3$) δ 0.38 (m, 3H), 1.56 (q, J=7.6 Hz, 2H), 2.11 (m, 2H), 2.51 (q, J=7.6 Hz, 1H), 2.87 (m, 3H), 3.41 (d, J=7.6 Hz, 1H), 3.59 s, 2H), 3.88 (s, 3H), 4.83 (s, 2H), 6.69 (d, J=7.6 Hz, 1H), 6.87 (s, 1H), 7.28-7.50 (m, 4H), 7.78 (d, J=7.8 Hz, 1H), 7.95 (m, 4H), 8.24 (d, J=7.6 Hz, 1H)

(4-6-11) (Z)-Methyl 4-(3-(1-cyclohexylpyrrolidin-3-ylamino)-2-((naphthalen-1-yloxy)methyl)prop-1-enyl)benzoate (XXVIIIk)

The procedure of Preparation Example (4-6-1) was repeated except for using 1-cyclohexylpyrrolidin-3-ylamine instead of 1-ethylpiperidin-4-ylamine as the amine compound, to obtain 463 mg of the title compound as pale yellow oil (yield 95%).

TLC (MeOH/MC=1/12) Rf 0.20

$^1$H-NMR (300 MHz, CDCl$_3$) δ 1.17 (m, 4H), 1.62 (m, 4H), 1.71 (s, 2H), 2.16 (m, 3H), 2.43 (q, J=7.8 Hz, 1H), 2.64 (m, 2H), 2.87 (m, 1H), 3.40 (d, J=7.8 Hz, 1H), 3.59 (s, 2H), 3.88 (s, 3H), 4.84 (s, 2H), 6.68 (d, J=7.4 Hz, 1H), 6.87 (s, 1H), 7.26-7.50 (m, 6H), 7.78 (d, J=7.8 Hz, 1H), 7.96 (d, J=7.6 Hz, 2H), 8.24 (d, J=7.6 Hz, 1H)

(4-6-12) (Z)-Methyl 4-(3-(ethyl-(2-morpholinoethyl) amino)-2-((naphthalen-1-yloxy)methyl)prop-1-enyl) benzoate (XXVIIIl)

The procedure of Preparation Example (4-6-1) was repeated except for using ethyl (2-morpholinoethyl)amine instead of 1-ethylpiperidin-4-ylamine as the amine compound, to obtain 401 mg of the title compound as pale yellow oil (yield 69%).

TLC (MeOH/MC=1/9) Rf 0.90

$^1$H-NMR (300 MHz, CDCl$_3$) δ 1.01 (m, 3H), 1.80 (m, 1H), 2.32 (m, 6H), 2.51 (m, 3H), 3.42 (s, 2H), 3.54 (m, 4H), 3.85 (s, 3H), 4.84 (s, 2H), 6.73 (d, J=7.4 Hz, 1H), 6.90 (s, 1H), 7.30-7.56 (m, 6H), 7.84 (d, J=7.8 Hz, 1H), 7.97 (d, J=7.8 Hz, 2H), 8.30 (d, J=7.6 Hz, 1H)

(4-6-13) (Z)-Methyl 4-(3-(1-methoxypropan-2-ylamino)-2-((naphthalen-1-yloxy)methyl)prop-1-enyl)benzoate (XXVIIIm)

The procedure of Preparation Example (4-6-1) was repeated except for using 1-methoxypropan-2-ylamine instead of 1-ethylpiperidin-4-ylamine as the amine compound, to obtain 240 mg of the title compound as pale yellow oil (yield 57%).

$^1$H-NMR (200 MHz, CDCl$_3$) δ 1.08 (d, J=6.4 Hz, 3H), 3.07 (m, 1H), 3.30 (m, 2H), 3.34 (s, 3H), 3.64 (dd, J=15.8 Hz, 14.4 Hz, 2H), 3.92 (s, 3H), 4.87 (s, 2H), 6.71 (d, J=7.4 Hz, 1H), 6.92 (s, 1H), 7.27-7.57 (m, 6H), 7.81 (m, 1H), 7.98 (d, J=8.2 Hz, 2H), 8.30 (m, 1H)

LC/MS (M$^+$H): 420

Preparation Example 4-7

Preparation of the Compound of Formula XXIX (4-7-1) (Z)-4-(3-(1-Ethylpiperidin-4-ylamino)-2-((naphthalen-1-yloxy)methyl)prop-1-enyl)benzoic acid (XXIXa)

(Z)-Methyl 4-(3-(1-ethylpiperidin-4-ylamino)-2-((naphthalen-1-yloxy)methyl)prop-1-enyl)benzoate (211 mg, 0.46 mmol) obtained in Preparation Example (4-6-1) was dissolved in tetrahydrofuran (1.2 ml) in a 100 ml vessel, and a solution of lithium hydroxide monohydrate (58 mg, 1.35 mmol, 3 eq.) in water (0.4 ml) was added thereto. The resulting mixture was stirred at room temperature for about 12 hours. After the completion of reaction, the aqueous layer was washed with ethyl acetate, acidified with 6N HCL aqueous solution. The resultant was concentrated under reduced pressure and extracted with ethyl acetate twice. The organic layer was separated, washed with brine, dried over anhydrous magnesium sulfate, filtered, and concentrated under reduced pressure. The residue thus obtained was subjected to a silica gel column chromatography to obtain 200 mg of the title compound as pale yellow foam (yield 98%).

TLC (MeOH/MC=1/6) Rf 0.25

(4-7-2) (Z)-4-(3-(1-Ethylpyrrolidin-3-ylamino)-2-((naphthalen-1-yloxy)methyl)prop-1-enyl)benzoic acid (XXIXb)

The procedure of Preparation Example (4-7-1) was repeated except for using the compound obtained in Preparation Example (4-6-2) as the amine compound, to obtain 149 mg of the title compound as pale yellow foam (yield 96%).

TLC (MeOH/MC=1/6) Rf 0.40

(4-7-3) (Z)-4-(2-((4-(Trifluoromethoxy)benzylamino)methyl)-3-(naphthalen-1-yloxy)prop-1-enyl) benzoic acid (XXIXc)

The procedure of Preparation Example (4-7-1) was repeated except for using the compound obtained in Preparation Example (4-6-3) as the amine compound, to obtain 164 mg of the title compound as pale yellow foam (yield 100%).

TLC (MeOH/MC=1/6) Rf 0.25

$^1$H-NMR (300 MHz, CD$_3$OD) δ 4.10 (s, 2H), 4.37 (s, 2H), 4.98 (s, 2H), 6.75 (d, J=7.4 Hz, 1H), 7.21 (s, 1H), 7.28 (q, J=7.6 Hz, 3H), 7.36-7.48 (m, 5H), 7.57 (d, J=7.8 Hz, 2H), 7.77 (d, J=7.4 Hz, 1H), 7.97 (d, J=7.8 Hz, 2H), 8.06 (d, J=7.4 Hz, 1H)

LC/MS (M$^+$H): 492

(4-7-4) (Z)-4-(3-(1-(t-Butoxycarbonyl)pyrrolidin-3-ylamino)-2-((naphthalen-1-yloxy)methyl)prop-1-enyl)benzoic acid (XXIXd)

The procedure of Preparation Example (4-7-1) was repeated except for using the compound obtained in Preparation Example (4-6-4) as the amine compound, to obtain 201 mg of the title compound as pale yellow foam (yield 98%).

TLC (MeOH/MC=1/6) Rf 0.45

(4-7-5) (Z)-4-(3-(1-(Cyclohexanecarbonyl)pyrrolidin-3-ylamino)-2-((naphthalen-1-yloxy)-methyl) prop-1-enyl)benzoic acid (XXIXe)

The procedure of Preparation Example (4-7-1) was repeated except for using the compound obtained in Preparation Example (4-6-5) as the amine compound, to obtain 144 mg of the title compound as pale yellow foam (yield 87%).

TLC (MeOH/MC=1/6) Rf 0.15

(4-7-6) (Z)-4-(3-(1-Cyclopentylpiperidin-4-ylamino)-2-((naphthalen-1-yloxy)methyl)prop-1-enyl)benzoic acid (XXIXf)

The procedure of Preparation Example (4-7-1) was repeated except for using the compound obtained in Preparation Example (4-6-6) as the amine compound, to obtain 96 mg of the title compound as pale yellow foam (yield 16%).
TLC (MeOH/MC=1/6) Rf 0.20

(4-7-7) (Z)-4-(3-(1-(Cyclohexylmethyl)pyrrolidin-3-ylamino)-2-((naphthalen-1-yloxy)methyl)prop-1-enyl)benzoic acid (XXIXg)

The procedure of Preparation Example (4-7-1) was repeated except for using the compound obtained in Preparation Example (4-6-7) as the amine compound, to obtain 125 mg of the title compound as pale yellow foam (yield 42%).
TLC (MeOH/MC=1/6) Rf 0.45

(4-7-8) (Z)-4-(3-(1-Benzylpyrrolidin-3-ylamino)-2-((naphthalen-1-yloxy)methyl)prop-1-enyl)benzoic acid (XXIXh)

The procedure of Preparation Example (4-7-1) was repeated except for using the compound obtained in Preparation Example (4-6-8) as the amine compound, to obtain 232 mg of the title compound as pale yellow foam (yield 96%).
TLC (MeOH/MC=1/6) Rf 0.45

(4-7-9) (Z)-4-(3-(1-Cyclopropylpiperidin-4-ylamino)-2-((naphthalen-1-yloxy)methyl)prop-1-enyl)benzoic acid (XXIXi)

The procedure of Preparation Example (4-7-1) was repeated except for using the compound obtained in Preparation Example (4-6-9) as the amine compound, to obtain 250 mg of the title compound as pale yellow foam (yield 100%).
TLC (MeOH/MC=1/6) Rf 0.30

(4-7-10) (Z)-4-(3-(1-Cyclopropylpyrrolidin-3-ylamino)-2-((naphthalen-1-yloxy)methyl)prop-1-enyl)benzoic acid (XXIXj)

The procedure of Preparation Example (4-7-1) was repeated except for using the compound obtained in Preparation Example (4-6-10) as the amine compound, to obtain 198 mg of the title compound as pale yellow foam (yield 67%).
TLC (MeOH/MC=1/6) Rf 0.45

(4-7-11) (Z)-4-(3-(1-Cyclohexylpyrrolidin-3-ylamino)-2-((naphthalen-1-yloxy)methyl)prop-1-enyl)benzoic acid (XXIXk)

The procedure of Preparation Example (4-7-1) was repeated except for using the compound obtained in Preparation Example (4-6-11) as the amine compound, to obtain 160 mg of the title compound as pale yellow foam (yield 67%).
TLC (MeOH/MC=1/6) Rf 0.30

(4-7-12) (Z)-4-(3-(Ethyl(2-morpholinoethyl)amino)-2-((naphthalen-1-yloxy)methyl)prop-1-enyl)benzoic acid (the Compound of Formula XXIXl)

The procedure of Preparation Example (4-7-1) was repeated except for using the compound obtained in Preparation Example (4-6-12) as the amine compound, to obtain 201 mg of the title compound as pale yellow foam (yield 100%).
TLC (MeOH/MC=1/9) Rf 0.35

(4-7-13) (Z)-4-(3-(1-Methoxypropan-2-ylamino)-2-((naphthalen-1-yloxy)methyl)prop-1-enyl)benzoic acid (XXIXm)

The procedure of Preparation Example (4-7-1) was repeated except for using the compound obtained in Preparation Example (4-6-13) as the amine compound, to obtain 210 mg of the title compound as pale yellow foam (yield 89%).
$^1$H-NMR (200 MHz, CDCl$_3$) δ 1.34 (d, J=6.4 Hz, 3H), 3.17 (s, 3H), 3.48 (m, 1H), 3.54 (s, 2H), 3.91 (dd, J=16.4 Hz, 13.6 Hz, 2H), 4.94 (s, 2H), 6.62 (d, J=7.8 Hz, 1H), 7.08 (s, 1H), 7.13 (d, J=8.2 Hz, 2H), 7.31 (m, 2H), 7.45 (m, 2H), 7.73 (m, 1H), 7.79 (d, J=8.2 Hz, 2H), 8.23 (m, 1H)
LC/MS (M$^+$H): 406

Preparation Example 4-8

Preparation of the Compound of Formula XXX (4-8-1) (Z)-4-(3-(1-Ethylpiperidin-4-ylamino)-2-((naphthalen-1-yloxy)methyl)prop-1-enyl)-N-(tetrahydro-2H-pyran-2-yloxy)benzamide (XXXa)

The compound of formula XXIXa (205 mg, 0.46 mmol, 1 eq.) obtained in Preparation Example (4-7-1) was dissolved in N,N'-dimethylformal (2.3 ml) in a 50 ml vessel. To the resulting solution, N-hydroxy-6-trifluorobenzotriazole (FOBt; 104 mg, 0.51 mmol, 1.1 eq.), 1-ethyl-3-(3-dimethylaminopropyl)carbodiimide hydrochloride (EDC.HCl; 114 mg, 0.60 mmol, 1.3 eq.), tetrahydro-2H-pyran-2-yloxyamine (THPONH$_2$; 81 mg, 0.64 mmol, 1.5 eq.) and triethylamine (0.19 ml, 1.38 mmol, 3 eq.) were added at 0° C. while stirring. The resulting mixture was stirred at room temperature for 12 hours. After the completion of reaction, to the reaction solution, 10% potassium carbonate aqueous solution (20 ml) was added, and the resulting mixture was extracted with 20 ml of ethyl acetate three times. The organic layer was separated, washed with an aqueous saturated sodium bicarbonate solution and brine in order, dried over anhydrous magnesium sulfate, and concentrated under reduced pressure. The residue thus obtained was subjected to a silica gel column chromatography to obtain 143 mg of the title compound as dark yellow foam (yield 41.3%).
$^1$H-NMR (200 MHz, CDCl$_3$) δ 1.07 (t, J=7.2 Hz, 3H), 1.45 (m, 2H), 1.59 (m, 4H), 1.80-2.08 (m, 6H), 2.37 (q, J=7.2 Hz, 2H), 2.58 (m, 1H), 2.87 (m, 2H), 3.60 (m, 1H), 3.65 (s, 2H), 3.97 (m, 1H), 4.81 (s, 2H), 5.05 (m, 1H), 6.70 (d, J=7.5 Hz, 1H), 6.87 (s, 1H), 7.37 (m, 3H), 7.48 (m, 4H), 7.67 (d, J=8.4 Hz, 2H), 7.79 (d, J=7.2 Hz, 1H), 8.23 (d, J=7.5 Hz, 1H)
LC/MS (M$^+$H): 544

(4-8-2) (Z)-4-(3-(1-Ethylpyrrolidin-3-ylamino)-2-((naphthalen-1-yloxy)methyl)prop-1-enyl)-N-(tetrahydro-2H-pyran-2-yloxy)benzamide (XXXb)

The procedure of Preparation Example (4-8-1) was repeated except for using the compound obtained in Preparation Example (4-7-2) as the starting material, to obtain 120 mg of the title compound as pale yellow foam (yield 64%).
$^1$H-NMR (200 MHz, CDCl$_3$) δ 1.28 (t, J=7.8 Hz, 3H), 1.55-2.02 (m, 8H), 2.26 (m, 2H), 2.84 (q, J=7.2 Hz, 2H), 3.16 (m, 2H), 3.49 (s, 2H), 3.63 (m, 2H), 3.98 (m, 1H), 4.84 (s, 2H), 5.06 (m, 1H), 6.70 (d, J=7.8 Hz, 1H), 6.88 (s, 1H), 7.27-7.54 (m, 6H), 7.70 (d, J=8.1 Hz, 2H), 7.80 (d, J=7.2 Hz, 1H), 8.21 (d, J=7.2 Hz, 1H)
LC/MS (M$^+$H): 530

(4-8-3) (Z)-4-(2-((4-(Trifluoromethoxy)-benzylamino)methyl)-3-(naphthalen-1-yloxy)prop-1-enyl)-N-(tetrahydro-2H-pyran-2-yloxy)benzamide (XXXc)

The procedure of Preparation Example (4-8-1) was repeated except for using the compound obtained in Preparation Example (4-7-3) as the starting material, to obtain 189 mg of the title compound as pale yellow foam (yield 99%).
TLC (MeOH/MC=1/6) Rf 0.70
$^1$H-NMR (300 MHz, CDCl$_3$) δ 0.88 (m, 2H), 1.03 (m, 2H), 1.25-1.43 (m, 4H), 3.61 (s, 2H), 3.89 (s, 2H), 4.83 (s, 2H), 5.05 (s, 1H), 6.69 (d, J=7.4 Hz, 1H), 6.88 (s, 1H), 7.11 (d, J=7.6 Hz, 2H), 7.26-7.52 (m, 4H), 7.68 (d, J=7.4 Hz, 2H), 7.79 (d, J=7.8 Hz, 1H), 8.17 (d, J=7.4 Hz, 1H)
LC/MS (M$^+$H): 591

(4-8-4) (Z)-t-Butyl-3-(2-((naphthalen-1-yloxy)methyl)-3-(4-(tetrahydro-2H-pyran-2-yloxycarbamoyl)phenyl)-allylamino)-pyrrolidine-1-carboxylate (XXXd)

The procedure of Preparation Example (4-8-1) was repeated except for using the compound obtained in Preparation Example (4-7-4) as the starting material, to obtain 184 mg of the title compound as pale yellow foam (yield 90%).
TLC (MeOH/MC=1/6) Rf 0.80
$^1$H-NMR (300 MHz, CDCl$_3$) δ 1.43 (s, 9H), 1.58-1.84 (m, 4H), 2.01 (q, J=7.4 Hz, 3H), 2.86 (d, J=7.6 Hz, 8H), 3.40-3.62 (m, 3H), 3.94 (t, J=7.8 Hz, 1H), 4.81 (s, 2H), 5.05 (s, 1H), 6.68 (d, J=7.4 Hz, 1H), 6.86 (s, 1H), 7.26-7.50 (m, 5H), 7.69-7.71 (d, J=7.8 Hz, 2H), 7.76 (d, J=7.6 Hz, 1H), 7.99 (s, 1H), 8.21 (d, J=7.8 Hz, 1H)
LC/MS (M$^+$H): 602

(4-8-5) (Z)-4-(3-(1-(Cyclohexanecarbonyl)pyrrolidin-3-ylamino)-2-((naphthalen-1-yloxy)methyl)prop-1-enyl)-N-(tetrahydro-2H-pyran-2-yloxy)benzamide (XXXe)

The procedure of Preparation Example (4-8-1) was repeated except for using the compound obtained in Preparation Example (4-7-5) as the starting material, to obtain 170 mg of the title compound as pale yellow foam (yield 89%).
TLC (MeOH/MC=1/6) Rf 0.55
$^1$H-NMR (300 MHz, CDCl$_3$) δ 1.19 (m, 3H), 1.45-1.82 (m, 8H), 1.86-2.03 (m, 2H), 2.83 (m, 6H), 3.38 (m, 1H), 3.54 (m, 7H), 3.97 (t, J=7.8 Hz, 1H), 4.79 (d, J=7.8 Hz, 2H), 5.06 (s, 1H), 6.68 (d, J=7.8 Hz, 1H), 6.81 (d, J=7.6 Hz, 1H), 7.32 (m, 3H), 7.48 (m, 2H), 7.73 (q, J=7.8 Hz, 3H), 7.96 (s, 1H), 8.20 (d, J=7.6 Hz, 1H)
LC/MS (M$^+$H): 612

(4-8-6) (Z)-4-(3-(1-Cyclopentylpiperidin-4-ylamino)-2-((naphthalen-1-yloxy)methyl)prop-1-enyl)-N-(tetrahydro-2H-pyran-2-yloxy)benzamide (XXXf)

The procedure of Preparation Example (4-8-1) was repeated except for using the compound obtained in Preparation Example (4-7-6) as the starting material, to obtain 122 mg of the title compound as pale yellow foam (yield 54%).
TLC (MeOH/MC=1/6) Rf 0.45
$^1$H-NMR (300 MHz, CDCl$_3$) δ 1.40 (m, 9H), 1.59 (m, 9H), 2.46 (m, 3H), 2.94 (m, 3H), 3.64 (s, 3H), 3.93 (m, 1H), 4.81 (s, 2H), 5.05 (s, 1H), 6.69 (d, J=7.4 Hz, 1H), 6.87 (s, 1H), 7.26 (m, 3H), 7.42 (m, 3H), 7.67 (d, J=7.8 Hz, 2H), 7.79 (d, J=7.8 Hz, 1H), 8.22 (d, J=7.6 Hz, 1H)
LC/MS (M$^+$H): 584

(4-8-7) (Z)-4-(3-(1-(Cyclomethyl)pyrrolidin-3-ylamino)-2-((naphthalen-1-yloxy)methylprop-1-enyl)-N-(tetrahydro-2H-pyran-2-yloxy)benzamide (XXXg)

The procedure of Preparation Example (4-8-1) was repeated except for using the compound obtained in Preparation Example (4-7-7) as the starting material, to obtain 204 mg of the title compound as pale yellow foam (yield 93%).
TLC (MeOH/MC=1/6) Rf 0.55
$^1$H-NMR (300 MHz, CDCl$_3$) δ 0.83 (m, 3H), 1.14 (m, 4H), 1.30 (m, 2H), 1.59-1.85 (m, 5H), 2.16 (m, 5H), 2.23 (m, 1H), 2.41 (d, J=7.6 Hz, 2H), 2.61 (s, 1H), 2.94 (s, 2H), 3.42 (d, J=7.4 Hz, 1H), 3.63 (s, 3H), 3.88 (m, 1H), 4.80 (s, 2H), 5.04 (s, 1H), 6.68 (d, J=7. Hz, 1H), 6.85 (s, 1H), 7.26-7.50 (m, 6H), 7.67 (d, J=7.8 Hz, 2H), 7.78 (s, 1H), 8.22 (d, J=7.6 Hz, 1H)
LC/MS (M$^+$H): 598

(4-8-8) (Z)-4-(3-(1-Benzylpyrrolidin-3-ylamino)-2-((naphthalen-1-yloxy)methyl)prop-1-enyl)-N-(tetrahydro-2H-pyran-2-yloxy)benzamide (XXXh)

The procedure of Preparation Example (4-8-1) was repeated except for using the compound obtained in Preparation Example (4-7-8) as the starting material, to obtain 196 mg of the title compound as pale yellow foam (yield 90%).
TLC (MeOH/MC=1/6) Rf 0.60
$^1$H-NMR (300 MHz, CDCl$_3$) δ 1.21 (m, 1H), 1.56 (d, J=7.6 Hz, 3H), 1.79 (m, 2H), 2.03 (m, 2H), 2.40 (d, J=7.6 Hz, 4H), 2.73 (q, J=7.6 Hz, 2H), 3.54 (m, 4H), 3.90 (s, 1H), 4.77 (s, 2H), 5.03 (s, 1H), 6.66 (d, J=7.6 Hz, 1H), 6.81 (s, 1H), 7.18 (m, 8H), 7.40-7.48 (m, 3H), 7.65 (d, J=7.8 Hz, 2H), 7.77 (d, J=7.6 Hz, 1H), 8.20 (d, J=7.6 Hz, 1H)
LC/MS (M$^+$H): 592

(4-8-9) (Z)-4-(3-(1-Cyclopropylpiperidin-4-ylamino)-2-((naphthalen-1-yloxy)methyl)prop-1-enyl)-N-(tetrahydro-2H-pyran-2-yloxy)benzamide (XXXi)

The procedure of Preparation Example (4-8-1) was repeated except for using the compound obtained in Preparation Example (4-7-9) as the starting material, to obtain 92 mg of the title compound as pale yellow foam (yield 43%).
TLC (MeOH/MC=1/6) Rf 0.40
$^1$H-NMR (300 MHz, CDCl$_3$) δ 0.41 (m, 4H), 1.36 (m, 3H), 1.52 (m, 3H), 1.80 (m, 4H), 2.27 (m, 2H), 2.59 (d, J=7.4 Hz, 1H), 2.96 (t, J=7.6 Hz, 2H), 3.64 (m, 4H), 3.97 (s, 1H), 4.81 (s, 2H), 5.04 (s, 1H), 6.69 (d, J=7.4 Hz, 1H), 6.87 (s, 1H), 7.26-7.50 (m, 6H), 7.67 (d, J=7.4 Hz, 2H), 7.79 (d, J=7.4 Hz, 1H), 8.22 (d, J=7.6 Hz, 1H)

(4-8-10) (Z)-4-(3-(1-Cyclopropylpyrrolidin-3-ylamino)-2-((naphthalen-1-yloxy)methyl)prop-1-enyl)-N-(tetrahydro-2H-pyran-2-yloxy)benzamide (XXXj)

The procedure of Preparation Example (4-8-1) was repeated except for using the compound obtained in Preparation Example (4-7-10) as the starting material, to obtain 244 mg of the title compound as pale yellow foam (yield 100%).
TLC (MeOH/MC=1/6) Rf 0.60
$^1$H-NMR (300 MHz, CDCl$_3$) δ 0.41 (m, 4H), 1.59 (t, J=7.6 Hz, 2H), 1.81 (m, 2H), 2.16 (m, 3H), 2.53 (m, 4H), 2.87 (m, 2H), 3.42 (m, 1H), 3.58 (m, 3H), 3.80 (m, 1H), 4.80 (s, 2H), 5.05 (s, 1H), 6.69 (d, J=7.6 Hz, 1H), 6.85 (s, 1H), 7.26-7.50 (m, 6H), 7.67 (d, J=7.8 Hz, 2H), 7.77 (d, J=7.6 Hz, 1H), 8.23 (d, J=7.6 Hz, 1H)

(4-8-11) (Z)-4-(3-(1-Cyclohexylpyrrolidin-3-ylamino)-2-((naphthalen-1-yloxy)methyl)prop-1-enyl)-N-(tetrahydro-2H-pyran-2-yloxy)benzamide (XXXk)

The procedure of Preparation Example (4-8-1) was repeated except for using the compound obtained in Preparation Example (4-7-11) as the starting material, to obtain 146 mg of the title compound as pale yellow foam (yield 77%).
TLC (MeOH/MC=1/6) Rf 0.60
$^1$H-NMR (300 MHz, CDCl$_3$) δ 1.25 (m, 5H), 1.57 (m, 5H), 1.79 (m, 7H), 2.11 (s, 1H), 2.38 (q, J=7.8 Hz, 1H), 2.59 (q, J=7.8 Hz, 2H), 2.85 (q, J=7.8 Hz, 1H), 3.40 (m, 2H), 3.57 (m, 3H), 3.96 (s, 1H), 4.79 (s, 2H), 5.03 (s, 1H), 6.67 (d, J=7.4 Hz, 1H), 6.84 (s, 1H), 7.26 (m, 3H), 7.49 (m, 3H), 7.66 (d, J=7.8 Hz, 2H), 7.78 (d, J=7.6 Hz, 1H), 8.23 (d, J=7.6 Hz, 1H)

(4-8-12) (Z)-4-(3-(Ethyl(2-morpholinoethyl)amino)-2-((naphthalen-1-yloxymethyl)prop-1-enyl)-N-(tetrahydro-2H-pyran-2-yloxy)benzamide (XXXl)

The procedure of Preparation Example (4-8-1) was repeated except for using the compound obtained in Preparation Example (4-7-12) as the starting material, to obtain 186 mg of the title compound as pale yellow foam (yield 93%).
TLC (MeOH/MC=1/6) Rf 0.30
$^1$H-NMR (300 MHz, CDCl$_3$) δ 0.99 (m, 3H), 1.25 (s, 1H), 2.30 (m, 5H), 2.57 (m, 5H), 2.86 (m, 4H), 3.39 (s, 2H), 3.57 (m, 6H), 3.93 (m, 1H), 4.79 (s, 2H), 5.04 (s, 1H), 6.71 (d, J=7.4 Hz, 1H), 6.85 (s, 1H), 7.26-7.49 (m, 5H), 7.67 (d, J=7.8 Hz, 2H), 7.78 (t, J=7.8 Hz, 1H), 8.00 (s, 1H), 8.23 (d, J=7.6 Hz, 1H)

(4-8-13) (Z)-4-(3-(1-Methoxypropan-2-ylamino)-(2-((naphthalen-1-yloxy)methyl)-3-(4-(tetrahydro-2H-pyran-2-yloxy-carbamoyl)phenyl)allyl)carbamate (XXXm)

The procedure of Preparation Example (4-8-1) was repeated except for using the compound obtained in Preparation Example (4-7-13) as the starting material, to obtain 209 mg of the title compound as pale yellow oil (yield 78.8%).
$^1$H-NMR (200 MHz, CDCl$_3$) δ 1.05 (d, J=6.2 Hz, 3H), 1.59 (m, 4H), 1.86 (m, 2H), 2.99 (m, 1H), 3.27 (s, 2H), 3.31 (s, 3H), 3.61 (d, J=17.2 Hz, 13.4 Hz, 2H), 3.66 (m, 1H), 3.97 (m, 1H), 4.82 (s, 2H), 5.06 (m, 1H), 6.69 (d, J=7.8 Hz, 1H), 6.88 (s, 1H), 7.27-7.56 (m, 6H), 7.67 (d, J=8.2 Hz, 2H), 7.78 (m, 1H), 8.25 (m, 1H)
LC/MS (M$^+$H): 505

Preparation Example 4-9

Preparation of the Compound of Formula XXVIII-1

(4-9-1) (Z)-Methyl 4-(3-(2-(1-methylpyrrolidin-2-yl)ethylamino)-2-((naphthalen-1-yloxy)methyl)prop-1-enyl)benzoate (XXVIII-1a)

Methyl 4-[2-bromomethyl-3-(naphthalen-1-yloxy)-propenyl]-benzoate (412 mg, 1 mmol) was dissolved acetonitrile (5 ml) in a 100 ml vessel at 0° C., and thereto triethylamine (0.21 ml, 1.5 mmol, 1.5 eq.) and 2-(1-methylpyrrolidin-2-yl)ethylamine (R$_1$'''NH$_2$; 0.22 ml, 1.5 mmol, 1.5 eq.) were added while stirring. The resulting mixture was heated from 0° C. to room temperature, and then reacted for 4 hours. After the completion of reaction, the solvent was distilled off, and the residue thus obtained was extracted with ethyl ester. The organic layer was separated, washed with an aqueous saturated sodium bicarbonate solution and brine in order, dried over anhydrous magnesium sulfate, and concentrated under reduced pressure. The residue thus obtained was subjected to a silica gel column chromatography to obtain 220 mg of the title compound as pale yellow oil (yield 48%).

$^1$H-NMR (200 MHz, CDCl$_3$) δ 1.61 (m, 2H), 1.95 (m, 4H), 2.25 (m, 1H), 2.37 (s, 3H), 2.58 (m, 1H), 2.81 (m, 2H), 3.22 (m, 1H), 3.67 (s, 2H), 3.89 (s, 3H), 4.86 (s, 2H), 6.71 (d, J=7.4 Hz, 1H), 6.91 (s, 1H), 7.28-7.58 (m, 6H), 7.79 (m, 1H), 7.97 (d, J=8.6 Hz, 2H), 8.22 (m, 1H)
LC/MS (M$^+$H): 459

(4-9-2) (Z)-Methyl 4-(3-(1-isopropylpiperidin-4-ylamino)-2-((naphthalen-1-yloxy)methyl)prop-1-enyl)benzoate (XXVIII-1b)

The procedure of Preparation Example (4-9-1) was repeated except for using 1-isopropylpiperidine instead of 2-(1-methylpyrrolidin-2-yl)ethylamine as the amine compound, to obtain 255 mg of the title compound as pale yellow oil (yield 54%).
$^1$H-NMR (200 MHz, CDCl$_3$) δ 1.16 (d, J=6.4 Hz, 6H), 1.90 (m, 2H), 2.37 (m, 2H), 2.73 (m, 2H), 3.09 (m, 4H), 3.64 (s, 2H), 3.92 (s, 3H), 4.89 (s, 2H), 6.71 (d, J=7.8 Hz, 1H), 6.89 (s, 1H), 7.28-7.60 (m, 6H), 7.81 (d, J=7.0 Hz, 1H), 8.00 (d, J=7.6 Hz, 2H), 8.21 (d, J=7.4 Hz, 1H)
LC/MS (M$^+$H): 473

(4-9-3) (Z)-Methyl 4-(3-(3-(1H-imidazol-1-yl)propylamino)-2-((naphthalen-1-yloxy)methyl)prop-1-enyl)benzoate (XXVIII-1c)

The procedure of Preparation Example (4-9-1) was repeated except for using 1H-imidazole-1-propylamine instead of 2-(1-methylpyrrolidin-2-yl)ethylamine as the amine compound, to obtain 263 mg of the title compound as pale yellow oil (yield 58%).
$^1$H-NMR (200 MHz, CDCl$_3$) δ 1.93 (m, 2H), 2.69 (t, J=6.4 Hz, 2H), 3.61 (s, 2H), 3.90 (s, 3H), 4.00 (t, J=7.0 Hz, 2H), 4.85 (s, 2H), 6.70 (d, J=7.4 Hz, 1H), 6.85 (s, 2H), 7.02 (s, 1H), 7.26-7.56 (m, 7H), 7.85 (m, 1H), 7.97 (d, J=8.2 Hz, 2H), 8.23 (m, 1H)
LC/MS (M$^+$H): 456

(4-9-4) (Z)-Methyl 4-(3-(4-hydroxyphenethylamino)-2-((naphthalen-1-yloxy)methyl)prop-1-enyl)benzoate (XXVIII-1d)

The procedure of Preparation Example (4-9-1) was repeated except for using 4-hydroxyphenethylamine instead of 2-(1-methylpyrrolidin-2-yl)ethylamine as the amine compound, to obtain 271 mg of the title compound as pale yellow oil (yield 52%).
$^1$H-NMR (200 MHz, CDCl$_3$) δ 2.76 (t, J=7.2 Hz, 2H), 2.94 (t, J=6.6 Hz, 2H), 3.65 (s, 2H), 3.89 (s, 3H), 4.76 (s, 2H), 6.65 (m, 3H), 6.82 (s, 1H), 7.01 (d, J=8.4 Hz, 2H), 7.31 (d, J=8.0 Hz, 3H), 7.49 (m, 3H), 7.78 (m, 1H), 7.95 (d, J=8.0 Hz, 2H), 8.19 (m, 1H)
LC/MS (M$^+$H): 468

(4-9-5) (Z)-Methyl 4-(3-(3-(dimethylamino)-2,2-dimethylpropylamino)-2-((naphthalen-1-yloxy)methyl)prop-1-enyl)-benzoate (XXVIII-1e)

The procedure of Preparation Example (4-9-1) was repeated except for using 3-dimethylamino-2,2-dimethylpropylamine instead of 2-(1-methylpyrrolidin-2-yl)ethylamine as the amine compound, to obtain 328 mg of the title compound as pale yellow oil (yield 71%).
$^1$H-NMR (200 MHz, CDCl$_3$) δ 1.13 (s, 6H), 2.28 (s, 6H), 2.57 (s, 2H), 3.04 (s, 2H), 3.90 (s, 3H), 3.93 (s, 2H), 4.95 (s, 2H), 6.75 (d, J=7.4 Hz, 1H), 7.18 (s, 1H), 7.27-7.56 (m, 6H), 7.80 (m, 1H), 7.98 (d, J=8.2 Hz, 2H), 8.23 (m, 1H)
LC/MS (M$^+$H): 461

(4-9-6) (Z)-Methyl 4-(3-(2-(diisopropylamino)ethylamino)-2-((naphthalen-1-yloxy)methyl)prop-1-enyl)benzoate (XXVIII-1f)

The procedure of Preparation Example (4-9-1) was repeated except for using 2-(diisopropylamino)ethylamine instead of 2-(1-methylpyrrolidin-2-yl)ethylamine as the amine compound, to obtain 316 mg of the title compound as pale yellow oil (yield 67%).
$^1$H-NMR (200 MHz, CDCl$_3$) δ 1.29 (d, J=6.6 Hz, 12H), 2.95 (t, J=5.8 Hz, 2H), 3.22 (t, J=6.4 Hz, 2H), 3.45 (m, 2H), 3.71 (s, 2H), 3.89 (s, 3H), 4.89 (s, 2H), 5.30 (br, 1H), 6.73 (d, J=7.6 Hz, 1H), 6.97 (s, 1H), 7.42 (m, 6H), 7.79 (m, 1H), 7.96 (d, J=8.4 Hz, 2H), 8.22 (m, 1H)
LC/MS (M$^+$H): 475

(4-9-7) (Z)-methyl 4-(3-(2-methoxyethylamino)-2-((naphthalen-1-yloxy)methyl)prop-1-enyl)benzoate (XXVIII-1g)

The procedure of Preparation Example (4-9-1) was repeated except for using 2-methoxyethylamine instead of 2-(1-methylpyrrolidin-2-yl)ethylamine as the amine compound, to obtain 239 mg of the title compound as pale yellow oil (yield 59%).
$^1$H-NMR (200 MHz, CDCl$_3$) δ 2.91 (t, J=5.4 Hz, 2H), 3.38 (s, 3H), 3.56 (t, J=5.4 Hz, 2H), 3.68 (s, 2H), 3.91 (s, 3H), 4.86 (s, 2H), 6.71 (d, J=7.8 Hz, 1H), 6.92 (s, 1H), 7.27-7.56 (m, 6H), 7.81 (m, 1H), 7.98 (d, J=8.2 Hz, 2H), 8.27 (m, 1H)
LC/MS (M$^+$H): 406

(4-9-8) (Z)-Methyl 4-(3-(cyclohexylamino)-2-((naphthalen-1-yloxy)methyl)prop-1-enyl)benzoate (XXVIII-1h)

The procedure of Preparation Example (4-9-1) was repeated except for using 3-cyclohexylamine instead of 2-(1-methylpyrrolidin-2-yl)ethylamine as the amine compound, to obtain 300 mg of the title compound as pale yellow oil (yield 70%).
$^1$H-NMR (200 MHz, CDCl$_3$) δ 1.03-1.41 (m, 4H), 1.49 (m, 2H), 1.73 (m, 2H), 1.92 (m, 2H), 2.58 (m, 1H), 3.68 (s, 2H), 3.91 (s, 3H), 4.86 (s, 2H), 6.72 (d, J=7.4 Hz, 1H), 6.91 (s, 1H), 7.27-7.58 (m, 6H), 7.81 (m, 1H), 7.98 (d, J=8.2 Hz, 2H), 8.26 (m, 1H)
LC/MS (M$^+$H): 430

(4-9-9) (Z)-Methyl 4-(2-((4-(dimethylamino)benzylamino)methyl)-3-((naphthalen-1-yloxyprop)-1-enyl)benzoate The procedure of Preparation Example (4-9-1) was repeated except for using 4-(dimethylamino)benzylamine instead of 2-(1-methylpyrrolidin-2-yl)ethylamine as the amine compound, to obtain 324 mg of the title compound as pale yellow oil (yield 77%).
TLC (EtOAc/Hex=1/2) Rf 0.10
$^1$H-NMR (300 MHz, CDCl$_3$) δ 3.00 (s, 6H), 3.70 (s, 2H), 3.80 (s, 2H), 3.90 (s, 3H), 4.82 (s, 2H), 6.66 (m, 4H), 6.90 (s, 1H), 7.18-7.42 (m, 7H), 7.38 (m, 2H), 7.80 (dd, J=14.8, 7.4 Hz, 1H), 7.90 (dd, J=14.8, 7.4 Hz, 2H), 8.21 (dd, J=14.8, 7.4 Hz, 1H)
LC/MS (M$^+$H): 481

(4-9-10) (Z)-Methyl 4-(3-(naphthalen-1-yloxy)-2-((thiophen-2-ylmethylamino)methyl)prop-1-enyl)benzoate (XXVIII-1j)

The procedure of Preparation Example (4-9-1) was repeated except for using 2-thiophen-2-methylamine instead of 2-(1-methylpyrrolidin-2-yl)ethylamine as the amine compound, to obtain 301 mg of the title compound as pale yellow oil (yield 61%).
TLC (EtOAc/Hex=1/2) Rf 0.30
$^1$H-NMR (300 MHz, CDCl$_3$) δ 3.68 (s, 2H), 3.88 (s, 3H), 4.08 (s, 2H), 4.84 (s, 2H), 6.69 (d, J=7.4 Hz, 1H), 6.89 (dd, J=14.4, 7.6 Hz, 3H), 7.30-7.48 (m, 7H), 7.78 (d, J=7.6 Hz, 1H), 7.97 (t, J=7.8, 7.8 Hz, 2H), 8.20 (d, J=7.6 Hz, 1H)
LC/MS (M$^+$H): 444

(4-9-11) (Z)-methyl 4-(2-((4-methoxyphenethylamino)methyl)-3-(naphthalen-1-yloxy)prop-1-enyl)-benzoate (XXVIII-1k)

The procedure of Preparation Example (4-9-1) was repeated except for using 4-methoxyphenethylamine instead of 2-(1-methylpyrrolidin-2-yl)ethylamine as the amine compound, to obtain 350 mg of the title compound as pale yellow oil (yield 77%).
TLC (EtOAc/Hex=2/1) Rf 0.35
$^1$H-NMR (300 MHz, CDCl$_3$) δ 2.77 (t, J=7.8 Hz, 2H), 2.94 (t, J=7.8 Hz, 2H), 3.63 (s, 2H), 3.74 (s, 3H), 3.88 (s, 3H), 4.76 (s, 2H), 6.64 (d, J=7.4 Hz, 1H), 6.78 (t, J=7.6 Hz, 3H), 7.09 (d, J=7.8 Hz, 2H), 7.24-7.50 (m, 6H), 7.79 (t, J=7.8 Hz, 1H), 7.95 (d, J=7.8 Hz, 2H), 8.21 (d, J=7.6H, 1 Hz)
LC/MS (M$^+$H): 482

Preparation Example 4-10

Preparation of the Compound of Formula XXXI

(4-10-1) (Z)-Methyl 4-(3-(t-butoxycarbonyl-(2-(1-methylpyrrolidin-2-yl)ethyl)amino)-2-((naphthalen-1-yloxy)methyl)prop-1-enyl)benzoate (XXXIa)

(Z)-Methyl 4-(3-(2-(1-methylpyrrolidin-2-yl)ethylamino)-2-((naphthalen-1-yloxy)methyl)prop-1-enyl)benzoate (220 mg, 0.48 mmol) obtained in Preparation Example (4-9-1) was dissolved in 2 ml of dichloromethane in a 100 ml flask at 0° C., and thereto were added triethylamine (0.08 ml, 0.58 mmol, 1.2 eq.) and t-butyl-dicarbonate ((t-Boc)$_2$O; 127 mg, 0.58 mmol, 1.2 eq.) while stirring. To the resulting mixture, a catalytic amount of 4-dimethylaminopyridine (DMAP; 4 mg, 0.05 eq.), and the resultant was heated from 0° C. to room temperature and reacted for 12 hours at that temperature. After the completion of reaction, the reaction solution was extracted with dichloromethane. The organic layer was separated, washed with a saturated sodium bicarbonate aqueous solution and brine in order, dried over anhydrous magnesium sulfate, and concentrated under reduced pressure. The residue thus obtained was subjected to a silica gel column chromatography to obtain 252 mg of the title compound as pale yellow oil (yield 94%).
$^1$H-NMR (200 MHz, CDCl$_3$) δ 1.33 (s, 9H), 1.61-2.24 (m, 8H), 2.54 (s, 3H), 3.36 (m, 2H), 3.51 (m, 1H), 3.89 (s, 3H), 4.25 (s, 2H), 4.75 (s, 2H), 6.66 (d, J=7.2 Hz, 1H), 6.74 (s, 1H), 7.28-7.58 (m, 6H), 7.81 (m, 1H), 7.96 (d, J=8.4 Hz, 2H), 8.24 (m, 1H)
LC/MS (M$^+$H): 559

(4-10-2) (Z)-Methyl 4-(3-(t-butoxycarbonyl-(1-isopropylpiperidin-4-yl)amino)-2-((naphthalen-1-yloxy)methyl)prop-1-enyl)benzoate (XXXIb)

The procedure of Preparation Example (4-10-1) was repeated except for using the compound of formula XXVIII-1b (255 mg) obtained in Preparation Example (4-9-2) as the starting material, to obtain 158 mg of the title compound as pale yellow oil (yield 52%).

$^1$H-NMR (200 MHz, CDCl$_3$) δ 1.07 (d, J=6.6 Hz, 6H), 1.45 (s, 9H), 1.86 (m, 5H), 2.29 (m, 2H), 2.79 (m, 1H), 2.97 (m, 2H), 3.91 (s, 3H), 4.23 (s, 2H), 4.77 (s, 2H), 6.69 (d, J=7.0 Hz, 1H), 6.72 (s, 1H), 7.33 (d, J=8.2 Hz, 3H), 7.49 (m, 3H), 7.81 (m, 1H), 7.96 (d, J=8.2 Hz, 2H), 8.28 (m, 1H)

LC/MS (M$^+$H): 573

(4-10-3) (Z)-Methyl 4-(3-((3-(1H-imidazol-1-yl)propyl)(t-butoxycarbonyl)amino)-2-((naphthalen-1-yloxy)methyl)-prop-1-enyl)benzoate (XXXIc)

The procedure of Preparation Example (4-10-1) was repeated except for using the compound of formula XXVIII-1c (253 mg) obtained in Preparation Example (4-9-3) as the starting material, to obtain 174 mg of the title compound as pale yellow oil (yield 53%).

$^1$H-NMR (200 MHz, CDCl$_3$) δ 1.32 (s, 9H), 2.02 (m, 2H), 3.31 (t, J=5.6 Hz, 2H), 3.89 (s, 3H), 3.89 (t, J=6.0 Hz, 2H), 4.19 (s, 2H), 4.74 (s, 2H), 6.65 (m, 2H), 6.85 (s, 1H), 7.03 (s, 1H), 7.26-7.56 (m, 7H), 7.79 (m, 1H), 7.96 (d, J=8.2 Hz, 2H), 8.21 (m, 1H)

LC/MS (M$^+$H): 556

(4-10-4) (Z)-Methyl 4-(3-(t-butoxycarbonyl-(4-hydroxyphenethyl)amino)-2-((naphthalen-1-yloxy)methyl)prop-1-enyl)benzoate (XXXId)

The procedure of Preparation Example (4-10-1) was repeated except for using the compound of formula XXVIII-1d (271 mg) obtained in Preparation Example (4-9-4) as the starting material, to obtain 32 mg of the title compound as pale yellow oil (yield 12%).

$^1$H-NMR (200 MHz, CDCl$_3$) δ 1.56 (s, 9H), 2.81 (t, J=6.2 Hz, 2H), 2.96 (t, J=6.6 Hz, 2H), 3.64 (s, 2H), 3.89 (s, 3H), 4.78 (s, 2H), 6.67 (d, J=7.2 Hz, 1H), 6.83 (s, 1H), 7.03 (d, J=8.4 Hz, 2H), 7.17 (d, J=8.6 Hz, 2H), 7.33 (m, 3H), 7.46 (m, 3H), 7.79 (m, 1H), 7.95 (d, J=8.0 Hz, 2H), 8.23 (m, 1H)

LC/MS (M$^+$H): 568

(4-10-5) (Z)-Methyl 4-(3-(t-butoxycarbonyl-(3-(dimethylamino)-2,2-dimethylpropyl)amino)-2-((naphthalen-1-yloxy)-methyl)prop-1-enyl)benzoate (XXXIe)

The procedure of Preparation Example (4-10-1) was repeated except for using the compound of formula XXVIII-1e (328 mg) obtained in Preparation Example (4-9-5) as the starting material, to obtain 148 mg of the title compound as pale yellow oil (yield 37%).

$^1$H-NMR (200 MHz, CDCl$_3$) δ 0.97 (s, 6H), 1.39 (s, 9H), 2.13 (s, 2H), 2.25 (s, 6H), 3.28 (s, 2H), 3.91 (s, 3H), 4.35 (s, 2H), 4.75 (s, 2H), 6.65 (s, 1H), 6.67 (d, J=7.6 Hz, 1H), 7.28-7.59 (m, 6H), 7.81 (m, 1H), 7.98 (d, J=7.8 Hz, 2H), 8.29 (m, 1H)

LC/MS (M$^+$H): 561

(4-10-6) (Z)-Methyl 4-(3-(t-butoxycarbonyl-(2-(diisopropylamino)ethyl)amino)-2-((naphthalen-1-yloxy)methyl)prop-1-enyl)benzoate (XXXIf)

The procedure of Preparation Example (4-10-1) was repeated except for using the compound of formula XXVIII-1f (316 mg) obtained in Preparation Example (4-9-6) as the starting material, to obtain 277 mg of the title compound as pale yellow oil (yield 72%).

$^1$H-NMR (200 MHz, CDCl$_3$) δ 1.27 (d, J=6.4 Hz, 12H), 1.39 (s, 9H), 2.64 (t, J=5.8 Hz, 2H), 3.34 (t, J=6.4 Hz, 2H), 3.45 (m, 2H), 3.71 (s, 2H), 3.91 (s, 3H), 4.89 (s, 2H), 6.73 (d, J=7.6 Hz, 1H), 6.97 (s, 1H), 7.42 (m, 6H), 7.79 (m, 1H), 7.96 (d, J=8.4 Hz, 2H), 8.22 (m, 1H)

LC/MS (M$^+$H): 575

(4-10-7) (Z)-Methyl 4-(3-(t-butoxycarbonyl-(2-methoxyethyl)amino)-2-((naphthalen-1-yloxy)methyl)prop-1-enyl)-benzoate (XXXIg)

The procedure of Preparation Example (4-10-1) was repeated except for using the compound of formula XXVIII-1g (239 mg) obtained in Preparation Example (4-9-7) as the starting material, to obtain 262 mg of the title compound as pale yellow oil (yield 88%).

$^1$H-NMR (200 MHz, CDCl$_3$) δ 1.36 (s, 9H), 3.35 (s, 3H), 3.56 (s, 4H), 3.91 (s, 3H), 4.37 (s, 2H), 4.75 (s, 2H), 6.68 (m, 2H), 7.27-7.57 (m, 6H), 7.81 (m, 1H), 7.97 (d, J=7.8 Hz, 2H), 8.27 (m, 1H)

LC/MS (M$^+$H): 506

(4-10-8) (Z)-Methyl 4-(3-(t-butoxycarbonyl-(cyclohexyl)amino)-2-((naphthalen-1-yloxy)methyl)prop-1-enyl)benzoate (XXXIh)

The procedure of Preparation Example (4-10-1) was repeated except for using the compound of formula XXVIII-1h (300 mg) obtained in Preparation Example (4-9-8) as the starting material, to obtain 289 mg of the title compound as pale yellow oil (yield 94%).

$^1$H-NMR (200 MHz, CDCl$_3$) δ 1.02-1.44 (m, 4H), 1.36 (s, 9H), 1.45 (m, 2H), 1.71 (m, 2H), 1.91 (m, 2H), 2.59 (m, 1H), 3.67 (s, 2H), 3.91 (s, 3H), 4.86 (s, 2H), 6.72 (d, J=7.4 Hz, 1H), 6.88 (s, 1H), 7.26-7.54 (m, 6H), 7.80 (m, 1H), 7.97 (d, J=8.2 Hz, 2H), 8.22 (m, 1H)

LC/MS (M$^+$H): 530

(4-10-9) (Z)-Methyl 4-(3-(t-butoxycarbonyl-(4-(dimethylamino)benzyl)amino)-2-((naphthalen-1-yloxy)methyl)prop-1-enyl)benzoate (XXXIi)

The procedure of Preparation Example (4-10-1) was repeated except for using the compound of formula XXVIII-1i (210 mg) obtained in Preparation Example (4-9-9) as the starting material, to obtain 181 mg of the title compound as pale yellow oil (yield 51%).

TLC (EtOAc/Hex=1/4) Rf 0.20

$^1$H-NMR (300 MHz, CDCl$_3$) δ 1.36 (s, 9H), 2.91 (s, 6H), 3.87 (d, J=14.8 Hz, 3H), 4.15 (s, 2H), 4.45 (s, 2H), 4.70 (s, 2H), 6.64 (t, J=14.8, 7.4 Hz, 4H), 7.11 (d, J=14.8, 7.4 Hz, 1H), 7.23-7.50 (m, 7H), 7.78 (d, J=14.8, 7.4 Hz, 1H), 7.95 (d, J=14.8, 7.4 Hz, 2H), 8.23 (d, J=14.8, 7.4 Hz, 1H)

LC/MS (M$^+$H): 581

(4-10-10) (Z)-Methyl 4-(2-((t-butoxycarbonyl-(thiophen-2-ylmethyl)amino)-2-(naphthalen-1-yloxy)-methyl)prop-1-enyl)benzoate (XXXIj)

The procedure of Preparation Example (4-10-1) was repeated except for using the compound of formula XXVIII-1j (180 mg) obtained in Preparation Example (4-9-10) as the starting material, to obtain 162 mg of the title compound as pale yellow oil (yield 55%).
TLC (EtOAc/Hex=1/4) Rf 0.70
$^1$H-NMR (300 MHz, CDCl$_3$) δ 1.37 (s, 9H), 3.88 (s, 3H), 4.26 (s, 2H), 4.67 (s, 2H), 4.73 (s, 2H), 6.65 (d, J=7.4 Hz, 2H), 6.88 (d, J=7.6 Hz, 2H), 7.20-7.50 (m, 7H), 7.79 (d, J=7.6 Hz, 1H), 7.96 (d, J=7.8 Hz, 2H), 8.24 (d, J=7.6H, 1 Hz)
LC/MS (M$^+$H): 544

(4-10-11) (Z)-Methyl 4-(2-((t-butoxycarbonyl-(4-methoxyphenethyl)amino)-2-(naphthalen-1-yloxy)methyl)prop-1-enyl)-benzoate (XXXIk)

The procedure of Preparation Example (4-10-1) was repeated except for using the compound of formula XXXIII-1k (262 mg) obtained in Preparation Example (4-9-11) as the starting material, to obtain 255 mg of the title compound as pale yellow oil (yield 75%).
TLC (EtOAc/Hex=1/4) Rf 0.50
$^1$H-NMR (300 MHz, CDCl$_3$) δ 1.35 (s, 9H), 2.80 (s, 2H), 3.48 (s, 2H), 3.75 (s, 3H), 3.88 (s, 3H), 4.15 (m, 2H), 4.71 (s, 2H), 6.66 (s, 1H), 6.78 (d, J=7.4 Hz, 2H), 7.05 (s, 2H), 7.25-7.51 (m, 7H), 7.79 (t, J=7.8 Hz, 1H), 7.95 (d, J=7.4 Hz, 2H), 8.23 (d, J=7.6 Hz, 1H)
LC/MS (M$^+$H): 582

Preparation Example 4-11

Preparation of the Compound of Formula XXXII

(4-11-1) (Z)-4-(3-(t-Butoxycarbonyl-(2-(1-methylpyrrolidin-2-yl)ethyl)amino)-2-((naphthalen-1-yloxy)methyl)prop-1-enyl)benzoic acid (XXXIIa)

(Z)-Methyl 4-(3-(t-butoxycarbonyl(2-(1-methylpyrrolidin-2-yl)ethyl)amino)-2-((naphthalen-1-yloxy)methyl)prop-1-enyl)benzoate (252 mg, 0.45 mmol) obtained in Preparation Example (4-10-1) was dissolved in tetrahydrofuran (1.2 ml) in a 100 ml vessel while stirring. To the resulting solution, a solution of lithium hydroxide monohydrate (57 mg, 1.35 mmol, 3 eq.) dissolved in water (0.4 ml) was added, and the resultant was stirred at room temperature for 12 hours. After the completion of reaction, the aqueous layer was washed with ethyl acetate and acidified to pH 4 with 6N HCl aqueous solution. The resultant was filtered, distilled under reduced pressure and extracted with ethyl acetate twice. The organic layer was separated, washed with brine, dried over anhydrous magnesium sulfate, filtered, and concentrated under reduced pressure to remove the solvent therefrom. The residue thus obtained was subjected to a silica gel column chromatography to obtain 245 mg of the title compound as pale yellow foam (yield 100%).

(4-11-2) (Z)-4-(3-(t-Butoxycarbonyl-(1-isopropylpiperidin-4-yl)amino)-2-((naphthalen-1-yloxy)methyl)prop-1-enyl)benzoic acid (XXXIIb)

The procedure of Preparation Example (4-11-1) was repeated except for using the compound of formula XXXIb (158 mg) obtained in Preparation Example (4-10-2) as the starting material, to obtain 145 mg of the title compound as pale yellow foam (yield 93%).

(4-11-3) (Z)-4-(3-((3-(1H-Imidazol-1-yl)propyl)(t-butoxycarbonyl)amino)-2-((naphthalen-1-yloxy)methyl)prop-1-enyl)benzoic acid (XXXIIc)

The procedure of Preparation Example (4-11-1) was repeated except for using the compound of formula XXXIc (174 mg) obtained in Preparation Example (4-10-3) as the starting material, to obtain 167 mg of the title compound as pale yellow foam (yield 100%).
$^1$H-NMR (200 MHz, CD$_3$OD) δ 1.30 (s, 9H), 2.10 (m, 2H), 3.36 (t, J=5.8 Hz, 2H), 4.14 (t, J=6.2 Hz, 2H), 4.23 (s, 2H), 4.73 (s, 2H), 6.70 (m, 3H), 7.10 (br, 1H), 7.29 (m, 4H), 7.46 (m, 3H), 7.77 (m, 1H), 7.97 (d, J=8.2 Hz, 2H), 8.21 (m, 1H), 8.92 (br, 1H)
LC/MS (M$^+$H): 542

(4-11-4) (Z)-4-(3-(t-Butoxycarbonyl-(4-hydroxyphenethyl)amino)-2-((naphthalen-1-yloxy)methyl)prop-1-enyl)-benzoic acid (XXXIId)

The procedure of Preparation Example (4-11-1) was repeated except for using the compound of formula XXXI-1d (32 mg) obtained in Preparation Example (4-10-4) as the starting material, to obtain 31 mg of the title compound as pale yellow foam (yield 100%).
$^1$H-NMR (200 MHz, CD$_3$OD) δ 1.36 (s, 9H), 2.79 (t, J=4.8 Hz, 2H), 3.49 (t, J=4.4 Hz, 2H), 4.13 (s, 2H), 4.72 (s, 2H), 6.69 (m, 4H), 6.75 (d, J=8.0 Hz, 2H), 7.27-7.57 (m, 6H), 7.79 (m, 1H), 7.99 (d, J=7.8 Hz, 2H), 8.21 (m, 1H)
LC/MS (M$^+$H): 554

(4-11-5) (Z)-4-(3-(t-Butoxycarbonyl-(3-(dimethylamino)-2,2-dimethylpropyl)amino)-2-((naphthalen-1-yloxy)-methyl)prop-1-enyl)benzoic acid (XXXIIe)

The procedure of Preparation Example (4-11-1) was repeated except for using the compound of formula XXXIe (148 mg) obtained in Preparation Example (4-10-5) as the starting material, to obtain 142 mg of the title compound as pale yellow foam (yield 100%).
$^1$H-NMR (200 MHz, CDCl$_3$) δ 1.28 (s, 6H), 1.36 (s, 9H), 2.84 (s, 6H), 2.95 (s, 2H), 3.33 (s, 2H), 4.30 (s, 2H), 4.77 (s, 2H), 6.60 (s, 1H), 6.63 (d, J=7.4 Hz, 1H), 7.26-7.56 (m, 6H), 7.81 (m, 1H), 8.00 (d, J=8.2 Hz, 2H), 8.21 (m, 1H)
LC/MS (M$^+$H): 547

(4-11-6) (Z)-4-(3-(t-Butoxycarbonyl-(2-(diisopropylamino)ethyl)amino)-2-((naphthalen-1-yloxy)methyl)prop-1-enyl)benzoic acid (XXXIIf)

The procedure of Preparation Example (4-11-1) was repeated except for using the compound of formula XXXIf (277 mg) obtained in Preparation Example (4-10-6) as the starting material, to obtain 267 mg of the title compound as pale yellow foam (yield 100%).
$^1$H-NMR (200 MHz, CDCl$_3$) δ 1.26 (br, 12H), 1.44 (s, 9H), 3.16 (m, 2H), 3.54 (m, 2H), 3.97 (m, 2H), 4.14 (s, 2H), 4.32 (s, 2H), 6.68 (d, J=7.4 Hz, 1H), 6.88 (s, 1H), 7.40 (m, 6H), 7.77 (m, 1H), 7.90 (d, J=8.0 Hz, 2H), 8.22 (m, 1H)
LC/MS (M$^+$H): 561

(4-11-7) (Z)-4-(3-(t-Butoxycarbonyl-(2-methoxyethyl)amino)-2-((naphthalen-1-yloxy)methyl)prop-1-enyl)-benzoic acid (XXXIIg)

The procedure of Preparation Example (4-11-1) was repeated except for using the compound of formula XXXIg (262 mg) obtained in Preparation Example (4-10-7) as the starting material, to obtain 225 mg of the title compound as pale yellow foam (yield 89%).

$^1$H-NMR (200 MHz, CDCl$_3$) δ 1.36 (s, 9H), 3.35 (s, 3H), 3.58 (s, 4H), 4.37 (s, 2H), 4.76 (s, 2H), 6.70 (m, 2H), 7.27-7.56 (m, 6H), 7.80 (m, 1H), 8.02 (d, J=8.2 Hz, 2H), 8.27 (m, 1H)

LC/MS (M$^+$H): 492

(4-11-8) (Z)-4-(3-(t-Butoxycarbonyl-(cyclohexyl) amino)-2-((naphthalen-1-yloxy)methyl)prop-1-enyl) benzoic acid (XXXIIh)

The procedure of Preparation Example (4-11-1) was repeated except for using the compound of formula XXXIh (289 mg) obtained in Preparation Example (4-10-8) as the starting material, to obtain 81 mg of the title compound as pale yellow foam (yield 23%).

$^1$H-NMR (200 MHz, CDCl$_3$) δ 1.35 (m, 4H), 1.46 (s, 9H), 1.67 (m, 2H), 1.80 (m, 4H), 4.03 (m, 1H), 4.17 (s, 2H), 4.80 (s, 2H), 6.69 (d, J=7.8 Hz, 1H), 6.73 (s, 1H), 7.27-7.58 (m, 6H), 7.82 (m, 1H), 8.02 (d, J=8.6 Hz, 2H), 8.28 (m, 1H)

LC/MS (M$^+$H): 516

(4-11-9) (Z)-4-(3-((t-Butoxycarbonyl-(4-dimethylamino)benzyl)amino)-2-((naphthalen-1-yloxy)methyl)prop-1-enyl)benzoic acid (XXXIIi)

The procedure of Preparation Example (4-11-1) was repeated except for using the compound of formula XXXII (181 mg) obtained in Preparation Example (4-10-9) as the starting material, to obtain 176 mg of the title compound as pale yellow foam (yield 99%).

TLC (EtOAc) Rf 0.20

(4-11-10) (Z)-4-(3-(t-Butoxycarbonyl-(thiophen-2-ylmethyl)amino)-2-((naphthalen-1-yloxy)methyl) prop-1-enyl)benzoic acid (XXXIIj)

The procedure of Preparation Example (4-11-1) was repeated except for using the compound of formula XXXIj (162 mg) obtained in Preparation Example (4-10-10) as the starting material, to obtain 156 mg of the title compound as pale yellow foam (yield 99%).

TLC (EtOAc) Rf 0.80

(4-11-11) (Z)-4-(3-(t-butoxycarbonyl-(4-methoxyphenethyl)amino)-2-((naphthalen-1-yloxy)methyl) prop-1-enyl)-benzoic acid (XXXIIk)

The procedure of Preparation Example (4-11-1) was repeated except for using the compound of formula XXXIk (255 mg) obtained in Preparation Example (4-10-11) as the starting material, to obtain 228 mg of the title compound as pale yellow foam (yield 93%).

TLC (EtOAc) Rf 0.80

$^1$H-NMR (300 MHz, CD$_3$OD) δ 1.17 (s, 9H), 2.68 (s, 2H), 3.22 (s, 2H), 3.44 (s,3H), 4.02 (s, 2H), 4.80 (s, 2H), 6.59-6.69 (m, 4H), 6.92 (d, J=7.4 Hz, 2H), 7.18 (t, J=7.8 Hz, 1H), 7.29-7.41 (m, 5H), 7.69 (d, J=7.8 Hz, 1H), 7.85 (d, J=7.4 Hz, 2H), 8.09 (d, J=7.6 Hz, 1H)

Preparation Example 4-12

Preparation of the Compound of Formula XXXIII (4-12-1) (Z)-t-Butyl-2-(1-methylpyrrolidin-2-yl)-ethyl-(2-((naphthalen-1-yloxy))-3-(4-(tetrahydro-2H-pyran-2-yloxy-carbamoyl)-phenyl)allyl)carbamate (XXXIIIa)

(Z)-4-(3-(t-Butoxycarbonyl(2-(1-methylpyrrolidin-2-yl) ethyl)amino)-2-((naphthalen-1-yloxy)methyl)prop-1-enyl) benzoate (305 mg, 0.56 mmol, 1 eq.) obtained in Preparation Example (4-11-1) was dissolved in 3 ml of N,N'-dimethylformal in a 100 ml vessel, and to the resulting solution, N-hydroxy-6-trifluorobenzotriazole (FOBt; 126 mg, 0.62 mmol, 1.1 eq.), 1-ethyl-3-(3-dimethylaminopropyl)carbodiimide hydrochloride (EDC.HCl; 140 mg, 0.73 mmol, 1.3 eq.), tetrahydro-2H-pyran-2-yloxyamine (THPONH$_2$; 99 mg, 0.84 mmol, 1.5 eq.) and triethylamine (0.12 ml, 0.84 mmol, 1.5 eq.) were added at 0° C., while stirring. The resulting mixture was stirred at room temperature for 12 hours. After the completion of reaction, to the reaction mixture, 10% aqueous potassium carbonate solution was added, and then the resultant was extracted with ethyl acetate. The organic layer was separated, washed with an aqueous saturated sodium bicarbonate solution and brine in order, dried over anhydrous magnesium sulfate, filtered and concentrated under reduced pressure to remove the solvent therefrom. The residue thus obtained was subjected to a silica gel column chromatography to obtain 170 mg of the title compound as dark yellow foam (yield 46%).

$^1$H-NMR (200 MHz, CDCl$_3$) δ 1.36 (s, 9H), 1.41-2.12 (m, 14H), 2.22 (m, 1H), 2.36 (s, 3H), 3.18 (m, 1H), 3.35 (m, 2H), 3.62 (m, 1H), 3.99 (m, 1H), 4.26 (s, 2H), 4.74 (s, 2H), 5.08 (m, 1H), 6.68 (d, J=9.4 Hz, 1H), 6.73 (s, 1H), 7.29-7.55 (m, 6H), 7.69 (d, J=7.8 Hz, 2H), 7.80 (m, 1H), 8.28 (m, 1H)

LC/MS (M$^+$H): 644

(4-12-2) (Z)-t-Butyl-1-isopropylpiperidin-4-yl-(2-((naphthalen-1-yloxy)methyl)-3-(4-(tetrahydro-2H-pyran-2-yloxy-carbamoyl)phenyl)-allyl)carbamate (XXXIIIb)

The procedure of Preparation Example (4-12-1) was repeated except for using the compound of formula XXXIIb (145 mg) obtained in Preparation Example (4-11-2) as the starting material, to obtain 122 mg of the title compound as pale yellow foam (yield 73%).

$^1$H-NMR (200 MHz, CDCl$_3$) δ 1.12 (d, J=6.6 Hz, 6H), 1.43 (s, 9H), 1.61 (m, 3H), 1.86 (m, 7H), 2.06 (m, 2H), 2.37 (m, 2H), 3.61 (m, 1H), 3.98 (m, 1H), 4.23 (s, 2H), 4.74 (s, 2H), 5.07 (m, 1H), 6.68 (d, J=7.4 Hz, 2H), 7.33 (m, 3H), 7.48 (m, 3H), 7.68 (d, J=8.6 Hz, 2H), 7.80 (m, 1H), 8.27 (m, 1H)

LC/MS (M$^+$H): 658

(4-12-3) (Z)-t-Butyl-3-(1H-imidazol-1-yl)propyl-(2-((naphthalen-1-yloxy)methyl)-3-(4-(tetrahydro-2H-pyran-2-yloxy-carbamoyl)phenyl)-alkyl)carbamate (XXXIIIc)

The procedure of Preparation Example (4-12-1) was repeated except for using the compound of formula XXXIIc (176 mg) obtained in Preparation Example (4-11-3) as the starting material, to obtain 205 mg of the title compound as pale yellow foam (yield 99%).

$^1$H-NMR (200 MHz, CDCl$_3$) δ 1.34 (s, 9H), 1.61 (m, 4H), 1.88 (m, 2H), 2.05 (m, 2H), 3.33 (t, J=7.0 Hz, 2H), 3.64 (m, 1H), 3.91 (t, J=6.8 hz, 2H), 3.95 (m, 1H), 4.21 (s, 2H), 4.73 (s, 2H), 5.08 (m, 1H0, 6.66 (d, J=7.6 Hz, 2H), 6.88 (s, 1H), 7.05 (s, 1H), 7.27-7.59 (m, 7H), 7.70 (d, J=8.2 Hz, 2H), 7.82 (m, 1H), 8.21 (m, 1H)

LC/MS (M$^+$H): 641

(4-12-4) (Z)-t-Butyl-4-hydroxyphenethyl-(2-((naphthalen-1-yloxy)methyl)-3-(4-(tetrahydro-2H-pyran-2-yloxy-carbamoyl)phenyl)-allyl)carbamate (XXXIIId)

The procedure of Preparation Example (4-12-1) was repeated except for using the compound of formula XXXIId (31 mg) obtained in Preparation Example (4-11-4) as the starting material, to obtain 36 mg of the title compound as pale yellow oil (yield 98%).

$^1$H-NMR (200 MHz, CDCl$_3$) δ 1.35 (s, 9H), 1.61 (m, 4H), 1.85 (m, 2H), 2.34 (m, 2H), 3.22 (m, 2H), 3.27 (s, 2H), 3.60 (m, 1H), 3.93 (m, 1H), 4.68 (s, 2H), 5.06 (m, 1H), 6.74 (m, 4H), 6.98 (m, 2H), 7.31 (m, 3H), 7.49 (m, 3H), 7.66 (d, J=7.6 Hz, 2H), 7.79 (m, 1H), 8.16 (m, 1H)

LC/MS (M$^+$H): 653

(4-12-5) (Z)-t-Butyl-3-(dimethylamino)-2,2-dimethylpropyl(2-((naphthalen-1-yloxy)methyl)-3-(4-(tetrahydro-2H-pyran-2-yloxy-carbamoyl)phenyl)allyl)carbamate (XXXIIIe)

The procedure of Preparation Example (4-12-1) was repeated except for using the compound of formula XXXIIe (159 mg) obtained in Preparation Example (4-11-5) as the starting material, to obtain 187 mg of the title compound as pale yellow oil (yield 100%).

$^1$H-NMR (200 MHz, CDCl$_3$) δ 0.96 (s, 6H), 1.39 (s, 9H), 1.61 (m, 4H), 1.88 (m, 2H), 2.24 (s, 2H), 3.28 (s, 2H), 3.67 (m, 1H), 3.99 (m, 1H), 4.35 (s, 2H), 4.73 (s, 2H), 5.08 (m, 1H), 6.63 (s, 1H), 6.67 (d, J=8.0 Hz, 1H), 7.27-7.57 (m, 6H), 7.69 (d, J=8.2 Hz, 2H), 7.80 (m, 1H), 8.28 (m, 1H)

LC/MS (M$^+$H): 646

(4-12-6) (Z)-t-Butyl-2-(diisopropylamino)ethyl-(2-((naphthalen-1-yloxy)methyl)-3-(4-(tetrahydro-2H-pyran-2-yloxy-carbamoyl)phenyl)-allyl)carbamate (XXXIIIf)

The procedure of Preparation Example (4-12-1) was repeated except for using the compound of formula XXXIIf (267 mg) obtained in Preparation Example (4-11-6) as the starting material, to obtain 317 mg of the title compound as pale yellow oil (yield 100%).

$^1$H-NMR (200 MHz, CDCl$_3$) δ 0.99 (d, J=6.6 Hz, 12H), 1.36 (s, 9H), 1.61 (m, 4H), 1.86 (m, 2H), 2.61 (t, J=7.0 Hz, 2H), 3.29 (t, J=6.4 Hz, 2H), 3.67 (m, 1H), 3.98 (m, 1H), 4.31 (s, 2H), 4.72 (s, 2H), 5.07 (m, 1H), 6.71 (m, 2H), 7.29-7.58 (m, 6H), 7.68 (d, J=8.2 Hz, 2H). 7.80 (d, J=7.0 Hz, 1H), 8.26 (d, J=7.4 Hz,

LC/MS (M$^+$H): 660

(4-12-7) (Z)-t-Butyl-2-methoxyethyl-(2-((naphthalen-1-yloxy)methyl)-3-(4-(tetrahydro-2H-pyran-2-yloxy-carbamoyl)phenyl)-allyl)carbamate (XXXIIIg)

The procedure of Preparation Example (4-12-1) was repeated except for using the compound of formula XXXIIg (225 mg) obtained in Preparation Example (4-11-7) as the starting material, to obtain 274 mg of the title compound as pale yellow oil (yield 100%).

$^1$H-NMR (200 MHz, CDCl$_3$) δ 1.33 (s, 9H), 1.59 (m, 4H), 1.85 (m, 2H), 3.33 (s, 3H), 3.53 (s. 4H), 3.59 (m, 1H), 3.91 (m, 1H), 4.33 (s, 2H), 4.71 (s, 2H), 5.05 (m, 1H), 6.67 (m, 2H), 7.27-7.55 (m, 6H), 7.66 (d, J=8.0 Hz, 2H), 7.78 (m, 1H), 8.24 (m, 1H)

LC/MS (M$^+$H): 592

(4-12-8) (Z)-t-Butyl-cyclohexyl-(2-((naphthalen-1-yloxy)methyl)-3-(4-(tetrahydro-2H-pyran-2-yloxy-carbamoyl)phenyl)allyl)carbamate (XXXIIIh)

The procedure of Preparation Example (4-12-1) was repeated except for using the compound of formula XXXIIh (81 mg) obtained in Preparation Example (4-11-8) as the starting material, to obtain 109 mg of the title compound as pale yellow oil (yield 98%).

$^1$H-NMR (200 MHz, CDCl$_3$) δ 1.05-1.41 (m, 4H), 1.43 (s, 9H), 1.59 (m, 6H), 1.69-1.95 (m, 6H), 2.54 (m, 1H), 3.66 (m, 1H), 3.97 (m, 1H), 4.14 (s, 2H), 4.74 (s, 2H), 5.06 (m, 1H), 6.68 (m, 2H), 7.30 (m, 3H), 7.47 (m, 3H), 7.67 (d, J=8.2 Hz, 2H), 7.80 (m, 1H), 8.26 (m, 1H)

LC/MS (M$^+$H): 616

(4-12-9) (Z)-t-Butyl-4-(dimethylamino)benzyl-(2-((naphthalen-1-yloxy)methyl)-3-(4-(tetrahydro-2H-pyran-2-yloxycarbamoyl)phenyl)-alkyl)carbamate (XXXIIIi)

The procedure of Preparation Example (4-12-1) was repeated except for using the compound of formula XXXIIi (176 mg) obtained in Preparation Example (4-11-9) as the starting material, to obtain 210 mg of the title compound as pale yellow oil (yield 98%).

TLC (EtOAc) Rf 0.80

$^1$H-NMR (300 MHz, CDCl$_3$) δ 1.23-1.27 (t, J=14.8, 7.4 Hz, 6H), 1.35 (s, 9H), 1.58 (s, 2H), 1.79 (d, J=14.8 Hz, 2H), 2.91 (s, 6H), 3.93-4.15 (m, 4H), 4.45 (s, 2H), 4.67 (s, 2H), 5.04 (s, 1H), 6.63 (d, J=7.4 Hz, 4H), 7.10 (dd, J=14.8, 7.4 Hz, 1H), 7.25-7.53 (m, 7H), 7.66 (d, J=14.8, 7.4 Hz, 2H), 7.78 (d, J=14.8, 7.4 Hz, 1H), 8.21 (d, J=14.8, 7.4 Hz, 1H)

LC/MS (M$^+$H): 616

(4-12-10) (Z)-t-Butyl-3-(4-((tetrahydro-2H-pyran-2-yloxy)carbamoyl)phenyl)-2-((naphthalen-1-yloxy)methyl)allyl-(thiophen-2-ylmethyl)carbamate (XXXIIIj)

The procedure of Preparation Example (4-12-1) was repeated except for using the compound of formula XXXIIj (156 mg) obtained in Preparation Example (4-11-10) as the starting material, to obtain 194 mg of the title compound as pale yellow oil (yield 97%).

TLC (EtOAc) Rf 0.85

$^1$H-NMR (300 MHz, CDCl$_3$) δ 1.25 (s, 2H), 1.36 (s, 9H), 1.58 (s, 2H), 1.85 (m, 2H), 3.60 (s, 1H), 3.98 (s, 1H), 4.25 (s, 2H), 4.67-4.70 (m, 4H), 5.05 (s, 1H), 6.65 (m, 2H), 6.88 (t, J=7.6, 7.6 Hz, 2H), 7.30 (m, 2H), 7.42-7.50 (m, 2H), 7.69 (d, J=7.4 Hz, 2H), 7.79 (d, J=7.8 Hz, 2H), 8.00 (s, 2H), 8.23 (d, J=7.6 Hz, 1H)

LC/MS (M$^+$H): 629

(4-12-11) (Z)-t-Butyl-3-(4-((tetrahydro-2H-pyran-2-yloxy)-carbamoyl)phenyl)-2-((naphthalen-1-yloxy)methyl)allyl-(4-methoxyphenethyl)carbamate (XXXIIIk)

The procedure of Preparation Example (4-12-1) was repeated except for using the compound of formula XXXIIk (228 mg) obtained in Preparation Example (4-11-11) as the starting material, to obtain 283 mg of the title compound as pale yellow oil (yield 98%).

TLC (EtOAc) Rf 0.90

$^1$H-NMR (300 MHz, CDCl$_3$) δ 1.34 (s, 9H), 1.58 (s, 3H), 1.71-1.88 (m, 3H), 2.80 (s, 2H), 3.45-3.50 (t, J=7.4 Hz, 2H), 3.59 (d, J=7.4 Hz, 1H), 3.75 (s, 3H), 3.95 (t, J=7.4 Hz, 1H), 4.10 (d, J=7.8 Hz, 2H), 4.57 (s, 2H), 5.03 (s, 1H), 6.64 (d, J=7.8 Hz, 2H), 6.78 (d, J=7.8 Hz, 2H), 7.26-7.33 (m, 4H), 7.41-7.53 (m, 4H), 7.66 (d, J=7.8 Hz, 2H), 7.79 (d, J=7.4 Hz, 1H), 8.21 (d, J=7.6 Hz, 1H)

LC/MS (M$^+$H): 667

Example 4-1

Preparation of (Z)-4-(3-(1-ethylpiperidin-4-ylamino)-2-((naphthalen-1-yloxy)methyl)prop-1-enyl)-N-hydroxybenzamide (4a)

The compound of formula XXXa (103 mg, 0.19 mmol) obtained in Preparation Example (4-8-1) as the starting material was dissolved in methanol (1.5 ml), and trifluoroacetic acid (0.07 ml, 0.95 mmol) was added dropwise thereto at room temperature. The resulting mixture was reacted for 8 hours to conduct a deprotection reaction of THP. After the completion of reaction, the reaction solution was concentrated under reduced pressure, and the residue thus obtained was purified by a preparative HPLC, to obtain 37 mg of the title compound as pale orange foam, which was used in the subsequent analysis.

$^1$H-NMR (300 MHz, CD$_3$OD) δ 1.31 (t, J=7.5 Hz, 3H), 2.03 (m, 2H), 2.44 (m, 2H), 3.01 (m, 2H), 3.18 (m, 3H), 3.68 (m, 2H), 4.12 (s, 2H), 4.96 (s, 2H), 6.78 (d, J=7.5 Hz, 1H), 7.24 (s, 1H), 7.31 (t, J=8.1 Hz, 1H), 7.46 (m, 5H), 7.70 (d, J=8.1 Hz, 2H), 7.79 (m, 1H), 8.18 (m, 1H)

LC/MS (M$^+$H): 460

Example 4-2

Preparation of (Z)-4-(3-(1-ethylpyrrolidin-3-ylamino)-2-((naphthalen-1-yloxy)methyl)prop-1-enyl)-N-hydroxybenzamide (4b)

The procedure of Example 4-1 was repeated except for using the compound of formula XXXb (120 mg) obtained in Preparation Example (4-8-2) as the starting material, to obtain 56 mg of the title compound as pale yellow oil, which was used in the subsequent analysis.

$^1$H-NMR (300 MHz, CD$_3$OD) δ 1.29 (t, J=7.3 Hz, 3H), 2.29 (m, 1H), 2.60 (m, 1H), 3.27 (q, J=7.3 Hz, 2H), 3.30 (m, 2H), 3.69 (m, 2H), 4.05 (s, 2H), 4.21 (m, 1H), 4.96 (s, 2H), 6.76 (d, J=7.6 Hz, 1H), 7.21 (s, 1H), 7.27 (t, J=8.0 Hz, 1H), 7.45 (m, 5H), 7.69 (d, J=8.2 Hz, 2H), 7.78 (d, J=7.0 Hz, 1H), 8.17 (d, J=7.1 Hz, 1H)

LC/MS (M$^+$H): 446

Example 4-3

Preparation of (Z)—N-hydroxy-4-(3-(naphthalen-1-yloxy)-2-((4-(trifluoromethoxy)benzylamino)methyl)prop-1-enyl)-benzamide (4c)

The procedure of Example 4-1 was repeated except for using the compound of formula XXXc (180 mg) obtained in Preparation Example (4-8-3) as the starting material, to obtain 92 mg of the title compound as pale yellow oil, which was used in the subsequent analysis.

TLC (MeOH/MC=1/6) Rf 0.45

$^1$H-NMR (300 MHz, CD$_3$OD) δ 4.09 (s, 2H), 4.37 (s, 2H), 4.94 (s, 2H), 6.73 (d, J=7.4 Hz, 1H), 7.18 (s, 1H), 7.27 (t, J=7.6 Hz, 3H), 7.35-7.47 (m, 5H), 7.55 (d, J=7.8 Hz, 2H), 7.68 (d, J=7.4 Hz, 2H), 7.76 (d, J=7.8 Hz, 1H), 8.07 (d, J=7.4 Hz, 1H)

LC/MS (M$^+$H): 507

Example 4-4

Preparation of t-butyl (Z)-3-(3-(4-(hydroxycarbamoyl)phenyl)-2-((naphthalen-1-yloxy)methyl)allylamino)-pyrrolidine-1-carboxylate (4d)

The procedure of Example 4-1 was repeated except for using the compound of formula XXXd (180 mg) obtained in Preparation Example (4-8-4) as the starting material, to obtain 84 mg of the title compound as pale yellow oil (yield 81%), which was used in the subsequent analysis.

TLC (MeOH/MC=1/6) Rf 0.75

$^1$H-NMR (300 MHz, CD$_3$OD) δ 1.37 (s, 9H), 1.79-2.12 (m, 2H), 3.14-3.26 (m, 4H), 3.33-3.51 m, 3H), 4.61 (s, 2H), 6.69 (d, J=7.4 Hz, 1H), 6.93 (s, 1H), 7.29-7.55 (m, 6H), 7.63 (t, J=7.8 Hz, 1H), 7.72 (d, J=7.6 Hz, 2H), 8.11 (d, J=7.6 Hz, 1H)

LC/MS (M$^+$H): 518

Example 4-5

Preparation of (Z)—N-hydroxy-4-(3-(naphthalen-1-yloxy)-2-((pyrrolidin-3-ylamino)methyl)prop-1-enyl)-benzamide (4e)

The compound of formula 4d (103 mg, 0.19 mmol) obtained in Example 4-4 was dissolved in dichloromethane (1.5 ml), and trifluoroacetic acid (0.07 ml, 0.95 mmol) was added dropwise thereto at room temperature. The resulting mixture was reacted at room temperature for 8 hours. After the completion of reaction, the reaction solution was concentrated under reduced pressure, and the residue thus obtained was purified by a preparative HPLC, to obtain 37 mg of the title compound as pale orange foam, which was used in the subsequent analysis.

TLC (MeOH/MC=1/4) Rf 0.55

$^1$H-NMR (300 MHz, CD$_3$OD) δ 2.45 (m, 2H), 3.33 (s, 3H), 3.57-3.73 (m, 3H), 4.09 (s, 1H), 4.77 (s, 2H), 6.69 (d, J=7.4 Hz, 1H), 7.19-7.55 (m, 7H), 7.56 (t, J=7.8 Hz, 2H), 7.67 (s, 1H), 8.11 (d, J=7.6 Hz, 1H)

LC/MS (M$^+$H): 418

Example 4-6

Preparation of (Z)-4-(3-(1-(cyclohexylcarbonyl)pyrrolidin-3-ylamino)-2-((naphthalen-1-yloxy)-methyl)prop-1-enyl)-N-hydroxybenzamide (4f)

The procedure of Example 4-1 was repeated except for using the compound of formula XXXe (160 mg) obtained in Preparation Example (4-8-5) as the starting material, to obtain 68 mg of the title compound as pale yellow oil (yield 71%), which was used in the subsequent analysis.

TLC (MeOH/MC=1/6) Rf 0.45

$^1$H-NMR (300 MHz, CD$_3$OD) δ 1.18-1.33 (m, 5H), 1.63 (m, 5H), 2.13-2.44 (m, 3H), 3.33-3.86 (m, 4H), 4.05 (t, J=7.4 Hz, 3H), 4.88 (s, 2H), 6.77 (s, 1H), 7.22 (d, J=7.6 Hz, 2H), 7.35-7.68 (m, 5H), 7.75 (t, J=7.8 Hz, 2H), 7.81 (d, J=7.6 Hz, 1H), 8.18 (s, 1H)

LC/MS (M$^+$H): 528

Example 4-7

Preparation of (Z)-4-(3-(1-cyclopentylpiperidin-4-ylamino)-2-((naphthalen-1-yloxy)methyl)prop-1-enyl)-N-hydroxybenzamide (4g)

The procedure of Example 4-1 was repeated except for using the compound of formula XXXf (120 mg) obtained in Preparation Example (4-8-6) as the starting material, to obtain 77 mg of the title compound as pale yellow oil (yield 44%), which was used in the subsequent analysis.

TLC (MeOH/MC=1/6) Rf 0.20

$^1$H-NMR (300 MHz, CD$_3$OD) δ 1.64 (m, 6H), 1.93 (m, 4H), 2.42 (s, 2H), 3.02-3.19 (m, 2H), 3.29-3.73 (m, 4H), 4.10 (s, 2H), 4.94 (s, 2H), 6.74 (d, J=7.4 Hz, 1H), 7.21 (m, 2H), 7.40 (m, 5H), 7.66 (d, J=7.8 Hz, 2H), 7.76 (t, J=7.8 Hz, 1H), 8.16 (d, J=7.6 Hz, 1H)

LC/MS (M$^+$H): 500

Example 4-8

Preparation of (Z)-4-(3-(1-(cyclohexylmethyl)pyrrolidin-3-ylamino)-2-((naphthalen-1-yloxy)-methyl)prop-1-enyl)-N-hydroxybenzamide (4h)

The procedure of Example 4-1 was repeated except for using the compound of formula XXXg (200 mg) obtained in Preparation Example (4-8-7) as the starting material, to obtain 121 mg of the title compound as pale yellow oil (yield 64%), which was used in the subsequent analysis.

TLC (MeOH/MC=1/6) Rf 0.50

$^1$H-NMR (300 MHz, CD$_3$OD) δ 1.46 (m, 2H), 1.69 (m, 4H), 2.20 (m, 5H), 2.63 (m, 2H), 3.55 (d, J=7.6 Hz, 2H), 3.77 (m, 4H), 4.57 (s, 2H), 4.72 (s, 1H), 5.48 (s, 2H), 7.30 (s, 1H), 7.47 (m, 5H), 7.71 (s, 1H), 7.81 (s, 1H), 8.19 (d, J=7.8 Hz, 2H), 8.29 (d, J=7.6 Hz, 1H), 8.71 (s, 1H)

LC/MS (M$^+$H): 514

Example 4-9

Preparation of (Z)-4-(3-(1-benzylpyrrolidin-3-ylamino)-2-((naphthalen-1-yloxy)methyl)prop-1-enyl)-N-hydroxybenzamide (4i)

The procedure of Example 4-1 was repeated except for using the compound of formula XXXh (180 mg) obtained in Preparation Example (4-8-8) as the starting material, to obtain 94 mg of the title compound as pale yellow oil (yield 77%), which was used in the subsequent analysis.

TLC (MeOH/MC=1/6) Rf 0.35

$^1$H-NMR (300 MHz, CD$_3$OD) δ 1.50 (m, 1H), 2.20 (m, 1H), 3.51 (m, 4H), 3.99 (s, 2H), 4.14 (s, 1H), 4.28 (d, J=7.8 Hz, 2H), 4.91 (s, 2H), 6.73 (d, J=7.6 Hz, 1H), 7.24 (t, J=7.8 Hz, 1H), 7.37-7.58 (m, 11H), 7.66 (d, J=7.8 Hz, 2H), 7.75 (d, J=7.6 Hz, 1H), 8.13 (d, J=7.6 Hz, 1H)

LC/MS (M$^+$H): 508

Example 4-10

Preparation of (Z)-4-(3-(1-cyclopropylpiperidin-4-ylamino)-2-((naphthalen-1-yloxy)methyl)prop-1-enyl)-N-hydroxybenzamide (4j)

The procedure of Example 4-1 was repeated except for using the compound of formula XXXi (90 mg) obtained in Preparation Example (4-8-9) as the starting material, to obtain 44 mg of the title compound as pale yellow oil (yield 57%), which was used in the subsequent analysis.

TLC (MeOH/MC=1/6) Rf 0.25

$^1$H-NMR (300 MHz, CD$_3$OD) δ 0.47 (m, 2H), 1.47 (m, 3H), 1.64 (t, J=7.4 Hz, 3H), 2.35 (m, 1H), 2.57 (s, 1H), 3.04 (d, J=7.4 Hz, 1H), 3.25 (m, 1H), 3.62 (m, 4H), 4.86 (s, 2H), 6.69 (d, J=7.4 Hz, 1H), 6.96 (s, 1H), 7.27-7.50 (m, 4H), 7.78 (d, J=7.4 Hz, 1H), 7.95 (t, J=7.4 Hz, 4H), 8.21 (d, J=7.6 Hz, 1H)

Example 4-11

Preparation of (Z)-4-(3-(1-cyclopropylpyrrolidin-3-ylamino)-2-((naphthalen-1-yloxy)methyl)prop-1-enyl)-N-hydroxybenzamide (4k)

The procedure of Example 4-1 was repeated except for using the compound of formula XXXj (200 mg) obtained in Preparation Example (4-8-10) as the starting material, to obtain 121 mg of the title compound as pale yellow oil (yield 71%), which was used in the subsequent analysis.

TLC (MeOH/MC=1/6) Rf 0.55

$^1$H-NMR (300 MHz, CD$_3$OD) δ 0.40 (m, 3H), 1.62 (m, 2H), 2.11 (m, 2H), 2.51 (q, J=7.6 Hz, 1H), 2.87 (m, 3H), 3.41 (d, J=7.6 Hz, 1H), 3.59 (s, 2H), 4.83 (s, 2H), 6.69 (d, J=7.6 Hz, 1H), 6.87 (s, 1H), 7.28-7.50 (m, 4H), 7.78 (d, J=7.8 Hz, 1H), 7.95 (m, 4H), 8.24 (d, J=7.6 Hz, 1H)

Example 4-12

Preparation of (Z)-4-(3-(1-cyclohexylpyrrolidin-3-ylamino)-2-((naphthalen-1-yloxy)methyl)prop-1-enyl)-N-hydroxybenzamide (4l)

The procedure of Example 4-1 was repeated except for using the compound of formula XXXk (130 mg) obtained in Preparation Example (4-8-11) as the starting material, to obtain 68 mg of the title compound as pale yellow oil (yield 55%), which was used in the subsequent analysis.

TLC (MeOH/MC=1/6) Rf 0.35

$^1$H-NMR (300 MHz, CD$_3$OD) δ 1.17 (m, 4H), 1.56 (m, 4H), 1.71 (s, 2H), 2.11 (m, 3H), 2.43 (m, 1H), 2.64 (m, 2H), 2.87 (m, 1H), 3.40 (d, J=7.8 Hz, 1H), 3.59 (s, 2H), 4.84 (s, 2H), 6.68 (d, J=7.4 Hz, 1H), 6.87 (s, 1H), 7.26 (m, 6H), 7.78 (d, J=7.8 Hz, 1H), 7.96 (d, J=7.6 Hz, 2H), 8.24 (d, J=7.6 Hz, 1H)

Example 4-13

Preparation of (Z)—N-hydroxy-4-(3-(1-methoxypropan-2-ylamino)-2-((naphthalen-1-yloxy)methyl)prop-1-enyl)benzamide (4m)

The procedure of Example 4-1 was repeated except for using the compound of formula XXXm (209 mg) obtained in Preparation Example (4-8-13) as the starting material, to obtain 170 mg of the title compound as pale yellow oil (yield 99%), which was used in the subsequent analysis.

$^1$H-NMR (200 MHz, CD$_3$OD) δ 1.40 (d, J=6.4 Hz, 3H), 3.30 (s, 3H), 3.53 (m, 1H), 3.68 (d, J=8.0 Hz, 2H), 4.13 (s, 2H), 5.00 (s, 2H), 6.80 (d, J=7.8 Hz, 1H), 7.26 (s, 1H), 7.34 (t, J=8.0 Hz, 1H), 7.49 (m, 5H), 7.73 (d, J=8.2 Hz, 2H), 7.81 (m, 1H), 8.23 (m, 1H)

LC/MS (M$^+$H): 421

Example 4-14

Preparation of (Z)—N-hydroxy-4-(3-(2-(1-methylpyrrolidin-2-yl)ethylamino)-2-((naphthalen-1-yloxy)methyl)prop-1-enyl)benzamide (4n)

(Z)-t-Butyl-2-(1-methylpyrrolidin-2-yl)ethyl(2-((naphthalen-1-yloxy)methyl)-3-(4-(tetrahydro-2H-pyran-2-yloxycarbamoyl)phenyl)allyl)-carbamate (170 mg, 0.26 mmol) obtained in Preparation Example (4-12-1) was dissolved in methanol (1.5 ml), and trifluoroacetic acid (0.10 ml, 1.3 mmol) was added dropwise thereto. The resulting mixture was reacted at room temperature for 8 hours, to conduct a deprotection reaction of THP. After the completion of reaction, the reaction solution was concentrated under reduced pressure, and the residue thus obtained was dissolved in trifluoroacetic acid (0.10 ml)/dichloromethane (1.5 ml). The resulting solution was stirred for 12 hours. After the completion of reaction, the reaction solution was concentrated under reduced pressure, and the residue thus obtained was purified by a preparative HPLC, to obtain 68 mg (yield 58%) of the title compound as pale orange foam, which was used in the subsequent analysis.

$^1$H-NMR (200 MHz, CD$_3$OD) δ 1.79 (m, 1H), 2.04 (m, 3H), 2.40 (m, 2H), 2.92 (s, 3H), 3.19 (m, 2H), 3.34 (m, 2H), 3.69 (m, 1H), 4.15 (s, 2H), 4.98 (s, 1H), 6.80 (d, J=6.2 Hz, 1H), 7.26 (s, 1H), 7.33 (t, J=8.0 Hz, 1H), 7.48 (m, 5H), 7.70 (d, J=8.0 Hz, 2H), 7.83 (m, 1H), 8.23 (m, 1H)

LC/MS (M$^+$H): 460

Example 4-15

Preparation of (Z)—N-hydroxy-4-(3-(1-isopropylpiperidin-4-ylamino)-2-((naphthalen-1-yloxy)methyl)prop-1-enyl)benzamide (4o)

The procedure of Example 4-14 was repeated except for using the compound of formula XXXIIIb (122 mg) obtained in Preparation Example (4-12-2) as the starting material, to obtain 55 mg of the title compound as pale yellow oil (yield 62%), which was used in the subsequent analysis.

$^1$H-NMR (200 MHz, CD$_3$OD) δ 1.34 (d, J=7.0 Hz, 6H), 2.17 (m, 2H), 2.51 (m, 2H), 3.16 (m, 2H), 3.60 (m, 4H), 4.17 (s, 2H), 4.98 (s, 2H), 6.77 (d, J=7.2 Hz, 1H), 7.27 (s, 1H), 7.31 (t, J=7.8 Hz, 1H), 7.47 (m, 5H), 7.68 (d, J=8.2 Hz, 2H), 7.81 (m, 1H), 8.23 (m, 1H)

LC/MS (M$^+$H): 474

Example 4-16

Preparation of (Z)-4-(3-(3-(1H-imidazol-1-yl)propylamino)-2-((naphthalen-1-yloxy)methyl)prop-1-enyl)-N-hydroxybenzamide (4p)

The procedure of Example 4-14 was repeated except for using the compound of formula XXXIIIc (205 mg) obtained in Preparation Example (4-12-3) as the starting material, to obtain 70 mg of the title compound as pale yellow oil (yield 47%), which was used in the subsequent analysis.

$^1$H-NMR (200 MHz, CD$_3$OD) δ 2.41 (m, 2H), 3.29 (t, J=6.2 Hz, 2H), 4.13 (s, 2H), 4.46 (t, J=6.4 Hz, 2H), 4.98 (s, 2H), 6.79 (d, J=7.4 Hz, 1H), 7.24 (s, 1H), 7.33 (t, J=7.4 Hz, 1H), 7.48 (m, 7H), 7.70 (t, J=8.2 Hz, 3H), 7.80 (m, 1H), 8.23 (m, 1H)

LC/MS (M$^+$H): 457

Example 4-17

Preparation of (Z)—N-hydroxy-4-(3-(4-hydroxyphenethylamino)-2-((naphthalen-1-yloxy)methyl)prop-1-enyl)-benzamide (4q)

The procedure of Example 4-14 was repeated except for using the compound of formula XXXIIId (36 mg) obtained in Preparation Example (4-12-4) as the starting material, to obtain 18 mg of the title compound as pale yellow oil (yield 67%), which was used in the subsequent analysis.

$^1$H-NMR (200 MHz, CD$_3$OD) δ 3.00 (t, J=5.8 Hz, 2H), 3.37 (m, 2H), 4.10 (s, 2H), 4.95 (s, 2H), 6.69 (d, J=8.6 Hz, 2H), 6.80 (d, J=7.8 Hz, 1H), 7.04 (d, J=8.6 Hz, 2H), 7.23 (s, 1H), 7.34 (t, J=8.2 Hz, 1H), 7.48 (m, 5H), 7.69 (d, J=8.6 Hz, 2H), 7.81 (m, 1H), 8.20 (m, 1H)

LC/MS (M$^+$H): 469

Example 4-18

Preparation of (Z)-4-(3-(3-(dimethylamino)-2,2-dimethylpropylamino)-2-((naphthalen-1-yloxy)methyl)prop-1-enyl)-N-hydroxybenzamide (4r)

The procedure of Example 4-14 was repeated except for using the compound of formula XXXIIIe (187 mg) obtained in Preparation Example (4-12-5) as the starting material, to obtain 65 mg of the title compound as pale yellow oil (yield 48%), which was used in the subsequent analysis.

$^1$H-NMR (200 MHz, CD$_3$OD) δ 1.29 (s, 6H), 2.93 (s, 6H), 3.34 (s, 4H), 4.20 (s, 2H), 5.00 (s, 2H), 6.84 (d, J=7.4 Hz, 1H), 7.30 (s, 1H), 7.36 (t, J=7.6 Hz, 1H), 7.51 (m, 5H), 7.71 (d, J=8.6 Hz, 2H), 7.83 (m, 1H), 8.23 (m, 1H)

LC/MS (M$^+$H): 462

Example 4-19

Preparation of (Z)-4-(3-(2-(diisopropylamino)ethylamino)-2-((naphthalen-1-yloxy)methyl)prop-1-enyl)-N-hydroxybenzamide (4s)

The procedure of Example 4-14 was repeated except for using the compound of formula XXXIIIf (317 mg) obtained in Preparation Example (4-12-6) as the starting material, to obtain 171 mg of the title compound as pale yellow oil (yield 75%), which was used in the subsequent analysis.

$^1$H-NMR (200 MHz, CD$_3$OD) δ 1.37 (d, J=6.6 Hz, 12H), 3.67 (m, 4H), 3.81 (m, 2H), 4.23 (s, 2H), 4.96 (s, 2H), 6.78 (d, J=7.8 Hz, 1H), 7.26 (s, 1H), 7.29 (t, J=7.6 Hz, 1H), 7.43 (m, 5H), 7.63 (d, J=8.0 Hz, 2H), 7.76 (m, 1H), 8.23 (m, 1H)

LC/MS (M$^+$H): 476

Example 4-20

Preparation of (Z)—N-hydroxy-4-(3-(2-methoxyethylamino)-2-((naphthalen-1-yloxy)methyl)prop-1-enyl)-benzamide (4t)

The procedure of Example 4-14 was repeated except for using the compound of formula XXXIIIg (274 mg) obtained in Preparation Example (4-12-7) as the starting material, to obtain 85 mg of the title compound as pale yellow oil (yield 45%), which was used in the subsequent analysis.

$^1$H-NMR (200 MHz, CD$_3$OD) δ 3.33 (s, 3H), 3.43 (t. J=4.8 Hz, 2H), 3.72 (t, J=4.6 Hz, 2H), 4.13 (s, 2H), 4.99 (s, 2H), 6.82 (d, J=6.8 Hz, 1H), 7.25 (s, 1H), 7.36 (t, J=7.8 Hz, 1H), 7.25 (s, 1H), 7.36 (t, J=7.8 Hz, 1H), 7.51 (m, 5H), 7.74 (d, J=8.2 Hz, 2H), 7.83 (m, 1H), 8.23 (m, 1H)

LC/MS (M$^+$H): 407

Example 4-21

Preparation of (Z)-4-(3-(cyclohexylamino)-2-((naphthalen-1-yloxy)methyl)prop-1-enyl)-N-hydroxybenzamide (4u)

The procedure of Example 4-14 was repeated except for using the compound of formula XXXIIIh (98 mg) obtained in Preparation Example (4-12-8) as the starting material, to obtain 26 mg of the title compound as pale yellow oil (yield 37%), which was used in the subsequent analysis.

$^1$H-NMR (200 MHz, CD$_3$OD) δ 1.20-1.58 (m, 5H), 1.73 (m, 1H), 1.92 (m, 2H), 2.20 (m, 2H), 3.32 (m, 1H), 4.11 (s, 2H), 5.00 (s, 2H), 6.82 (d, J=7.2 Hz, 1H), 7.27 (s, 1H), 7.36 (t, J=6.2 Hz, 1H), 7.52 (m, 5H), 7.74 (d, J=8.2 Hz, 2H), 7.84 (m, 1H), 8.23 (m, 1H)

LC/MS (M$^+$H): 431

Example 4-22

Preparation of (Z)—N-hydroxy-4-(3-(naphthalen-1-yloxy)-2-((thiophen-2-ylmethylamino)methyl)prop-1-enyl)benzamide (4v)

The procedure of Example 4-14 was repeated except for using the compound of formula XXXIIIi (130 mg) obtained in Preparation Example (4-12-9) as the starting material, to obtain 6 mg of the title compound as pale yellow oil, which was used in the subsequent analysis.

$^1$H-NMR (200 MHz, CD$_3$OD) δ 4.14 (s, 2H), 4.64 (s, 2H), 4.98 (s, 2H), 6.78 (d, J=7.4 Hz, 1H), 7.09 (m, 1H), 7.23 (s, 1H), 7.33 (m, 2H), 7.48 (m, 6H), 7.71 (d, J=8.2 Hz, 2H), 7.80 (m, 1H), 8.14 (m, 1H)

LC/MS (M$^+$H): 445

Example 4-23

Preparation of (Z)—N-hydroxy-4-(3-(4-methoxyphenethylamino)-2-((naphthalen-1-yloxy)methyl)prop-1-enyl)-benzamide (4w)

The procedure of Example 4-14 was repeated except for using the compound of formula XXXIIIj (150 mg) obtained in Preparation Example (4-12-10) as the starting material, to obtain 20 mg of the title compound as pale yellow oil, which was used in the subsequent analysis.

$^1$H-NMR (200 MHz, CD$_3$OD) δ 3.01 (t, J=7.4 Hz, 2H), 3.40 (t, J=6.4 Hz, 2H), 3.72 (s, 3H), 4.12 (s, 2H), 4.95 (s, 2H), 6.79 (d, J=9.0 Hz, 3H), 7.15 (d, J=8.4 Hz, 2H), 7.24 (s, 1H), 7.34 (t, J=7.6 Hz, 1H), 7.48 (m, 5H), 7.70 (d, J=8.4 Hz, 2H), 7.82 (m, 1H), 8.21 (m, 1H)

LC/MS (M$^+$H): 483

Example 4-24

Preparation of (Z)-4-(3-(4-(dimethylamino)benzylamino))-2-((naphthalen-1-yloxy)methyl)prop-1-enyl)-N-hydroxybenzamide (4x)

The procedure of Example 4-14 was repeated except for using the compound of formula XXXIIIk (211 mg) obtained in Preparation Example (4-12-11) as the starting material, to obtain 19 mg of the title compound as pale yellow oil, which was used in the subsequent analysis.

$^1$H-NMR (200 MHz, CD$_3$OD) δ 3.06 (s, 6H), 4.10 (s, 2H), 4.35 (s, 2H), 4.97 (s, 2H), 6.76 (d, J=8.0 Hz, 1H), 7.09 (d, J=8.6 Hz, 2H), 7.21 (s, 1H), 7.32 (t, J=8.0 Hz, 1H), 7.48 (m, 7H), 7.76 (d, J=8.0 Hz, 2H), 7.80 (m, 1H), 8.12 (m, 1H)

LC/MS (M$^+$H): 482

Test Example 4-1

Analysis of Inhibitory Activity Against HDAC

HDAC activity was analyzed using BIOMOL Quantizyme™ Assay system which comprised two steps of 1) enzyme reaction between HDAC and a substrate and 2) determination of the level of HDAC inhibitory activity.

In step 1), 42 μl of a buffer solution (25 mM Tris-HCl [pH 8.0], 137 mM NaCl, 2.7 mM KCl, 1 mM MgCl$_2$) and 5 μl of 250 μM Fluor de Lys™ substrate were added to each well of a 96-well plate, to which 2.5 μl of a test compound (compounds of Examples 4-1 to 4-24) at a concentration of 0.01, 0.1, 1, 10 and 100 μM, respectively, was added. 0.5 μl of HeLa nuclear organic layer (10 μM) (a source of HDAC enzymes) was then added thereto to a final concentration of 100 nM. The enzyme reaction was carried out for 1 hr.

Subsequently, in step 2), 2 μM tricostatin A was added to 50 μl of Flour de Lys™ developer, followed by allowing the mixture to react at room temperature for 15 minutes. The light excited at 355 nm and emitted at 460 nm from the fluorophore was measured with a fluorometric plate reader. The intensity of the fluorescence increases as the enzyme activity is higher. The HDAC inhibitory activity of each of the test compounds was determined and compared with that of the control. And suberoylanilide hydroxamic acid (SAHA) (Biomol) was used at the same level with the test compounds as a comparative control.

The HDAC inhibitory concentrations (IC$_{50}$) of the test compounds of Examples 4-1 to 4-24 are shown in Table 7.

TABLE 7

| HDAC Inhibitory conc. (IC$_{50}$, μM/ml) | |
| --- | --- |
| Compound | IC$_{50}$ (μM/ml) |
| SAHA | 0.160 |
| Example 4-1 | 0.014 |
| Example 4-2 | 0.017 |
| Example 4-3 | 0.140 |
| Example 4-4 | 0.208 |
| Example 4-5 | 0.020 |
| Example 4-6 | 0.061 |
| Example 4-7 | 0.016 |
| Example 4-8 | 0.045 |
| Example 4-9 | 0.046 |
| Example 4-10 | 0.011 |
| Example 4-11 | 0.023 |
| Example 4-12 | 0.040 |
| Example 4-13 | 0.005 |
| Example 4-14 | 0.013 |
| Example 4-15 | 0.014 |
| Example 4-16 | 0.003 |
| Example 4-17 | 0.003 |
| Example 4-18 | 0.006 |
| Example 4-19 | 0.016 |
| Example 4-20 | 0.010 |
| Example 4-21 | 0.030 |
| Example 4-22 | 0.020 |
| Example 4-23 | 0.040 |
| Example 4-24 | 0.011 |

As shown in Table 7, each of the inventive naphthalenyloxypropenyl derivatives of formula (4) has an inhibitory activity against HDAC, which is comparable to or markedly higher than that of SAHA known as a HDAC inhibitor.

Test Example 4-2

Analysis of Inhibitory Activity Against Proliferation of Cancer Cells

Inhibitory activities of naphthalenyloxypropenyl derivatives synthesized in Examples 4-1 to 4-24 against proliferation of cancer cells were examined by SRB (Sulforhodamine B) analysis using colon cancer cells HCT116 (Korean Cell Line Bank, KCLB 10247) as follows:

Cancer cells were inoculated into a 96-well microplate at a concentration of $1\times10^3\sim3\times10^3$ cells/well and incubated under the condition of 37° C., 5% $CO_2$ for 24 hrs. After the incubation was completed, 0.2, 1, 5, 25, or 100 μM of each of the compounds of Examples was added to the plate, and then the reactant was incubated for 48 hrs. After the substrate was stained with SRB, the anti-cancer activity was determined by comparing the amount of protein in the cells treated with the compound of Examples with that of protein in untreated cells.

Specifically, after the incubation was completed, the culture medium was removed from each well, and the cells were washed 3 times with PBS (pH 7.4). Then, a solution of 50% trichloroacetic acid (TCA) was added to each well in an amount of 50 μl/well at 4° C. for 1 hr to fix them. Then, the microplate was washed 5 times with distilled water and dried in air.

50 μl of a staining solution prepared by dissolving 0.4% SRB in 1% acetic acid was added to the wells, and the microplate was kept at room temperature for 1 hr. The well plate was then washed 5 times with 1% acetic acid to remove unbound SRB and dried in air. The stained cells were treated with 150 μl/well of 10 mM Tris-HCl solution (pH 10.5) to elute SRB from the cells, and the absorbance of the cells treated with the compounds of examples at 540 nm was measured, based on the absorbance of an untreated cell. The $EC_{50}$ value representing inhibition of the cancer cell growth by the extent of 50% was calculated from the measured absorbance, and the results are shown in Table 8.

When cancer cells were treated with a HDAC inhibitor, histone deacetylation would be inhibited, leading to an increase in the amount of acetyl-histone. In this test, the increased amount of acetyl-histone in the cancer cells was determined by using Western blotting, after the treatment with each of the compounds of Examples.

The cells to be tested were inoculated into a 6-well microplate at a concentration of $1.5\times10^8$ cells/well and incubated overnight under the condition of 37° C., 5% $CO_2$. 10 μM of each compound of Examples, and suberoylanilide hydroxamic acid (SAHA) as a control was added to the plate and the plate was incubated again for 24 hrs.

The cells cultured in the presence of the test compound were harvested and subjected to fractionation to separate the nuclei from the cells. The cells were allowed to swell in a hypotonic solution, lysed by several rounds of freezing-thawing cycles, and then centrifuged of 1,300 rpm for 5 min to collect the nuclei. The nuclei was lysed in a lysis buffer solution (20 mM HEPES (pH 7.9), 25% glycerol, 420 mM KCl, 1.5 mM $MgCl_2$, 0.2 mM EDTA) to obtain a protein extract. In order to conduct Western blotting, the resulting protein organic layer was subjected to SDS-PAGE to separate the proteins by the size and transferred onto the nitrocellulose membrane according to the conventional method. The amount of acetylated histone H4 was measured using anti-acetyl histone H4 antibody (Upstate, USA) and evaluated the HDAC inhibitory activity of the inventive compounds by comparing the degree of increase of acetylated histone H4 relative to the control (SAHA). The results are shown in Table 8.

TABLE 8

| Compound | Inhibitory conc. against cancer cell growth ($EC_{50}$ μM) HCT116 | Effect on increase of acetyl-Histone H4 compared with SAHA |
| --- | --- | --- |
| Example 4-1 | 1.1 | + |
| Example 4-2 | 0.8 | + |

TABLE 8-continued

| Compound | Inhibitory conc. against cancer cell growth ($EC_{50}$ μM) HCT116 | Effect on increase of acetyl-Histone H4 compared with SAHA |
| --- | --- | --- |
| Example 4-7 | 10 | + |
| Example 4-10 | 0.5 | + |
| Example 4-11 | 1.0 | + |
| Example 4-13 | <0.2 | + |
| Example 4-15 | 0.4 | + |
| Example 4-16 | 0.7 | + |
| Example 4-17 | <0.2 | + |
| Example 4-18 | 0.31 | + |
| Example 4-19 | 0.8 | + |
| Example 4-20 | <0.2 | + |
| Example 4-22 | 1.3 | + |
| Example 4-23 | 0.8 | + |
| Example 4-24 | 0.5 | + |
| SAHA | 1.6 | + |

As shown in Table 8, the inventive naphthalenyloxypropenyl derivatives of formula (4) has a markedly enhanced inhibitory activity against HDAC, which leads to effective suppression of the cancer cell proliferation.

It should be understood that Examples, while indicating preferred embodiments of the invention, are given by way of illustration only. From the above Examples, one skilled in the art can ascertain the essential characteristics of this invention, and without departing from the spirit and scope thereof, can make various changes and modifications of the invention to adapt it to various usage and conditions.

What is claimed is:

1. A naphthalenyloxypropenyl derivative of formula (1) or its pharmaceutically acceptable salt:

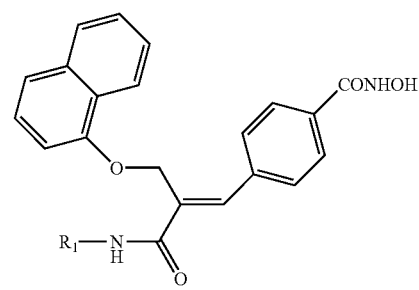

(1)

wherein, $R_1$ is substituted or unsubstituted $C_{1-6}$alkyl with one or more substituents selected from the group consisting of di$C_{1-3}$alkylamino, pyrrolidinyl, oxopyrrolidinyl, methoxypyrrolidinyl, $C_{1-3}$alkylpiperidinyl, morpholinyl, imidazolyl, methoxy, ethoxy, tetrahydrofuranyl, $C_{3-8}$cycloalkenyl, furanyl, thiophenyl, fluorophenyl, di$C_{1-3}$alkylaminophenyl and methoxyphenyl; piperidinyl substituted with $C_{1-6}$alkyl; or $C_{3-8}$cycloalkyl.

2. The compound of claim 1, which is selected from the group consisting of:

(E)-4-(3-(1-methylpiperidin-4-ylamino)-2-((naphthalen-1-yloxy)methyl)-3-oxoprop-1-enyl)-N-hydroxybenzamide;

(E)-4-(3-(3-(1H-imidazol-1-yl)propylamino)-2-((naphthalen-1-yloxy)-methyl)-3-oxopropenyl)-N-hydroxybenzamide;

(E)-4-(3-(4-methoxyphenethylamino)-2-((naphthalen-1-yloxy)-methyl)-3-oxoprop-1-enyl)-N-hydroxybenzamide;

(E)-4-(3-(3-dimethylamino)-2,2-dimethylpropylamino)-2-((naphthalen-1-yloxy)methyl)-3-oxoprop-1-enyl)-N-hydroxybenzamide;

(E)-4-(3-(2-diisopropylamino)ethylamino)-2-((naphthalen-1-yloxy)-methyl)-3-oxoprop-1-enyl)-N-hydroxybenzamide;

(E)-4-(3-(1-methoxypropan-2-ylamino)-2-((naphthalen-1-yloxy)-methyl)-3-oxoprop-1-enyl)-N-hydroxybenzamide;

(E)-4-(3-(4-methoxybenzylamino)-2-((naphthalen-1-yloxy)methyl)-3-oxo-prop-1-enyl)-N-hydroxybenzamide;

(E)-4-(3-(4-fluorophenethylamino)-2-((naphthalen-1-yloxy)methyl)-3-oxo-prop-1-enyl)-N-hydroxybenzamide;

(E)-4-(3-(tetrahydrofuran-2-yl)methylamino)-2-((naphthalen-1-yloxy)-methyl)-3-oxoprop-1-enyl)-N-hydroxybenzamide;

(E)-4-(3-(2-cyclohexenylethylamino)-2-((naphthalen-1-yloxy)methyl)-3-oxoprop-1-enyl)-N-hydroxybenzamide;

(E)-4-(3-(3-(2-oxopyrrolidin-1-yl)propylamino)-2-((naphthalen-1-yloxy)-methyl)-3-oxoprop-1-enyl)-N-hydroxybenzamide;

(E)-4-(3-(furan-2-ylmethylamino)-2-((naphthalen-1-yloxy)methyl)-3-oxo-prop-1-enyl)-N-hydroxybenzamide;

(E)-4-(3-(4-(dimethylamino)benzylamino)-2-((naphthalen-1-yloxy)-methyl)-3-oxoprop-1-enyl)-N-hydroxybenzamide;

(E)-4-(3-(2-methoxyethylamino)-2-((naphthalen-1-yloxy)methyl)-3-oxo-prop-1-enyl)-N-hydroxybenzamide;

(E)-4-(3-(cyclohexylamino)-2-((naphthalen-1-yloxy)methyl)-3-oxoprop-1-enyl)-N-hydroxybenzamide;

(E)-4-(3-(thiophen-2-ylmethylamino)-2-((naphthalen-1-yloxy)methyl)-3-oxoprop-1-enyl)-N-hydroxybenzamide;

(E)-4-(3-(1-ethylpiperidin-4-ylamino)-2-((naphthalen-1-yloxy)methyl)-3-oxoprop-1-enyl)-N-hydroxybenzamide;

(E)-4-(3-(3-morpholinopropylamino)-2-((naphthalen-1-yloxy)methyl)-3-oxoprop-1-enyl)-N-hydroxybenzamide;

(E)-(3-(3-(2-methylpiperidin-1-yl)propylamino)-2-((naphthalen-1-yloxy)-methyl)-3-oxoprop-1-enyl)-N-hydroxybenzamide;

(E)-(3-(3-pyrrolidin-1-yl)propylamino)-2-((naphthalen-1-yloxy)methyl)-3-oxoprop-1-enyl)-N-hydroxybenzamide;

(E)-4-(3-(3-ethoxypropylamino)-2-((naphthalen-1-yloxy)methyl)-3-oxo-prop-1-enyl)-N-hydroxybenzamide;

(E)-4-(3-(2-(1-methylpyrrolidin-2-yl)ethylamino)-2-((naphthalen-1-yloxy)-methyl)-3-oxoprop-1-enyl)-N-hydroxybenzamide; and (E)-4-(3-(1-isopropylpiperidin-4-ylamino)-2-((naphthalen-1-yloxy)methyl)-3-oxoprop-1-enyl)-N-hydroxybenzamide.

3. A naphthalenyloxypropenyl derivative of formula (2) or its pharmaceutically acceptable salt:

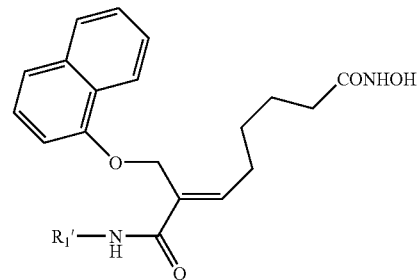

(2)

wherein, $R_1'$ is substituted or unsubstituted $C_{1-3}$alkyl with one or more substituents selected from the group consisting of halophenyl, $C_{1-3}$alkoxy, $C_{1-3}$alkoxy$C_{1-3}$alkyl, cyclohexanyl, furanyl, thiophenyl, imidazole, imidazolidyl$C_{1-3}$alkyl, $C_{1-3}$-alkylamino, di$C_{1-3}$alkylamino, hydroxyphenyl, tetrahydrofuranyl, cyclohexyl, cyclohexenyl, oxopyrrolidinyl, $C_{1-3}$alkoxyphenyl, di$C_{1-3}$-alkylaminophenyl and trifluoromethoxyphenyl; substituted or unsubstituted pyrrolidinyl with a substituent selected from $C_{3-8}$cycloalkyl, $C_{3-8}$cycloalkyl$C_{1-3}$alkyl, benzyl, $C_{1-3}$-alkyl or $C_{3-8}$cycloalkylcarbonyl; piperidinyl substituted with $C_{1-3}$alkyl or $C_{3-8}$-cycloalkyl; furanyl; or $C_{3-8}$cycloalkyl.

4. The compound of claim 3, which is selected from the group consisting of:

(E)-N1-(3-(1H-imidazol-1-yl)propyl)-N8-hydroxy-2-((naphthalen-1-yloxy)-methyl)octenediamide;

(E)-N8-hydroxy-N1-(4-hydroxyphenethyl)-2-((naphthalen-1-yloxy)methyl)-2-octenediamide;

(E)-N1-(3-(dimethylamino)-2,2-dimethylpropyl)-N8-hydroxy-2-((naphthalen-1-yloxy)methyl)octenediamide;

(E)-N1-(2-(diisopropylamino)ethyl)-N8-hydroxy-2-((naphthalen-1-yloxy)-methyl)octenediamide;

(E)-N8-hydroxy-N1-(1-methoxypropan-2-yl)-2-((naphthalen-1-yloxy)-methyl)-2-octenediamide;

(E)-N8-hydroxy-N1-(4-methoxybenzyl)-2-((naphthalen-1-yloxy)methyl)-2-octenediamide;

(E)-N1-(4-fluorophenethyl)-N8-hydroxy-2-((naphthalen-1-yloxy)methyl)-2-octenediamide;

(E)-N8-hydroxy-2-((naphthalen-1-yloxy)methyl)-N1-(tetrahydrofuran-2-yl)-methyl)-2-octenediamide;

(E)-N1-(2-cyclohexenylethyl)-N8-hydroxy-2-((naphthalen-1-yloxy)methyl)-2-octenediamide;

(E)-N8-hydroxy-2-((naphthalen-1-yloxy)methyl)-N1-(3-(2-oxopyrrolidin-1-yl)propyl)-2-octenediamide;

(E)-N1-(furan-2-ylmethyl)-N8-hydroxy-2-((naphthalen-1-yloxy)-methyl)-2-octenediamide (E)-N1-(4-(dimethylamino)benzyl)-N8-hydroxy-2-((naphthalen-1-yloxy)-methyl)-2-octenediamide;

(E)-N8-hydroxy-N1-(2-methoxyethyl)-2-((naphthalen-1-yloxy)methyl)-2-octenediamide;

(E)-N1-cyclohexyl-N8-hydroxy-2-((naphthalen-1-yloxy)methyl)-2-octenediamide;

(E)-N8-hydroxy-2-((naphthalen-1-yloxy)methyl)-N1-(thiophen-2-ylmethyl)-2-octenediamide;

(E)-N8-hydroxy-N1-(4-methoxyphenethyl)-2-((naphthalen-1-yloxy)-methyl)-2-octenediamide;

(E)-N8-hydroxy-2-((naphthalen-1-yloxy)methyl)-N1-(4-(trifluoromethoxy)-benzyl)-2-octenediamide;

(E)-N1-(1-cyclohexylmethyl)pyrrolidin-3-yl)-N8-hydroxy-2-((naphthalen-1-yloxy)methyl)-2-octenediamide;

(E)-N1-(1-cyclopentylpiperidin-4-yl)-N8-hydroxy-2-((naphthalen-1-yloxy)-methyl)-2-octenediamide;
(E)-N1-(1-benzylpyrrolidin-3-yl)-N8-hydroxy-2-((naphthalen-1-yloxy)-methyl)-2-octene diamide;
(E)-N8-hydroxy-N1-(1-isopropylpyrrolidin-3-yl)-2-((naphthalen-1-yloxy)-methyl)-2-octenediamide;
(E)-N1-(1-(cyclohexanecarbonyl)pyrrolidin-3-yl)-N8-hydroxy-2-((naphthalen-1-yloxy)methyl)-2-octenediamide;
t-butyl (E)-3-(8-(hydroxyamino)-2-((naphthalen-1-yloxy)methyl)-8-oxo-2-octeneamido)pyrrolidine-1-carboxylate;
(E)-N8-hydroxy-2-((naphthalen-1-yloxy)methyl)-N1-(pyrrolidin-3-yl)-2-octenediamide;
(E)-N1-(1-cyclohexylpyrrolidin-3-yl)-N8-hydroxy-2-((naphthalen-2-yloxy)-methyl)-2-octenediamide;
(E)-N1-(1-cyclopropylpyrrolidin-3-yl)-N8-hydroxy-2-((naphthalen-1-yloxy)methyl)-2-octenediamide;
(E)-N1-(1-cyclopropylpiperidin-4-yl)-N8-hydroxy-2-((naphthalen-1-yloxy)-methyl)-2-octenediamide;
(E)-N1-(1-ethylpiperidin-4-yl)-N8-hydroxy-2-((naphthalen-1-yloxy)-methyl)-2-octenediamide;
(E)-N1-(1-ethylpyrrolidin-3-yl)-N8-hydroxy-2-((naphthalen-1-yloxy)-methyl)-2-octenediamide; and
(E)-N8-hydroxy-N1-(1-isopropylpiperidin-4-yl)-2-((naphthalen-1-yloxy)-methyl)-2-octenediamide.

5. A naphthalenyloxypropenyl derivative of formula (3) or its pharmaceutically acceptable salt:

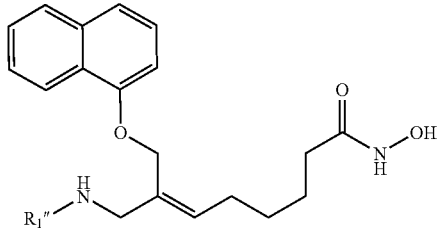

(3)

wherein,
R$_1$" is C$_{1-3}$ alkyl optionally having one or more substituents selected from the group consisting of C$_{1-3}$alkyl, C$_{1-3}$alkoxy, hydroxyC$_{1-3}$alkyl, halophenyl, piperidinyl, morpholinyl, cyanomethyl, piperazinyl, diC$_{1-3}$alkylamino, diC$_{1-3}$-alkylaminoC$_{1-3}$alkyl, piperidinylC$_{1-3}$alkyl, C$_{1-3}$alkoxyC$_{1-3}$alkyl, morpholinoC$_{1-3}$-alkyl, piperazinoC$_{1-3}$alkyl, pyrrolidinyl, oxopyrrolidinyl, C$_{1-3}$alkylpyrrolidinyl, imidazolyl, imidazolylC$_{1-3}$alkyl and thiophenyl.

6. The compound of claim 5, which is selected from the group consisting of:
(Z)—N-hydroxy-8-(2-morpholinoethylamino)-7-((naphthalen-1-yloxy)-methyl)oct-6-en-amide;
(Z)—N-hydroxy-8-(1-methoxypropan-2-ylamino)-7-((naphthalen-1-yloxy)-methyl)oct-6-enamide;
(Z)—N-hydroxy-8-(naphthalen-1-yloxy)-7-((3-(2-oxopyrrolidin-1-yl)propyl-amino)methyl)oct-6-enamide;
(Z)-8-(3-(1H-imidazol-1-yl)propylamino)-N-hydroxy-7-((naphthalen-1-yloxy)methyl)oct-6-enamide;
(Z)—N-hydroxy-8-(3-(2-methylpiperidin-1-yl)propylamino)-7-((naphthalen-1-yloxy)methyl)oct-6-enamide;
(Z)-8-(3-(dimethylamino)propylamino)-N-hydroxy-7-((naphthalen-1-yloxy)methyl)oct-6-enamide;
(Z)-8-(3-(dimethylamino)-2,2-dimethylpropylamino)-N-hydroxy-7-((naphthalen-1-yloxy)methyl)oct-6-enamide;
(Z)—N-hydroxy-8-(naphthalen-1-yloxy)-7-((2-(pyrrolidin-1-yl)ethylamino)-methyl)oct-6-enamide;
(Z)-8-(4-fluorophenethylamino)-N-hydroxy-7-((naphthalen-1-yloxy)-methyl)oct-6-enamide;
(Z)—N-hydroxy-8-(2-methoxyethylamino)-7-((naphthalen-1-yloxy)methyl)-oct-6-enamide
(Z)—N-hydroxy-8-(1-isopropylpiperidin-4-ylamino)-7-((naphthalen-1-yloxy)methyl)oct-6-enamide;
(Z)-8-(3-(diethylamino)propylamino)-N-hydroxy-7-((naphthalen-1-yloxy)-methyl)oct-6-enamide;
(Z)-8-(2-diisopropylamino)ethylamino))-N-hydroxy-7-((naphthalen-1-yloxy)methyl)oct-6-enamide; and
(Z)—N-hydroxy-8-(naphthalen-1-yloxy)-7-(thiophen-2-ylmethylamino)-methyl)oct-6-enamide.

7. A naphthalenyloxypropenyl derivative of formula (4) or its pharmaceutically acceptable salt:

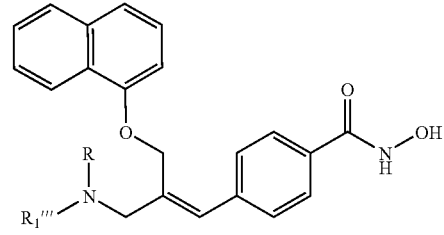

(4)

wherein,
R is hydrogen or C$_{1-3}$alkyl;
R$_1$''' is substituted or unsubstituted C$_{1-6}$alkyl with one or more substituents selected from the group consisting of diC$_{1-3}$alkylamino, C$_{1-3}$alkylpyrrolidinyl, imidazolyl, methoxy and thiophenyl; C$_{1-6}$alkyl substituted with hydroxyphenyl, diC$_{1-3}$-alkylaminophenyl, methoxyphenyl or trifluoromethoxyphenyl; substituted or unsubstituted pyrrolidine with a substituent selected from C$_{1-3}$alkyl, C$_{3-8}$cycloalkyl, C$_{3-8}$-cycloalkylC$_{1-3}$alkyl, benzyl or C$_{3-8}$cycloalkylcarbonyl; piperidinyl substituted with C$_{3-8}$cycloalkyl or C$_{1-6}$alkyl; or C$_{3-8}$cycloalkyl.

8. The compound of claim 7, which is selected from the group consisting of:
(Z)-4-(3-(1-ethylpiperidin-4-ylamino)-2-((naphthalen-1-yloxy)methyl)-prop-1-enyl)-N-hydroxybenzamide;
(Z)-4-(3-(1-ethylpyrrolidin-3-ylamino)-2-((naphthalen-1-yloxy)methyl)-prop-1-enyl)-N-hydroxybenzamide;
(Z)—N-hydroxy-4-(3-(naphthalen-1-yloxy)-2-((4-(trifluoromethoxy)-benzylamino)methyl)prop-1-enyl)benzamide;
t-butyl (Z)-3-(3-(4-(hydroxycarbamoyl)phenyl-2-((naphthalen-1-yloxy)-methyl)allylamino)pyrrolidine-1-carboxylate;
(Z)—N-hydroxy-4-(3-(naphthalen-1-yloxy)-2-((pyrrolidin-3-ylamino)-methyl)prop-1-enyl)benzamide;
(Z)-4-(3-(1-(cyclohexylcarbonyl)pyrrolidin-3-ylamino)-2-((naphthalen-1-yloxy)methyl)prop-1-enyl)-N-hydroxybenzamide;
(Z)-4-(3-(1-cyclopentylpiperidin-4-ylamino)-2-((naphthalen-1-yloxy)-methyl)prop-1-enyl)-N-hydroxybenzamide;

(Z)-4-(3-(1-(cyclohexylmethyl)pyrrolidin-3-ylamino)-2-((naphthalen-1-yloxy)methyl)prop-1-enyl)-N-hydroxybenzamide;

(Z)-4-(3-(1-benzylpyrrolidin-3-yl-amino)-2-((naphthalen-1-yloxy)methyl)-prop-1-enyl)-N-hydroxybenzamide (Z)-4-(3-(1-cyclopropylpiperidin-4-ylamino)-2-((naphthalen-1-yloxy)-methyl)prop-1-enyl)-N-hydroxybenzamide;

(Z)-4-(3-(1-cyclopropylpyrrolidin-3-ylamino)-2-((naphthalen-1-yloxy)-methyl)prop-1-enyl)-N-hydroxybenzamide;

(Z)-4-(3-(1-cyclohexylpyrrolidin-3-ylamino)-2-((naphthalen-1-yloxy)-methyl)prop-1-enyl)-N-hydroxybenzamide;

(Z)—N-hydroxy-4-(3-(1-methoxypropan-2-ylamino)-2-((naphthalen-1-yloxy)methyl)prop-1-enyl)benzamide;

(Z)—N-hydroxy-4-(3-(2-(1-methylpyrrolidin-2-yl)ethylamino)-2-((naphthalene-1-yloxy)methyl)prop-1-enyl)benzamide;

(Z)—N-hydroxy-4-(3-(2-(1-isopropylpiperidin-4-ylamino)-2-((naphthalen-1-yloxy)methyl)prop-1-enyl)benzamide;

(Z)-4-(3-(3-(1H-imidazol-1-yl)propylamino)-2-((naphthalen-1-yloxy)-methyl)prop-1-enyl)-N-hydroxybenzamide;

(Z)—N-hydroxy-4-(3-(4-hydroxyphenethylamino)-2-((naphthalen-1-yloxy)-methyl)prop-1-enyl)benzamide;

(Z)-4-(3-(3-(dimethylamino)-2,2-dimethylpropylamino)-2-((naphthalen-1-yloxy)methyl)prop-1-enyl)-N-hydroxybenzamide;

(Z)-4-(3-(2-(diisopropylamino)ethylamino)-2-((naphthalen-1-yloxy)-methyl)prop-1-enyl)-N-hydroxybenzamide;

(Z)—N-hydroxy-4-(3-(2-methoxyethylamino)-2-((naphthalen-1-yloxy)-methyl)prop-1-enyl)benzamide;

(Z)-4-(3-(cyclohexylamino)-2-((naphthalen-1-yloxy)methyl)prop-1-enyl)-N-hydroxybenzamide;

(Z)—N-hydroxy-4-(3-(naphthalen-1-yloxy)-2-((thiophen-2-ylmethylamino)-methyl)prop-1-enyl)benzamide;

(Z)—N-hydroxy-4-(3-(4-methoxyphenethylamino)-2-((naphthalen-1-lyoxy)-methyl)prop-1-enyl)benzamide; and (Z)-4-(3-(4-(dimethylamino)benzylamino))-2-((naphthalen-1-yloxy)-methyl)prop-1-enyl)-N-hydroxybenzamide.

9. An anti-cancer composition comprising a naphthalenyloxypropenyl derivative of claim 1.

10. An anti-cancer composition comprising a naphthalenyloxypropenyl derivative of claim 3.

11. An anti-cancer composition comprising a naphthalenyloxypropenyl derivative of claim 5.

12. An anti-cancer composition comprising a naphthalenyloxypropenyl derivative of claim 7.

13. The compound of claim 3, wherein $R'_1$ is a $C_{1-3}$alkyl substituted with diC1-3alkylamino group.

* * * * *